(12) United States Patent
Allard et al.

(10) Patent No.: US 11,141,174 B1
(45) Date of Patent: Oct. 12, 2021

(54) PATIENT SPECIFIC INSTRUMENTS AND METHODS OF USE

(71) Applicant: Paragon 28, Inc., Englewood, CO (US)

(72) Inventors: Randy Allard, Golden, CO (US);
Francis D. Barmes, Parker, CO (US);
Mark Ray Dalton, Austin, TX (US);
Joseph Dogué, Aurora, CO (US);
Aaron Kannard, Los Angeles, CA (US); Daniel J. Lee, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 17/304,048

(22) Filed: Jun. 14, 2021

Related U.S. Application Data

(63) Continuation of application No. PCT/US2019/066336, filed on Dec. 13, 2019.

(60) Provisional application No. 62/890,611, filed on Aug. 22, 2019, provisional application No. 62/779,436, filed on Dec. 13, 2018.

(51) Int. Cl.
*A61F 5/00* (2006.01)
*A61B 17/17* (2006.01)
*A61B 34/10* (2016.01)

(52) U.S. Cl.
CPC ............. *A61B 17/17* (2013.01); *A61B 34/10* (2016.02); *A61B 17/1775* (2016.11); *A61B 2034/108* (2016.02)

(58) Field of Classification Search
CPC combination set(s) only.
See application file for complete search history.

(56) References Cited

U.S. PATENT DOCUMENTS

| | | | |
|---|---|---|---|
| 7,468,075 | B2 | 12/2008 | Lang |
| 7,534,263 | B2 | 5/2009 | Burdulis, Jr. |
| 7,618,451 | B2 | 11/2009 | Berez |
| 7,981,158 | B2 | 7/2011 | Fitz |
| 8,062,302 | B2 | 11/2011 | Lang |
| 8,083,745 | B2 | 12/2011 | Lang |
| 8,105,330 | B2 | 1/2012 | Fitz |
| 8,357,166 | B2 | 1/2013 | Aram |
| 8,366,771 | B2 | 2/2013 | Burdulis, Jr. |
| 8,460,304 | B2 | 6/2013 | Fitz |
| 8,585,708 | B2 | 11/2013 | Fitz |
| 8,617,172 | B2 | 12/2013 | Fitz |

(Continued)

FOREIGN PATENT DOCUMENTS

WO    2019213122    11/2019

OTHER PUBLICATIONS

Wright Medical Technology, Inc., Prophecy Infinity Preoperative Navigation Guides, Surgical Technique, https://www.wightemedia.com/ProductFiles/Files/PDFs/011940_EN_LR_LE.pdf, 39 pages, Feb. 8, 2018 (retrieved from the internet on Mar. 16, 2020).

(Continued)

*Primary Examiner* — Sameh R Boles
(74) *Attorney, Agent, or Firm* — Heslin Rothenberg Farley & Mesiti P.C.; Jacquelyn A. Graff, Esq.

(57) ABSTRACT

Patient specific instruments, systems and methods for maintaining, correcting and/or resurfacing joint surfaces. A tibia alignment guide including a body with a first surface and a second surface, a base portion coupled to and extending away from the first surface of the body, and a tower portion coupled to and extending away from a top surface of the body.

30 Claims, 82 Drawing Sheets

(56) References Cited

U.S. PATENT DOCUMENTS

| | | |
|---|---|---|
| 8,657,827 B2 | 2/2014 | Fitz |
| 8,951,259 B2 | 2/2015 | Fitz et al. |
| 8,951,260 B2 | 2/2015 | Lang |
| 8,965,088 B2 | 2/2015 | Tsougarakis et al. |
| 9,023,050 B2 | 5/2015 | Lang |
| 9,066,728 B2 | 6/2015 | Burdulis, Jr. |
| 9,072,531 B2 | 7/2015 | Fitz et al. |
| 9,107,680 B2 | 8/2015 | Fitz et al. |
| 9,125,672 B2 | 9/2015 | Fitz et al. |
| 9,125,673 B2 | 9/2015 | Fitz et al. |
| 9,186,161 B2 | 11/2015 | Lang |
| 9,220,517 B2 | 12/2015 | Lang |
| 9,326,780 B2 | 5/2016 | Wong et al. |
| 9,358,018 B2 | 6/2016 | Fitz |
| 2010/0217338 A1 | 8/2010 | Carroll |
| 2011/0218542 A1 | 9/2011 | Lian |
| 2015/0305753 A1* | 10/2015 | McGinley ............ A61F 2/4606 606/96 |
| 2017/0238946 A1 | 8/2017 | van der Walt et al. |
| 2018/0280069 A1 | 10/2018 | Barmes et al. |

OTHER PUBLICATIONS

International Search Report and Written Opinion of the International Searching Authority for PCT/US2019/066336, dated Apr. 1, 2020, 17 pages.

\* cited by examiner

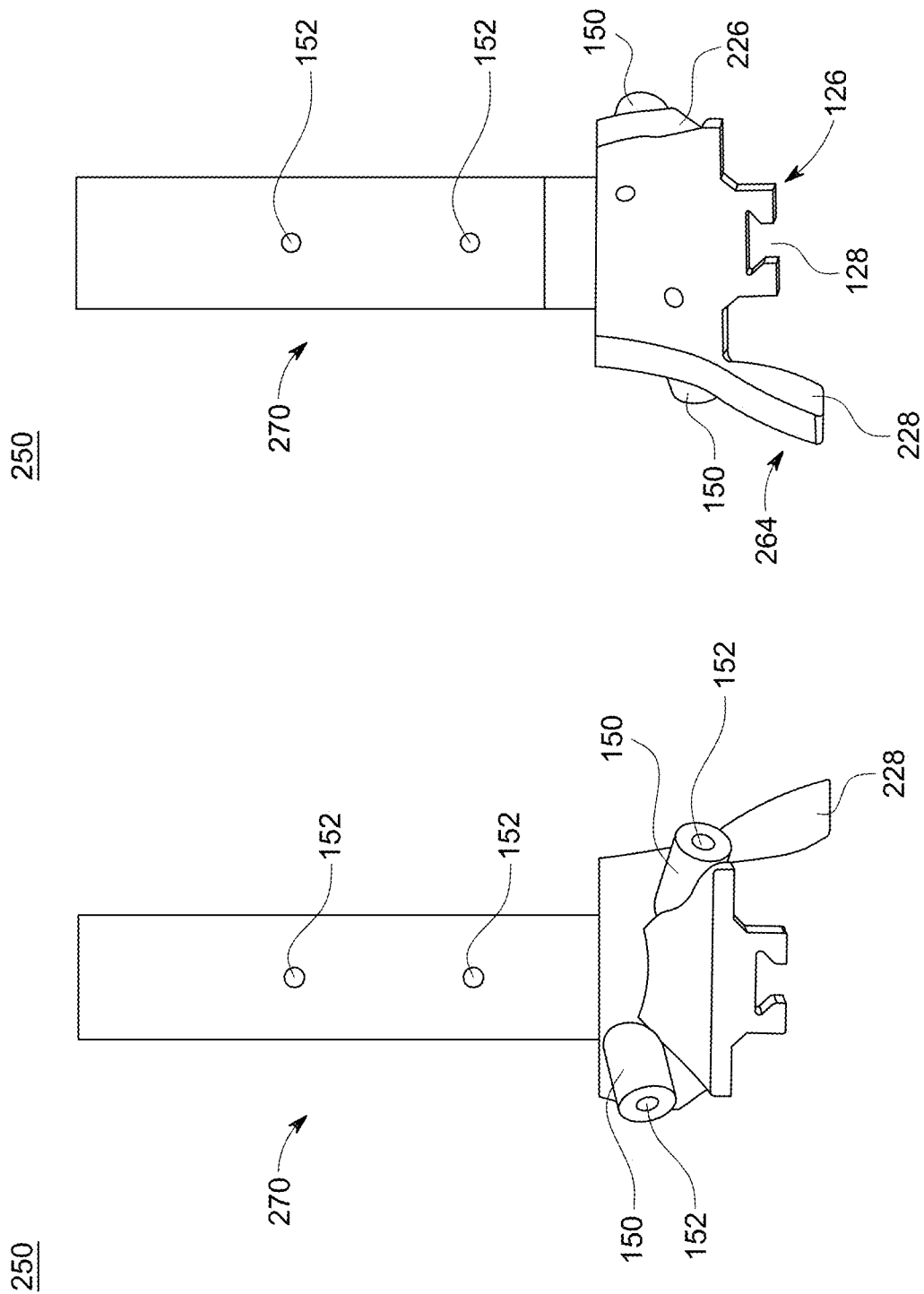

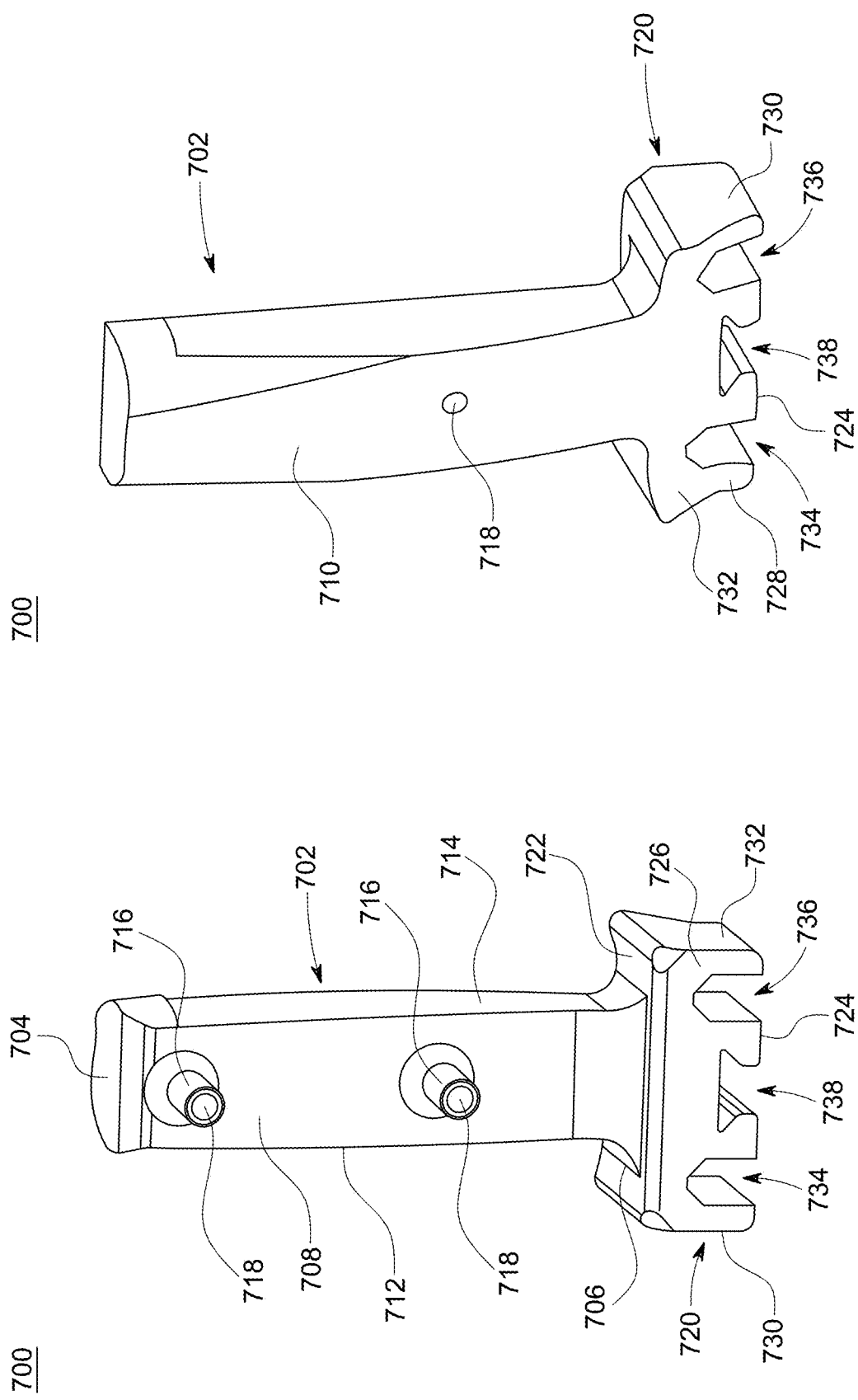

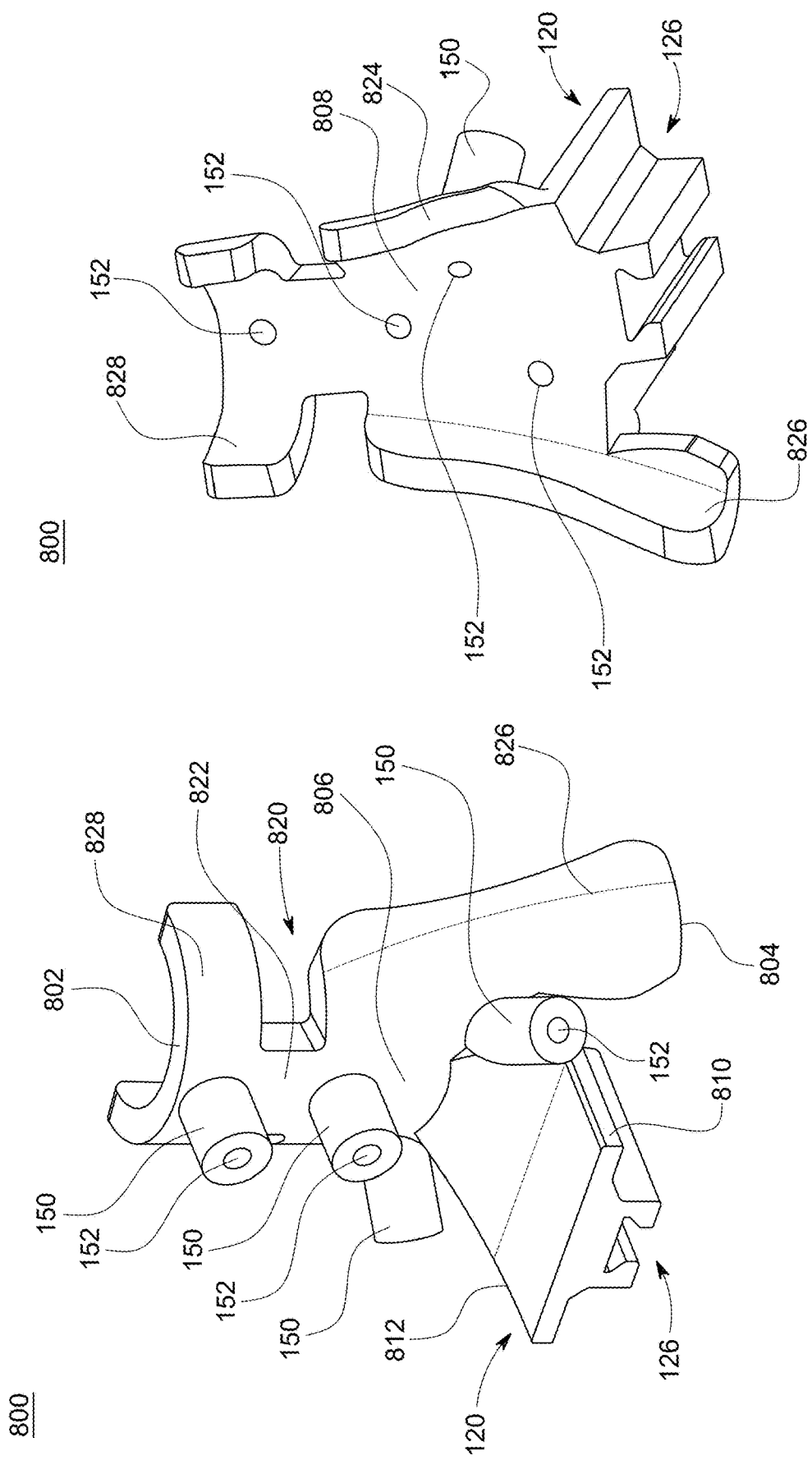

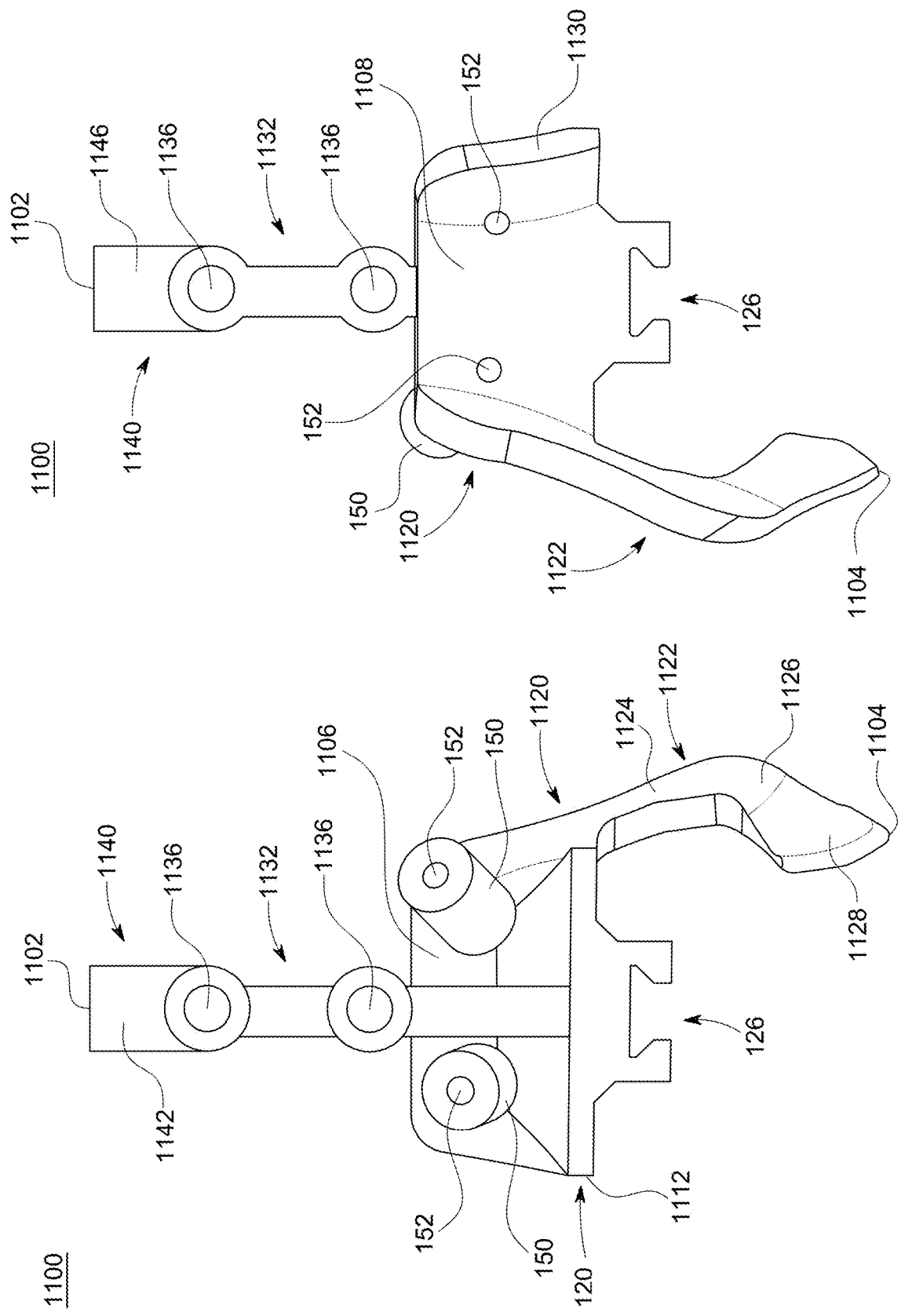

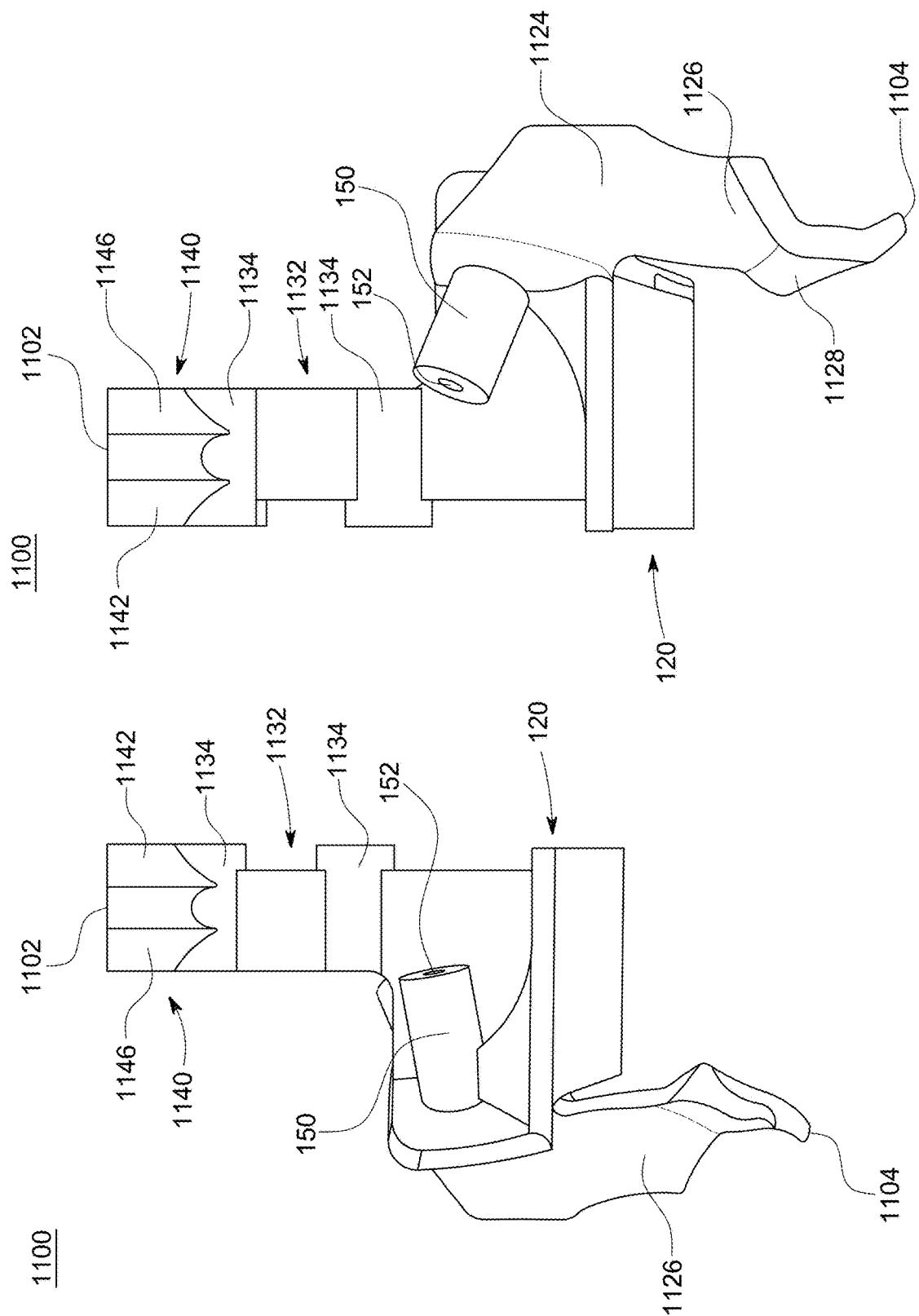

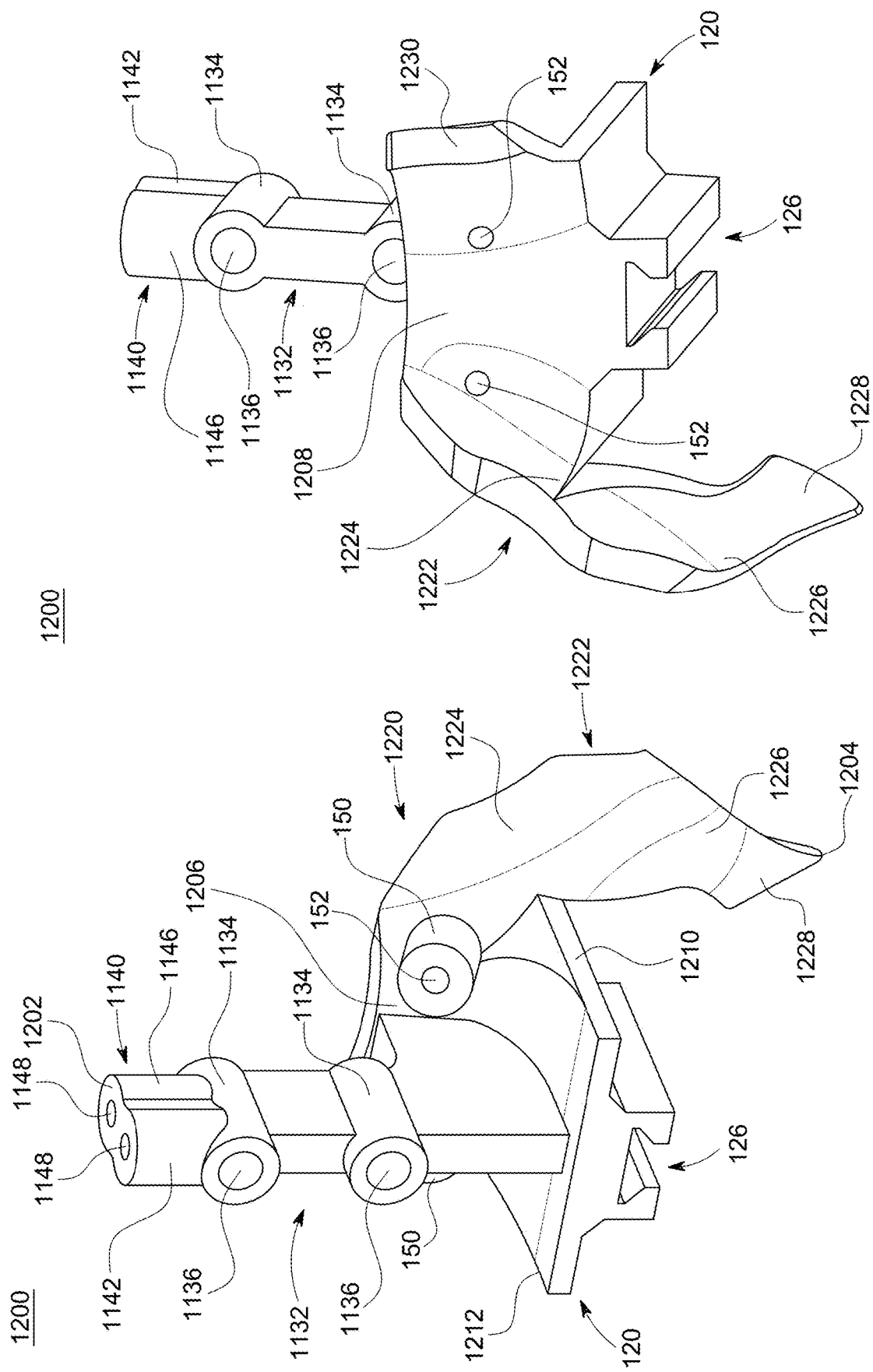

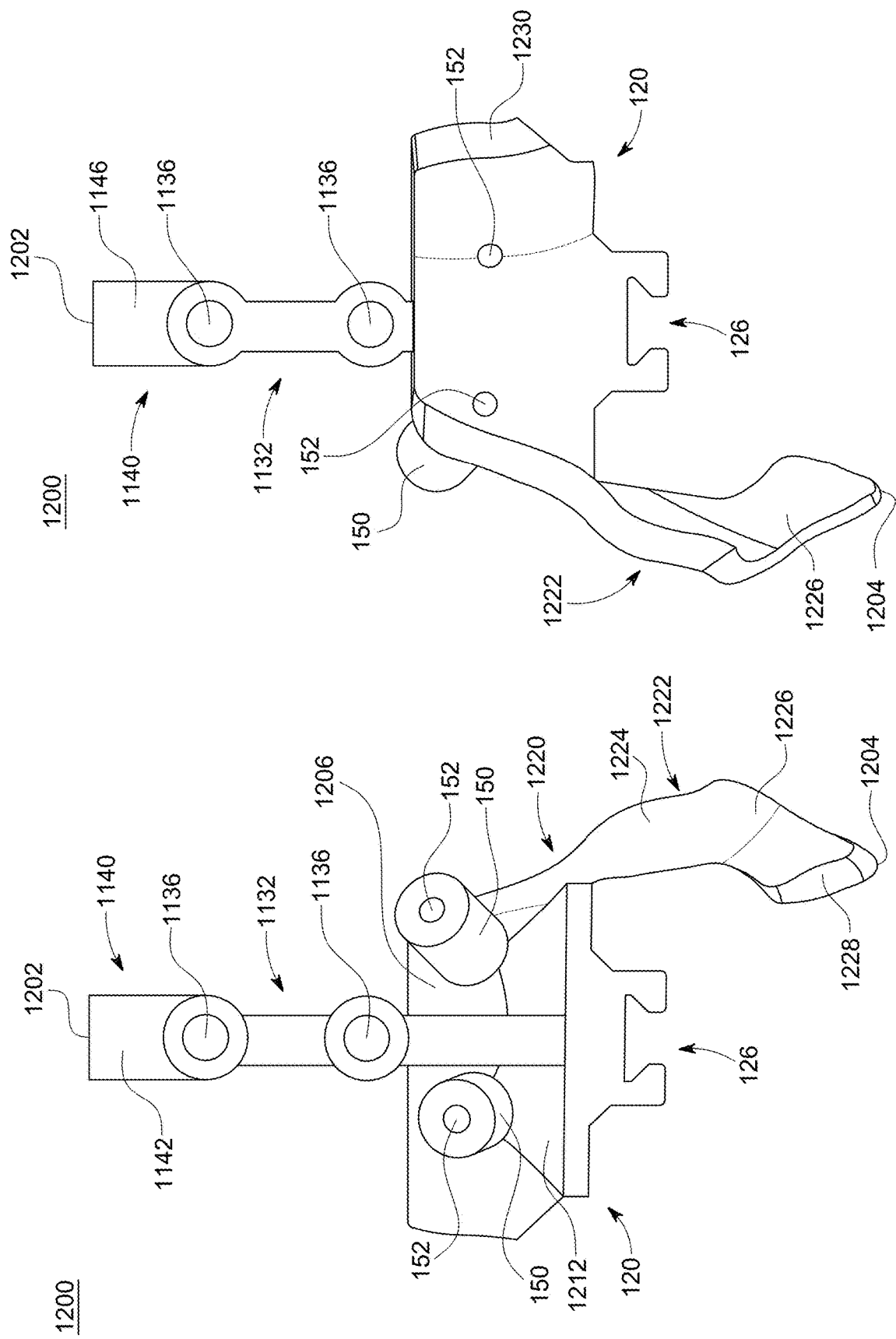

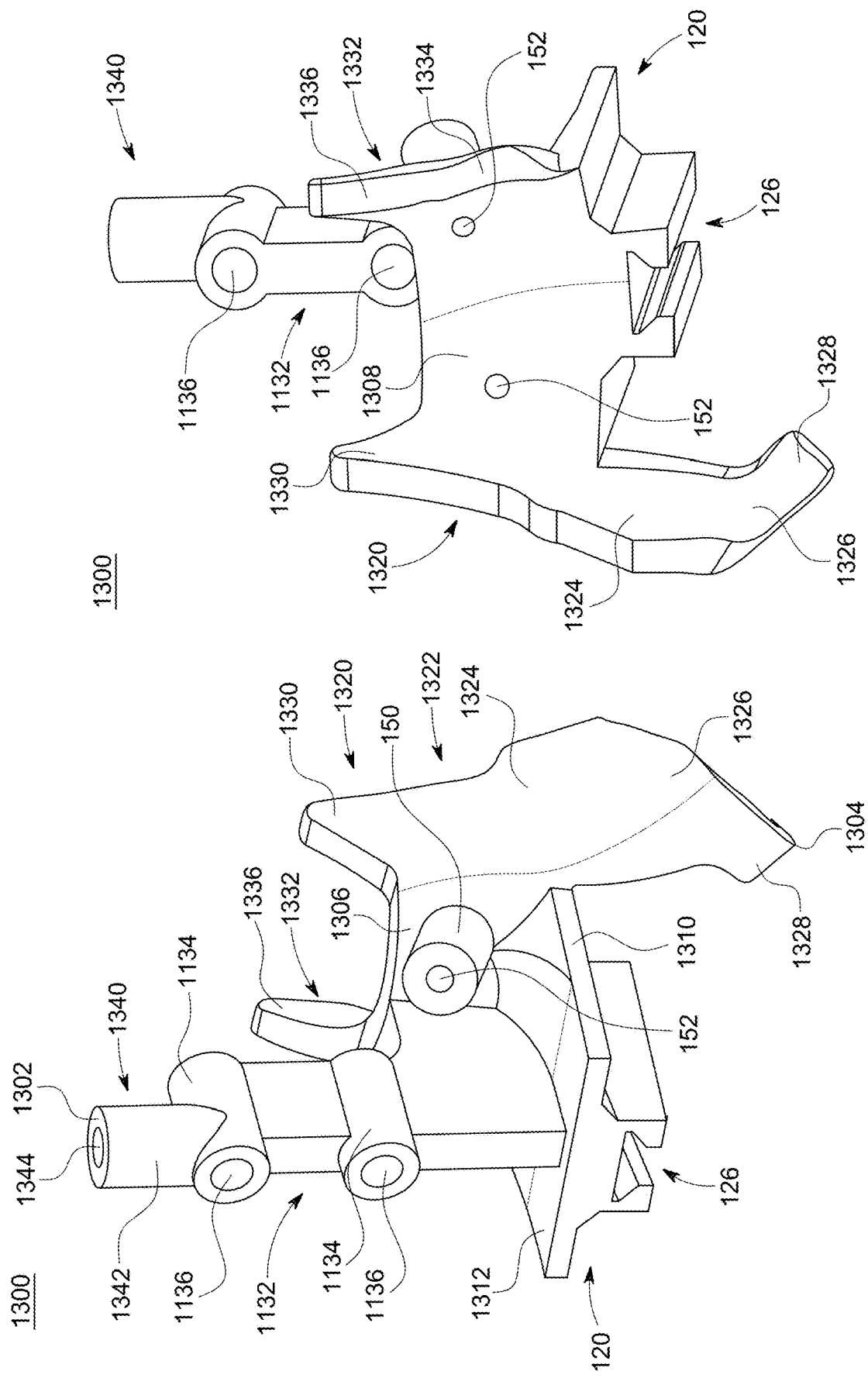

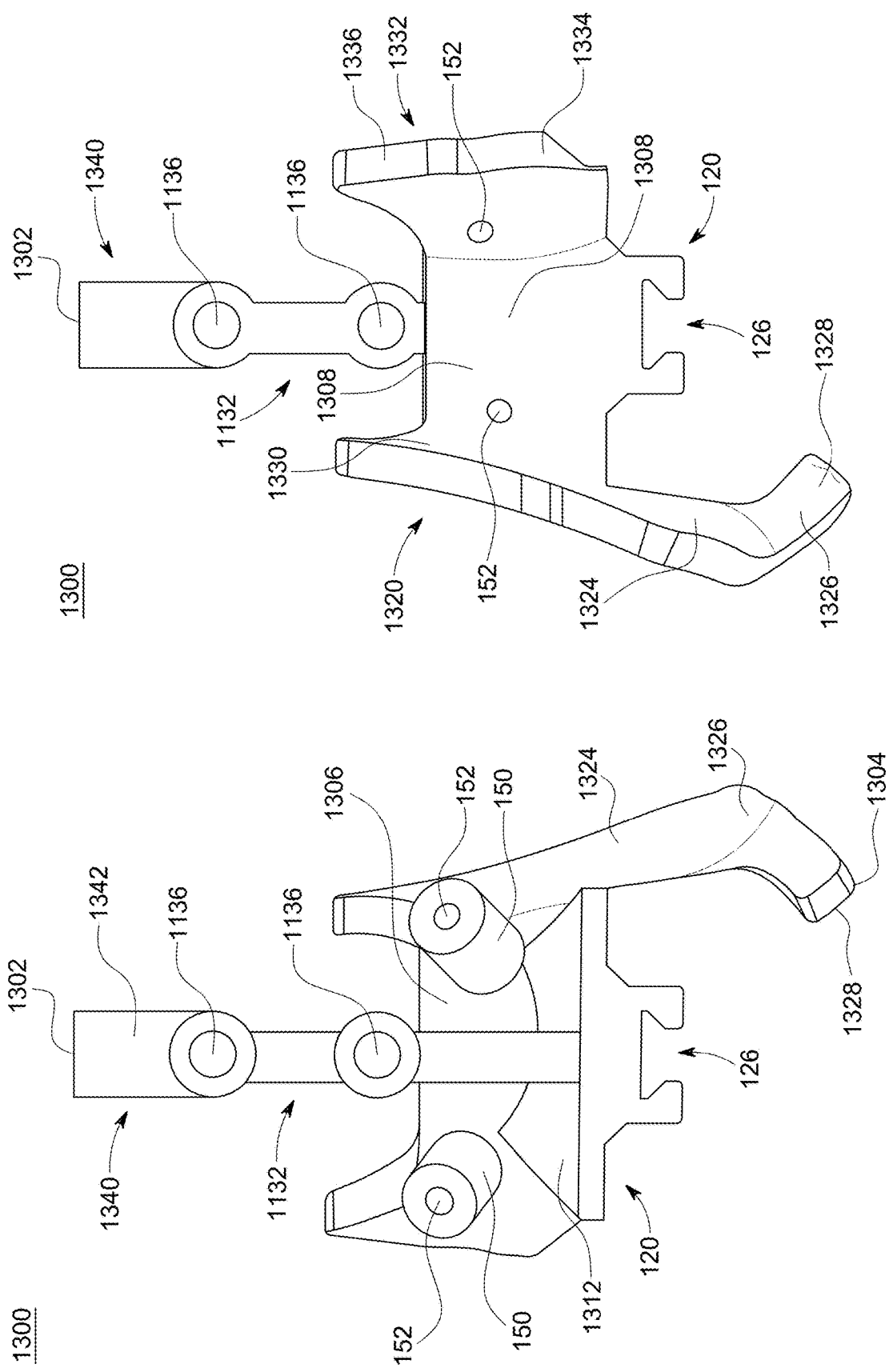

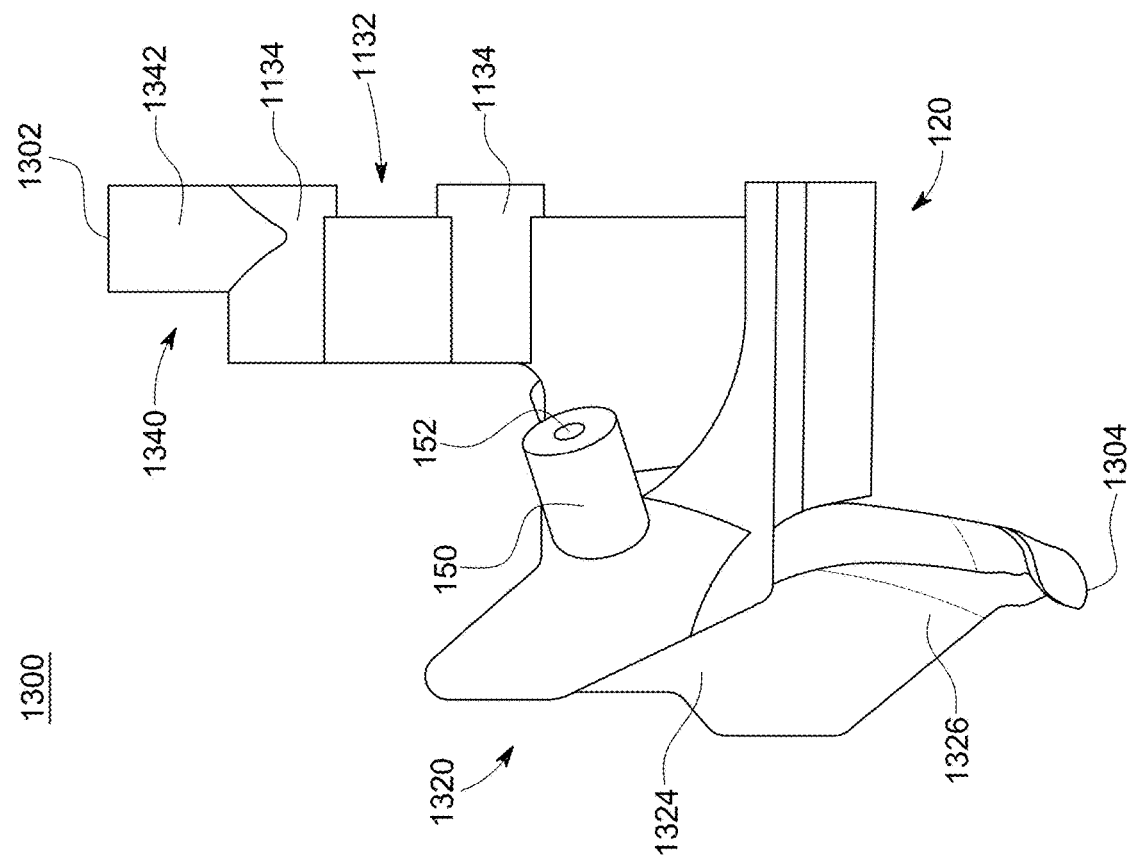
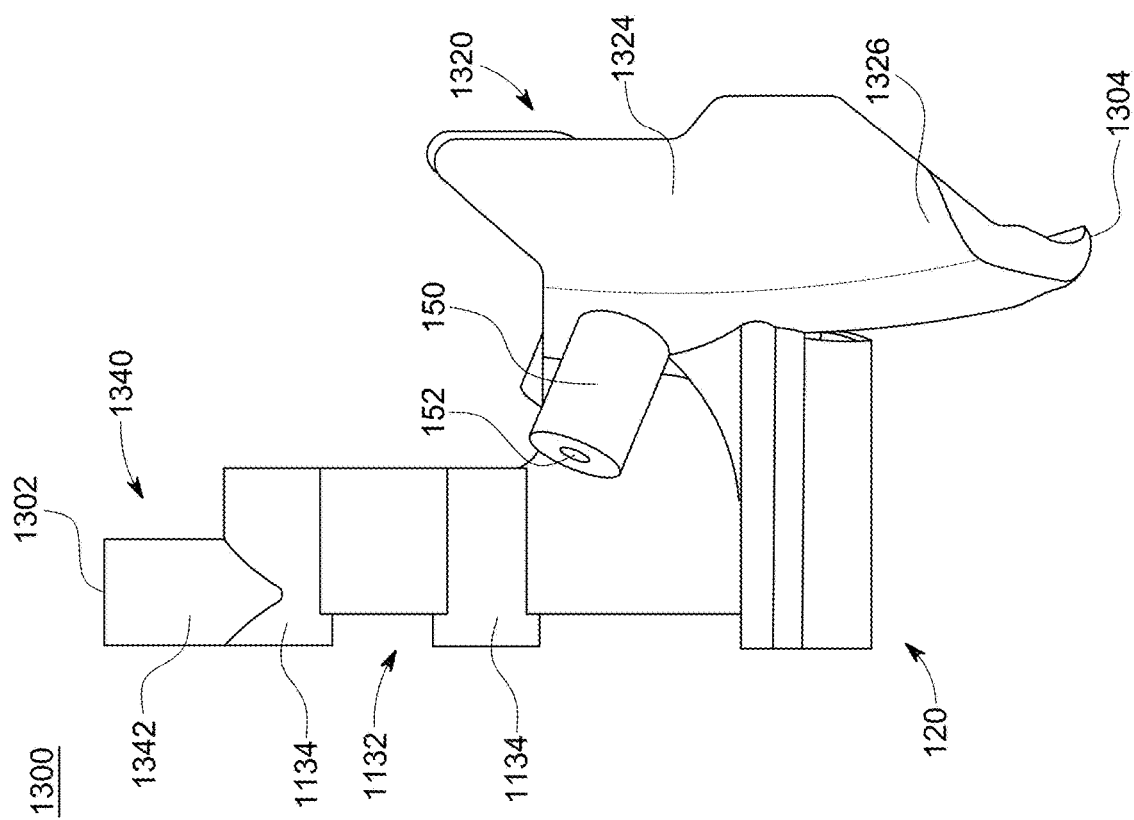

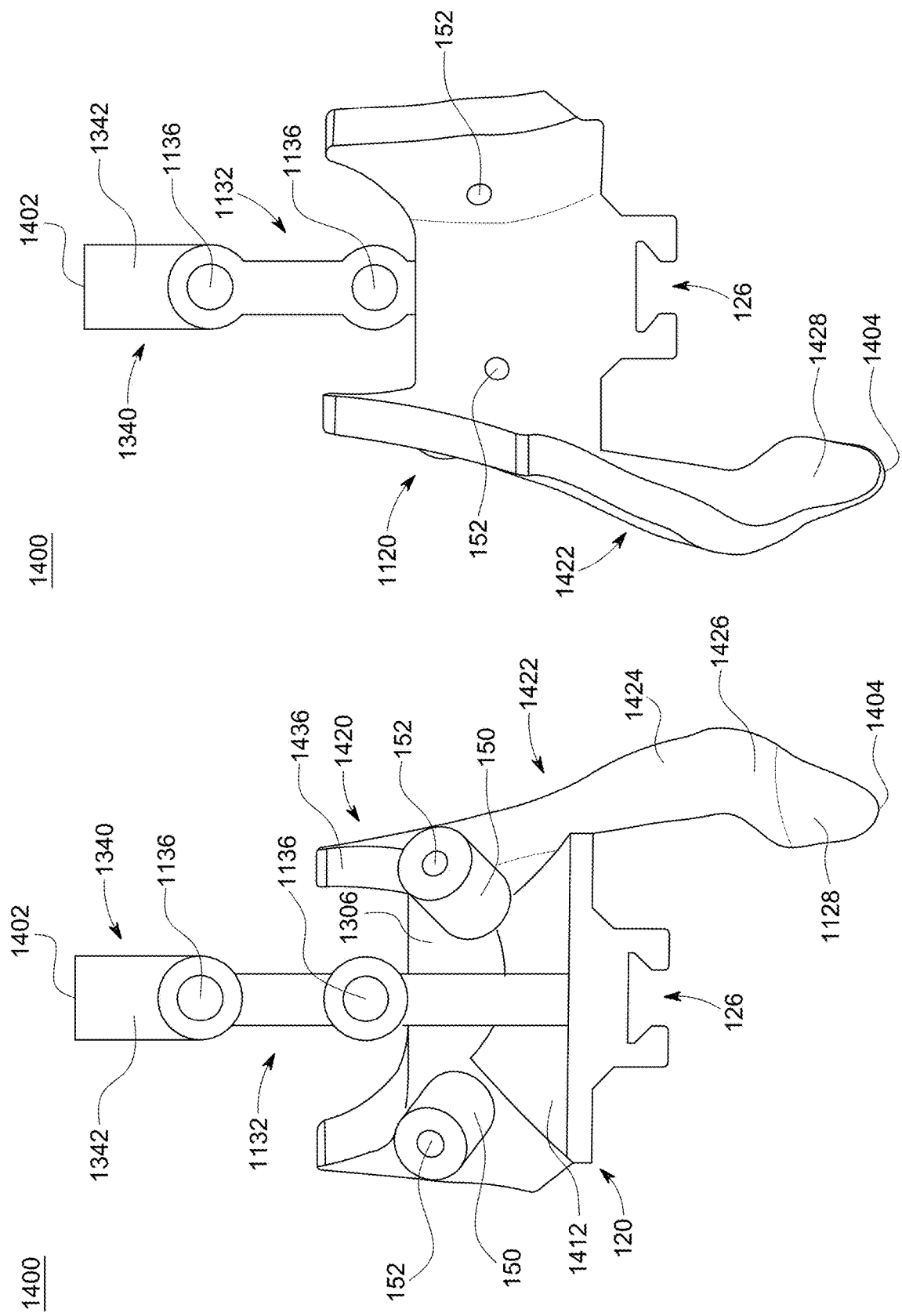

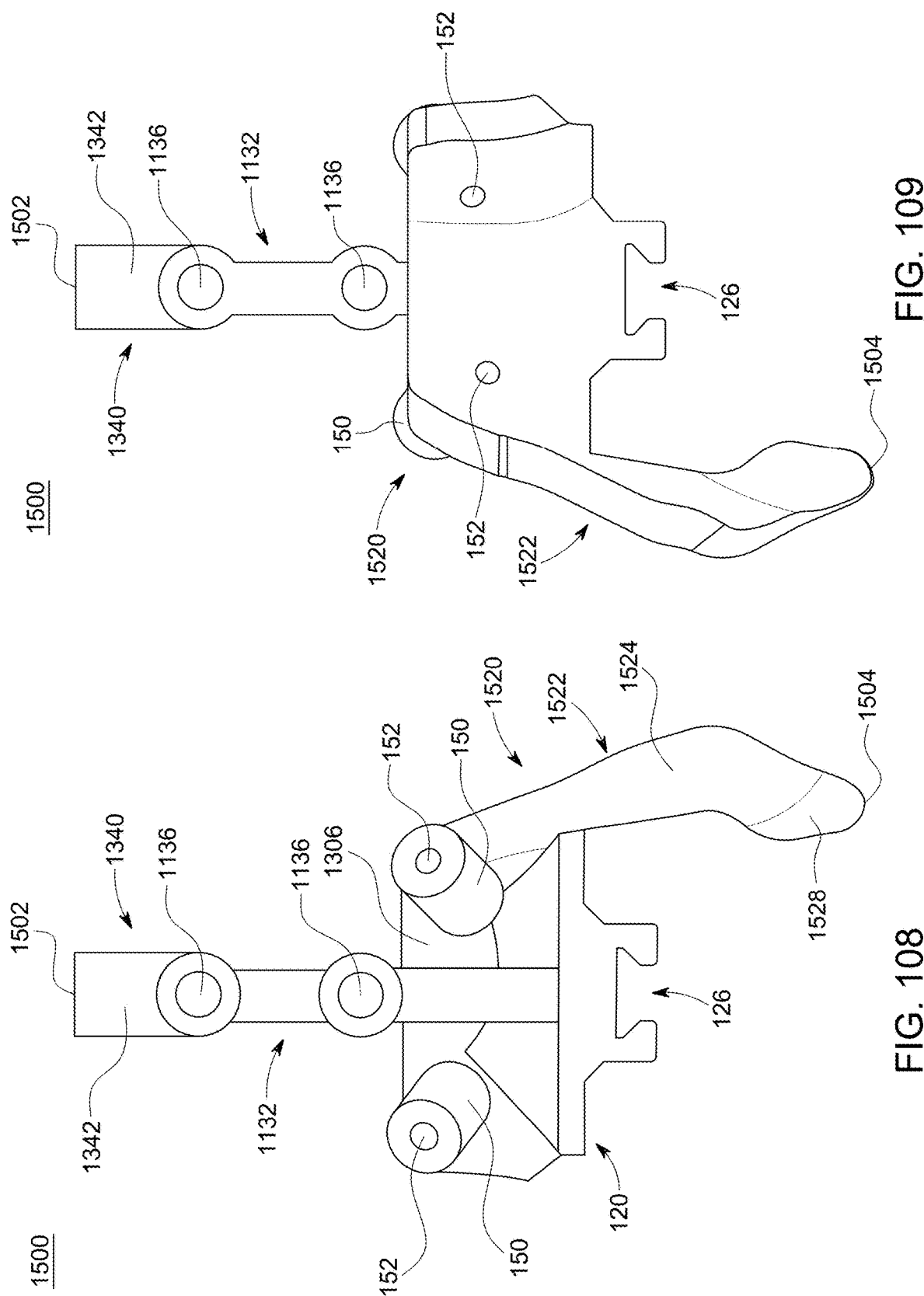

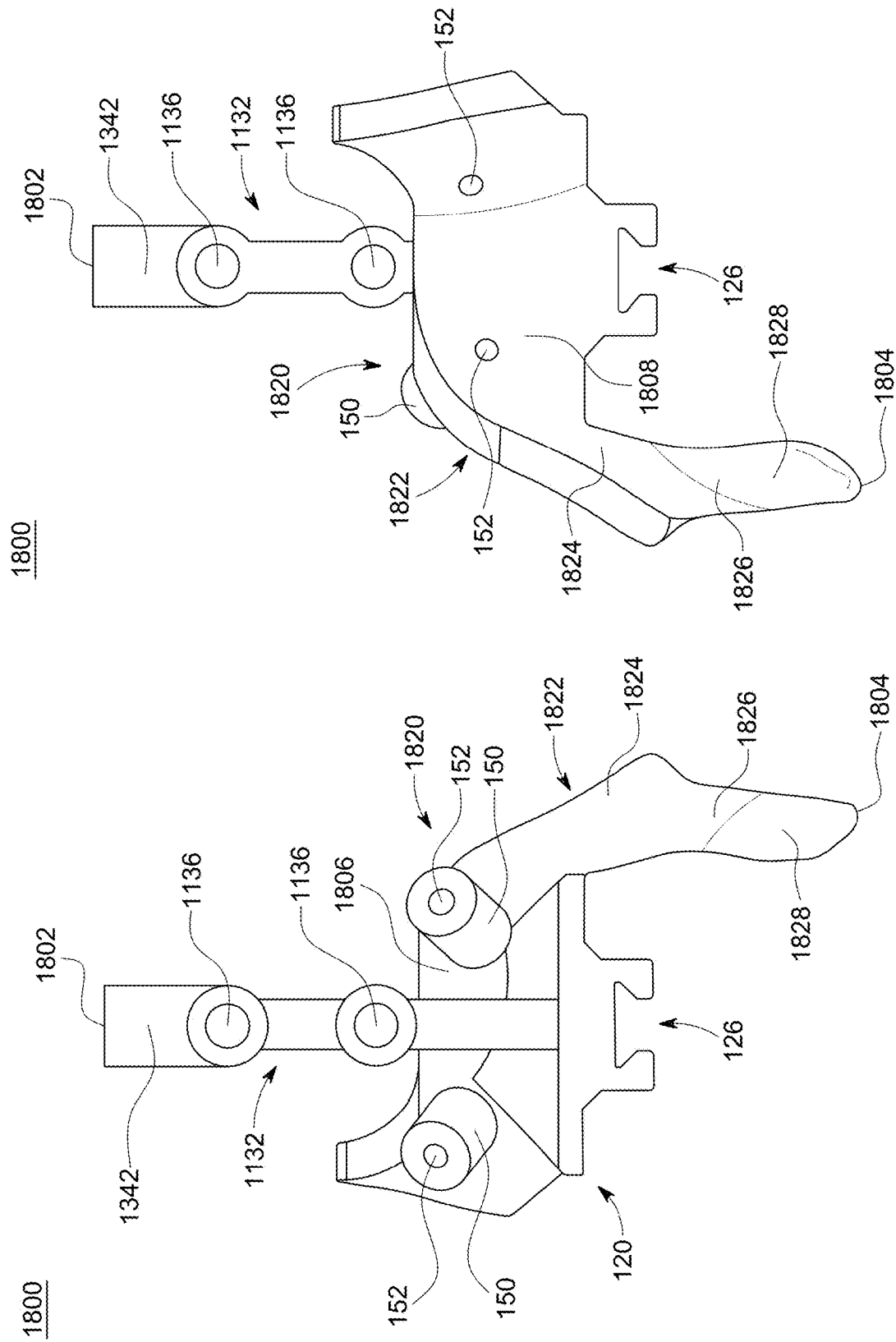

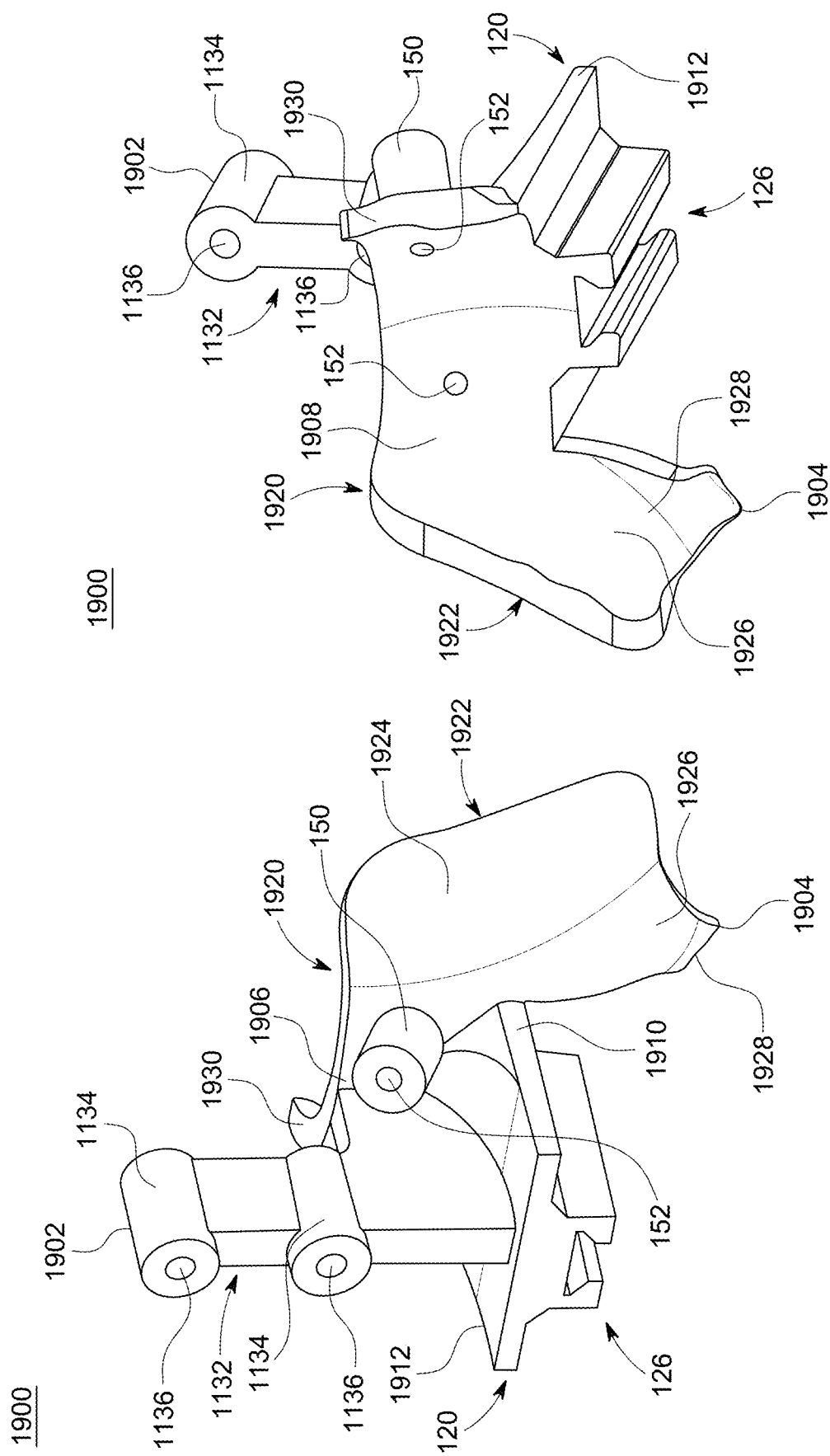

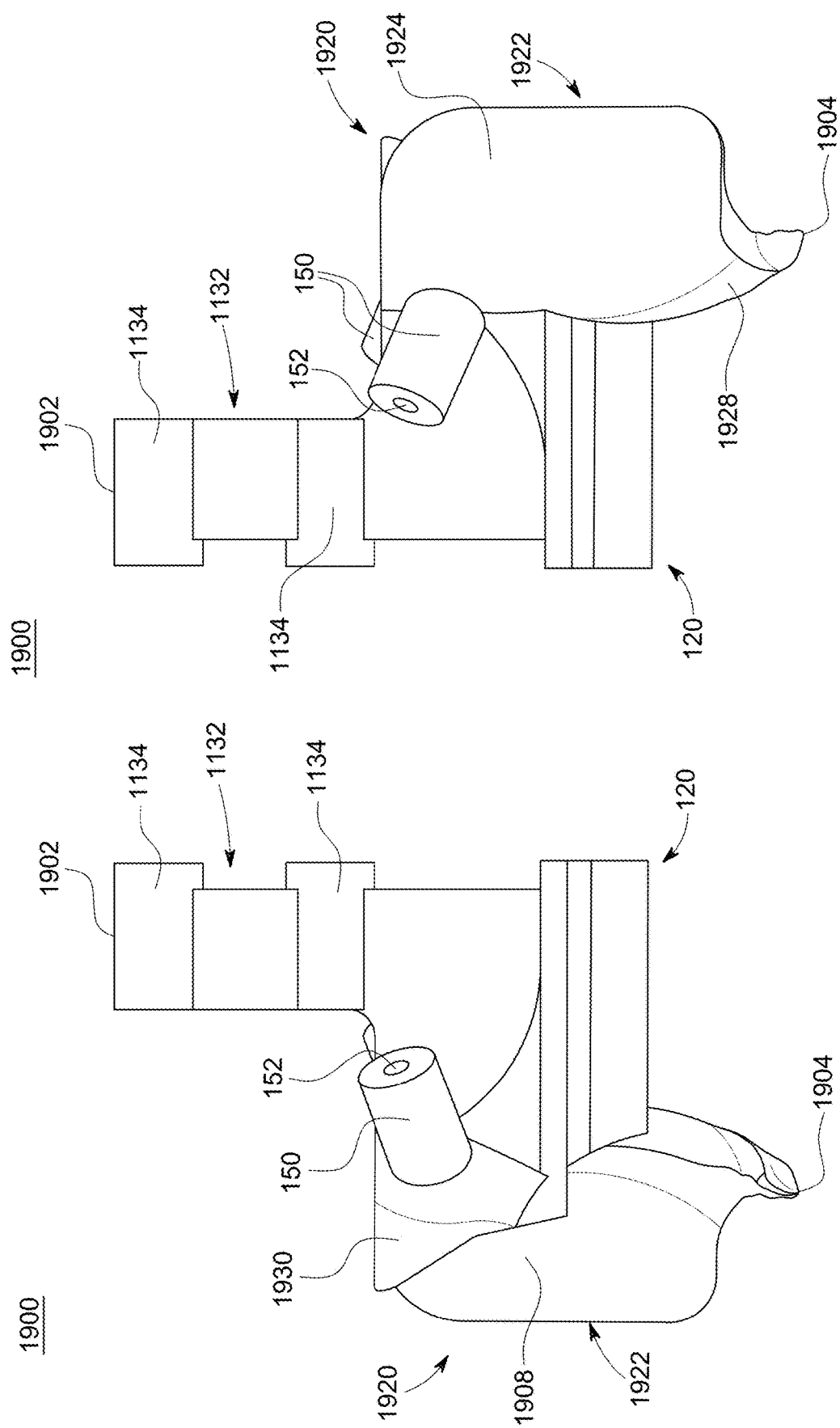

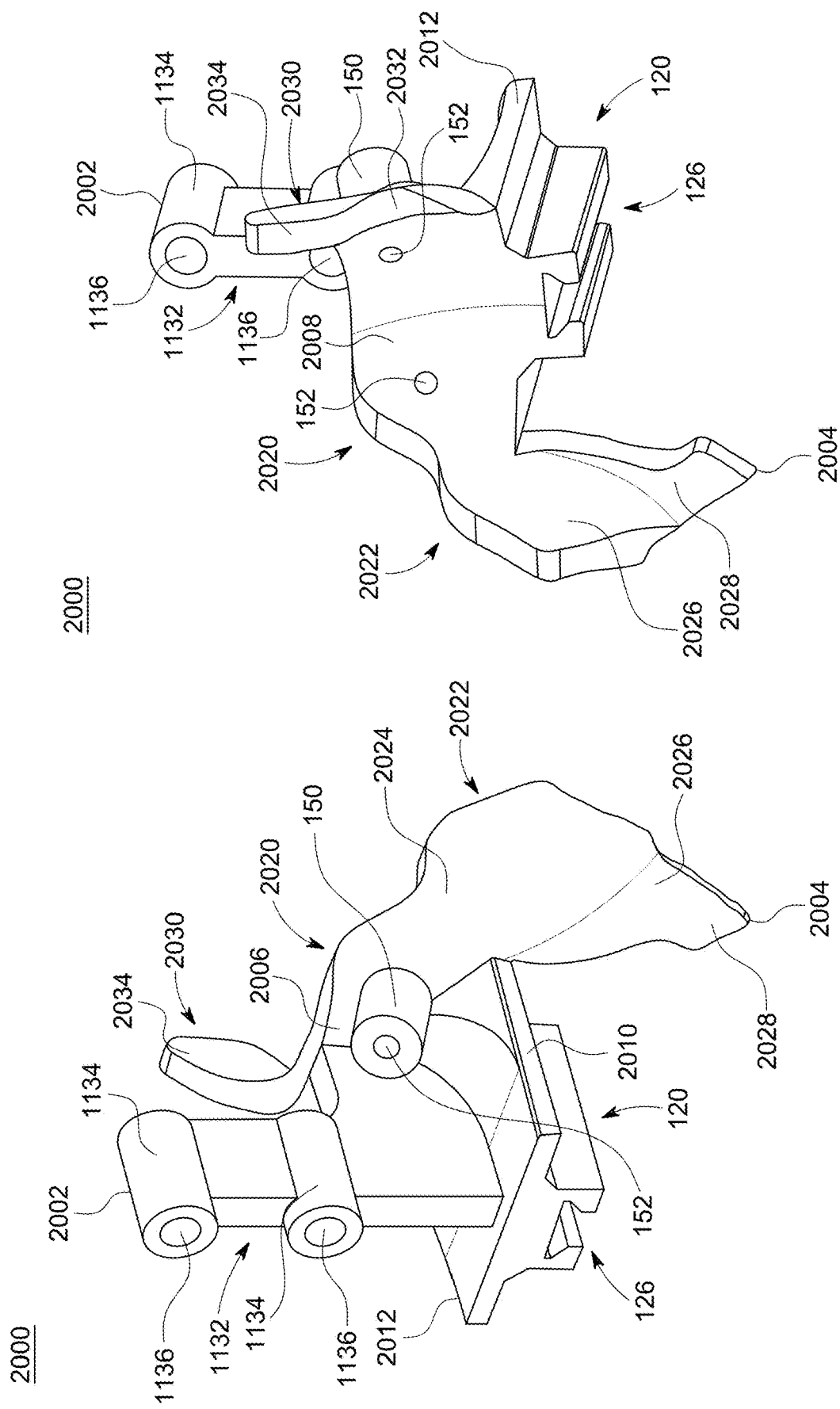

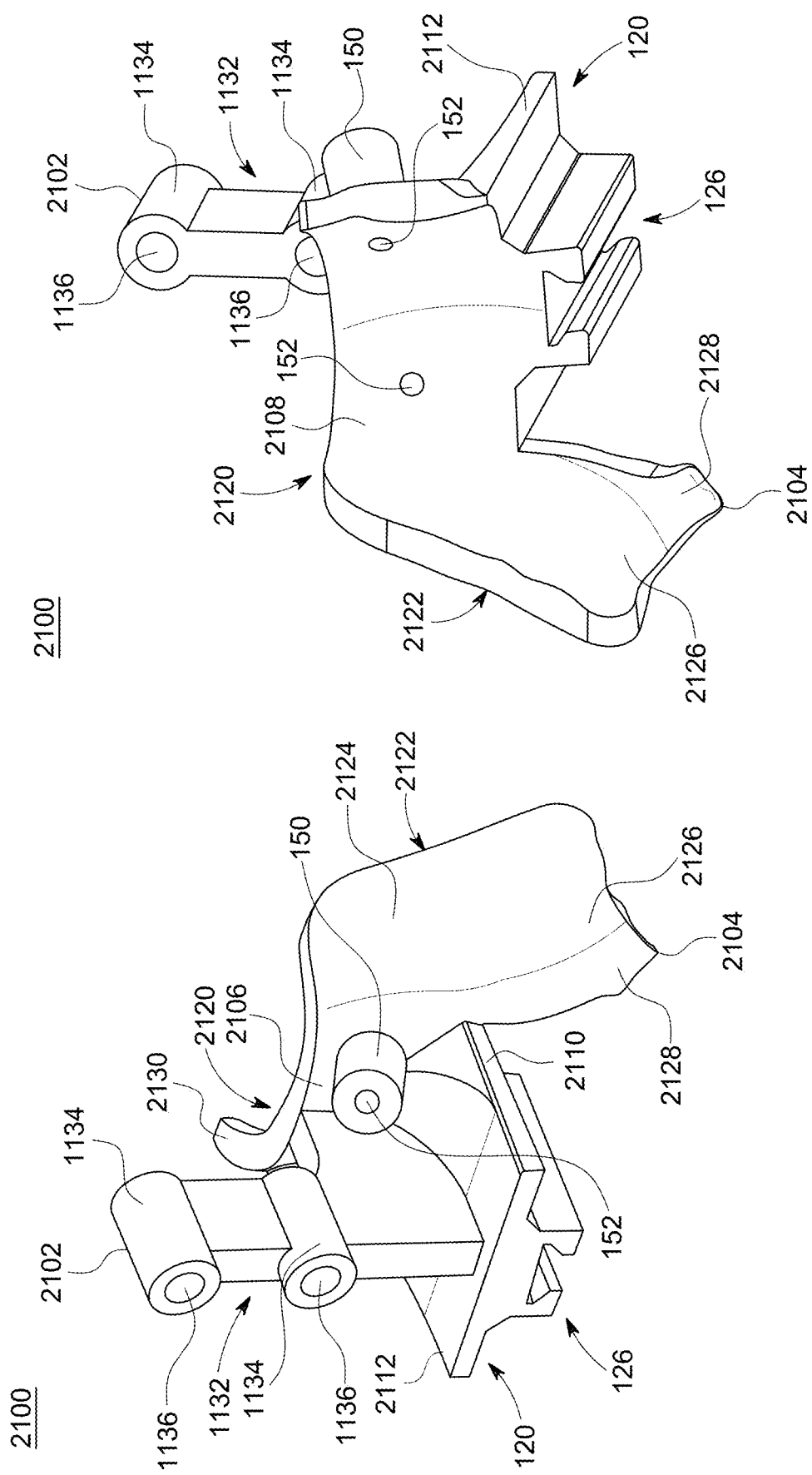

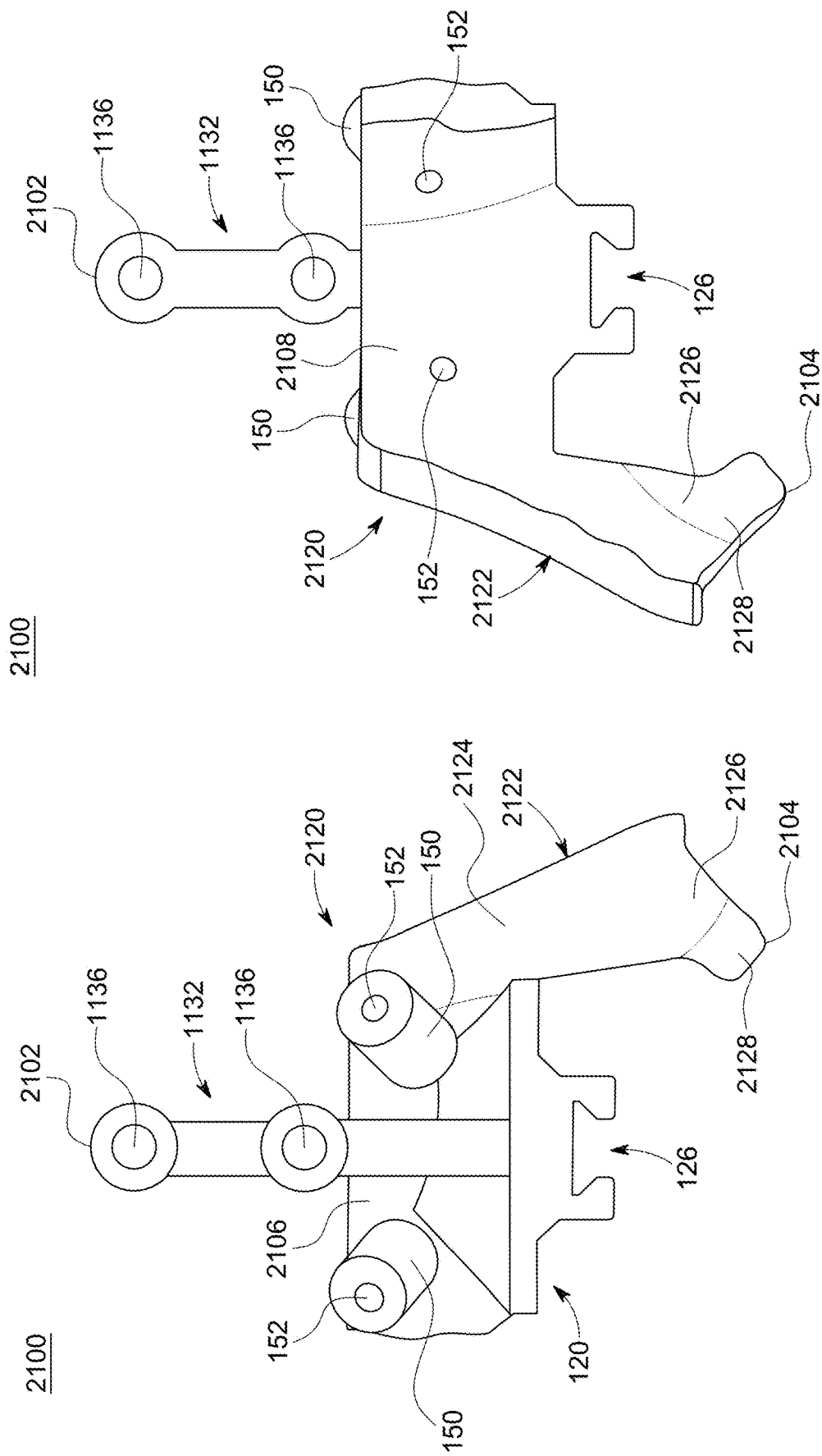

// PATENT SPECIFIC INSTRUMENTS AND METHODS OF USE

CROSS REFERENCE TO RELATED APPLICATIONS

This application is a continuation of PCT/US2019/066336 filed on Dec. 13, 2019 and entitled Patient Specific Instruments and Methods of Use, which claims priority benefit under 35 U.S.C. § 119(e) of U.S. Provisional Application No. 62/890,611 filed Aug. 22, 2019 and entitled Patient Specific Instruments and Methods of Use, and U.S. Provisional Application No. 62/779,436 filed Dec. 13, 2018 and entitled Joint Replacement Systems and Methods of Use and Assembly, which is incorporated herein by reference in its entirety.

FIELD OF THE INVENTION

The present invention relates generally to general surgery, podiatric, and orthopaedic instruments used for correcting bone deformities. More specifically, but not exclusively, the present invention relates to patient specific instruments, systems and methods for maintaining, correcting and/or resurfacing joint surfaces.

BACKGROUND OF THE INVENTION

Many currently available patient specific instruments for total ankle replacements do not allow the user to quickly check the achieved alignment of the guide. Furthermore, currently available patient specific instruments do not provide a means to easily transfer the alignment attained using the patient specific guides to the traditional alignment guides for translational, rotational, and angular adjustments if adjustments are desired. Thus, new instruments and methods of use are needed to overcome the above-noted drawbacks and provide for patient specific instruments that easily transfer the attained alignment to traditional alignment guides.

SUMMARY OF THE INVENTION

Aspects of the present invention provide instruments, systems and methods for correcting bone deformities in the ankle.

In one aspect, provided herein is an alignment guide. The alignment guide including, a body with a first surface and a second surface, a base portion coupled to and extending away from the first surface of the body, and a tower portion coupled to and extending away from a top surface of the body.

In another aspect, provided herein is an alignment guide. The alignment guide including a body and a base portion extending away from a first surface of the body.

In a further aspect, provided herein is a resection system. The resection system including a tibia alignment guide including at least one pin for insertion through at least one pin tower, a tibia trial system comprising at least one through hole for receiving the at least one pin; and a talus guide.

In yet another aspect, provided herein is a surgical method of using an alignment guide system. The method including exposing a patient's ankle joint and obtaining a tibia alignment guide. The method also includes positioning the tibia alignment guide on a patient's tibia and inserting at least one pin through the tibia alignment guide to secure the tibia alignment guide to a patient's tibia. The method further includes preparing the tibia for an implant and obtaining a tibia trial system. In addition, the method includes coupling the tibia trial system to the tibia and testing alignment and fit of the tibia implant and obtaining a talus guide. The method also includes positioning the talus guide on a patient's talus and inserting at least one pin through the talus guide to secure the talus guide to the talus. Still further, the method includes preparing the talus for a talar implant and completing the testing of the trial implants and removing the tibia trial system and talus guide from the patient's bones. Finally, the method may include implanting the tibia and talus implants and completing the surgical procedure.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 26 is a front view of the alignment guide of FIG. 20, in accordance with an aspect of the present invention;

FIG. 27 is a back view of the alignment guide of FIG. 20, in accordance with an aspect of the present invention;

FIG. 51 is a first perspective view of another alignment guide, in accordance with an aspect of the present invention;

FIG. 52 is a second perspective view of the alignment guide of FIG. 51, in accordance with an aspect of the present invention;

FIG. 56 is a first perspective view of another alignment guide, in accordance with an aspect of the present invention;

FIG. 57 is a second perspective view of the alignment guide of FIG. 56, in accordance with an aspect of the present invention;

FIG. 84 is a front view of the alignment guide of FIG. 82, in accordance with an aspect of the present invention;

FIG. 85 is a back view of the alignment guide of FIG. 82, in accordance with an aspect of the present invention;

FIG. 88 is a first side view of the alignment guide of FIG. 82, in accordance with an aspect of the present invention;

FIG. 89 is a second side view of the alignment guide of FIG. 82, in accordance with an aspect of the present invention;

FIG. 90 is a first perspective view of yet another alignment guide, in accordance with an aspect of the present invention;

FIG. 91 is a second perspective view of the alignment guide of FIG. 90, in accordance with an aspect of the present invention;

FIG. 92 is a front view of the alignment guide of FIG. 90, in accordance with an aspect of the present invention;

FIG. 93 is a back view of the alignment guide of FIG. 90, in accordance with an aspect of the present invention;

FIG. 94 is a first perspective view of another alignment guide, in accordance with an aspect of the present invention;

FIG. 95 is a second perspective view of the alignment guide of FIG. 94, in accordance with an aspect of the present invention;

FIG. 96 is a front view of the alignment guide of FIG. 94, in accordance with an aspect of the present invention;

FIG. 97 is a back view of the alignment guide of FIG. 94, in accordance with an aspect of the present invention;

FIG. 100 is a first side view of the alignment guide of FIG. 94, in accordance with an aspect of the present invention;

FIG. 101 is a second side view of the alignment guide of FIG. 94, in accordance with an aspect of the present invention;

FIG. 104 is a front view of the alignment guide of FIG. 102, in accordance with an aspect of the present invention;

FIG. 105 is a rear view of the alignment guide of FIG. 102, in accordance with an aspect of the present invention;

FIG. 108 is a front view of the alignment guide of FIG. 106, in accordance with an aspect of the present invention;

FIG. 109 is a back view of the alignment guide of FIG. 106, in accordance with an aspect of the present invention;

FIG. 120 is a front view of the alignment guide of FIG. 118, in accordance with an aspect of the present invention;

FIG. 121 is a back view of the alignment guide of FIG. 118, in accordance with an aspect of the present invention;

FIG. 122 is a first perspective view of yet another alignment guide, in accordance with an aspect of the present invention;

FIG. 123 is a back perspective view of the alignment guide of FIG. 122, in accordance with an aspect of the present invention;

FIG. 124 is a front view of the alignment guide of FIG. 122, in accordance with an aspect of the present invention;

FIG. 125 is a back view of the alignment guide of FIG. 122, in accordance with an aspect of the present invention;

FIG. 126 is a first end view of the alignment guide of FIG. 122, in accordance with an aspect of the present invention;

FIG. 127 is a second end view of the alignment guide of FIG. 122, in accordance with an aspect of the present invention;

FIG. 128 is a first side view of the alignment guide of FIG. 122, in accordance with an aspect of the present invention;

FIG. 129 is a second side view of the alignment guide of FIG. 122, in accordance with an aspect of the present invention;

FIG. 130 is a first perspective view of another alignment guide, in accordance with an aspect of the present invention;

FIG. 131 is a second perspective view of the alignment guide of FIG. 130, in accordance with an aspect of the present invention;

Figures 132, 133:
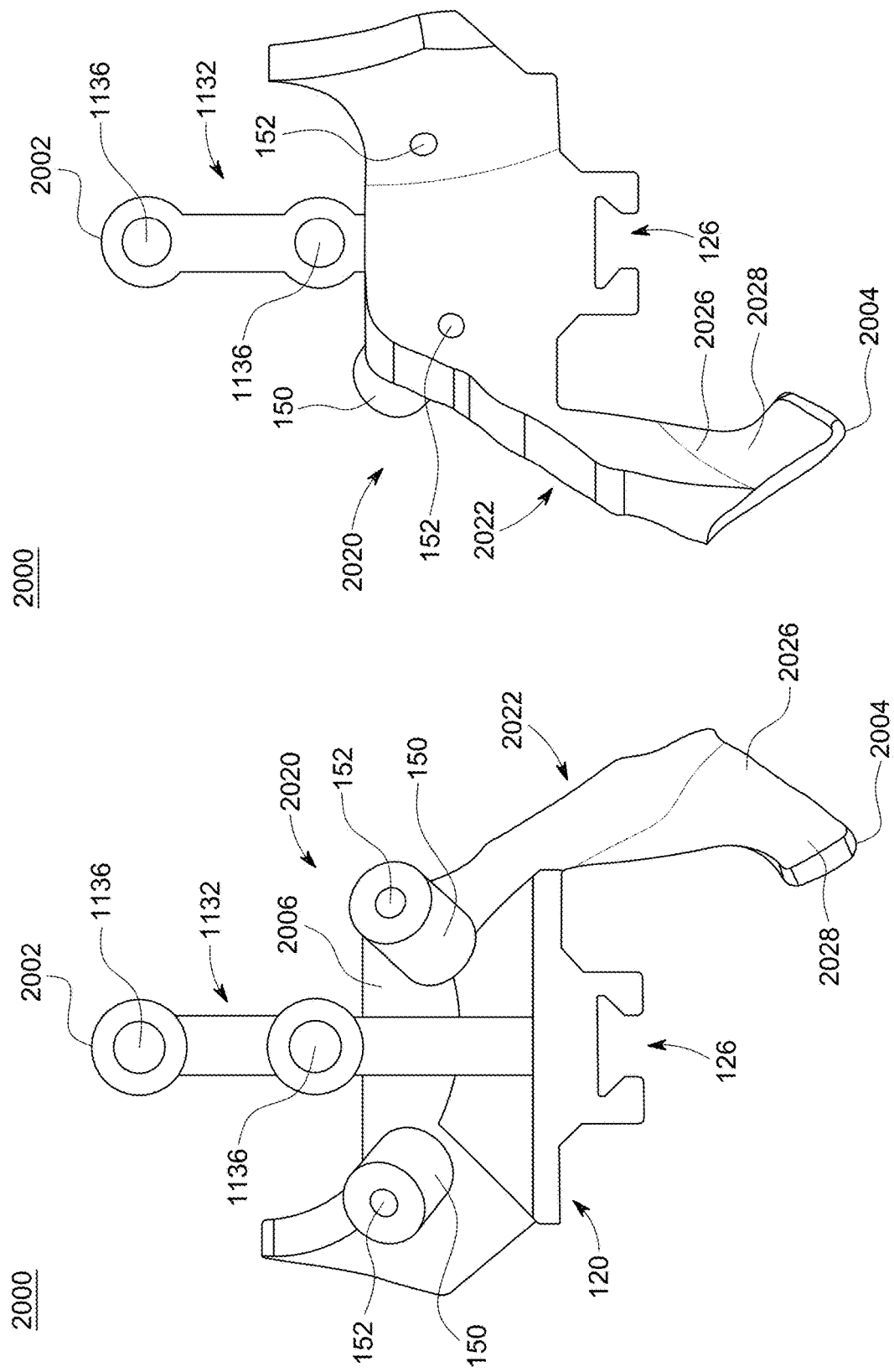
Figure 139:
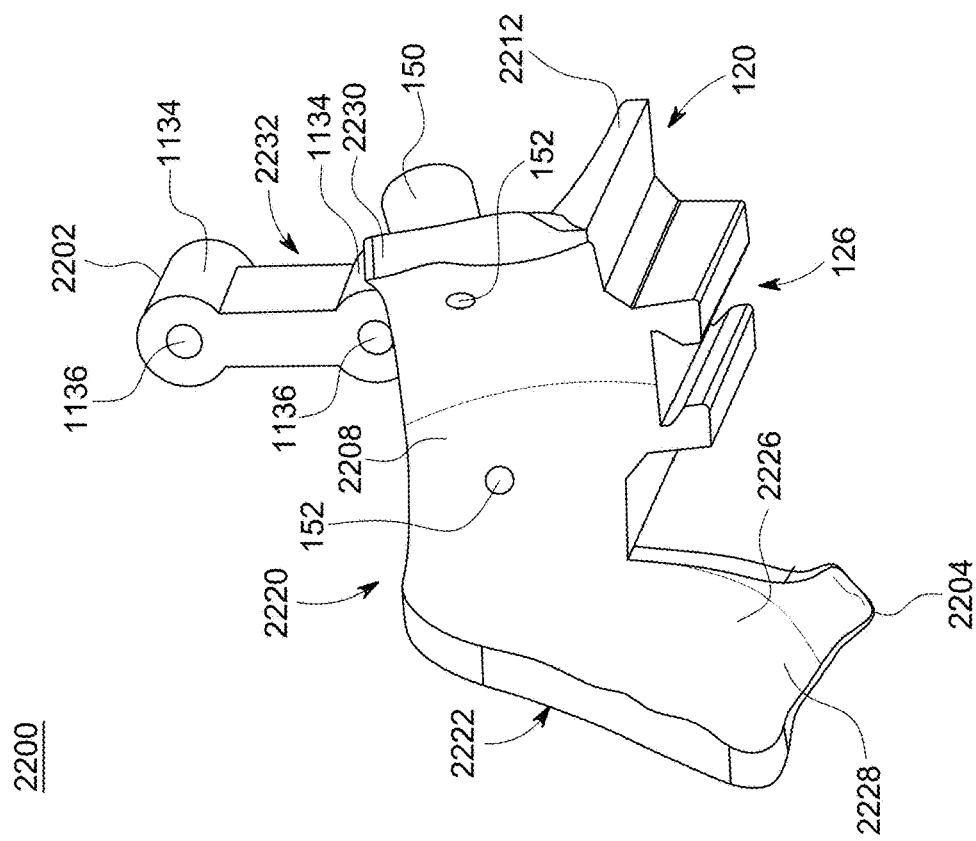
Figure 138:
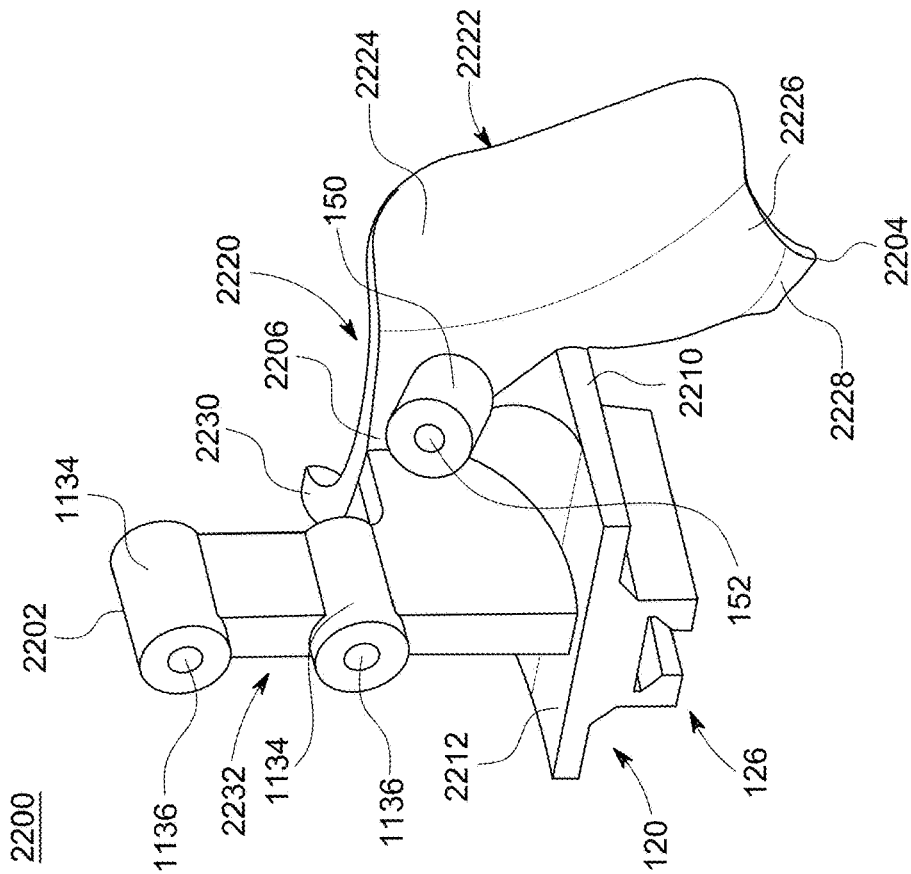
Figure 141:
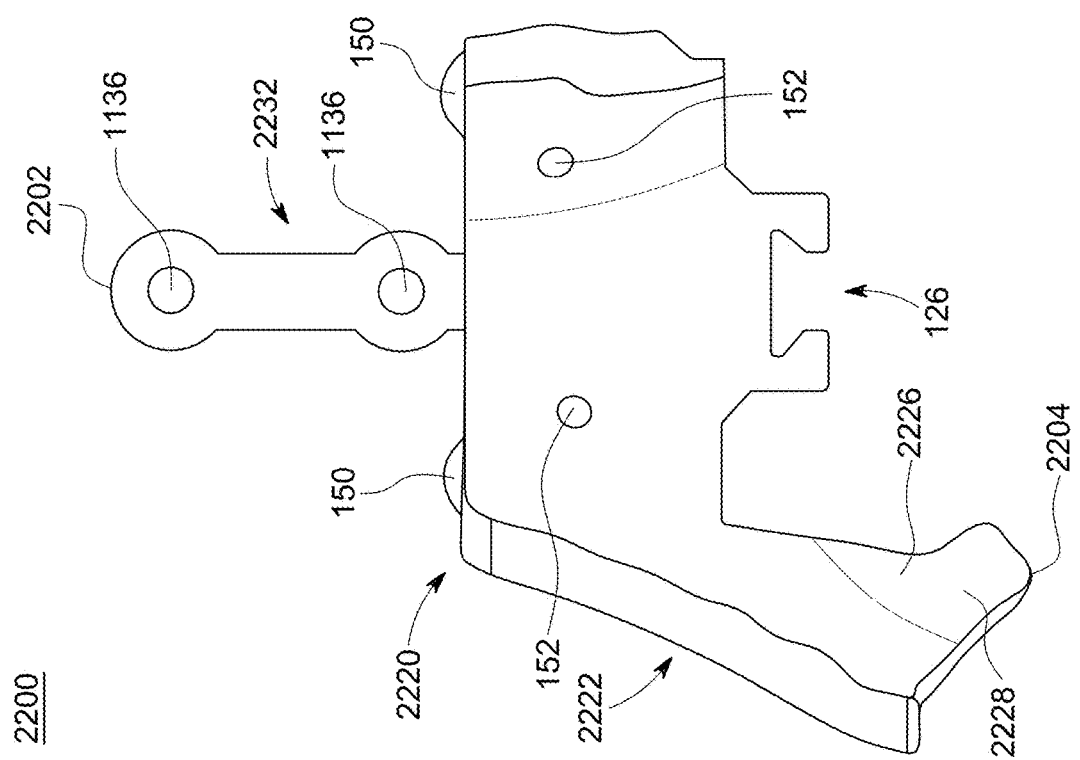
Figure 140:
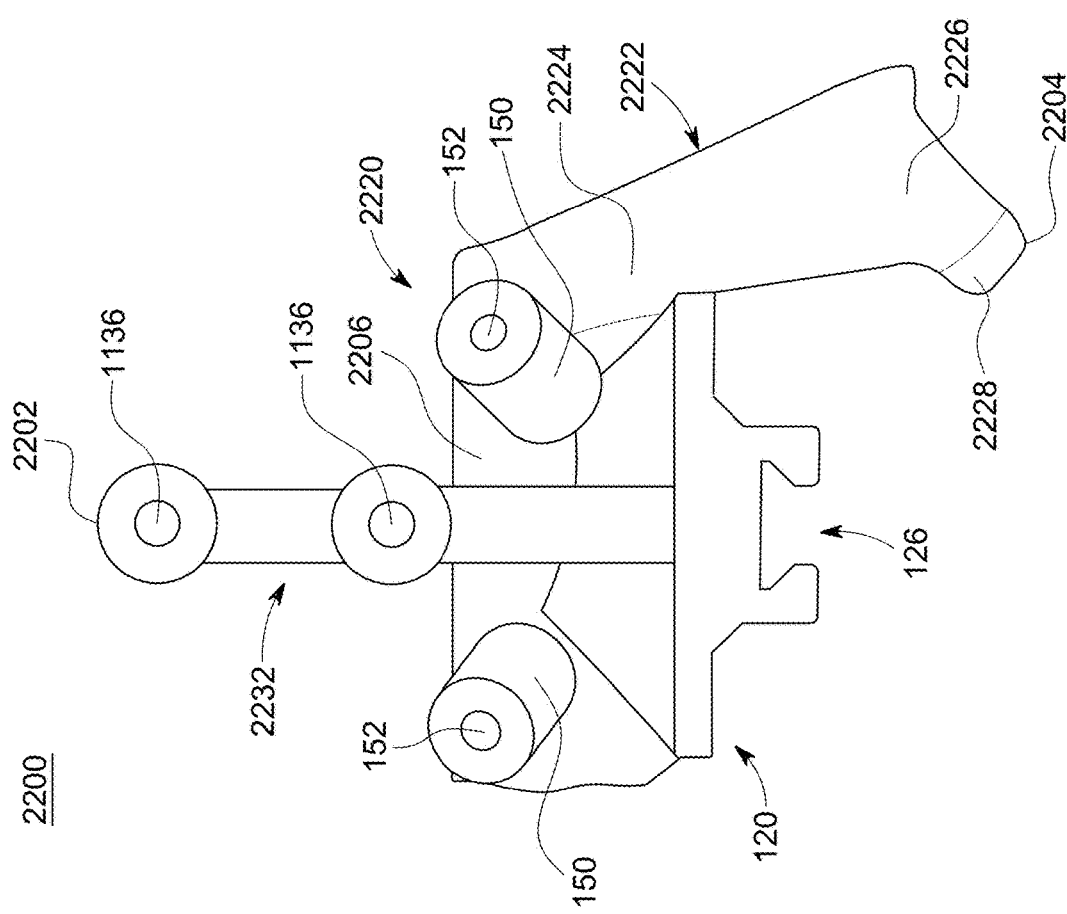
Figure 142:
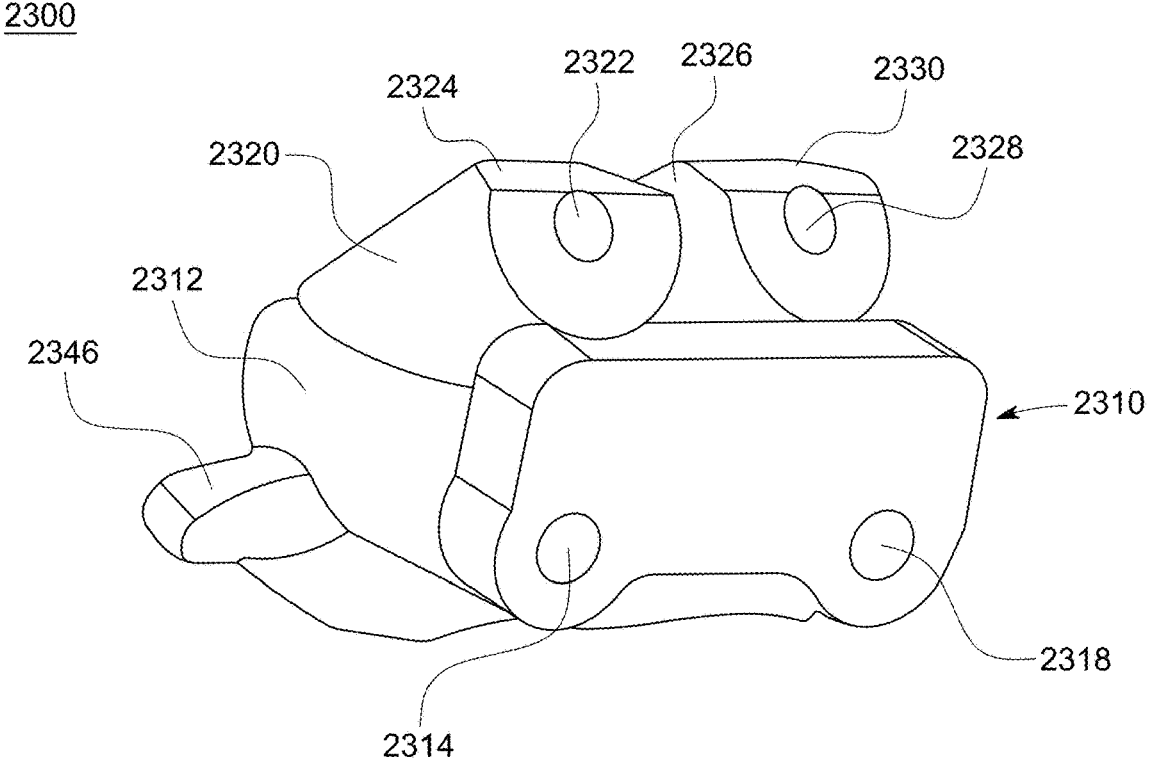
Figure 143:
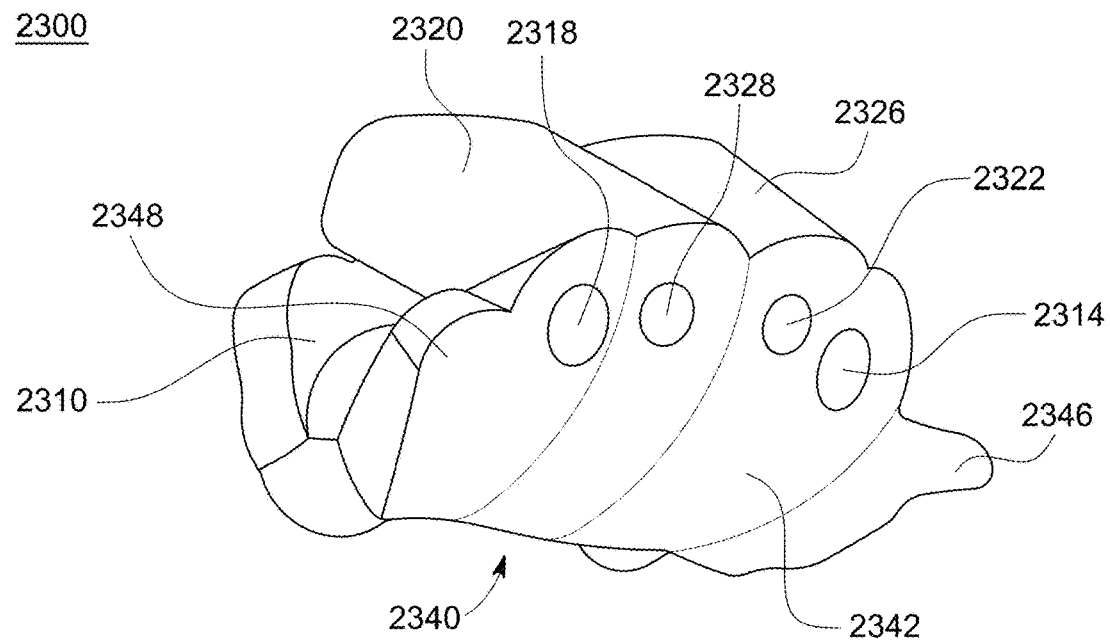
Figure 144:
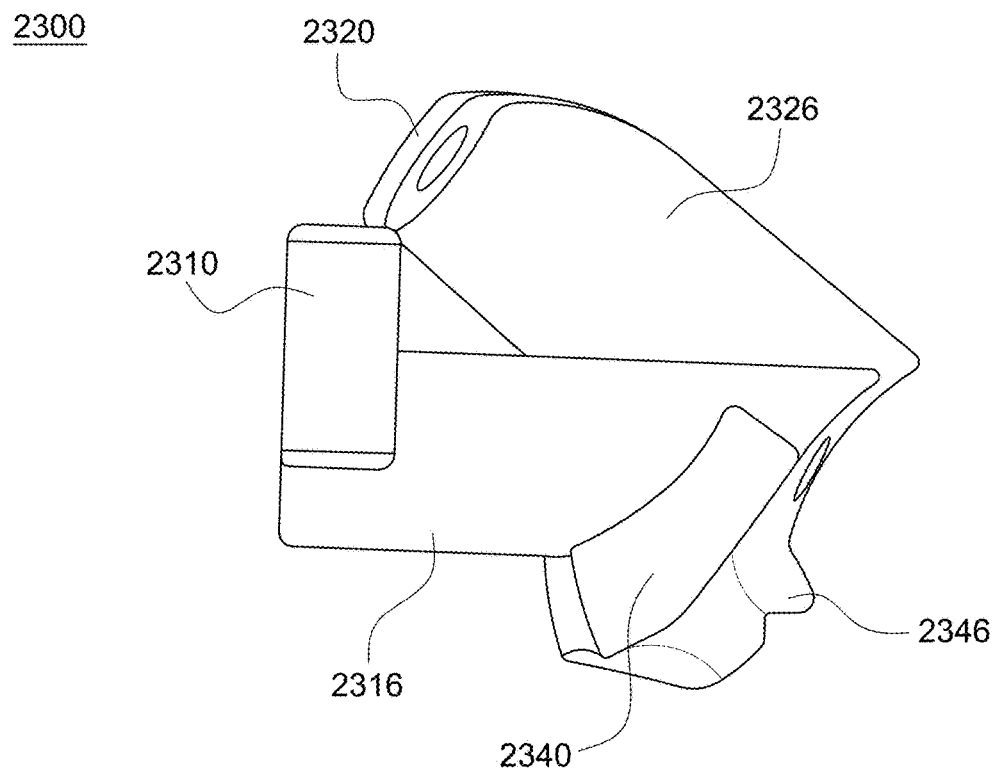
Figure 145:
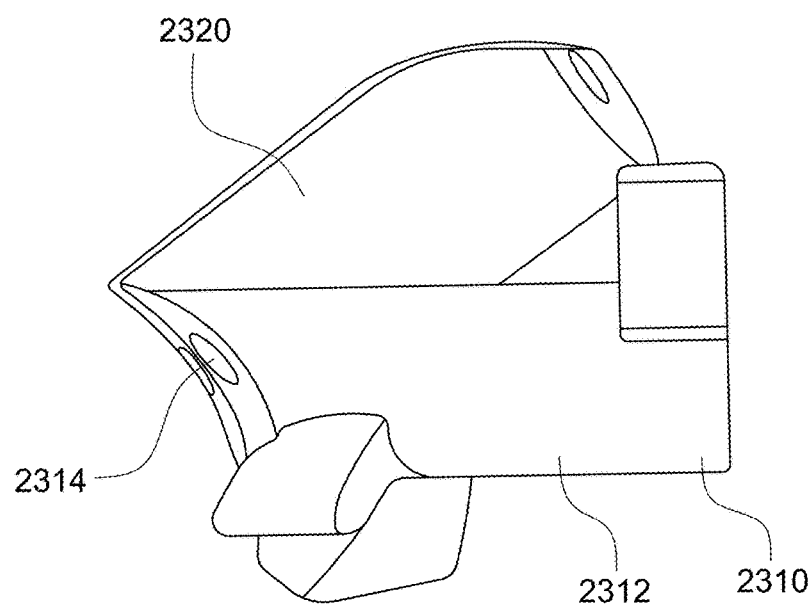
Figure 146:
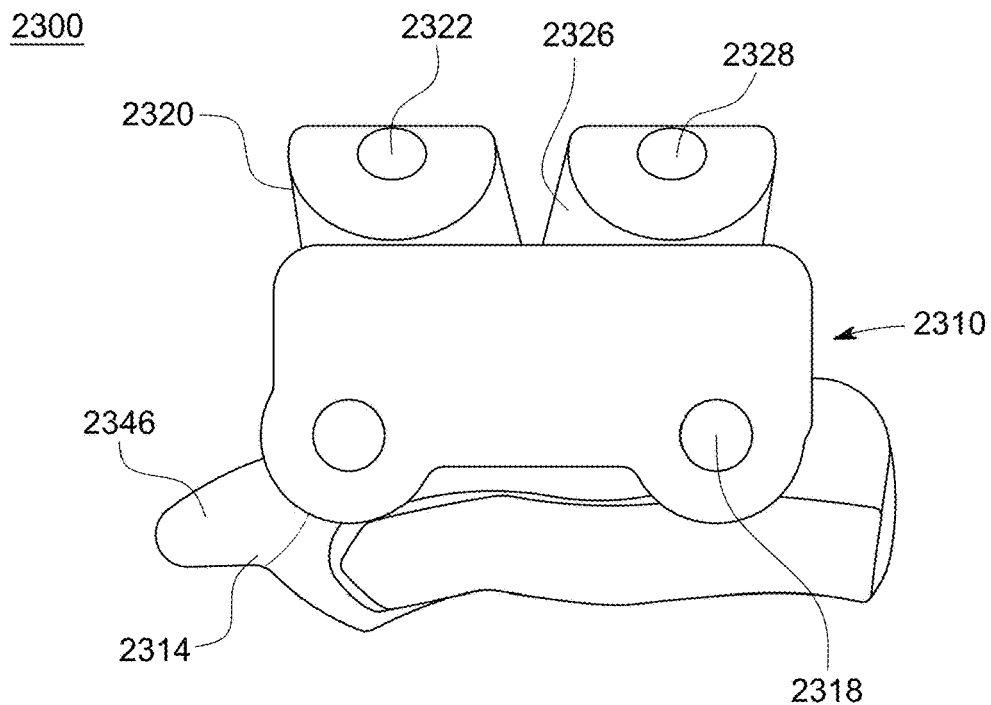
Figure 147:
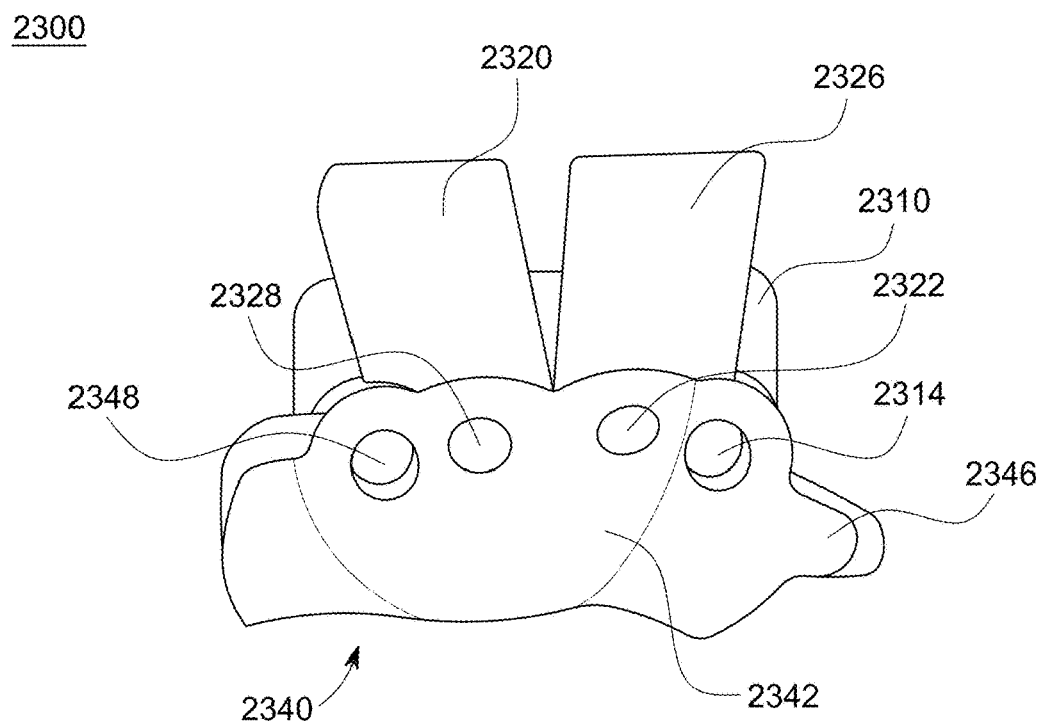
Figure 148:
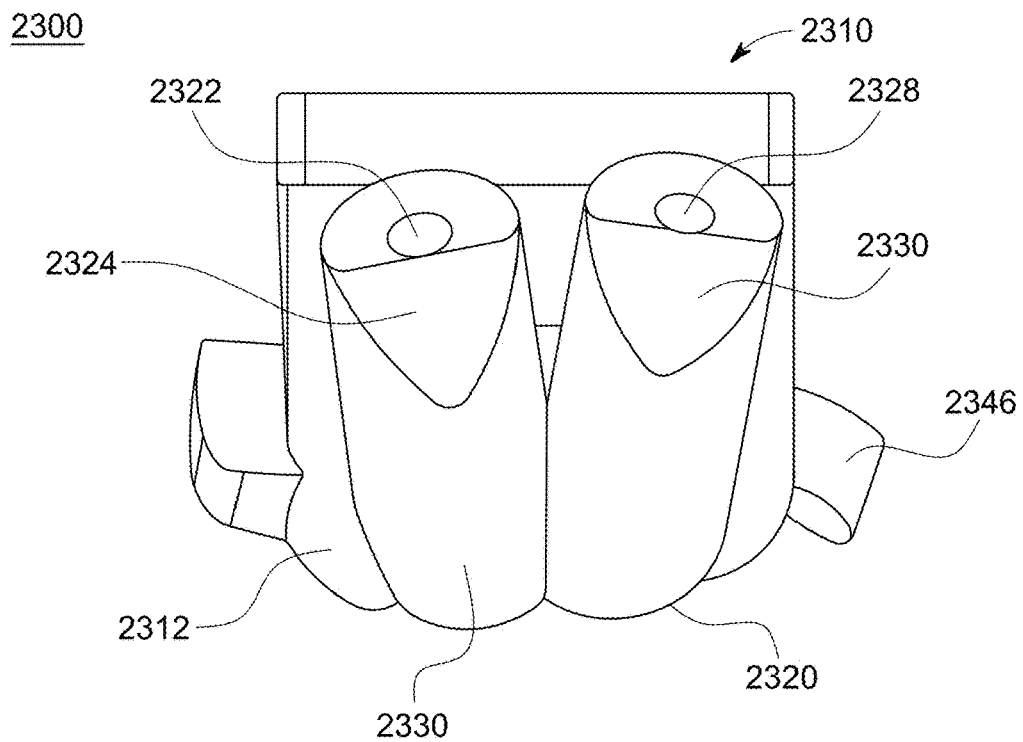
Figure 149:
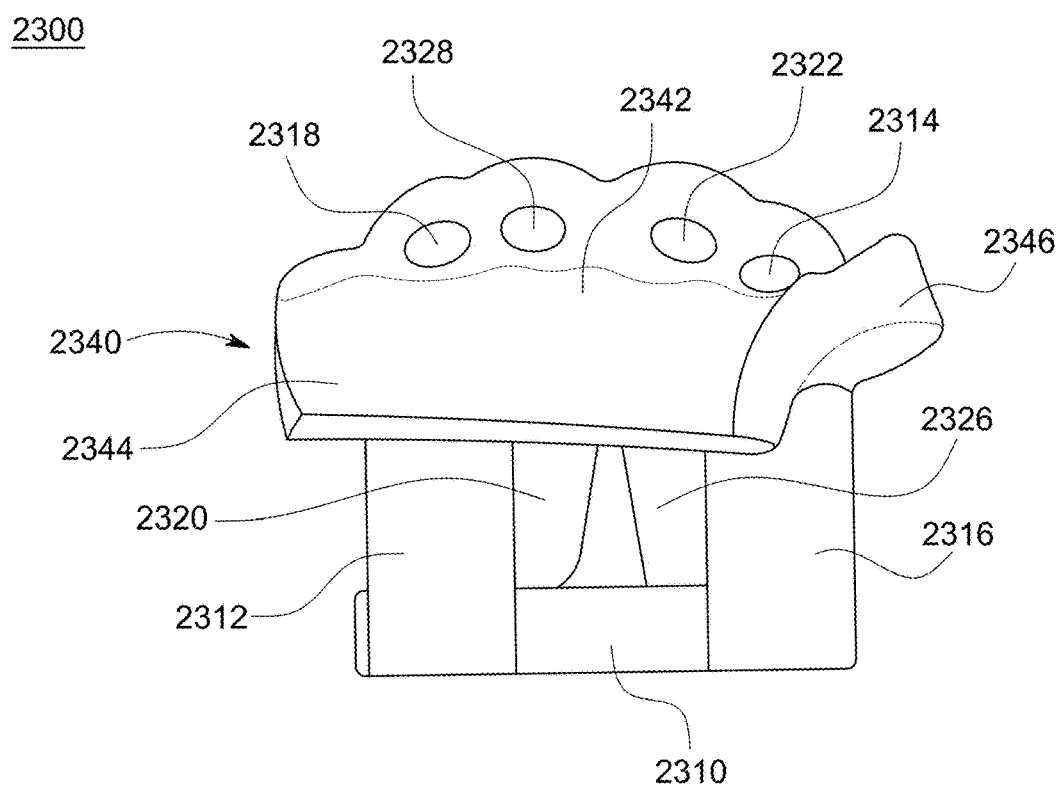

FIG. 132 is a front view of the alignment guide of FIG. 130, in accordance with an aspect of the present invention;

FIG. 133 is a back view of the alignment guide of FIG. 130, in accordance with an aspect of the present invention;

FIG. 134 is a first perspective view of yet another alignment guide, in accordance with an aspect of the present invention;

FIG. 135 is a second perspective view of the alignment guide of FIG. 134, in accordance with an aspect of the present invention;

FIG. 136 is a front view of the alignment guide of FIG. 134, in accordance with an aspect of the present invention;

FIG. 137 is a back view of the alignment guide of FIG. 134, in accordance with an aspect of the present invention;

FIG. 138 is a first perspective view of another alignment guide, in accordance with an aspect of the present invention;

FIG. 139 is a second perspective view of the alignment guide of FIG. 138, in accordance with an aspect of the present invention;

FIG. 140 is a front view of the alignment guide of FIG. 138, in accordance with an aspect of the present invention;

FIG. 141 is a back view of the alignment guide of FIG. 138, in accordance with an aspect of the present invention;

FIG. 142 is a first perspective view of another alignment guide, in accordance with an aspect of the present invention;

FIG. 143 is a second perspective view of the alignment guide of FIG. 142, in accordance with an aspect of the present invention;

FIG. 144 is a first side view of the talus alignment guide of FIG. 146, in accordance with an aspect of the present invention;

FIG. 145 is a second side view of the talus alignment guide of FIG. 146, in accordance with an aspect of the present invention;

FIG. 146 is a first end view of the talus alignment guide of FIG. 146, in accordance with an aspect of the present invention;

FIG. 147 is second end view of the talus alignment guide of FIG. 146, in accordance with an aspect of the present invention;

FIG. 148 is a top view of the talus alignment guide of FIG. 146, in accordance with an aspect of the present invention; and FIG. 149 is bottom view of the talus alignment guide of FIG. 146, in accordance with an aspect of the present invention.

DETAILED DESCRIPTION FOR CARRYING OUT THE INVENTION

Generally stated, disclosed herein are patient specific instruments and systems for maintaining, correcting and/or resurfacing joint surfaces. Further, methods for maintaining, correcting and/or resurfacing joint surfaces using instruments and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the leg for brevity purposes, but it should be understood that the devices, systems, instrumentation and methods may be used with other bones of the body having similar structures.

Figure 1:
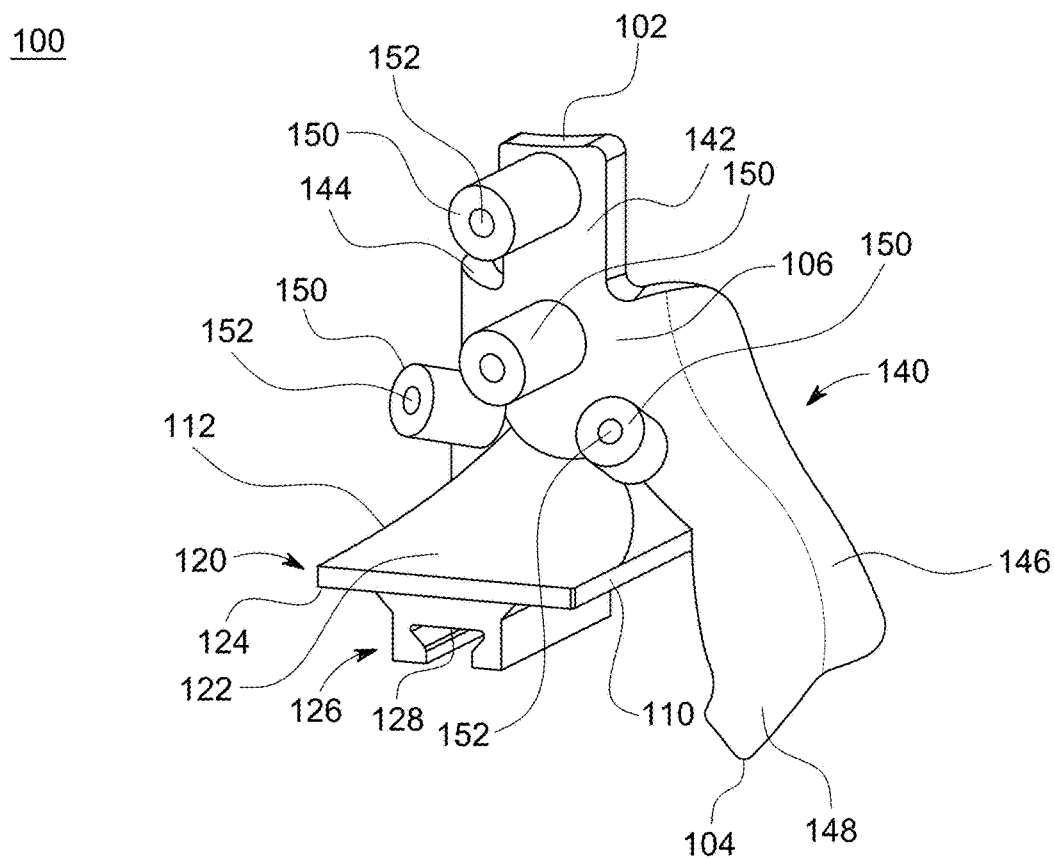
FIG. 1 is a first perspective view of an embodiment of an alignment guide, in accordance with an aspect of the present invention.
Figure 2:
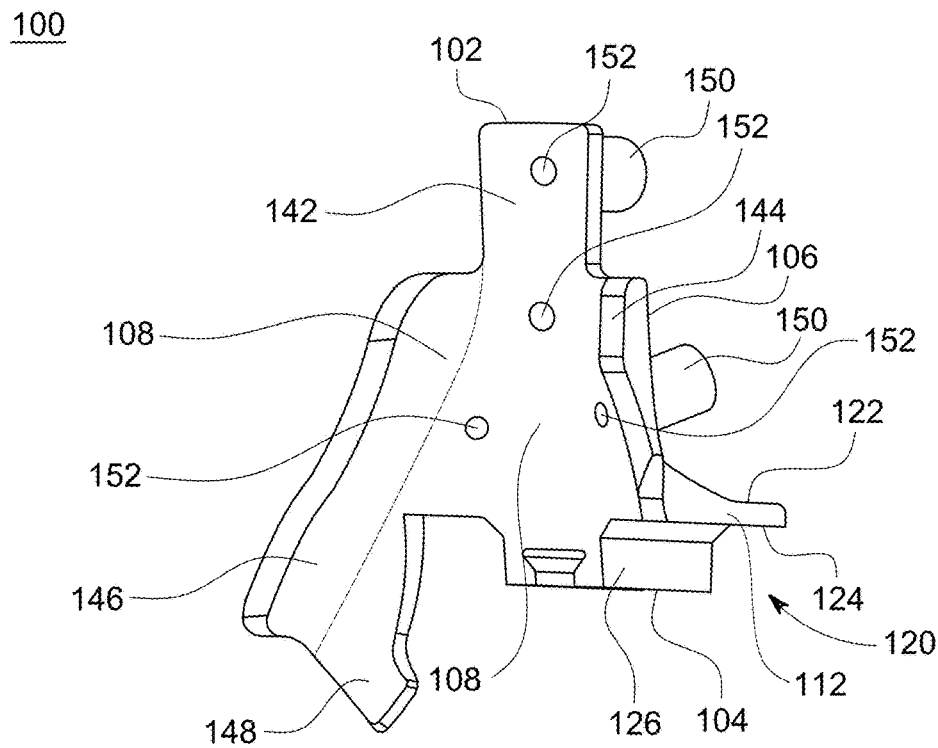
FIG. 2 is a second perspective view of the alignment guide of FIG. 1, in accordance with an aspect of the present invention.
Figure 3:
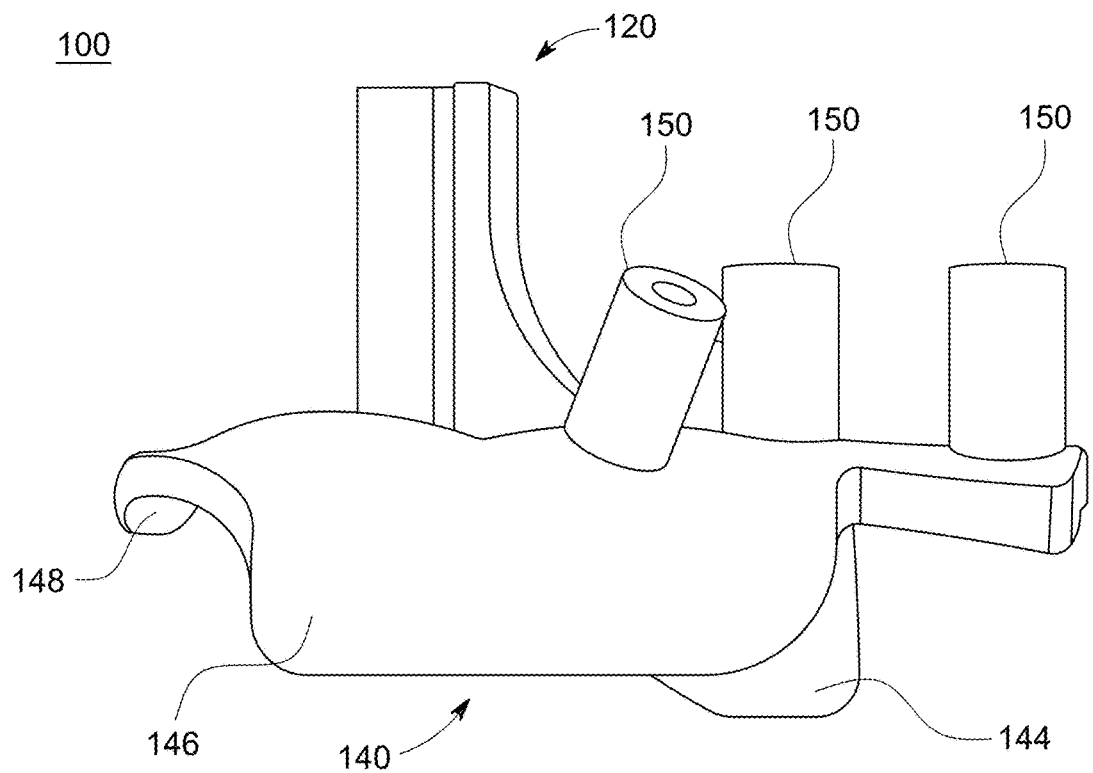
FIG. 3 is a first side view of the alignment guide of FIG. 1, in accordance with an aspect of the present invention.
Figure 4:
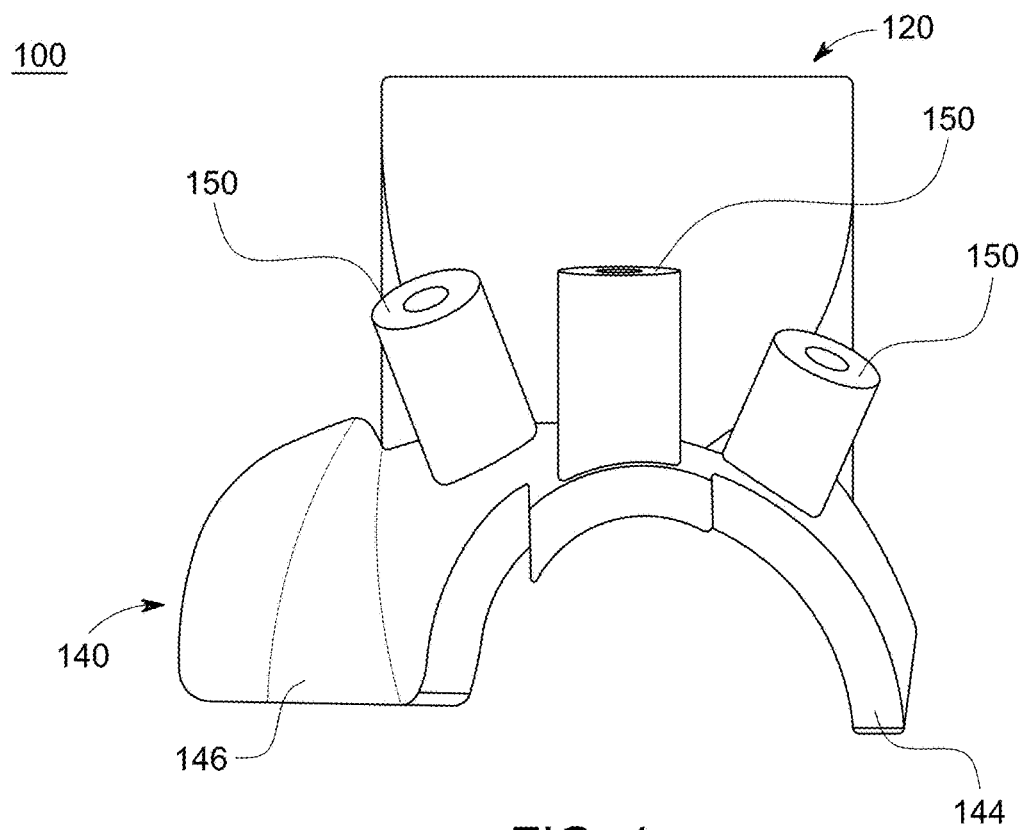
FIG. 4 is a first end view of the alignment guide of FIG. 1, in accordance with an aspect of the present invention.
Figure 5:
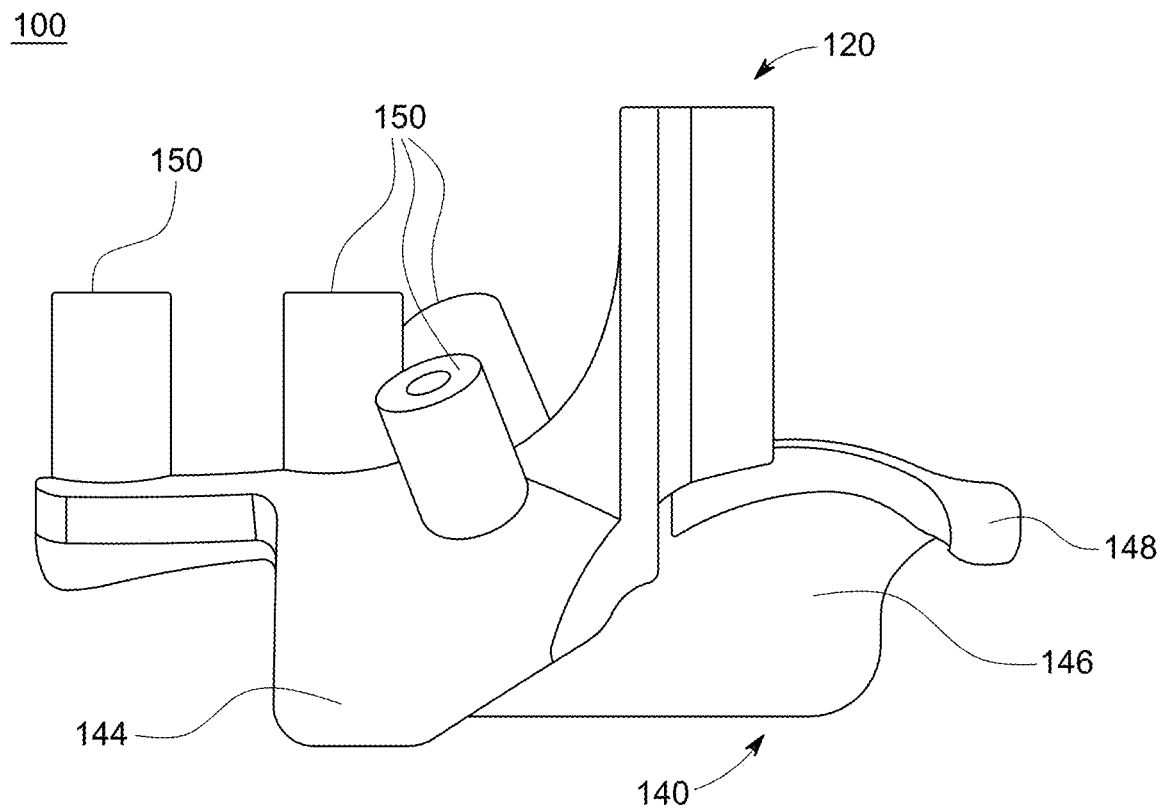
FIG. 5 is a second side view of the alignment guide of FIG. 1, in accordance with an aspect of the present invention.
Figure 6:
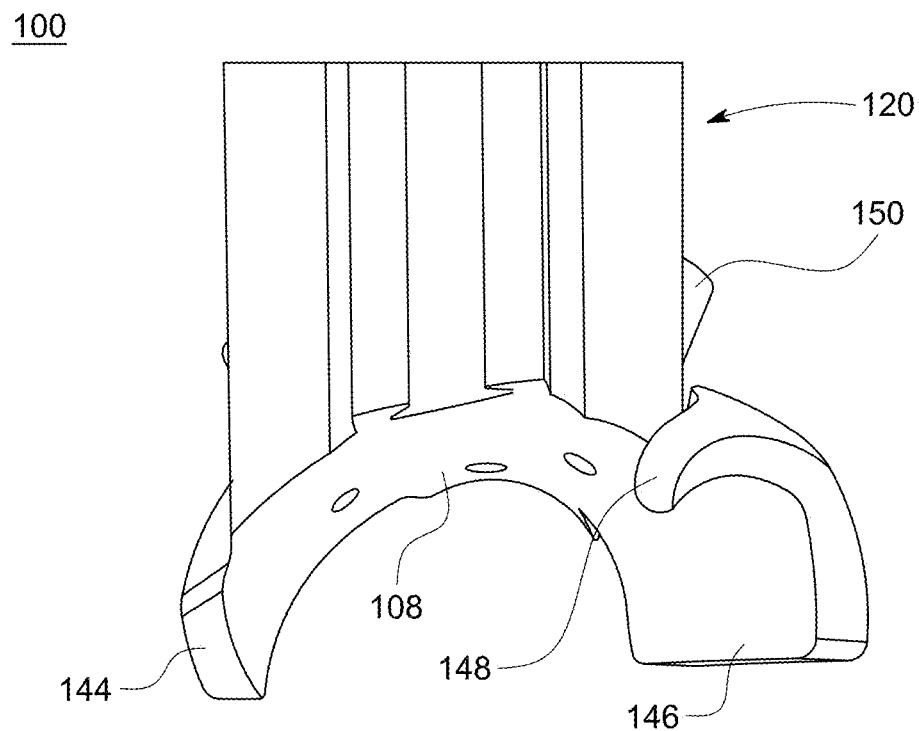
FIG. 6 is a second end view of the alignment guide of FIG. 1, in accordance with aspect of the present invention.
Figure 8:
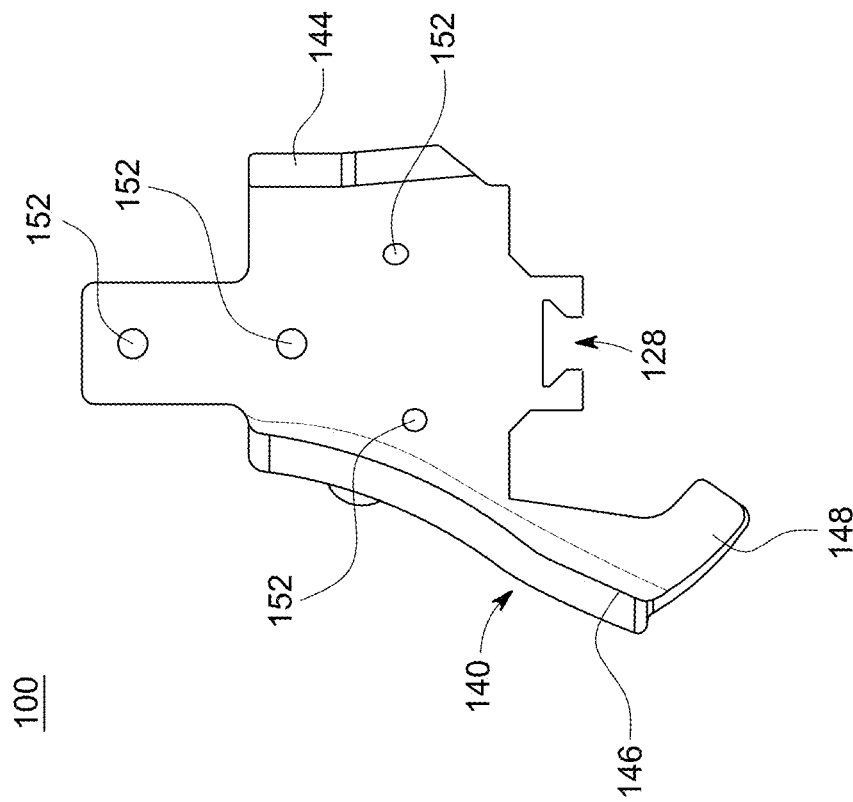
FIG. 8 is a back view of the alignment guide of FIG. 1, in accordance with aspect of the present invention.

Referring now to FIGS. 1-141, alignment guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 are shown. The alignment guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 may be, for example, patient specific guides. The guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 may be, for example, modeled and formed to a patient's anatomy based on medical imagines, such as, CT scans or other tissue determining images. The imagines may be utilized to create a three-dimensional (3D) bone model of the patient's anatomy. The 3D model may be used to determine the axes for alignment of the subsequent guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 and implants (not shown). Specifically, the 3D models can be used to determine the mechanical and/or anatomic axes in both the coronal (front) and sagittal (side) planes. In addition, the 3D model can be used to determine a joint line for alignment of the subsequent guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 and implants (not shown). Specifically, the 3D model can be used to determine the joint line in the sagittal (side) plane for the ankle. Then, the 3D bone model may be used to create a guide 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 directly interfaces with and conforms to the patient's bone.

As discussed in greater detail below, the guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 also match and attach to the bone for alignment of the subsequent resection blocks and implants (not shown). The guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 allow for alignment of the resection blocks without the need for traditional external alignment guides. The guides 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 allow for the resection blocks to be installed directly into the guide 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200 by, for example, a dovetail or other locking or attachment feature. In addition to visualizing placement and use of the guide 100, 180, 190, 200, 250, 300, 400, 450, 500, 600, 700, 750, 800, 900, 1000, 1100, 1200, 1300, 1400, 1500, 1600, 1700, 1800, 1900, 2000, 2100, 2200, the bone model may also be used pre-operatively by the surgeon to estimate implant sizing and placement to restore the ankle joint and ankle joint line.

Figure 7:
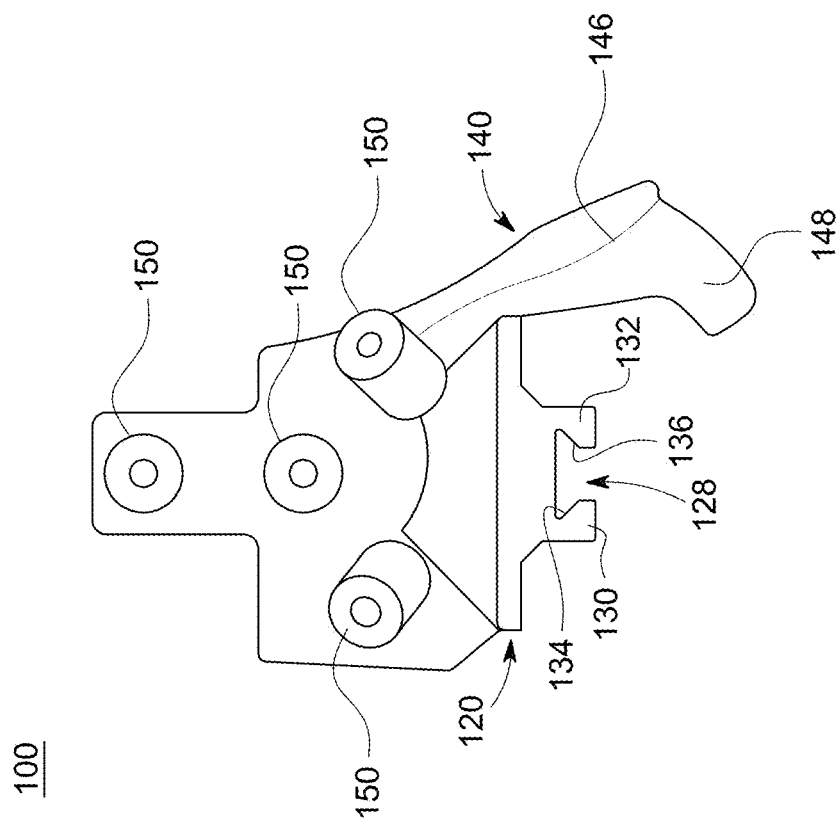
FIG. 7 is a front view of the alignment guide of FIG. 1, in accordance with aspect of the present invention.
Figure 9:
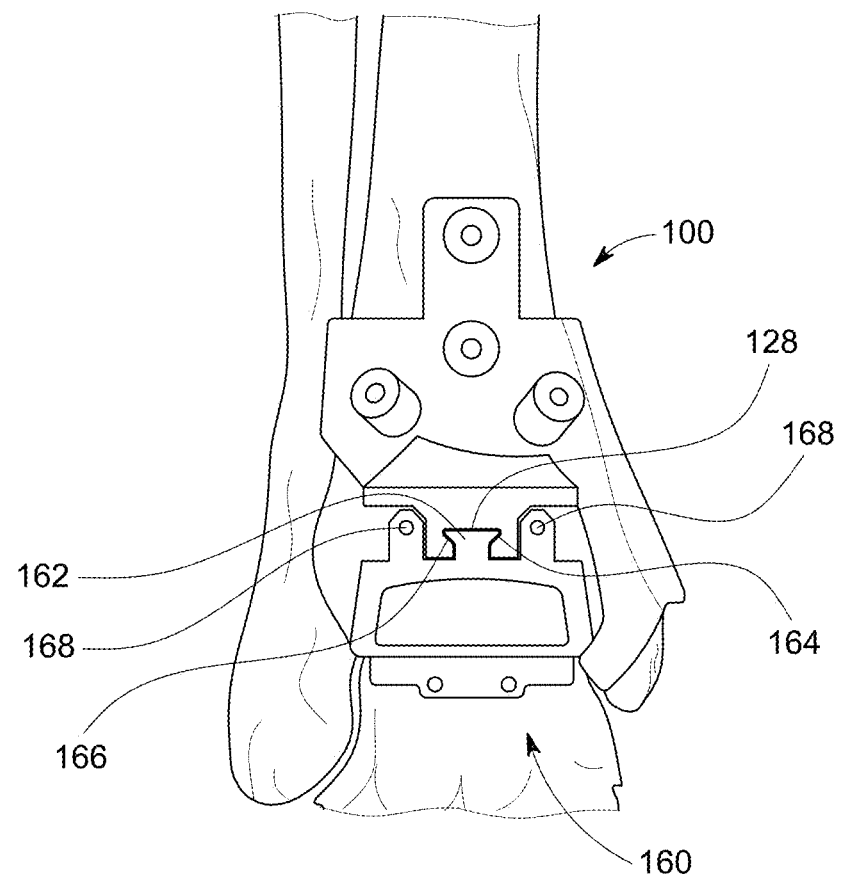
FIG. 9 is a front view of the alignment guide of FIG. 1 shown on a patient's bones with a cut guide attached, in accordance with an aspect of the present invention.

Referring now to FIGS. 1-9, an alignment guide 100 is shown. The alignment guide 100 includes a first or proximal end 102, a second or distal end 104, a first or anterior surface 106, a second or posterior surface 108, a first or medial side 110, and a second or lateral side 112. The alignment guide 100 may include a base portion 120 with a top surface 122 and a bottom surface 124. The base portion 120 may extend out from a body 140 of the alignment guide 100 in an anterior direction, as shown in FIGS. 3-6. The bottom surface 124 may include a fastening system 126, for example, a dovetail fastener. The fastener 126 may include a channel 128 for receiving a corresponding dovetail portion 162 on a resection block 160, as shown in FIG. 9. The fastener 126 may include a first leg 130 spaced apart from a second leg 132. The first leg 130 may include a first undercut 134 and the second leg 132 may include a second undercut 136, as shown in FIG. 7. The first and second undercuts 134, 136 may be for engaging corresponding protrusions 164, 166 on the resection block 160, as shown in FIG. 9.

With continued reference to FIGS. 1-9, the body 140 is formed using imaging, such as CT scans or other tissue determining images. The second or posterior surface 108 of the body 140 is formed to match or correspond to the distal end of a patient's tibia. The body 140 includes a tab 142 extending in a proximal direction toward the first end 102. In addition, the body 140 includes a lateral protrusion 144 and a medial protrusion 146. The lateral protrusion 144 extends away from the second side 112 and matches the patient's anatomy. The lateral protrusion 144 may, for example, wrap around the posterior aspect (for example, apex) of the tibia to allow the guide 100 to couple to or grip the patient's tibia making additional fasteners optional. The medial protrusion 146 extends away from the first side 110 and extends in a distal direction past the base portion 120 and the fastener 126. The medial protrusion 146 includes an extension 148 that wraps around the anterior aspect (for example, apex) of a tibia and/or, more specifically, the notch of Harty, if present, and at the junction of the medial malleolus and anterior tibial plafond, extending inferior along the medial malleolus. The body 140 may also include at least one pin tower 150 extending away from the first surface 106 of the body 140. The at least one pin tower 150 may also include a through hole 152 extending through each pin tower 150 and the body 140. As shown, the body 140 may include two pin towers 150 positioned along a longitudinal axis of the body 140. In addition, the body 140 may include at least one pin tower 150 positioned on a medial side of the body 140 and at least one pin tower 150 positioned on a lateral side of the body 140. Alternative arrangements of the pin towers 150 are also contemplated in order to place the fixation pins in a position for use with the rest of the total ankle procedure.

Figure 10:
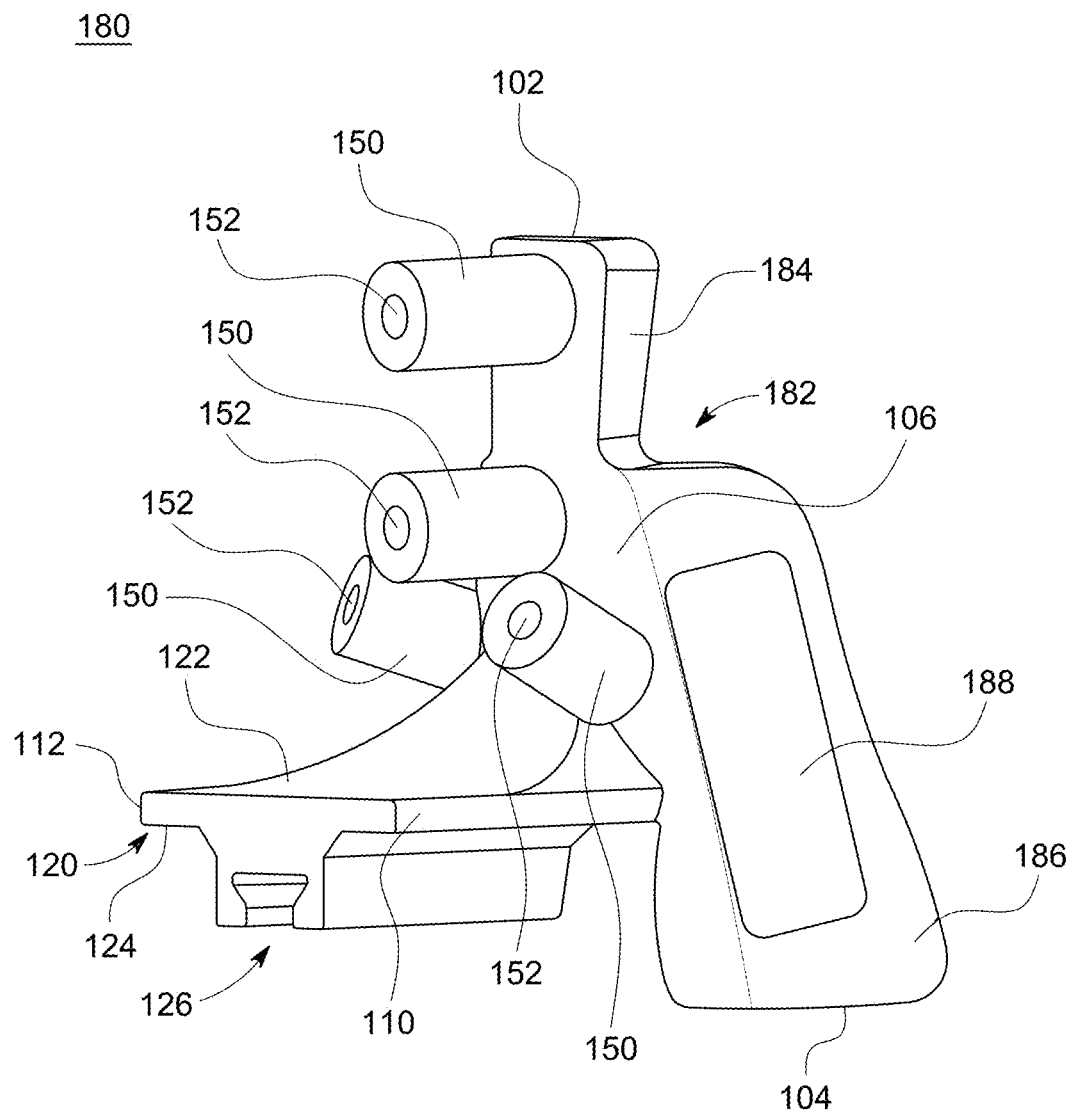
FIG. 10 is a first perspective view of another alignment guide, in accordance with an aspect of the present invention.

An alternative embodiment of the guide 100 is shown in FIG. 10. The guide 180 includes a body 182 and a base portion 120 extending away from the body 182. The base portion 120 is as described in greater detail above and will not be described again here for brevity sake. The body 182 is formed using imaging, such as CT scans or other tissue determining images. The second or posterior surface 108 of the body 182 is formed to match or correspond to the distal end of a patient's tibia. The body 182 includes a tab 184 extending in a proximal direction toward the first end 102. In addition, the body 182 includes a lateral protrusion (not shown) and a medial protrusion 186. The lateral protrusion may be the same or similar to the lateral protrusion 144 as described in greater detail above with reference to guide 100 and which will not be described again here for brevity sake. The medial protrusion 186 extends away from the first side 110 and extends in a distal direction past the base portion 120 and the fastener 126. The medial protrusion 186 may include, for example, a flat distal surface. The medial protrusion 186 may also include at least one window 188 for providing additional visualization of the patient's bones.

The window 188 would allow for assessment of the fit of the guide 180 onto at least one bone. In addition, the window 188 may provide space for the interior soft tissue protuberances providing for an improved fit of the guide 180. The body 182 may further include at least one pin tower 150 extending away from the first surface 106 of the body 182. The at least one pin tower 150 and through hole 152 are as described in greater detail above and which will not be described again here for brevity sake.

Figure 11:
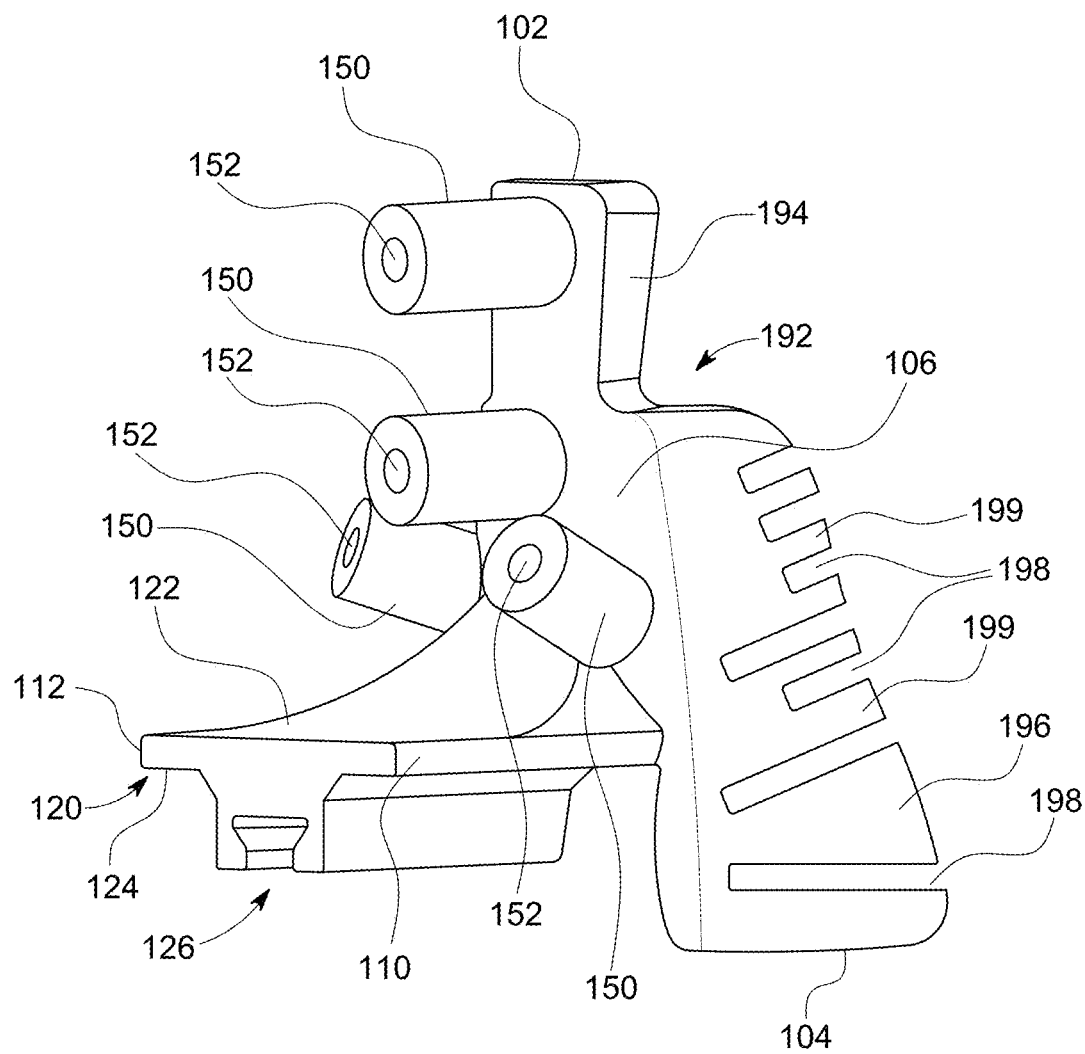
FIG. 11 is a first perspective view of yet another alignment guide, in accordance with an aspect of the present invention.

Another alternative embodiment of the guide 100 is shown in FIG. 11. The guide 190 includes a body 192 and a base portion 120 extending away from the body 192. The base portion 120 is as described in greater detail above and will not be described again here for brevity sake. The body 192 is formed using imaging, such as CT scans or other tissue determining images. The second or posterior surface 108 of the body 192 is formed to match or correspond to the distal end of a patient's tibia. The body 192 includes a tab 194 extending in a proximal direction toward the first end 102. In addition, the body 192 includes a lateral protrusion (not shown) and a medial protrusion 196. The lateral protrusion may be the same or similar to the lateral protrusion 144 as described in greater detail above with reference to guide 100 and which will not be described again here for brevity sake. The medial protrusion 196 extends away from the first side 110 and extends in a distal direction past the base portion 120 and the fastener 126. The medial protrusion 196 may include, for example, a flat distal surface. The medial protrusion 196 may also include at least one slot 198 extending from the first or medial side of the medial protrusion 196 toward the base portion 120. As shown in FIG. 11, when the guide 190 includes multiple slots 198, extension portions or fingers 199 may be formed between the slots 198. The fingers 199 may provide a better fit and gripping to allow for variances in contour matching. Further, individual fingers 199 may be removable to allow for additional clearance or adaptation to local bone anomalies. The at least one slot 198 would also allow for assessment of the fit of the guide 190 onto the bone. The body 192 may further include at least one pin tower 150 extending away from the first surface 106 of the body 192. The at least one pin tower 150 and through hole 152 are as described in greater detail above and which will not be described again here for brevity sake.

Referring now to FIGS. 12-19, another guide 200 is shown. The guide 200 includes a first or proximal end 202, a second or distal end 204, a first or anterior surface 206, a second or posterior surface 208, a first or medial side 210, and a second or lateral side 212. The alignment guide 200 may include a first or coupling member 220 and an extension member or tongue 230 removably coupled to or engaged with the coupling member 220. The first member 220 may be formed using imaging, such as CT scans or other tissue determining images. The second or posterior surface 108 of the first member 220 may be formed to match or correspond to the distal end of a patient's tibia. The first member 220 may include an engagement surface 222 with a protrusion 224 extending away from the engagement surface 222. The protrusion 224 may have, for example, a first end that is larger than the second end. The protrusion 224 may be, for example, a male portion of a dovetail including protrusions for engagement with a corresponding female dovetail or alternative interlocking member.

The first member 220 may also include a lateral protrusion 226 and a medial protrusion 228, as shown in FIGS. 13, 15, and 17-19. The lateral protrusion 226 may be the same or similar to the lateral protrusion 144, as described in greater detail above with reference to guide 100 and which will not be described again here for brevity sake. The medial protrusion 228 may extend away from the first side 110 and in a distal direction past the base portion 120 and the fastener 126. The medial protrusion 228 may include, for example, a flat distal surface.

With continued reference to FIGS. 12-19, the first member 220 may further include at least one pin tower 150 extending away from the first surface 106. The at least one pin tower 150 may be, for example, two pin towers 150, a first pin tower 150 positioned on a medial side of the first member 220 and a second pin tower 150 positioned on a lateral side of the first member 220. The at least one pin tower 150 and through hole 152 may be as described in greater detail above, and which will not be described again here for brevity sake. In addition, the first member 220 may include a base portion 120 extending away from the first surface 106. The base portion 120 is as described in greater detail above and will not be described again here for brevity sake.

As shown in FIGS. 12-19, the extension member or tongue 230 may include a base portion 232 with at least one pin tower 150 extending away from a front surface 238 of the base portion 232. The base portion 232 may be, for example, generally rectangular shaped. The base portion 232 may include a first or proximal end 234, a second or distal end 236, a first, front or anterior surface 238, a second, back or posterior surface 240, a first or medial side 242, and a second or lateral side 244. The distal end 236 of the base portion 232 may include an opening or engagement opening 246 for receiving the protrusion 224 of the first member 220. The opening 246 may be, for example, wider at the proximal end than at the distal end or opening. The opening 246 may be, for example, a female portion of a dovetail including recesses for engagement with a corresponding male dovetail or alternative interlocking member, as would be known by one of ordinary skill in the art. The at least one pin tower 150 extending away from the base portion 232 may be, for example, two pin towers 150 positioned along a longitudinal axis of the base portion 232. The at least one pin tower 150 and through hole 152 are as described in greater detail above and which will not be described again here for brevity sake.

Figure 13:
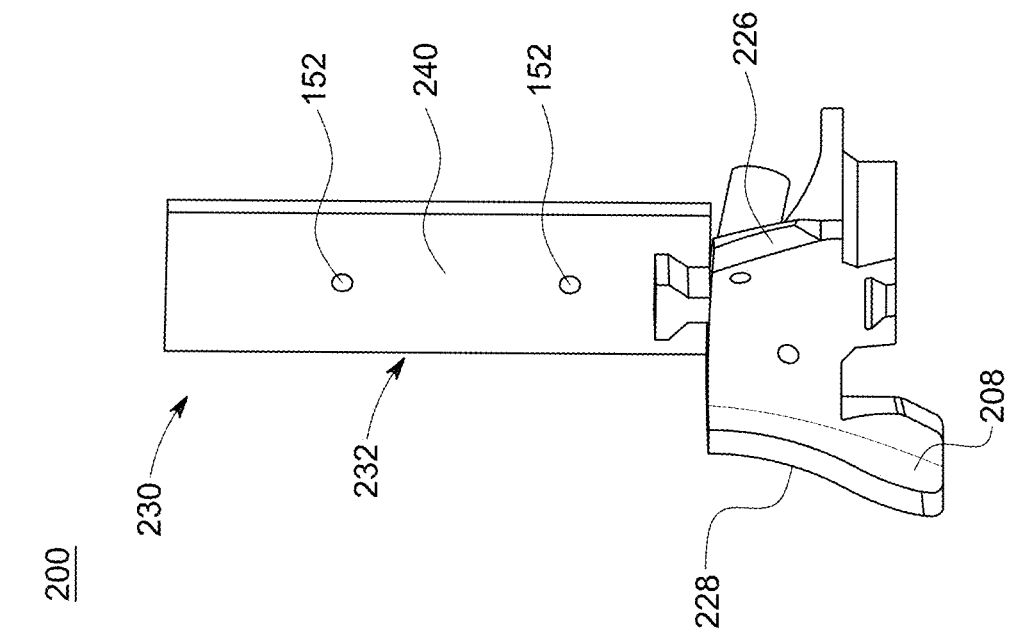
FIG. 13 is a second perspective view of the alignment guide of FIG. 12, in accordance with an aspect of the present invention.
Figure 12:
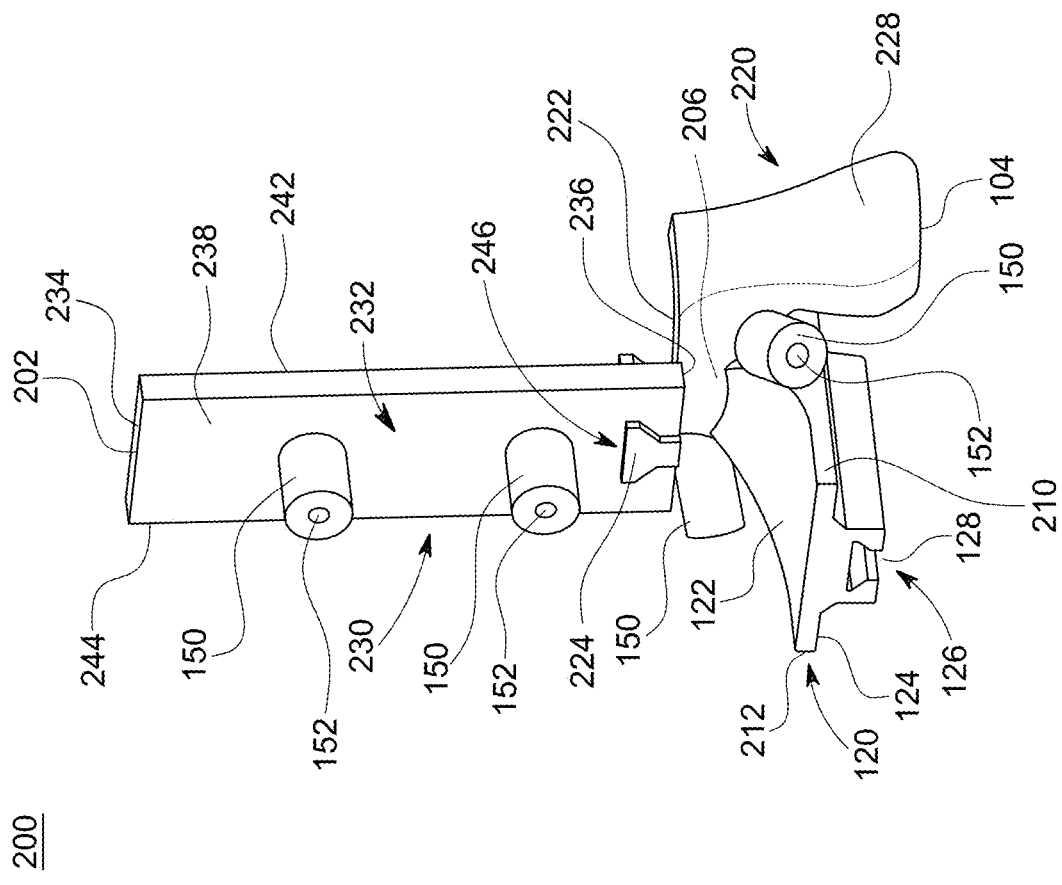
FIG. 12 is a first perspective view of another alignment guide, in accordance with an aspect of the present invention
Figure 14:
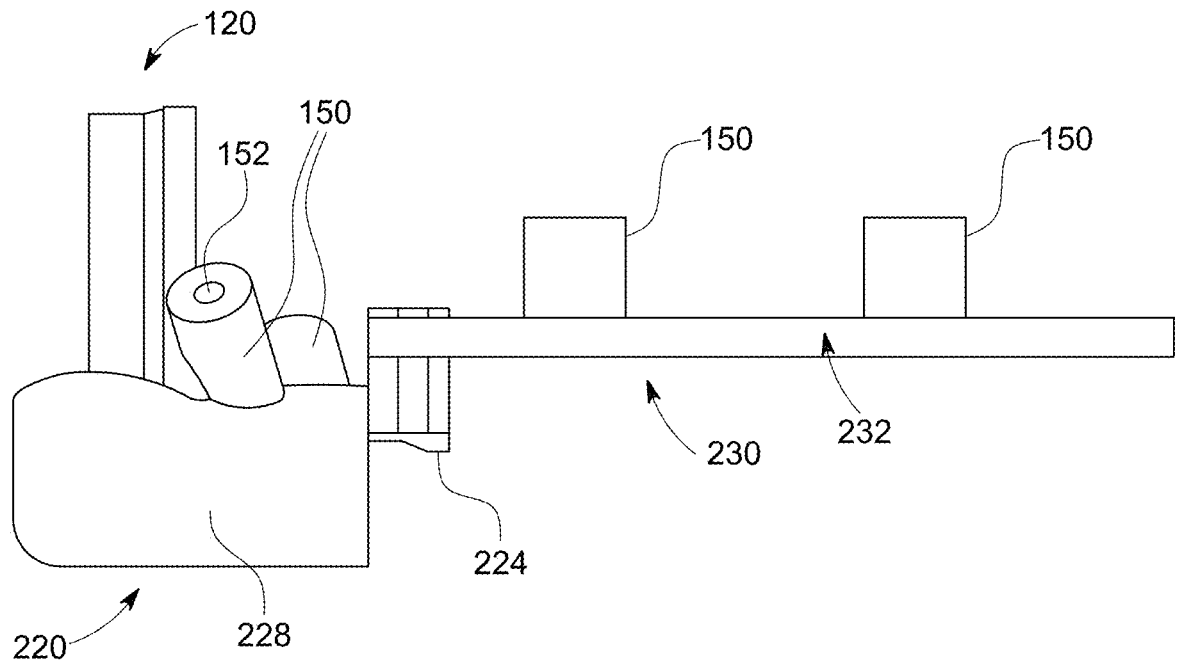
FIG. 14 is a first side view of the alignment guide of FIG. 12, in accordance with aspect of the present invention.
Figure 15:
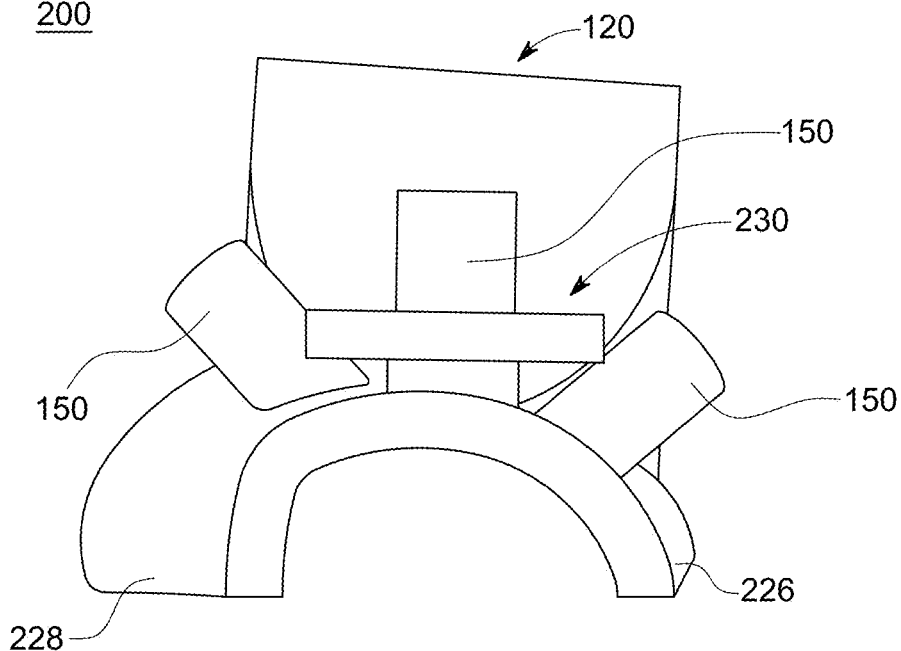
FIG. 15 is a first end view of the alignment guide of FIG. 12, in accordance with an aspect of the present invention.
Figure 16:
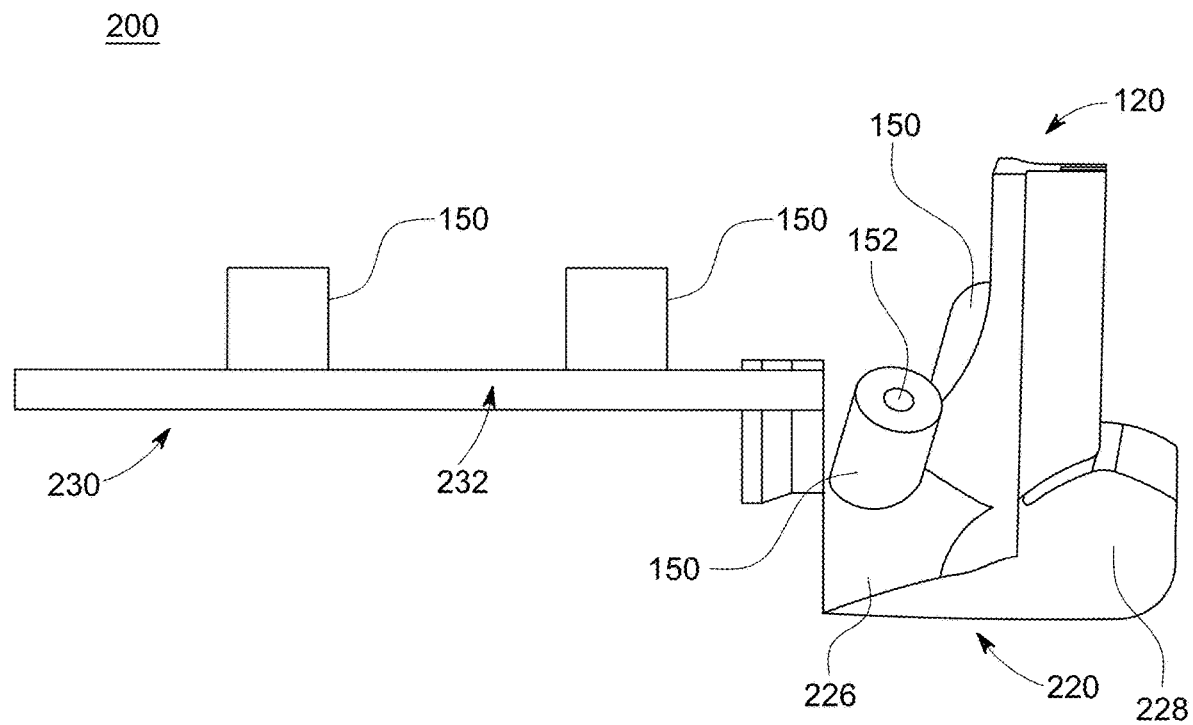
FIG. 16 is a second side view of the alignment guide of FIG. 12, in accordance with an aspect of the present invention.
Figure 17:
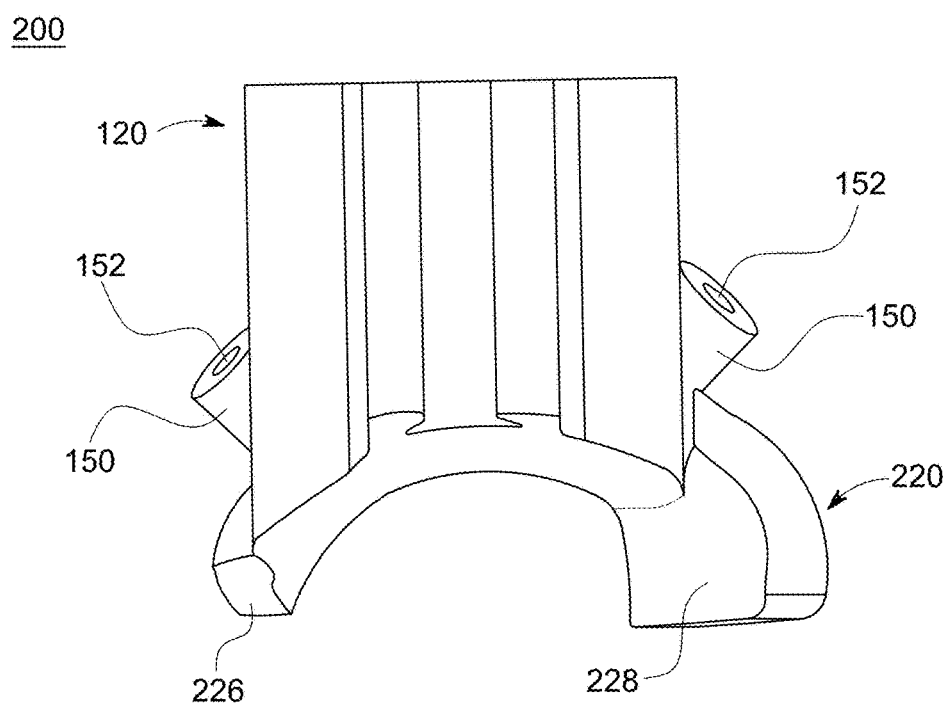
FIG. 17 is a second end view of the alignment guide of FIG. 12, in accordance with aspect of the present invention.
Figure 19:
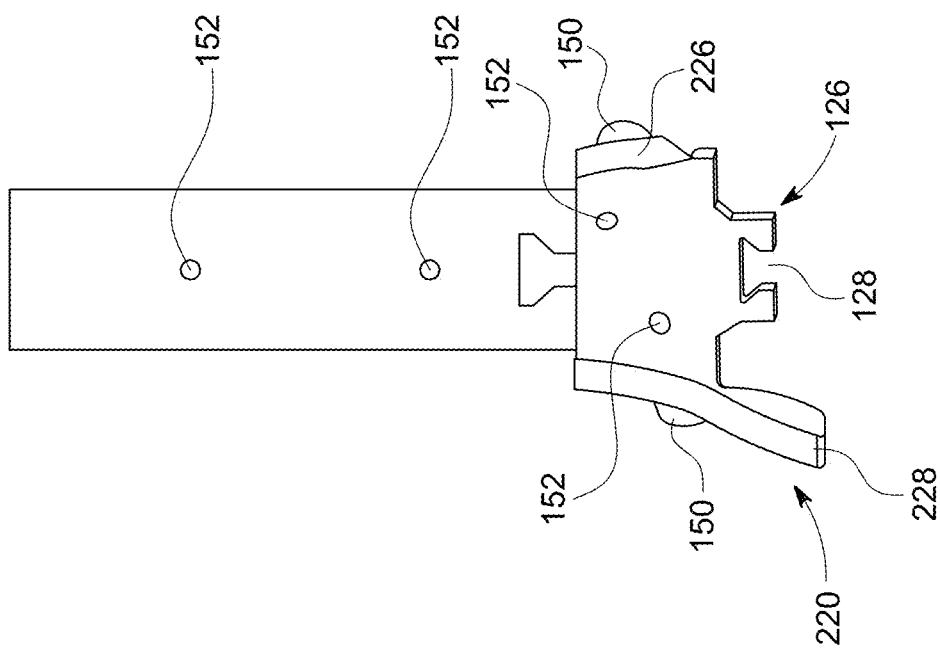
FIG. 19 is a back view of the alignment guide of FIG. 12, in accordance with aspect of the present invention.
Figure 18:
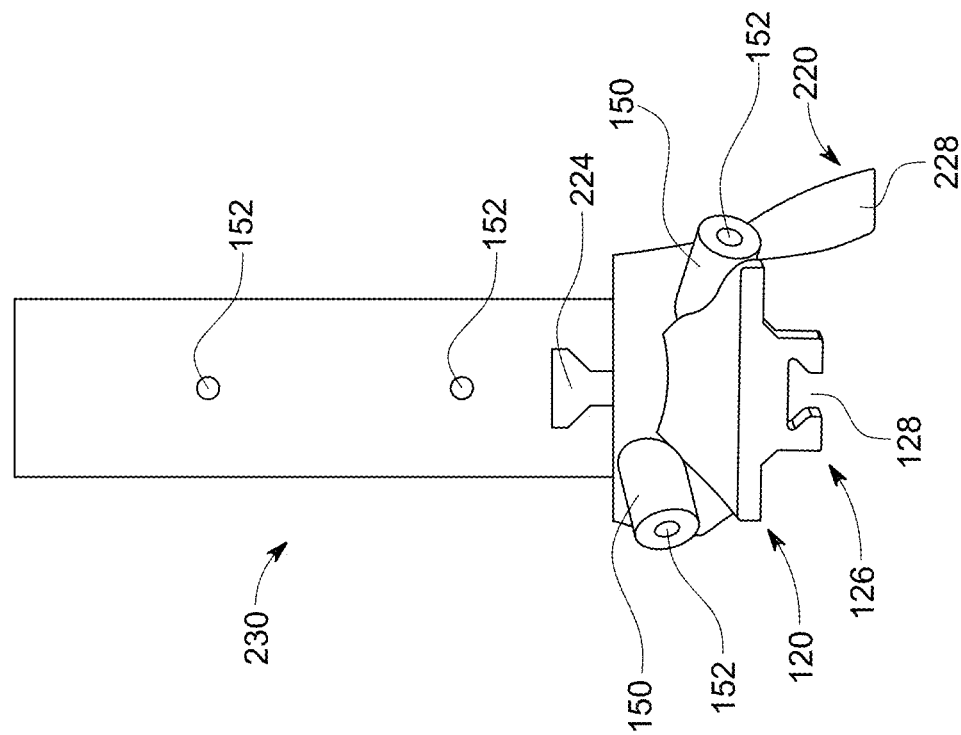
FIG. 18 is a front view of the alignment guide of FIG. 12, in accordance with an aspect of the present invention.

The extension member 230 may be modular and removable to enable the first member 220 to be inserted into the patient's incision and the extension member 230 to be positioned extracorporeal or outside the patient's incision during the surgical procedure. The two part guide 200 allows for the surgeon to make, for example, a smaller incision. Further, as shown in FIGS. 13, 14 and 16, the extension member 230 may slide or translate along the protrusion 224 of the first member 220. The translation of the extension member 230 allows for the extension member 230 to be positioned closer to the incision site while lessening the angularity error or skiving on the bone during the procedure.

Referring now to FIGS. 20-27, another guide 250 is shown. The guide 250 includes a first or proximal end 252, a second or distal end 254, a first or anterior surface 256, a second or posterior surface 258, a first or medial side 260, and a second or lateral side 262. The alignment guide 250 may include a first or coupling member 264 and an extension member or tongue 270 coupled to and extending away from an engagement surface 222 of the coupling member 264. The extension member 270 may be, for example, directly coupled to the first member 264 on the engagement surface 222. The first member 264 may be similar to the first member 220 as described above with reference to guide 200 and which will not be described again here for brevity sake. The first member 264 may include a lateral protrusion 226, a medial protrusion 228, a base portion 120, and at least one pin tower 150, as described in greater detail above with reference to guide 200. However, the first member 264 does not include the protrusion 246.

As shown in FIGS. 20-27, the extension member or tongue 270 may include a base portion 272 with at least one pin tower 150 extending away from a front surface 278 of the base portion 272. The base portion 272 may be, for example, generally rectangular shaped. The base portion 272 may include a first or proximal end 274, a second or distal end 276, a first, front or anterior surface 278, a second, back or posterior surface 280, a first or medial side 282, and a second or lateral side 284. The distal end 276 of the base portion 272 may include a coupling portion 286 for coupling or attaching to the first member 264. The at least one pin tower 150 extending away from the base portion 272 may be, for example, two pin towers 150 positioned along a longitudinal axis of the base portion 272. The at least one pin tower 150 and through hole 152 are as described in greater detail above and which will not be described again here for brevity sake.

Figure 21:
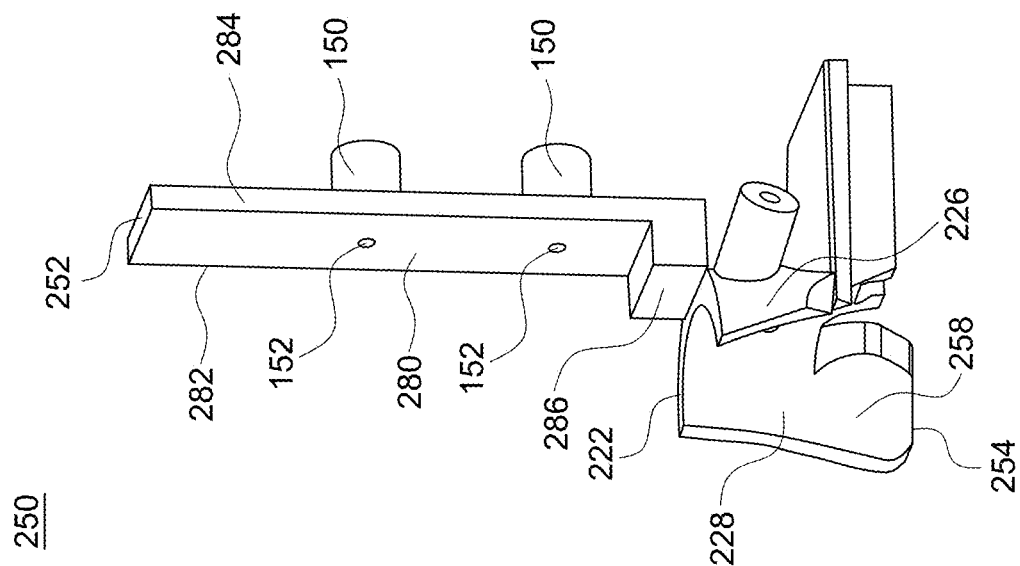
FIG. 21 is a second perspective view of the alignment guide of FIG. 20, in accordance with an aspect of the present invention.
Figure 20:
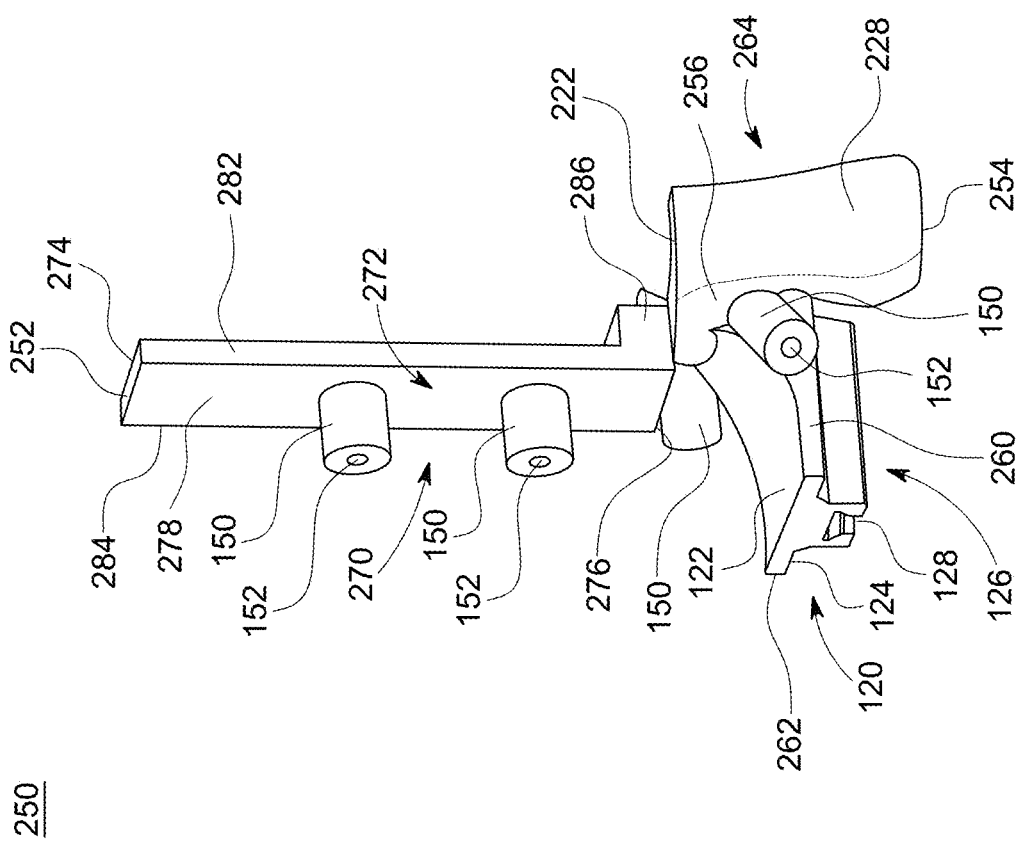
FIG. 20 is a first perspective view of another embodiment of an alignment guide, in accordance with aspect of the present invention.
Figure 22:
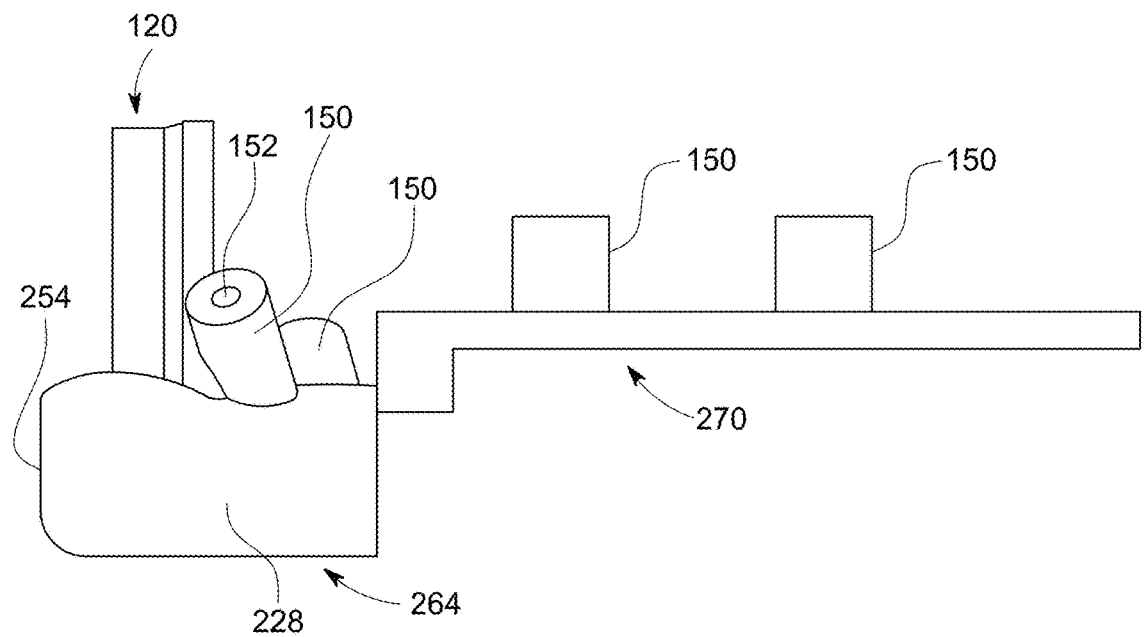
FIG. 22 is a first side view of the alignment guide of FIG. 20, in accordance with an aspect of the present invention.
Figure 23:
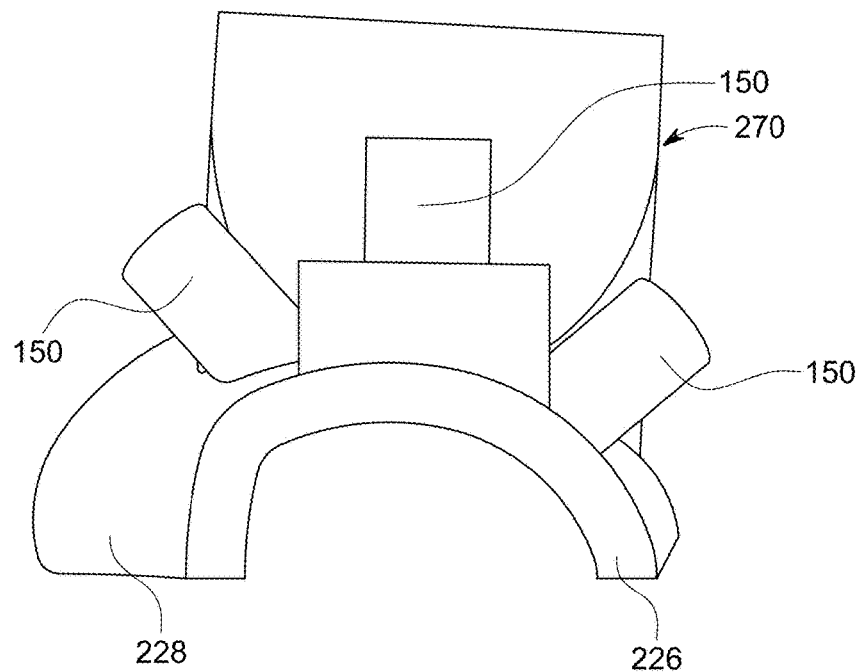
FIG. 23 is a first end view of the alignment guide of FIG. 20, in accordance with an aspect of the present invention.
Figure 24:
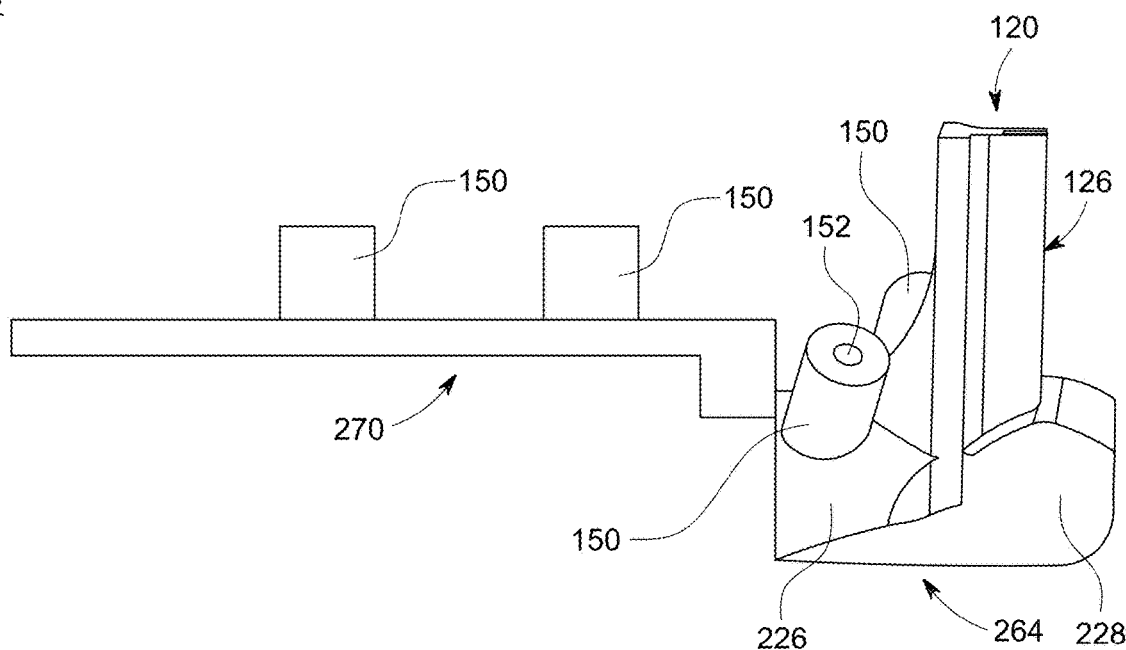
FIG. 24 is a second side view of the alignment guide of FIG. 20, in accordance with an aspect of the present invention.
Figure 25:
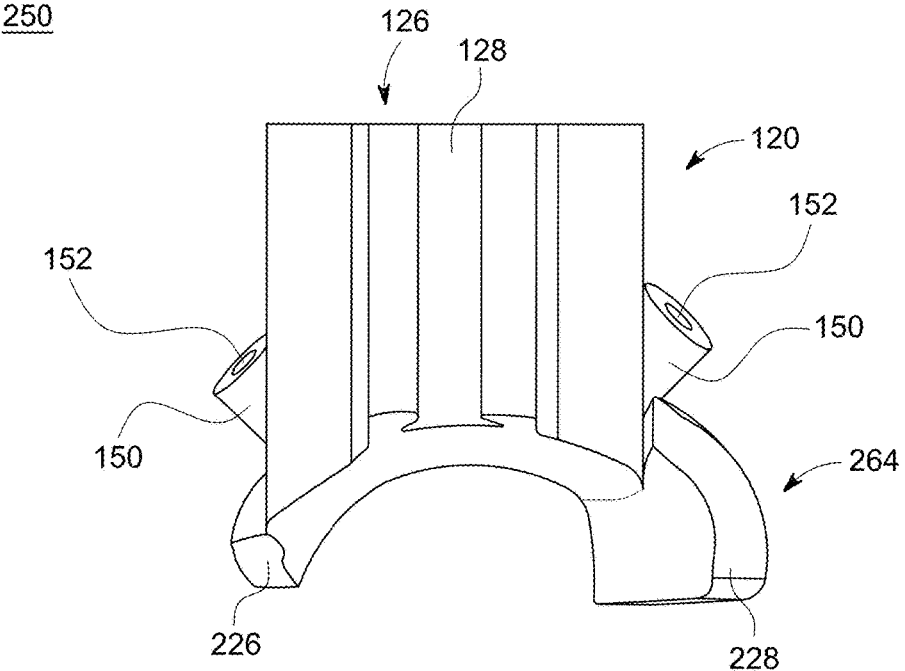
FIG. 25 is a second end view of the alignment guide of FIG. 20, in accordance with an aspect of the present invention.

The extension member 270 may be, for example, one-piece, monolithic, a single construct, or integral with the first member 264. The truncated first member 264 allows for the guide 250 to be inserted into the patient's incision and the extension member 270 to be positioned extracorporeal or outside the patient's incision during the surgical procedure. Further, as shown in FIGS. 21, 22 and 24, the extension member 270 may be formed or printed with an offset from the first member 264 to account for the extension member 270 being positioned outside the patient's incision. The extension member 270 may be formed to allow for removal of the extension member 270 during the surgical procedure, if necessary. The extension member 270 may be, for example, snapped off at the coupling portion 286.

Figure 29:
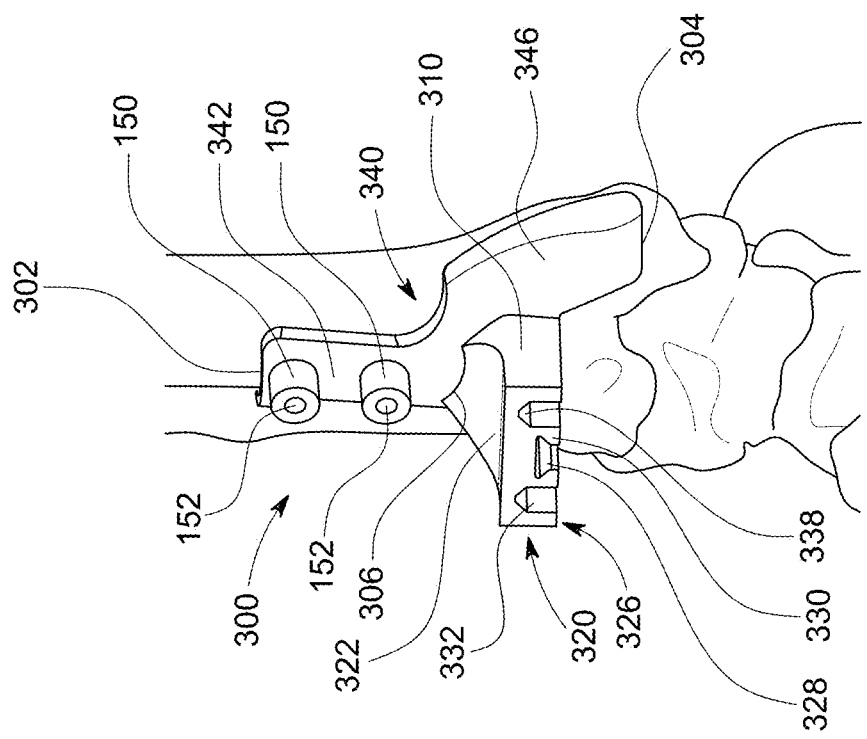
FIG. 29 is a second perspective view of the alignment guide and patient's leg of FIG. 28, in accordance with an aspect of the present invention.
Figure 28:
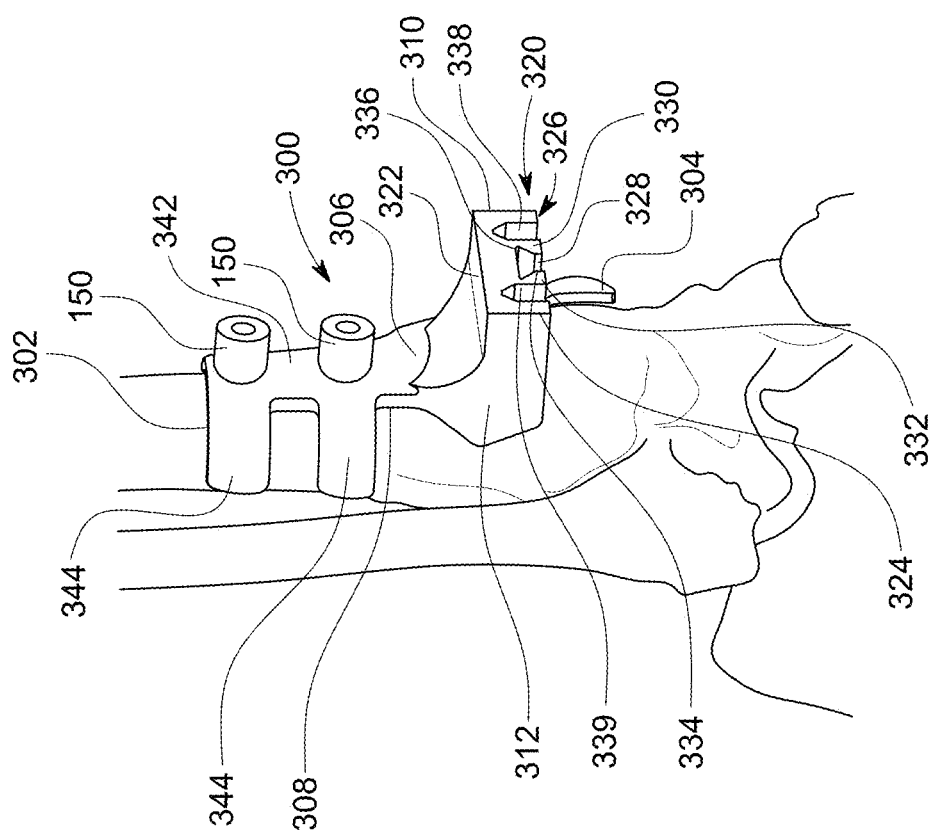
FIG. 28 is a first perspective view of another alignment guide positioned on a patient's leg, in accordance with an aspect of the present invention.
Figure 30:
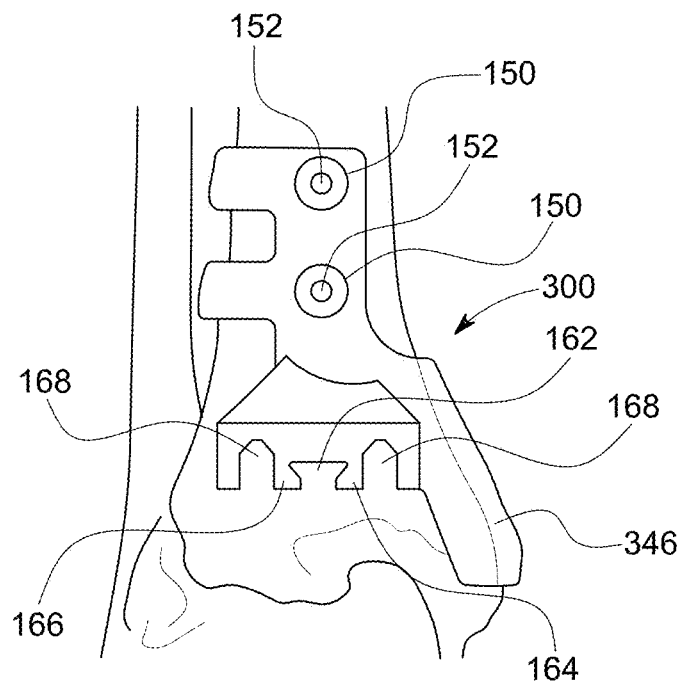
FIG. 30 is a front view of the alignment guide and patient's leg of FIG. 28, in accordance with an aspect of the present invention.
Figure 31:
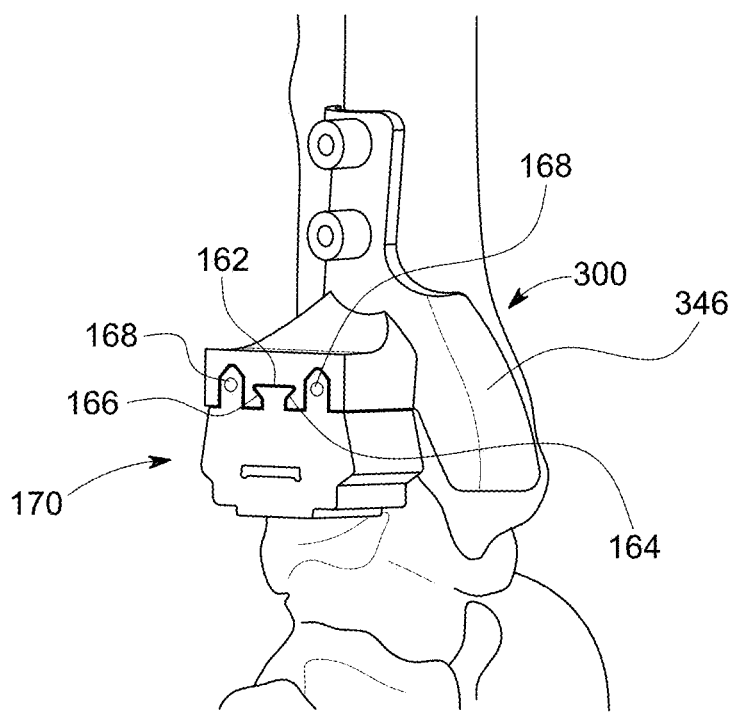
FIG. 31 is the second perspective view of the alignment guide and leg of FIG. 29 with a resection guide coupled to the alignment guide, in accordance with an aspect of the present invention.

Referring now to FIGS. 28-31, another guide 300 is shown. The guide 300 includes a first or proximal end 302, a second or distal end 304, a first or anterior surface 306, a second or posterior surface 308, a first or medial side 310, and a second or lateral side 312. The alignment guide 300 may include a base portion 320 with a top surface 322 and a bottom surface 324. The base portion 320 may extend out from a body 340 of the alignment guide 300 in an anterior direction, as shown in FIGS. 28, 29, and 31. The bottom surface 324 may include a fastening system 326, for example, a dovetail fastener. The fastener 326 may include a channel 328 for receiving a corresponding dovetail portion 162 on a resection block 170, as shown in FIG. 31. The fastener 326 may include a first leg 330 spaced apart from a second leg 332. The first leg 330 may include a first undercut 334 and the second leg 332 may include a second undercut 336, as shown in FIG. 28. The first and second undercuts 334, 336 may be for engaging corresponding protrusions 164, 166 on the resection block 170, as shown in FIG. 31. The fastening system 326 may also include a first alignment groove 338 positioned adjacent to the channel 328 on a first side and a second alignment groove 339 positioned adjacent to the channel 328 on a second side. As shown in FIG. 31, the alignment grooves 338, 339 may receive the protrusions 168 extending away from a top surface of the resection block 170.

With continued reference to FIGS. 28-31, the body 340 is formed using imaging, such as CT scans or other tissue determining images. The second or posterior surface 308 of the body 340 is formed to match or correspond to the distal end of a patient's tibia. The body 340 includes a tab 342 extending in a proximal direction toward the first end 302.

In addition, the body 340 includes at least one lateral protrusion 344 and a medial protrusion 346. The at least one lateral protrusion 344 extends away from the second side 312 and matches the patient's anatomy. In the depicted embodiment, the at least one lateral protrusion 344 is two lateral protrusions 344. The lateral protrusion 344 may, for example, wrap around the posterior aspect of the tibia to allow the guide 300 to couple to or grip the patient's tibia making additional fasteners optional. The medial protrusion 346 extends away from the first side 310 and extends in a distal direction past the base portion 320 and the fastener 326. The medial protrusion 346 includes a flat or planar end surface near the anterior aspect (for example, apex) of a tibia and/or, more specifically, the notch of Harty, if present, and at the junction of the medial malleolus and anterior tibial plafond, extending inferior along the medial malleolus. The body 340 may also include at least one pin tower 150 extending away from the first surface 306 of the body 340. The at least one pin tower 150 may also include a through hole 152 extending through each pin tower 150. As shown, the body 340 may include two pin towers 150 positioned along a longitudinal axis of the body 340. Alternative arrangements of the pin towers 150 are also contemplated in order to place the fixation pins in a position for use with the rest of the total ankle procedure.

Figure 32:
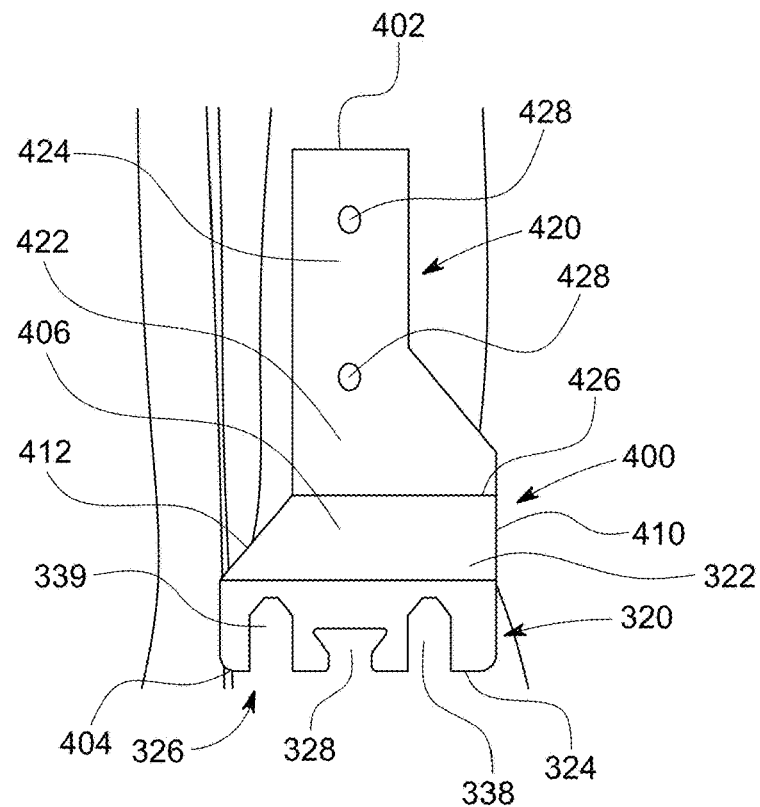
FIG. 32 is a front view of another alignment guide positioned on a patient's bone, in accordance with an aspect of the present invention.

Referring now to FIG. 32, a guide 400 is shown. The guide 400 is another embodiment of a low profile, one-piece guide, similar to guide 250, as described in greater detail above. The guide 400 may include a first or proximal end 402, a second or distal end 404, a first or anterior surface 406, a second or posterior surface positioned on the bone, a first or medial side 410, and a second or lateral side 412. The alignment guide 400 may include a first or coupling member 320 and an extension member or tongue 420 extending away from a top surface or engagement surface 322 of the coupling member 320. The extension member 420 may be, for example, directly coupled to the first member 320 on the engagement surface 322. The first member 320 may be as described above with reference to guide 300 and which will not be described again here for brevity sake.

The extension member or tongue 420 may include a first portion 422 and a second portion 424. The first portion 422 may include an end 426 for engaging the coupling member 320. The end 426 of the first portion 422 may be, for example, coupled to the coupling member 320. The first portion 422 may extend away from the coupling member 320 to the second portion 424 and toward the first end 402 of the guide 400. The first member 422 may be, for example, wider than the second member 424. A second side 412 of the first portion 422 and the second portion 424 may be, for example, aligned along the length of the extension member 420. The first portion 422 may include a parallel portion and an angled portion as the first portion 422 extends between the coupling member 320 and the second portion 424. The first member 422 may have, for example, a first width at the point where the first member 422 engages the coupling member 320. The second member 424 may have, for example, a second width and the first width may be larger than the second width. The extension member 420 may also include at least one through hole 428. The at least one through hole 428 may extend through the extension member 420 from an anterior surface 406 to posterior surface (not shown). The at least one through hole 428 may be, for example, two through holes 150 positioned along a longitudinal axis of the extension member 420. The extension member 420 and coupling member 320 of the guide 400 may be, for example, one-piece, monolithic, a single construct, or integral.

The base portion 320 may be as described above in greater detail with respect to FIGS. 28-31 and which will not be described again here, in detail, for brevity sake. The base portion 320 includes a top surface 322 and a bottom surface 324. The base portion 320 may extend out from the extension member 420 of the alignment guide 400 in an anterior direction. The bottom surface 324 includes the fastening system 326, for example, a dovetail fastener.

Figure 33:
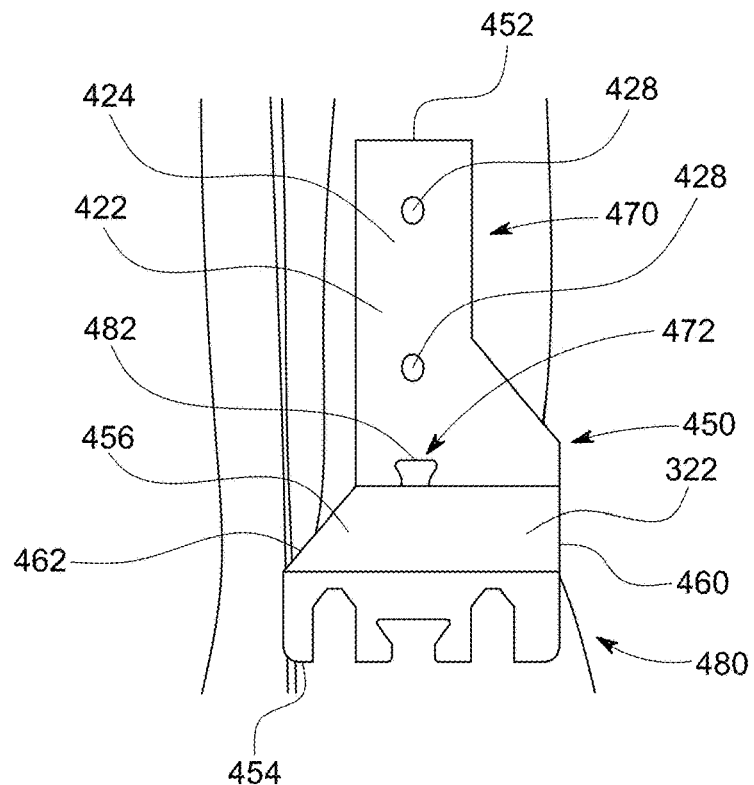
FIG. 33 is a front view of yet another alignment guide positioned on a patient's bone, in accordance with an aspect of the present invention.

Referring now to FIG. 33, a guide 450 is shown. The guide 450 is another embodiment of a low profile, modular guide, similar to guides 200 and 400, as described in greater detail above. The guide 450 may include a first or proximal end 452, a second or distal end 454, a first or anterior surface 456, a second or posterior surface positioned on the bone, a first or medial side 460, and a second or lateral side 462. The alignment guide 450 may include an extension member or tongue 470 and a first or coupling member 480. The extension member 470 may be similar to the extension member 420, as described in greater detail above and which will not be described again here for brevity sake. The coupling member 480 may be similar to the coupling member 320, as described in greater detail above and which will not be described again here for brevity sake.

The extension member 470 may extend away from a top surface or engagement surface 322 of the coupling member 480. The extension member 470 may include an opening or engagement opening 472 positioned at the distal end of the extension member 470. The opening 472 may be, for example, wider at the proximal end than at the distal end or opening. The opening 472 may be, for example, a female portion of a dovetail including recesses for engagement with a corresponding male dovetail or alternative interlocking member, as would be known by one of ordinary skill in the art. The coupling member 320 may also include a protrusion 482 extending away from the engagement surface 322. The protrusion 482 may have, for example, a first end that is larger than the second end. The protrusion 482 may be, for example, a male portion of a dovetail including protrusions for engagement with a corresponding female dovetail 472 of the extension member 470 or an alternative interlocking member, as would be known by one of ordinary skill in the art. The extension member 470 may be, for example, coupled to the first member 320 on the engagement surface 322 by the engagement opening 472 and the protrusion 482.

Figure 34:
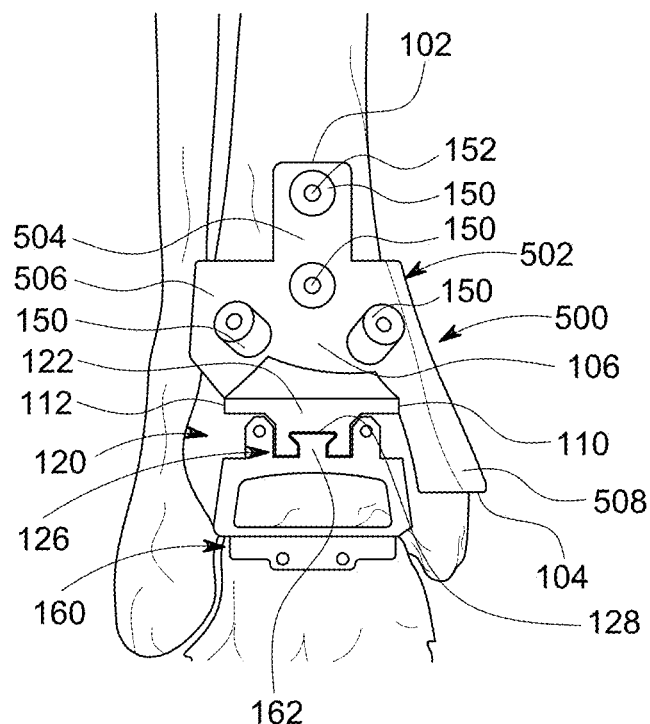
FIG. 34 is a front view of a further alignment guide positioned on a patient's bone, in accordance with an aspect of the present invention.
Figure 35:
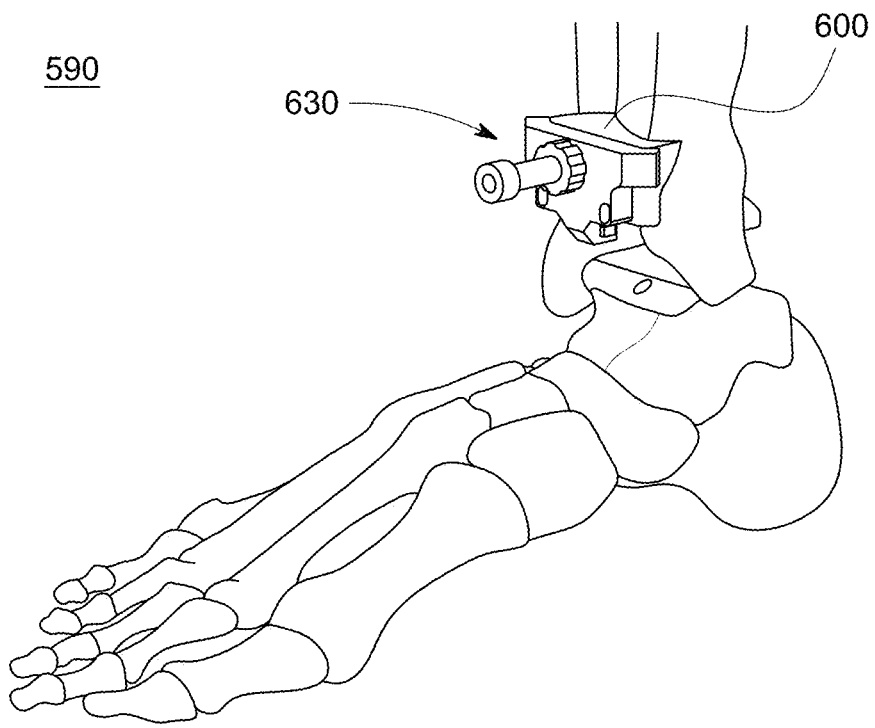
FIG. 35 is a first perspective view of a tibia trial system with a tibia insert and tibia trial positioned on a patient's leg, in accordance with an aspect of the present invention.
Figure 36:
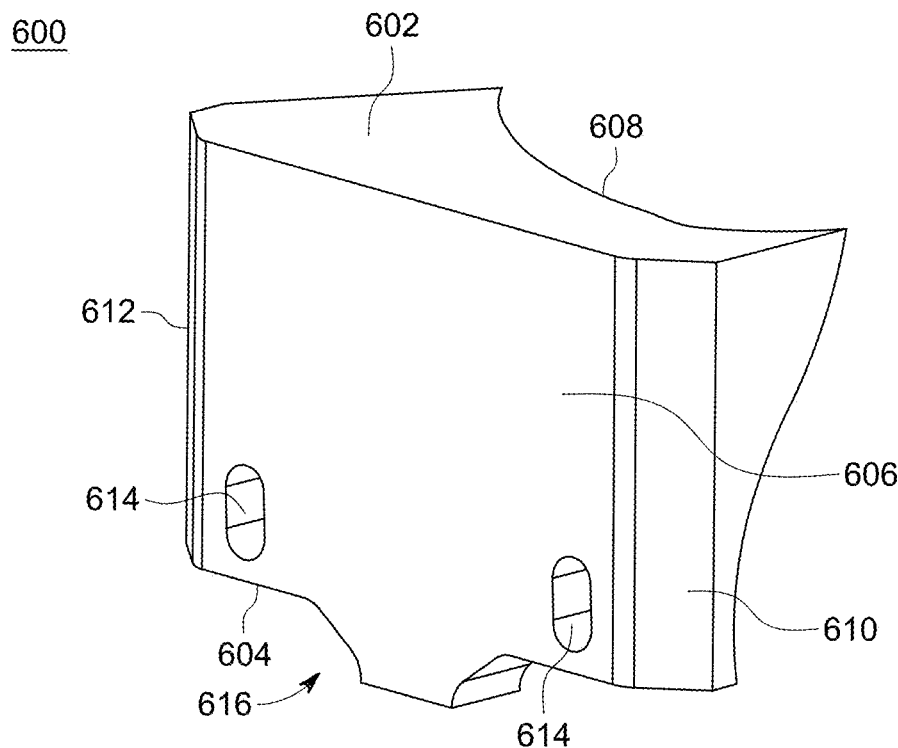
FIG. 36 is a first perspective view of the tibia insert of FIG. 35, in accordance with an aspect of the present invention.
Figure 37:
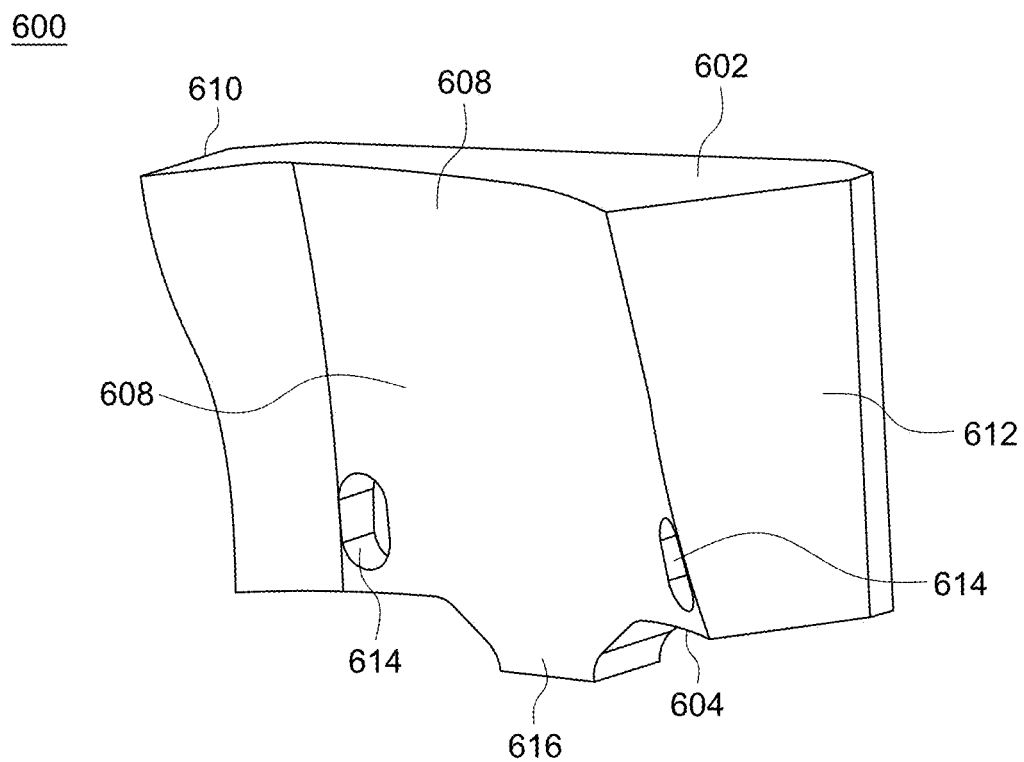
FIG. 37 is a second perspective view of the tibia insert of FIG. 35, in accordance with an aspect of the present invention.
Figure 38:
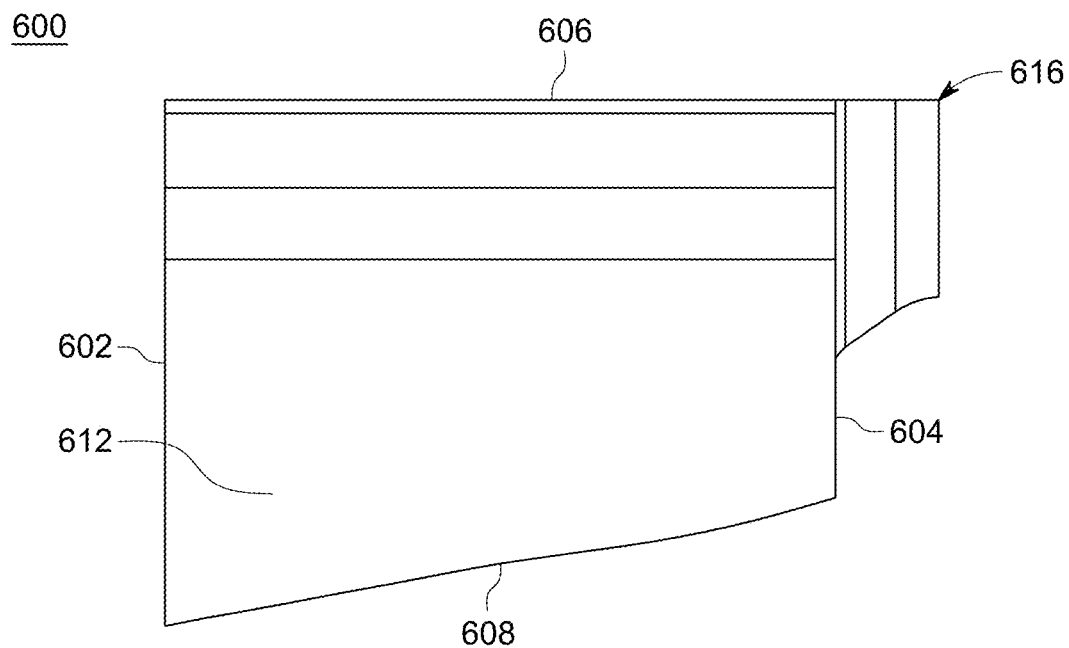
FIG. 38 is a first side view of the tibia trial of FIG. 35, in accordance with an aspect of the present invention.
Figure 39:
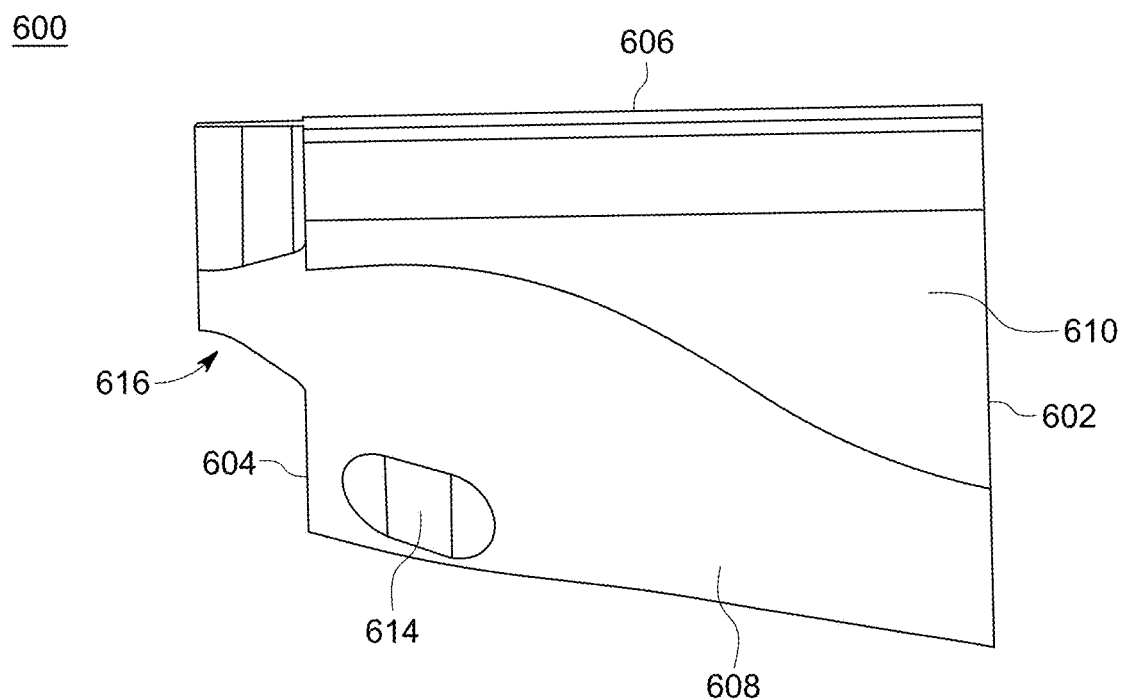
FIG. 39 is a second side view of the tibia trial of FIG. 35, in accordance with an aspect of the present invention.
Figure 40:
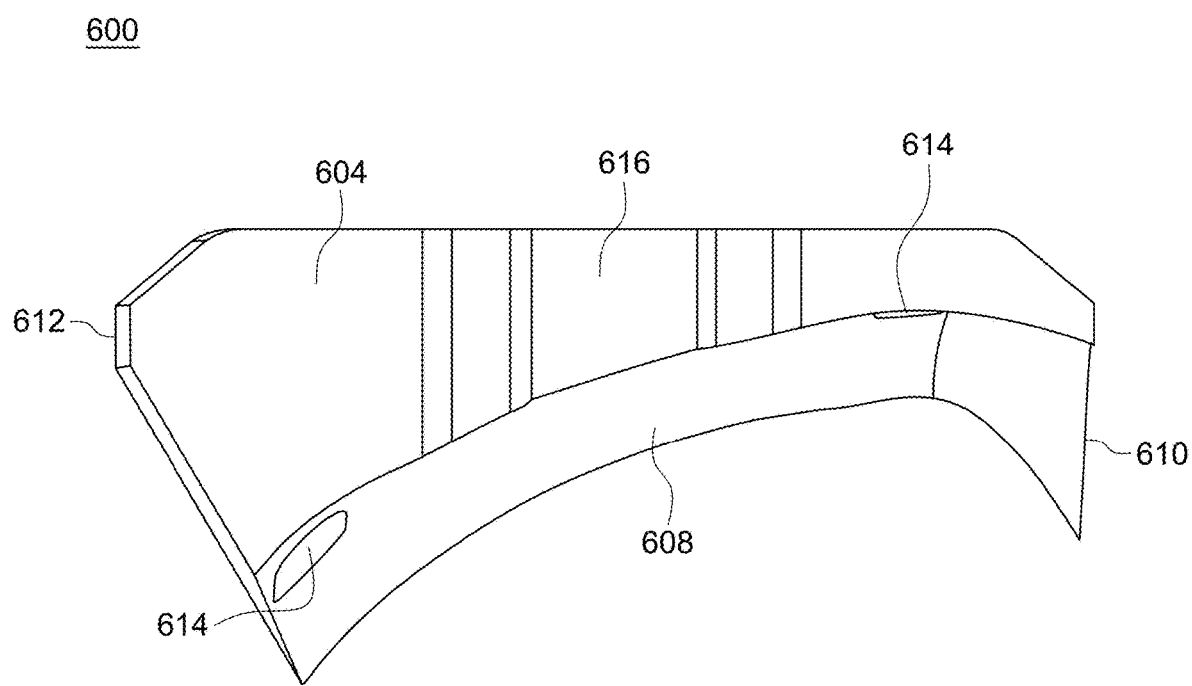
FIG. 40 is a bottom view of the tibia trial of FIG. 35, in accordance with an aspect of the present invention.

Referring now to FIG. 34, a guide 500 is shown. The guide 500 is another embodiment of guide 100, as described in greater detail above. The guide 500 includes a body 502 and a base portion 120 extending away from the body 502. The base portion 120 is as described in greater detail above and will not be described again here for brevity sake. The body 502 is formed using imaging, such as CT scans or other tissue determining images. The second or posterior surface (positioned on the bone) of the body 502 is formed to match or correspond to the distal end of a patient's tibia. The body 502 includes a tab 504 extending in a proximal direction toward the first end 102. In addition, the body 502 includes a lateral protrusion 506 and a medial protrusion 508. The lateral protrusion 506 may extend away from the second side 112 and matches the patient's anatomy. The lateral protrusion 506 may, for example, wrap around the posterior aspect of the tibia to allow the guide 500 to couple to or grip the patient's tibia making additional fasteners optional. The medial protrusion 508 extends away from the first side 110 and extends in a distal direction past the base portion 120 and the fastener 126. The medial protrusion 508 has a flat or planar distal surface positioned near the anterior aspect (for example, apex) of a tibia and/or the notch of Harty, if present, and at the junction of the medial malleolus and anterior tibial plafond, extending inferior along the medial malleolus. The body 502 may further include at least one pin tower 150 extending away from the first surface 106 of the body 502. The at least one pin tower 150 and through hole 152 are as described in greater detail above with reference to guide 100 and which will not be described again here for brevity sake.

Referring now to FIGS. 35-50, a patient specific tibia trail system 590 is shown. The tibia trial system 590 includes a tibia insert or patient specific tibia insert 600 and a tibia trial 630. The tibia insert 600 may have a first or proximal end 602, a second or distal end 604, a first or anterior surface 606, a second or posterior surface 608, a first or medial side 610, and a second or lateral side 612. The insert 600 may include at least one alignment opening 614 extending through the insert 600 from a first surface 606 to a second surface 608. The insert 600 may also include an engagement member 616 extending away from a second end 604 of the insert 600. The first end 602 may be, for example, a generally planar or flat surface. The second end 604 may be, for example, shaped to match or correspond to the shape of the second end of the tibia trial 630. The first surface 606 may be, for example, generally planar or flat. The second surface 608 may be, for example, shaped or contoured to match a specific patient's tibia 620, specifically the anterior portion of the tibia 620. The insert 600, specifically the second surface 606 may be formed using imaging, such as CT scans or other tissue determining images. The first side 610 and second side 612 may each be angled to connect the first surface 606 to the second surface 608.

Figure 45:
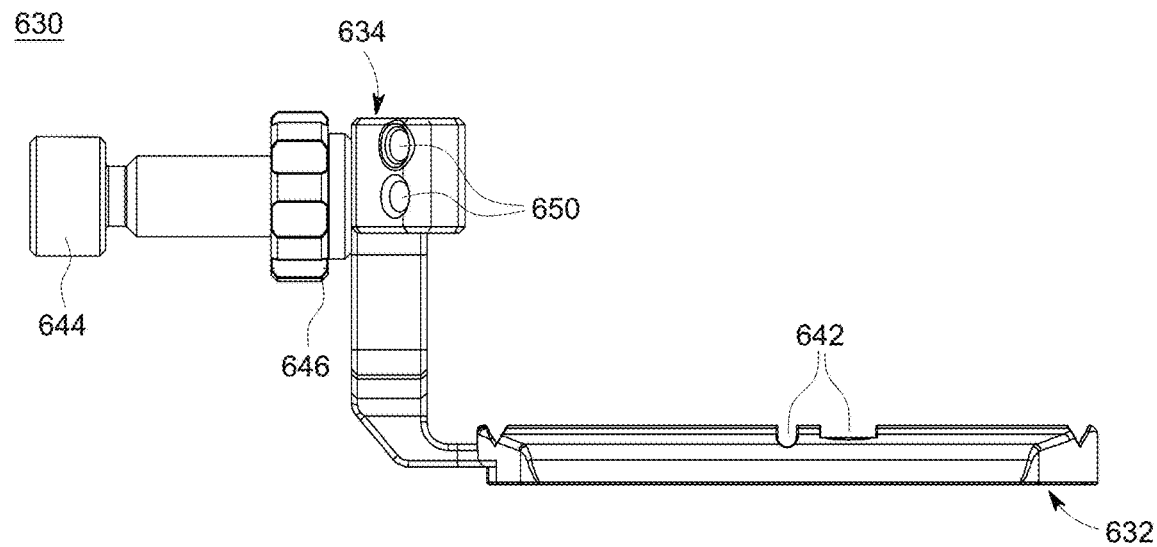
FIG. 45 is a first side view of the tibia trial of FIG. 35, in accordance with an aspect of the present invention.
Figure 46:
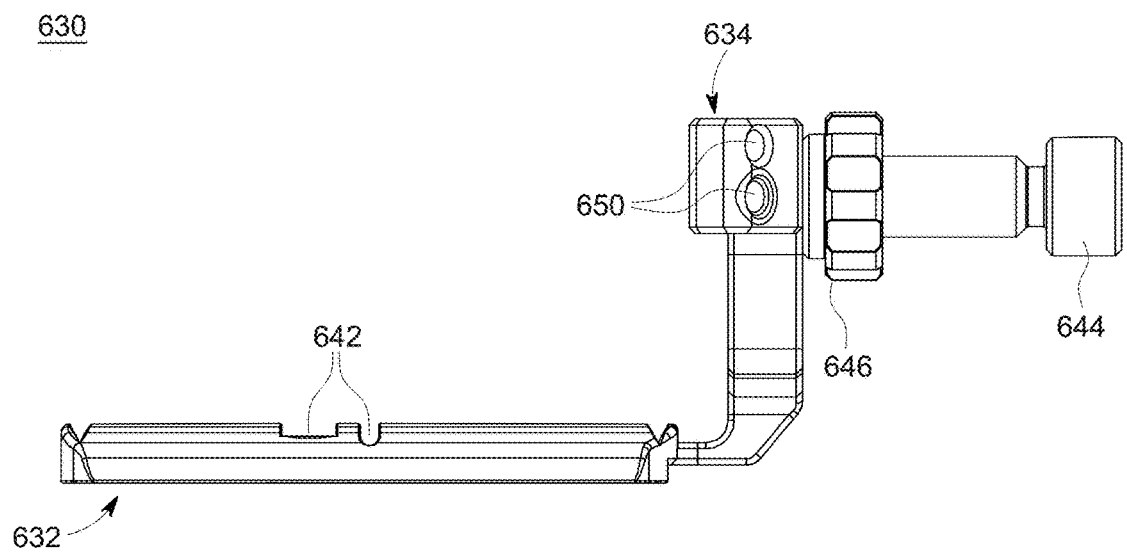
FIG. 46 is a second side view of the tibia trial of FIG. 35, in accordance with an aspect of the present invention.
Figure 47:
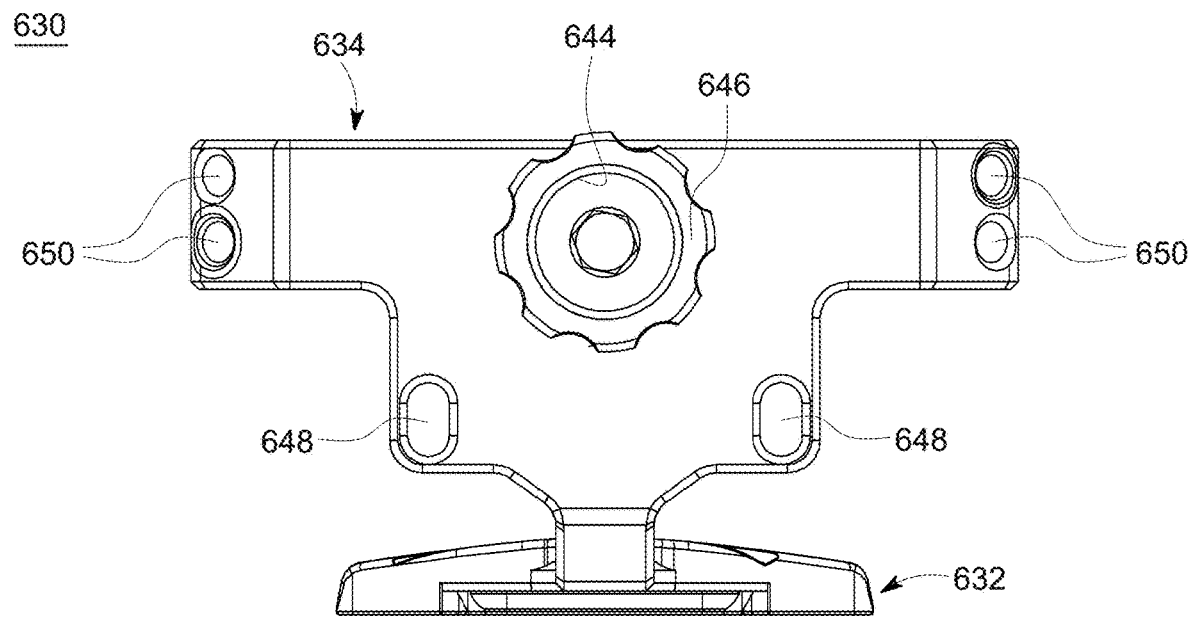
FIG. 47 is a first end view of the tibia trial of FIG. 35, in accordance with an aspect of the present invention.
Figure 48:
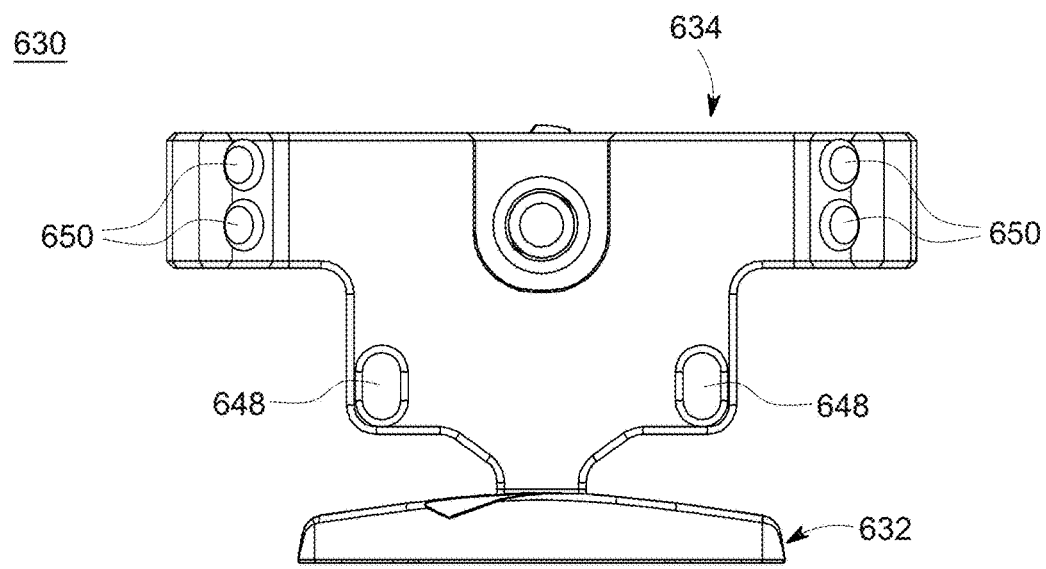
FIG. 48 is a second end view of the tibia trial of FIG. 35, in accordance with an aspect of the present invention.

The tibia trial 630 may be the same or similar to the tibia trial component 112 described in greater detail in U.S. provisional application No. 62/779,092, which is hereby incorporated by reference in its entirety herein. The tibial trial 630 is configured to be coupled to a distal tibia (e.g., a resected portion thereof) and be utilized as a sizing and orientation trial instrument, and/or a punch/drill/cut guide to the distal tibia 620, for one or more corresponding tibial components (not shown). Referring now to FIGS. 35 and 41-50, the tibial trial 630 may include a base portion 632 and an arm or wing portion 634. The base portion 632 includes a proximal bone engagement surface or side 363 configured to engage/abut the distal tibia 620 (potentially resected) of a patient. In some embodiments, the proximal bone engagement surface 363 of the base portion 632 is convex (e.g., arcuately convex) along the medial-lateral direction, as shown in FIG. 47. In some other embodiments (not shown), the proximal bone engagement surface 363 of the base portion 632 is flat/planar along the medial-lateral direction, as shown in FIG. 47.

Figure 43:
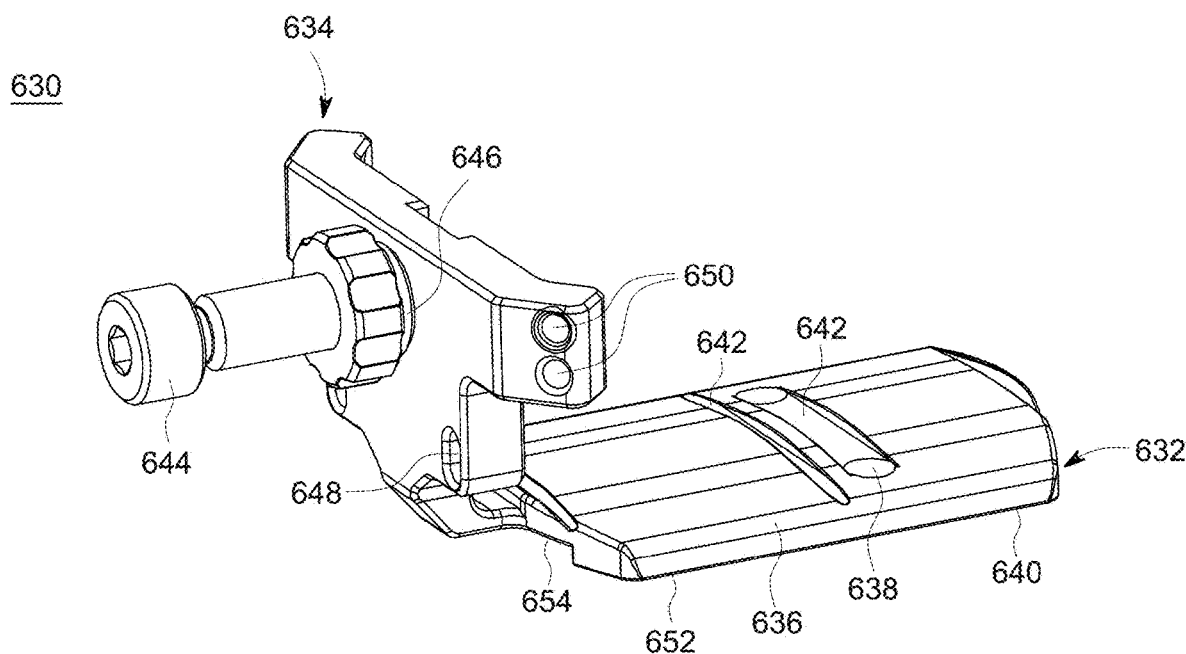
FIG. 43 is a first perspective view of the tibia trial of FIG. 35, in accordance with an aspect of the present invention.
Figure 44:
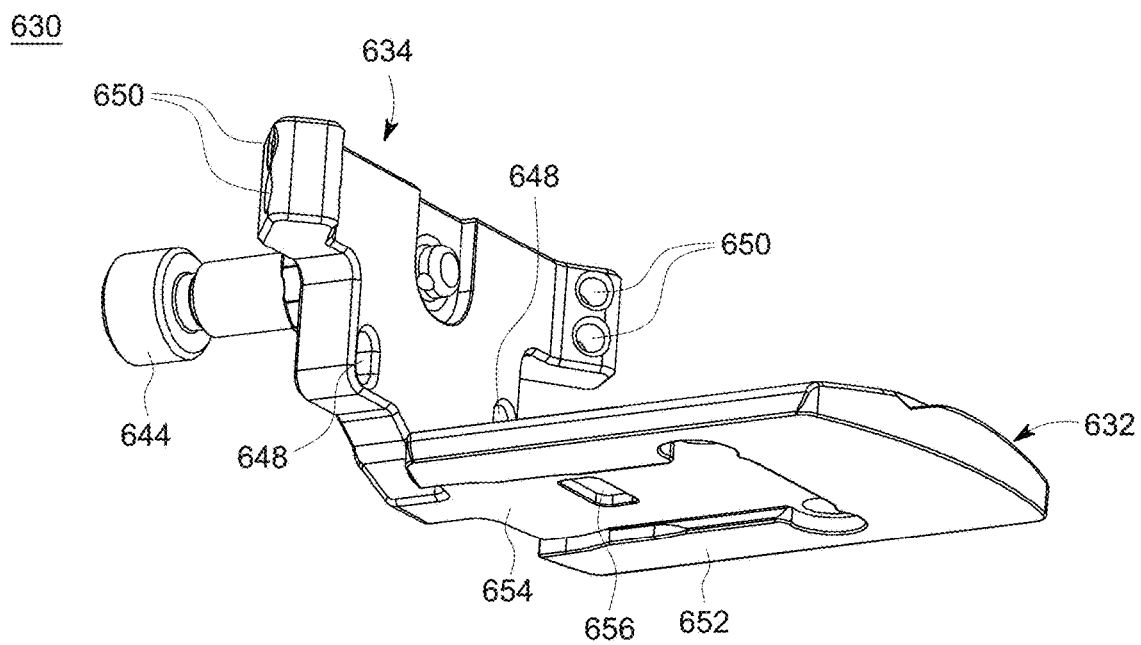
FIG. 44 is a second perspective view of the tibia trial of FIG. 35, in accordance with an aspect of the present invention.
Figure 49:
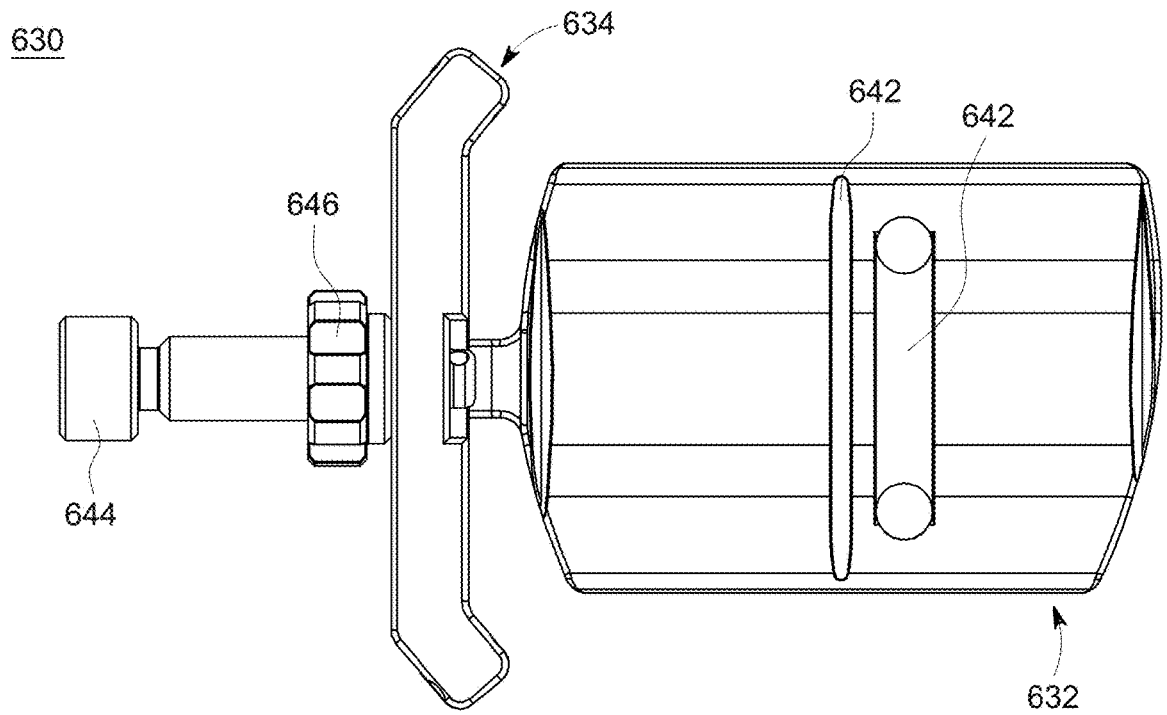
FIG. 49 is a top view of the tibia trial of FIG. 35, in accordance with an aspect of the present invention.
Figure 50:
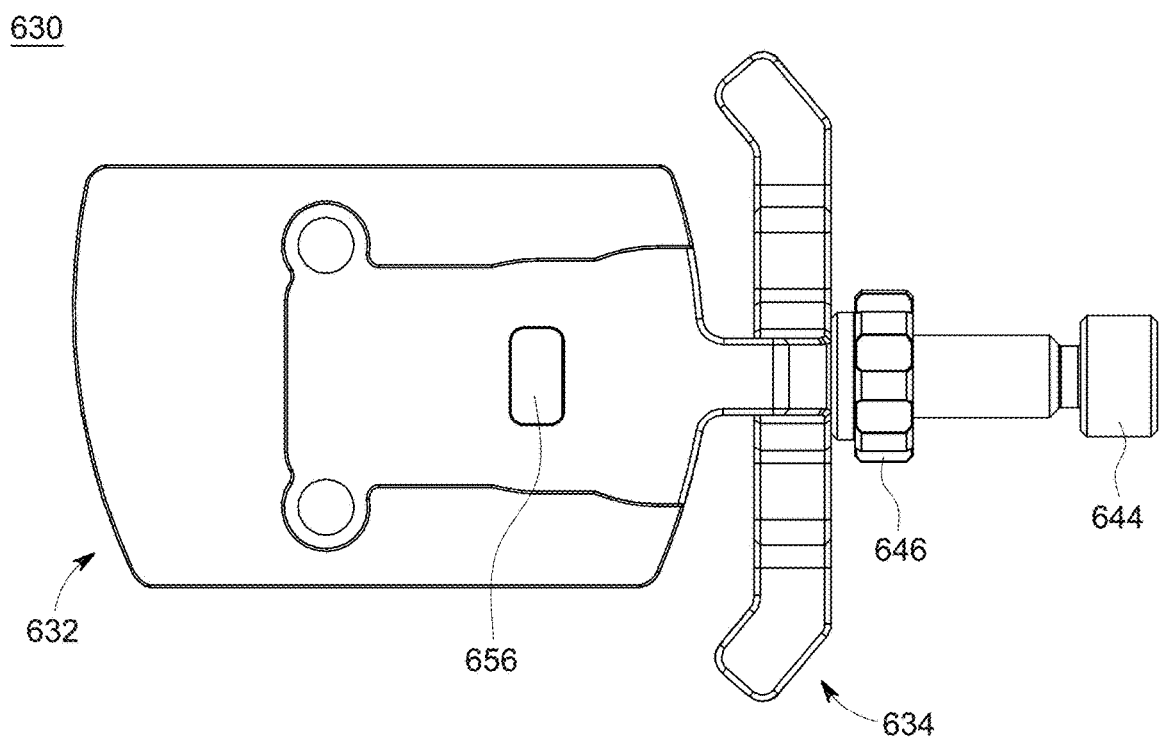
FIG. 50 is a bottom view of the tibia trial of FIG. 35, in accordance with an aspect of the present invention.

The base portion 632 includes at least one through hole or aperture 638 that extends through the base portion 632 along the proximal-distal direction from the proximal bone engagement surface 636 to a distal insert engagement surface or side 640 that opposes the proximal bone engagement surface 636, as shown in at least FIGS. 44 and 50. In some embodiments, the base portion 632 includes a plurality of through holes 638. The at least one through hole 638 is configured as a guide hole for a cutting instrument (e.g., a sharp tipped trocar, drill, etc.) to remove portions of the distal tibia 620 to accommodate at least one peg of a corresponding tibial component (not shown). The at least one through hole 638 may thereby correspond to the position/location (and potentially size and/or orientation) of at least one implantable post of a corresponding tibial component (not shown). It is noted that differing tibial trial components 630 may correspond to differing corresponding tibial components (e.g., differing sized components), and thereby may include differing numbers, locations and/or configurations of the at least one through hole 638 to correspond to the at least one implantable peg of a respective corresponding tibial trial component 630. As shown in FIGS. 43, 44, 49 and 50, the illustrative embodiment includes two through holes 638 including a posterior and medial through hole 638 and a posterior and lateral through hole 638.

The proximal bone engagement surface 636 may include at least one slot or indentation 642 extending therein, such as at least one slot that is elongated along the medial lateral direction, as shown in FIGS. 43 and 49. The at least one slot 642 may extend at least through the proximal apex or highest surface portion of the bone engagement surface 636 such that the at least one slot 642 (i.e., the edges thereof) is visible when viewed along the medial-lateral direction (e.g., visible under fluoroscopy or other imaging in situ), as shown in FIGS. 45 and 46. In this way, the at least one slot 642 may be utilized to identify portions or aspects of the base portion 632 that may not be visible, or may be difficult to decipher when viewed at least along the medial-lateral direction (e.g., under fluoroscopy or other imaging in situ). In some embodiments, the base portion 632 may include a plurality of slots 642 in the proximal bone engagement surface 636. For example, the tibial trial 630 includes an anterior slot 642 and a posterior slot 642 that passes through or corresponds to the anterior through holes 638 and the posterior through holes 638, respectively. As another example, the trial component also includes an intermediate slot 642 that passes through or corresponds to the center of the base portion 632 (and thereby the corresponding tibial component) along the anterior-posterior direction, which may be utilized to align the base portion 632 to the long and/or mechanical axis of the tibia 620 along the anterior-posterior direction. Still further, the trial 630 may also include at least one posterior end slot 642 that passes through a posterior end portion of the base portion 632 that corresponds to at least one posterior end of at least one first "standard" corresponding tibial component and/or tibial insert. The posterior end of the base portion 632 may correspond to the posterior end of at least one second "long" corresponding tibial component and/or tibial insert. The at least one posterior end slot 642 and the posterior end of the base portion 632 may thereby be utilized to correctly position the base portion 632 and/or the tibial component (not shown) relative to the tibia 620 (e.g., align a center thereof with an axis of the tibia along the anterior-posterior direction) and determine an appropriately size (e.g., "standard" or "long") of the tibial component and/or tibial insert to be used with the particular tibia 620 (e.g., a tibial component that extends over the maximum area of the tibia to distribute the forces acting through the joint).

Figure 41:
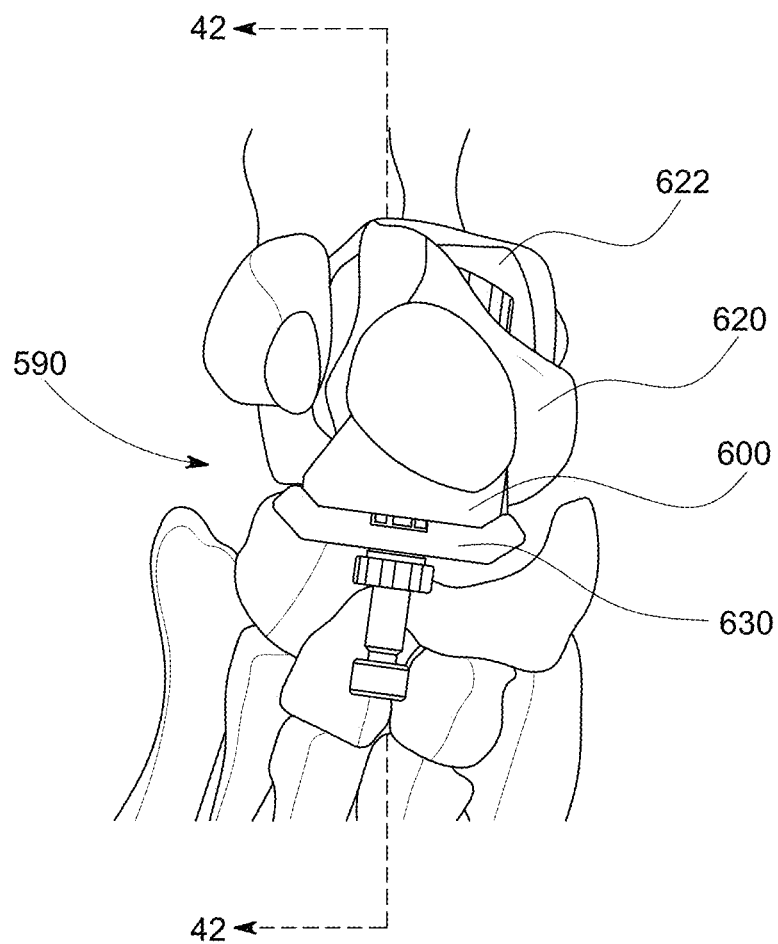
FIG. 41 is a top view of the tibia trial system of FIG. 35 on the patient's leg, in accordance with an aspect of the present invention.
Figure 42:
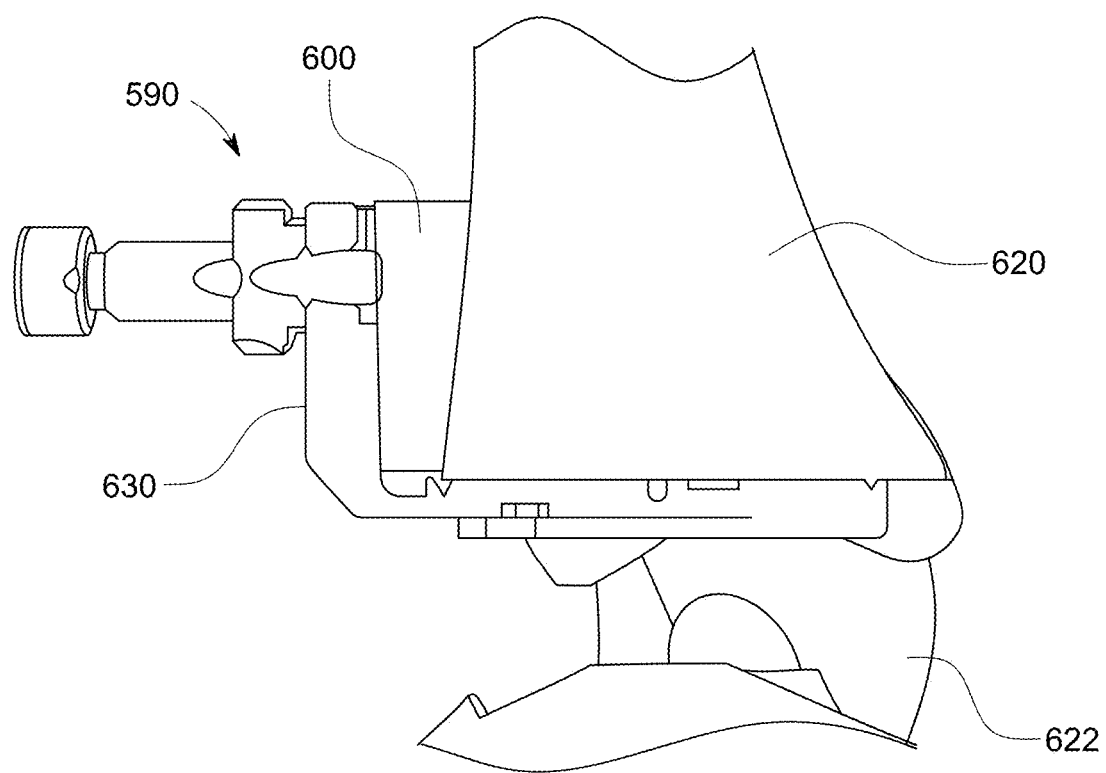
FIG. 42 is a cross-sectional view of the tibia trial system and patient's leg of FIG. 35 take along line 42-42 of FIG. 41, in accordance with an aspect of the present invention.

As shown in FIGS. 43-46, 49 and 50, the arm portion 634 of the tibial component 630 extends proximally from the anterior end of the base portion 632. The proximal end of the arm portion 634 may be wider in the medial-lateral direction than the distal end thereof. The arm portion 634 includes an adjustment screw 644 threadably extending through an adjustment aperture 646 along the anterior-posterior direction. The position of the adjustment screw 644 relative to the arm portion 634 along the anterior-posterior direction may be adjusted by rotation of the adjustment screw 644. The anterior-posterior position/location of the adjustment screw 644 relative to the arm portion 634 may be adjusted with the posterior tip of the adjustment screw 644 contacting the anterior face of the tibia 620 proximal to the resected portion thereof (e.g., the anterior crown of the tibia 620), as shown in FIGS. 41-42. In this way, the anterior-posterior position/location of the base portion 632 on the distal tibia 620 can be adjusted via anterior-posterior adjustment (e.g., via rotation) of the adjustment screw 644. In some embodiments, the adjustment screw 644 may include a nut or other mechanism that selectively locks the anterior-posterior position of the adjustment screw 644 in at least one direction along the anterior-posterior direction. The adjustment screw 644 and adjustment aperture 646 may be aligned with, or positioned proximate to, the medial-lateral midline of the base portion 632.

As shown in FIGS. 5, 6, 10, 11, 17 and 18, the arm portion 634 of the tibial component 630 may include a plurality of pin apertures 648, 650 extending therethrough along the anterior-posterior direction. The pin apertures 648, 650 may be configured to accept a pin, k-wire or other bone fixation member therethrough and into the tibia 620. For example, as shown, the arm portion 634 may include at least a pair of first pin apertures 648 that are aligned with each other and in the anterior-posterior direction (i.e., extend normal to the coronal plane (and parallel to the sagittal plane)). The arm portion 634 may also include at least one pair of second pin apertures 650 that converge (or diverge) as they extend posteriorly (i.e., are angled with respect to the sagittal plane). The pair of first pin apertures 648, and/or the pair of second pin apertures 650, may each include a pin aperture positioned on a medial side of the medial-lateral midline of the base portion 632, and a pin aperture positioned on a lateral side of the medial-lateral midline of the base portion 632. The at least one pair of second pin apertures 650 may include, for example, a superior pair of second pin apertures 650 and an inferior pair of second pin apertures 650. The first and second pin apertures 648, 650 may be configured to house pins or other fixation members extending therethrough and into the tibia 620.

The first pin apertures 648 may facilitate insertion of first pins or other fixation members therethrough and into the tibia 620 with the proximal bone engagement surface 636 of the base portion 632 engaged with the distal end (e.g., resected) of the tibia 620 between the tibia 620 and the talus 622 (see FIG. 42). The adjustment screw 644 can then be adjusted to translate the tibial component 630 over the first pins along the anterior-posterior to adjust the anterior-posterior position of the base portion 632 on the distal tibia 620 (e.g., to align the center thereof, potentially indicated by a slot 642) with the axis of the tibia 620. The first pins extending through the first pin apertures 648 may thereby fix the tibial component 630 along the medial-lateral and proximal-distal directions while allowing adjustment of the tibial component 630 (particularly the base portion 632 thereof) along the anterior-posterior direction along the first pins via the adjustment screw 644. It is noted that the adjustment screw 644 (which may be fixed via a nut or other mechanism) may also prevent the tibial component 630 from translating posteriorly toward the tibia 620. Once the base portion 632 is positioned in a desirable location (e.g., the center thereof aligned with the anatomical and/or mechanical axis of the tibia 620), the second pins or other fixation members may be inserted through the second pin apertures 650 and the tibia 620 to lock the anterior-posterior position of the tibial component 630 (and particularly the base portion 632 thereof).

The distal insert side 652 of the base portion 632 includes a distal recessed portion 654, as shown in at least FIGS. 44 and 50. The recessed portion 654 of the distal insert side 652 engages and couples with the tibial trial insert (not shown). As shown in FIGS. 44 and 47, the sides of the recessed portion 654 may include an undercut or otherwise be angled toward (or away) from the periphery of the base portion 632 as they extend proximally to a planar proximal end surface to form a sliding dovetail socket or female portion. The recessed portion 654 (and thereby the socket/female portion formed thereby) may be open on one side thereof. For example, in the illustrative embodiment the recessed portion 654 (and thereby the socket/female portion formed thereby) is open at the anterior end of the base portion 632 distal to the arm portion 634. The proximal end surface of the recessed portion 654 may include a slot or indentation 656, as shown in FIGS. 44 and 50.

Figure 53:
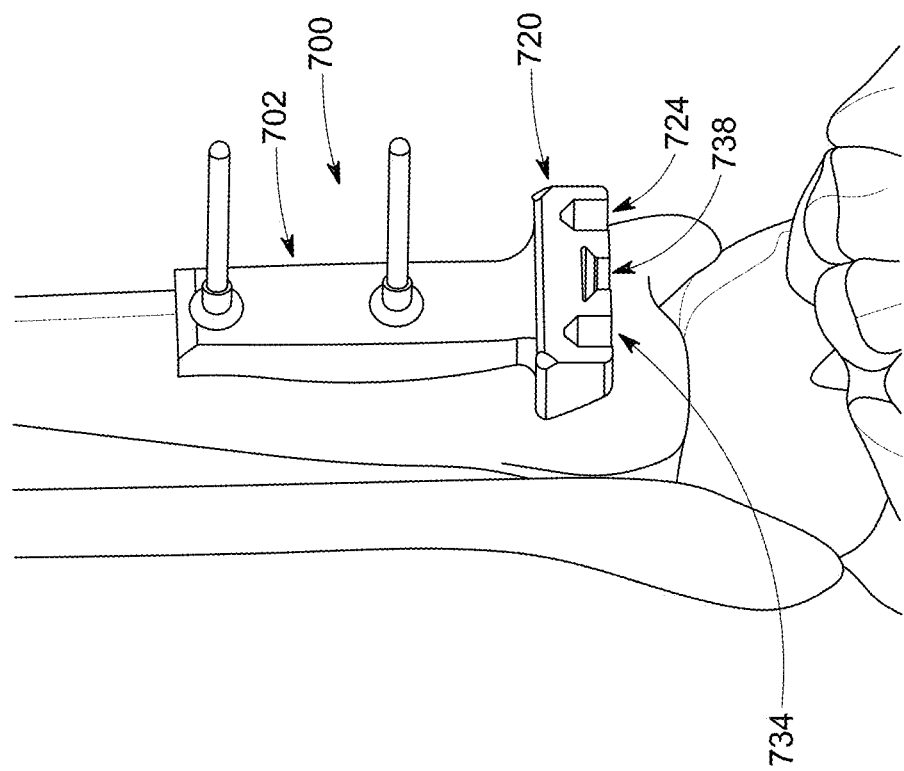
FIG. 53 is a perspective view of the alignment guide of FIG. 51 positioned on a patient's leg with two guide wires, in accordance with an aspect of the present invention.

Referring now to FIG. 51-53, another guide 700 is shown. Guide 700 includes a body portion 702 and a fastening system 720. The body portion 702 may include a first end 704, a second end 706, a first or anterior surface 708, a second or posterior surface 710, a first side 712, and a second side 714. The body portion 702 may also include at least one pin tower 716 and each pin tower 716 may include a through hole 718 extending through each pin tower 716 and body portion 702. The second end 706 of the body portion 702 may be coupled to the fastening system 720. The fastening system 720 may include a first end 722 coupled to the second end 706 of the body portion 702 and a second end 724. The fastening system 720 may also include a first or anterior surface 726 and a second or posterior surface 728. In addition, the fastening system 720 may include a first side 730 and a second side 732. The fastening system 720 may also include a first alignment opening 734 and a second alignment opening 736 extending into the fastening system 720 from the second end 724 toward the first end 722. In addition, the fastening system 720 may include a channel 738 extending into the fastening system 720 from the second end 724 toward the first end 722. The channel 738 may be positioned between the first alignment opening 734 and the second alignment opening 736.

Figure 54:
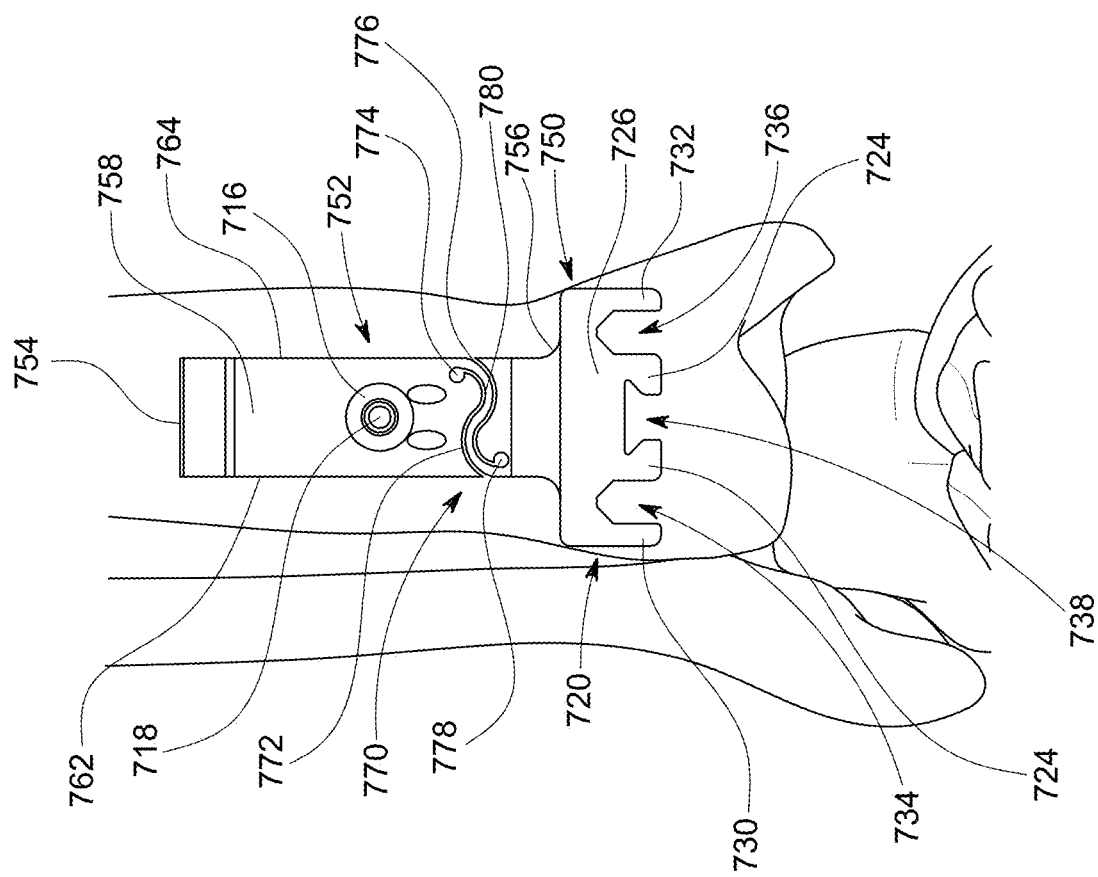
FIG. 54 is a front view of yet another alignment guide positioned on a patient's leg, in accordance with an aspect of the present invention.
Figure 55:
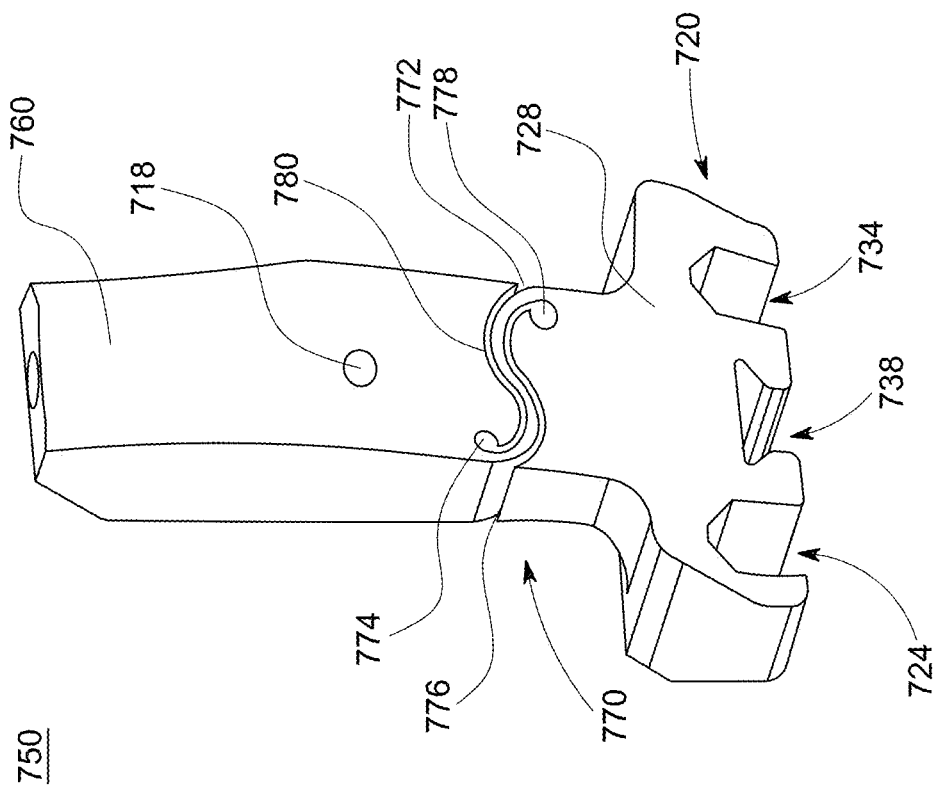
FIG. 55 is a perspective view of the alignment guide of FIG. 54, in accordance with an aspect of the present invention.
Figure 58:
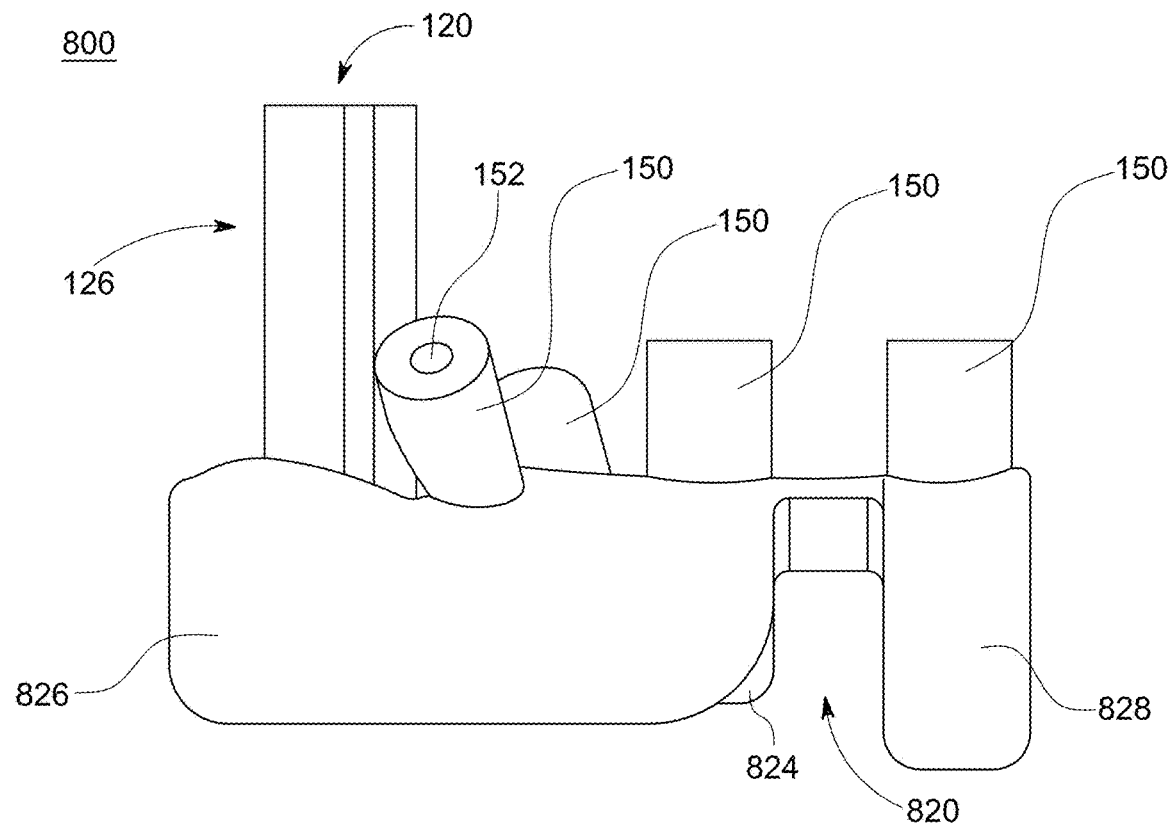
FIG. 58 is a first side view of the alignment guide of FIG. 56, in accordance with an aspect of the present invention.
Figure 59:
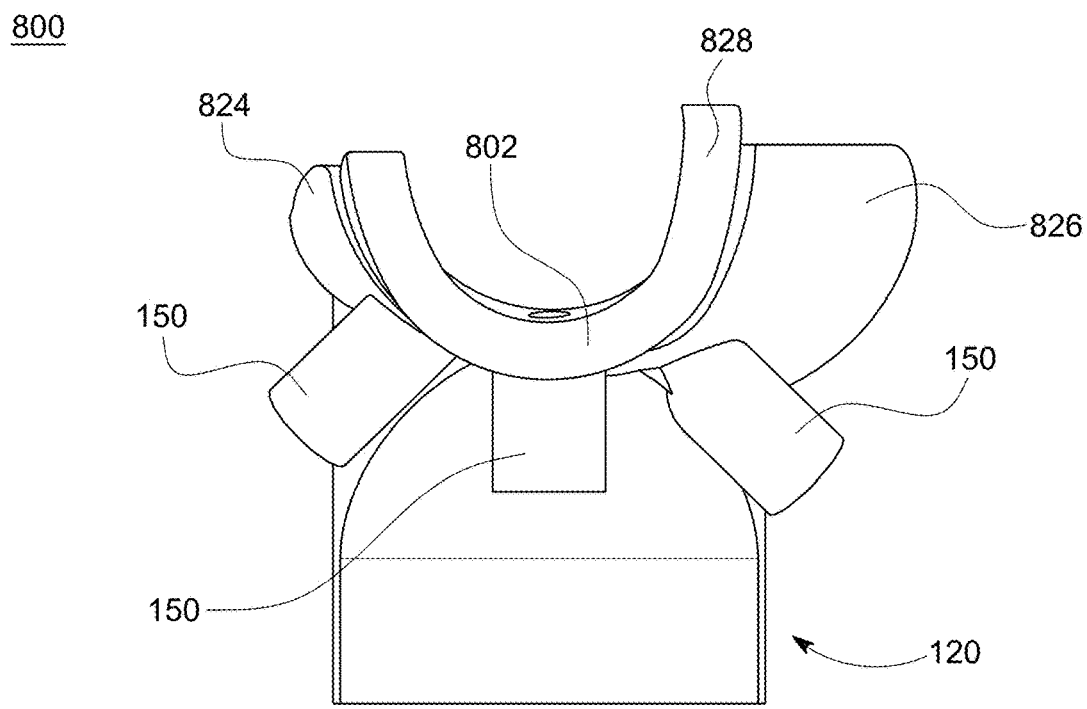
FIG. 59 is a first end view of the alignment guide of FIG. 56, in accordance with an aspect of the present invention.
Figure 60:
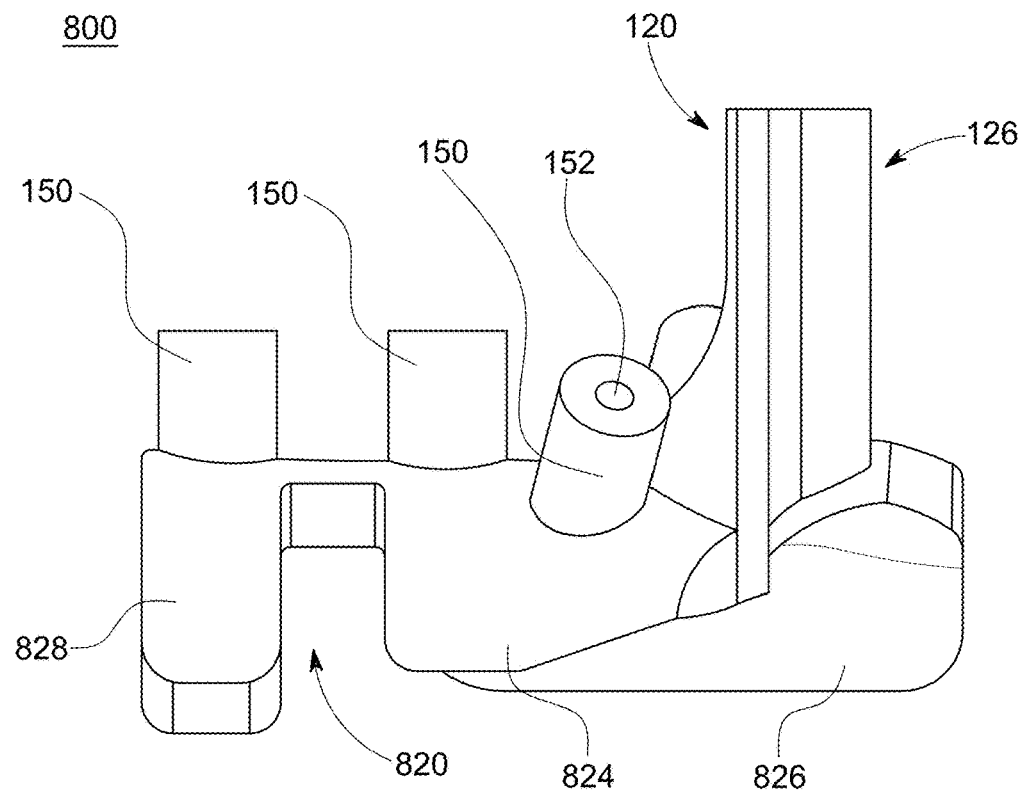
FIG. 60 is a second side view of the alignment guide of FIG. 56, in accordance with an aspect of the present invention.
Figure 61:
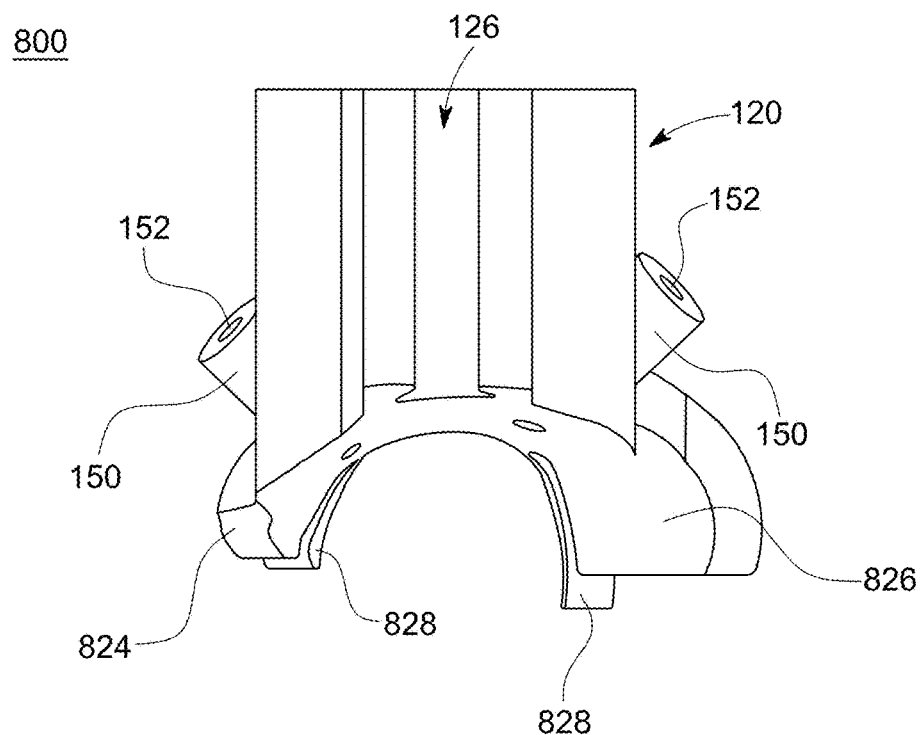
FIG. 61 is a second end view of the alignment guide of FIG. 56, in accordance with an aspect of the present invention.
Figure 63:
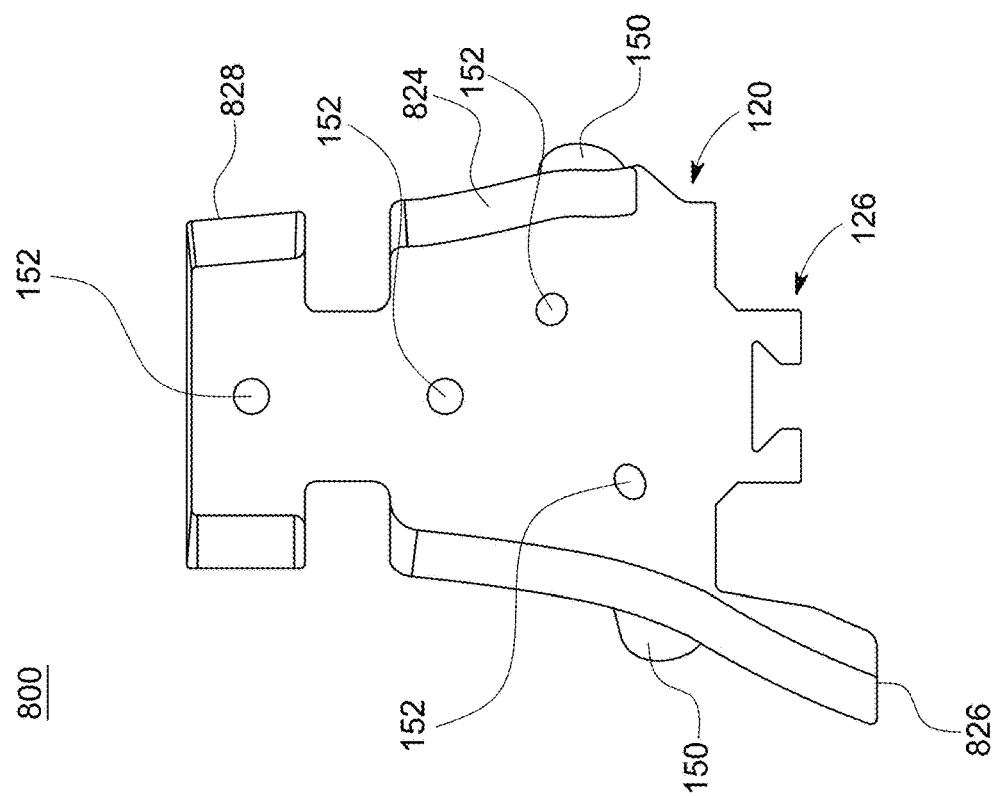
FIG. 63 is a back view of the alignment guide of FIG. 56, in accordance with an aspect of the present invention.
Figure 62:
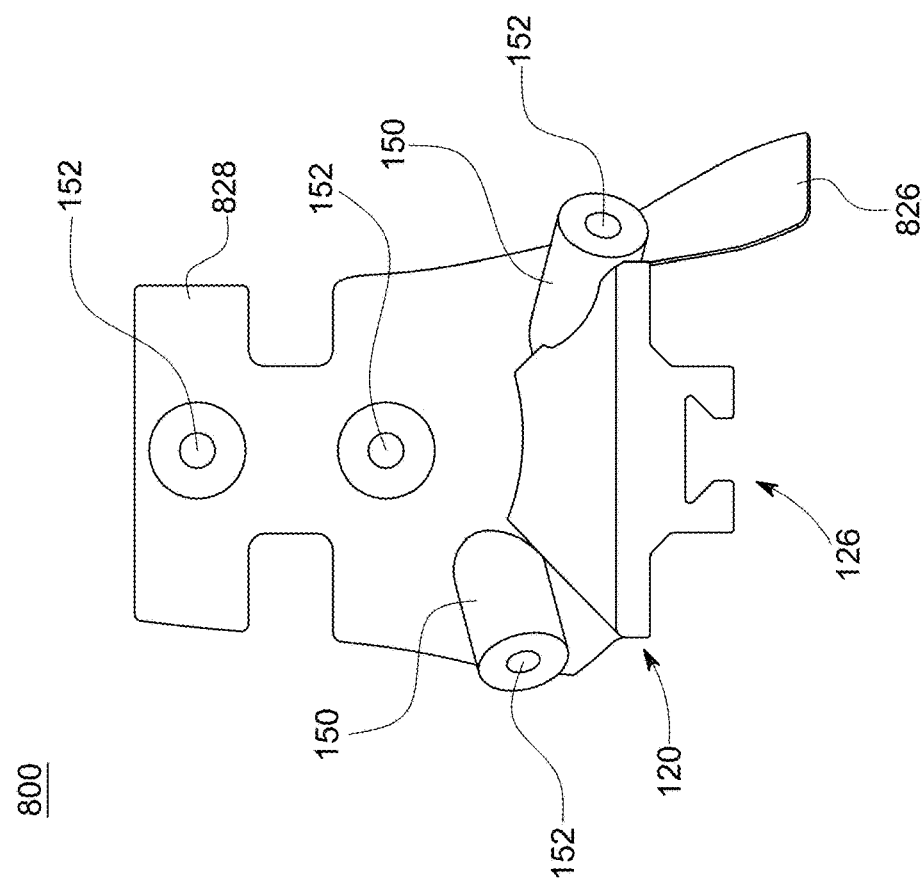
FIG. 62 is a front view of the alignment guide of FIG. 56, in accordance with an aspect of the present invention.

Referring now to FIGS. 54 and 55, another guide 750 is shown. The guide 750 includes a body portion 752 and a fastening system 720. The second end 756 of the body portion 752 may be coupled to the fastening system 720. The fastening system 720 may be as described above with reference to guide 700 and will not be described again here for brevity sake. The body portion 752 may include a first end 754, a second end 756, a first or anterior surface 758, a second or posterior surface 760, a first side 762, and a second side 764. The guide 750 includes a body portion 752 with an elastic region 770. The elastic region 770 includes a first slot 772 extending into the body portion 752 from the first side 762. The first slot 772 may end in an opening 774 near the second side 764. The first slot 772 may be, for example, curved at least once as it extends from the first side 762 toward the second side 764. The elastic region 770 may also include a second slot 776 extending into the body portion 752 from the second side 764. The second slot 776 may end in an opening 778 near the first side 762. The second slot 776 may be, for example, curved at least one as it extends from the second side 762 toward the first side 764. The first slot 772 and second slot 776 may have, for example, the same shape. The first slot 772 and the second slot 776 may be, for example, spaced apart from each other to form an elastic member 780. The elastic member 780 may likewise be, for example, curved between the first side 762 and the second side 764. The body portion 752 may also include at least one pin tower 716 with a through hole 718 extending through each pin tower 716 and body portion 752. In the depicted embodiment, guide 750 includes one pin tower 716 positioned superior to the elastic region 770.

Referring now to FIGS. 56-63, shows another alignment guide 800. The alignment guide 800 may be, for example, similar to the alignment guide 100, as described in greater detail above. The guide 800 includes a first or proximal end 802, a second or distal end 804, a first or anterior surface 806, a second or posterior surface 808, a first or medial side 810, and a second or lateral side 812. The guide 800 also includes a body 820 and a base portion 120 extending away from the body 820. The base portion 120 is as described in greater detail above with respect to guide 100 and will not be described again here for brevity sake. The body 820 may be, for example, formed using imaging, such as CT scans or other tissue determining images. The second or posterior surface 808 of the body 820 is formed to match or correspond to the distal end of a patient's tibia. The body 820 includes a tab 822 extending in a proximal direction toward the first end 802. In addition, the body 820 includes a lateral protrusion 824 and a medial protrusion 826. The lateral protrusion 824 may extend away from the second side 812 and matches the patient's anatomy. The lateral protrusion 824 may, for example, wrap around the posterior aspect of the tibia to allow the guide 800 to couple to or grip the patient's tibia making additional fasteners optional. The medial protrusion 826 extends away from the first side 810 and extends in a distal direction past the base portion 120 and the fastener 126. The medial protrusion 826 may include, for example, a flat distal surface. The medial protrusion 826 may also include a rounded anterior surface for engaging or wrapping partially around the anterior aspect (for example, apex) of a tibia and/or, more specifically, the notch of Harty, if present, and at the junction of the medial malleolus and anterior tibial plafond, extending inferior along the medial malleolus. The body 820 of the guide 800 may further include an additional bone coupling feature or coupler 828 positioned near the first or proximal end 802 of the alignment guide 800. The bone coupling feature 828 may be, for example, semicircular or hemispherical to wrap at least partially around a patient's tibia. The bone coupling feature 828 may extend away from the tab 822 in both a medial and lateral direction. The coupler 828 may include a medial portion extending toward the medial side 810 and a lateral portion extending toward the lateral side 812. The medial portion and the lateral portion may each be curved as the portions extend away from the tab 822. The body 820 may further include at least one pin tower 150 extending away from the first surface 806 of the body 820. The at least one pin tower 150 may include a through hole 152 extending through the pin tower 150 and the body 820. The pin tower 150 and through hole 152 may be as described in greater detail above with respect to guide 100 and which will not be described again here for brevity sake.

Figure 64:
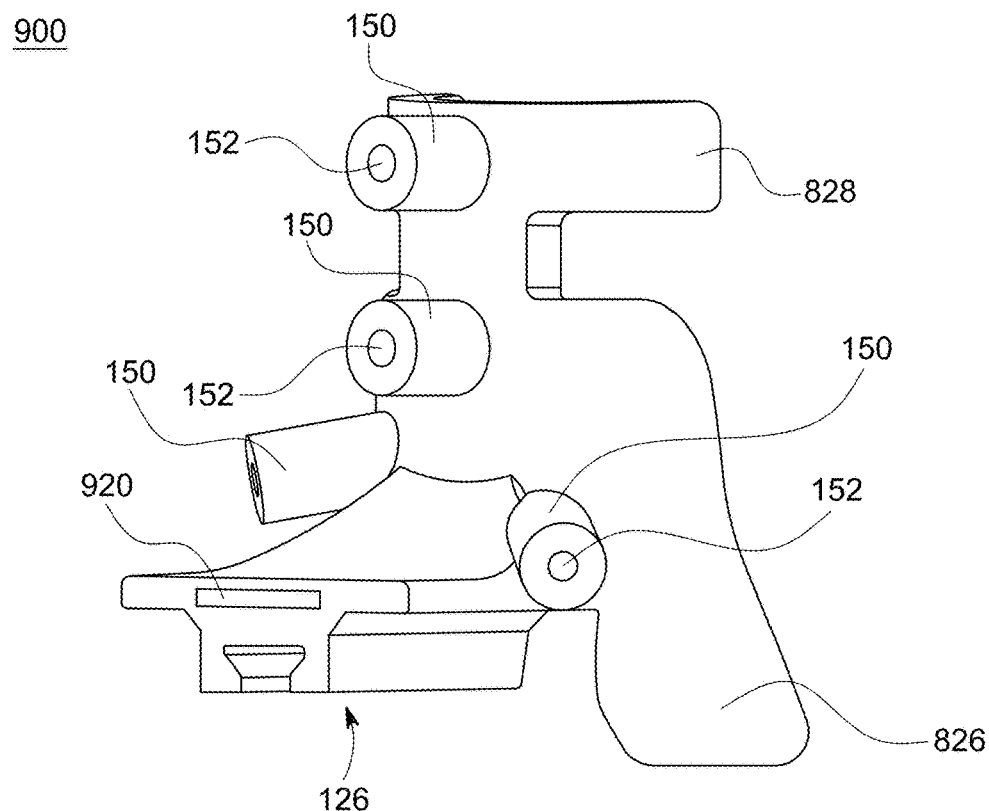
FIG. 64 is a first perspective view of another alignment guide, in accordance with an aspect of the present invention.
Figure 65:
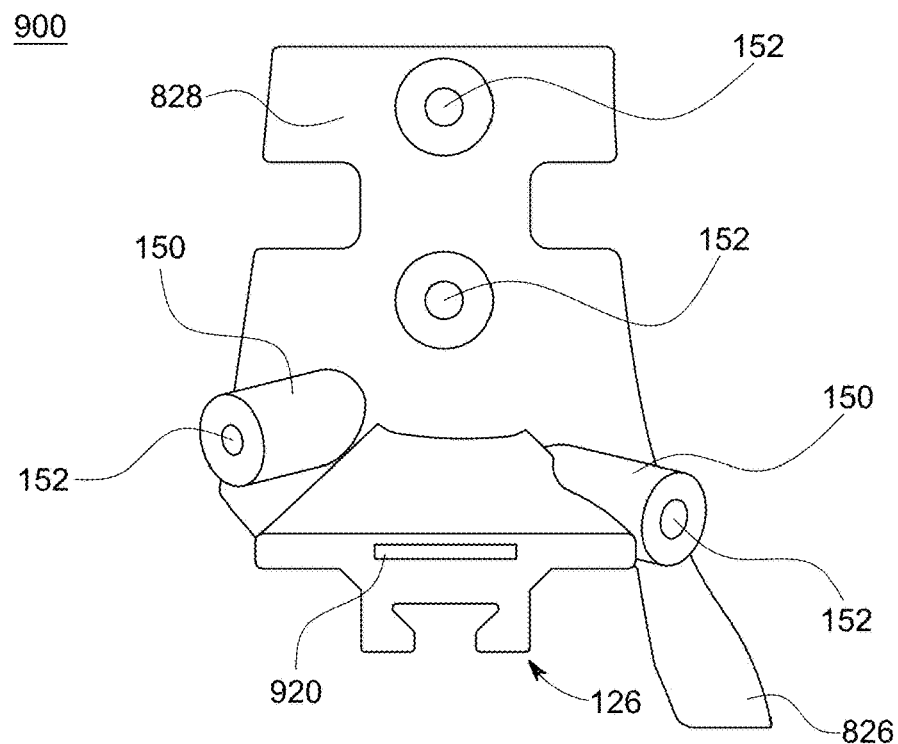
FIG. 65 is a front view of the alignment guide of FIG. 64, in accordance with an aspect of the present invention.
Figure 66:
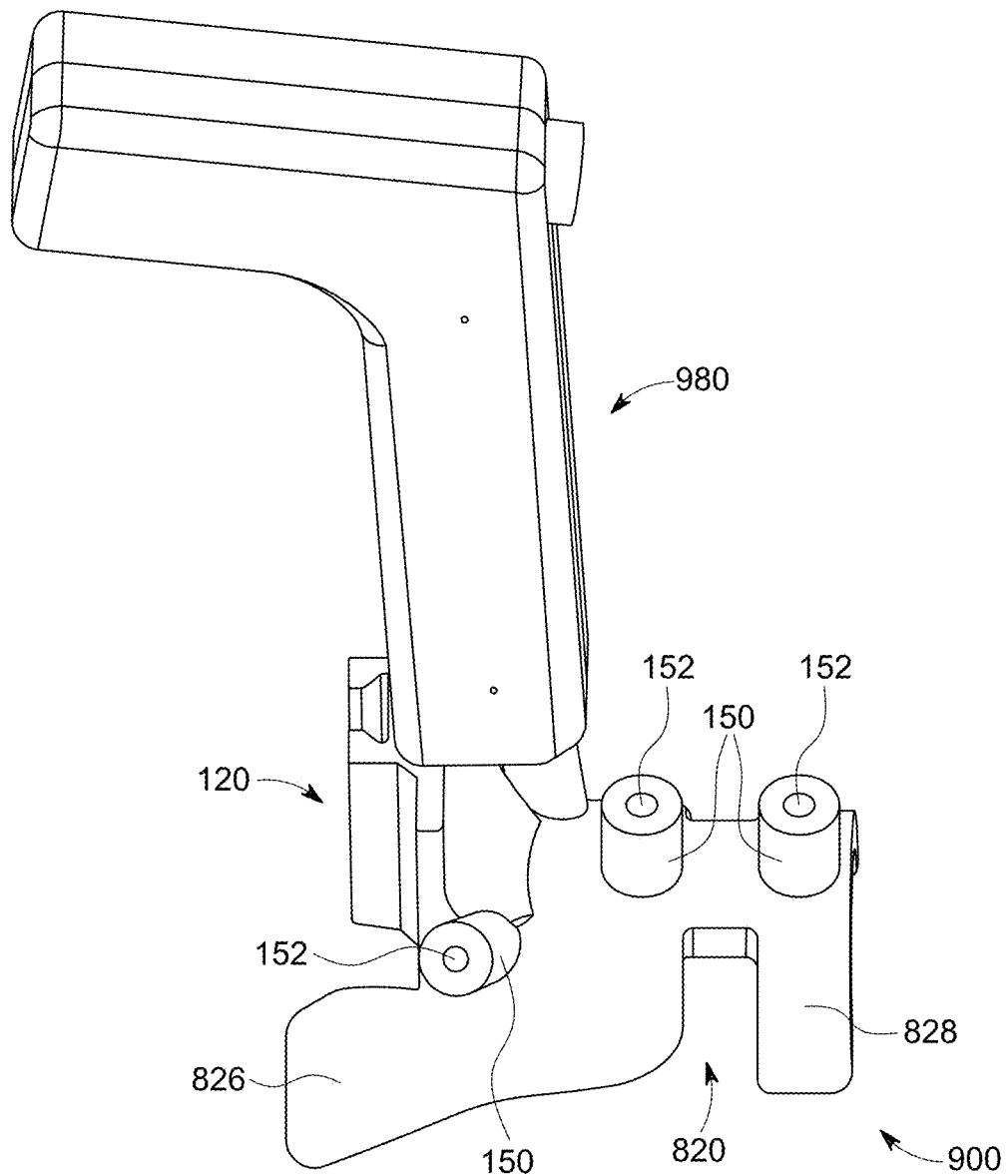
FIG. 66 is a first perspective view of the alignment guide of FIG. 64 with a coupled laser device, in accordance with an aspect of the present invention.
Figure 67:
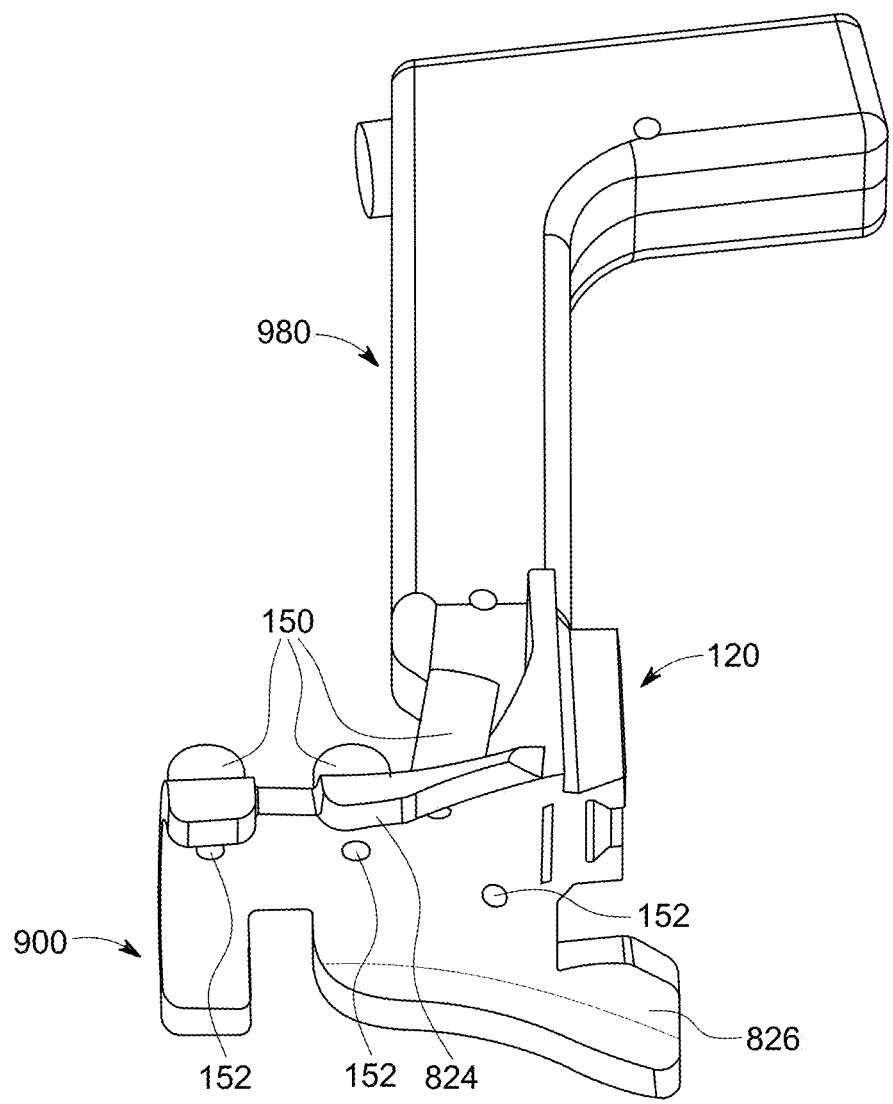
FIG. 67 is a second perspective view of the alignment guide and laser device of FIG. 66, in accordance with an aspect of the present invention.
Figure 69:
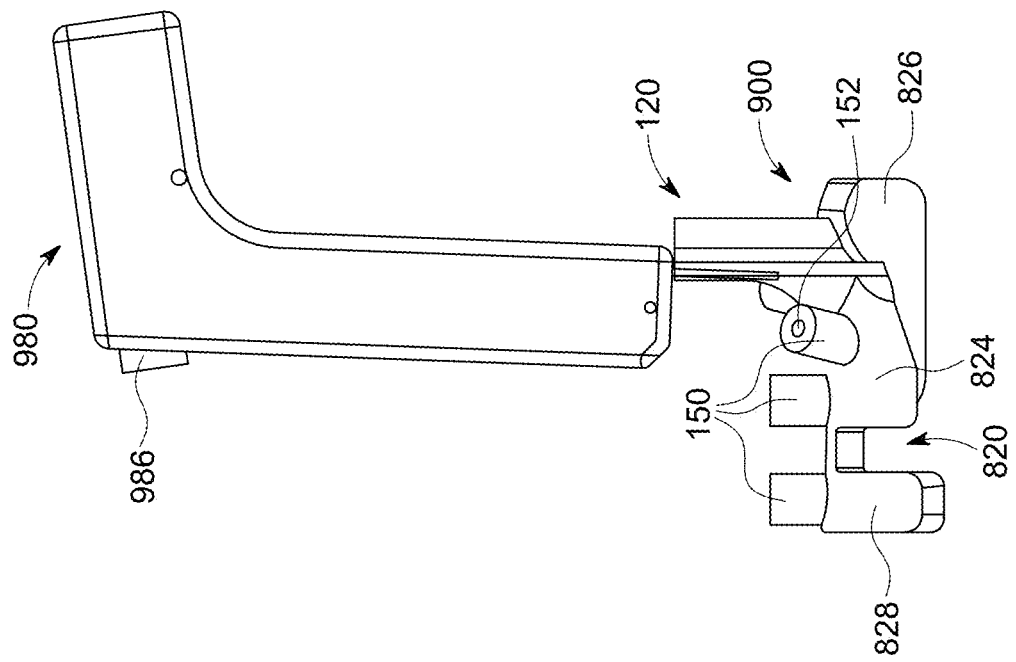
FIG. 69 is a second side view of the alignment guide and laser device of FIG. 66, in accordance with an aspect of the present invention.
Figure 68:
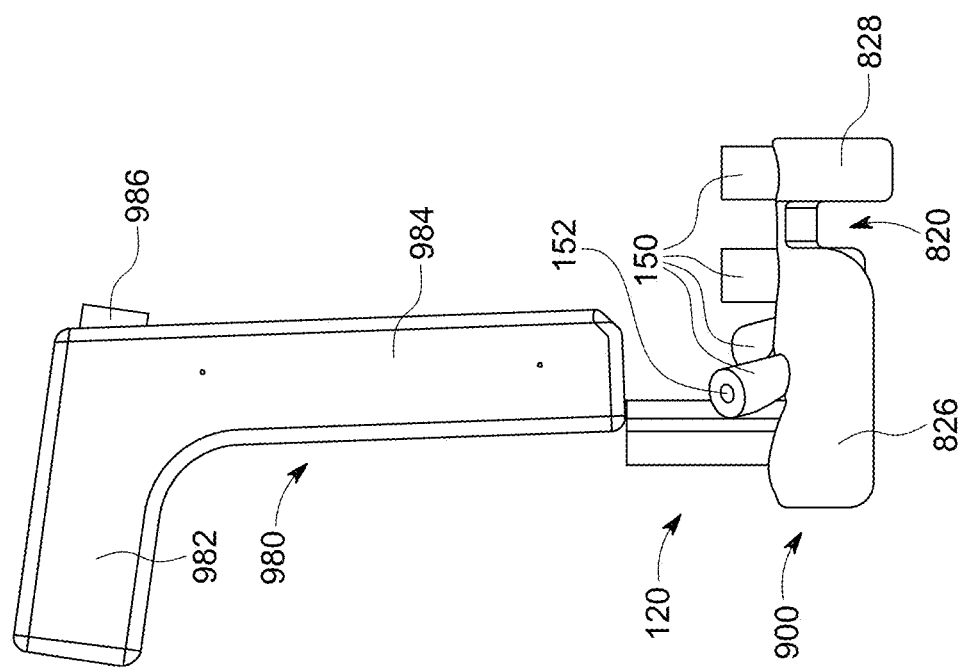
FIG. 68 is a first side view of the alignment guide and laser device of FIG. 66, in accordance with an aspect of the present invention.
Figure 70:
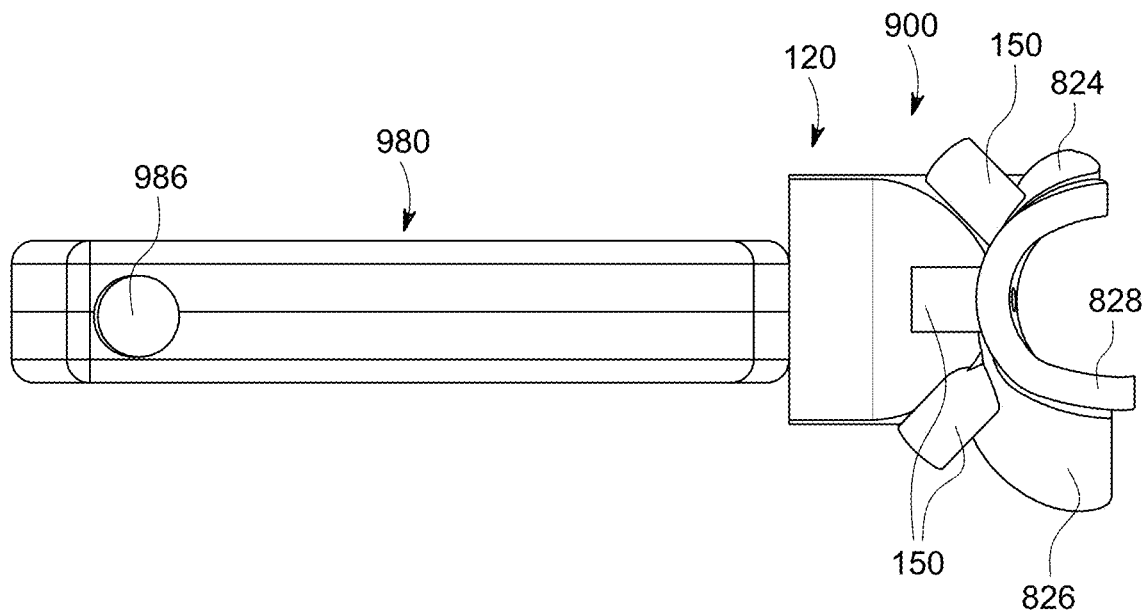
FIG. 70 is a first end view of the alignment guide and laser device of FIG. 66, in accordance with an aspect of the present invention.
Figure 71:
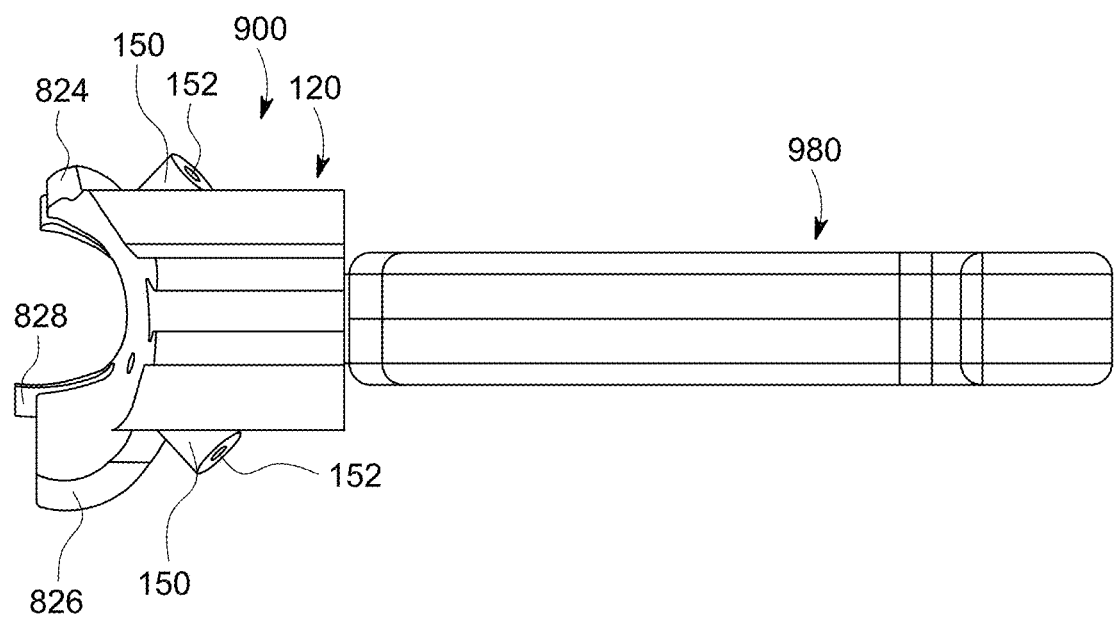
FIG. 71 is a second end view of the alignment guide and laser device of FIG. 66, in accordance with an aspect of the present invention.
Figure 72:
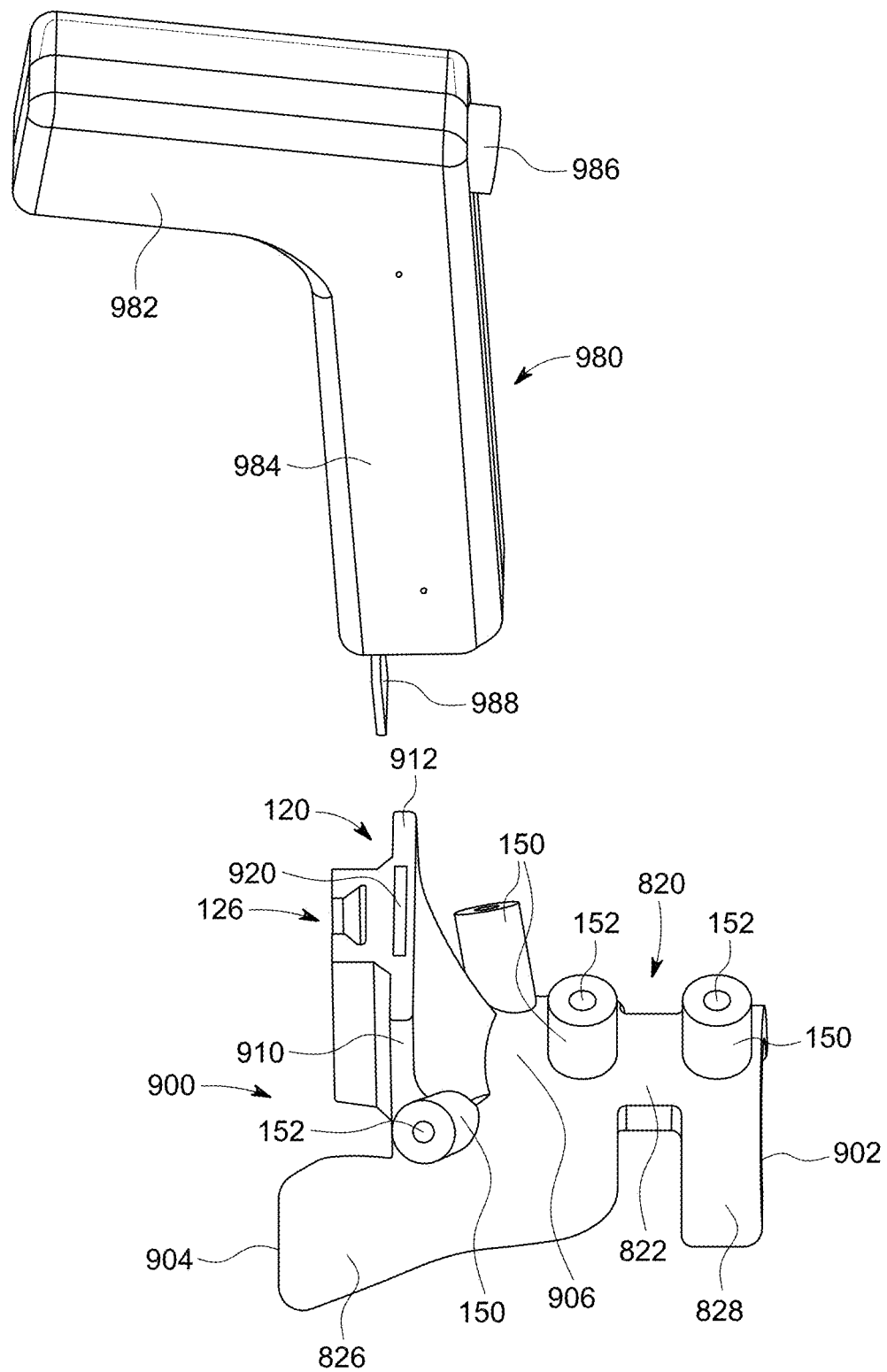
FIG. 72 is an exploded, perspective view of the alignment guide and laser device of FIG. 66, in accordance with an aspect of the present invention.
Figure 74:
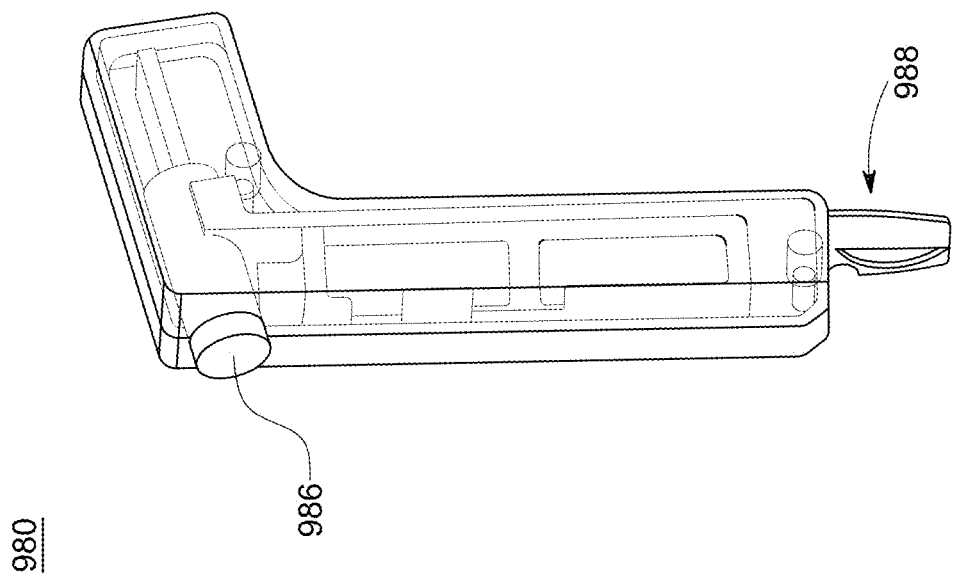
FIG. 74 is a second perspective view of the laser device of FIG. 66, in accordance with an aspect of the present invention.
Figure 73:
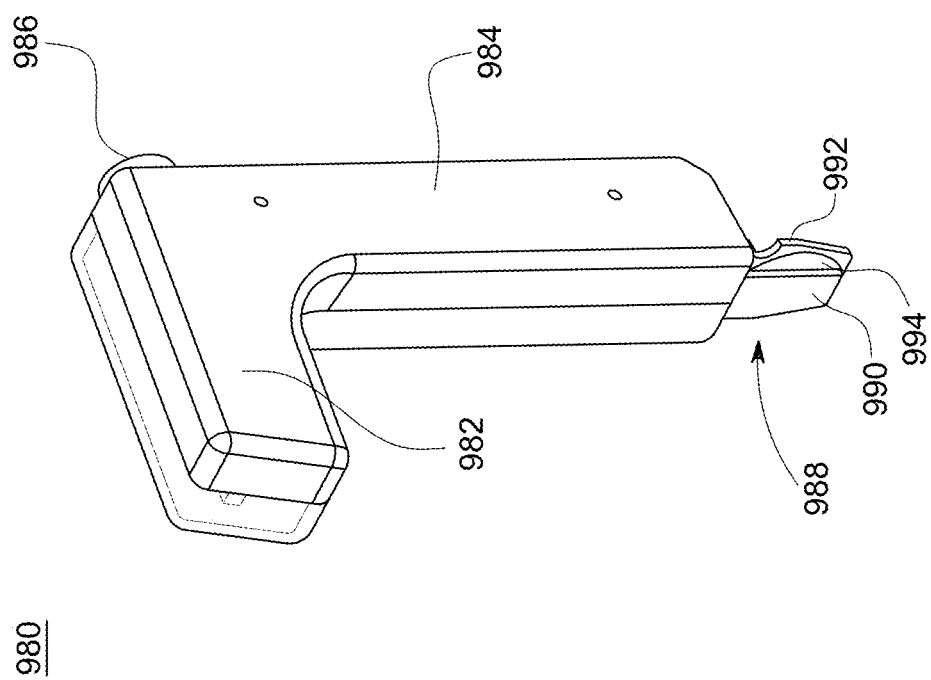
FIG. 73 is a first perspective view of the laser device of FIG. 66, in accordance with an aspect of the present invention.
Figure 76:
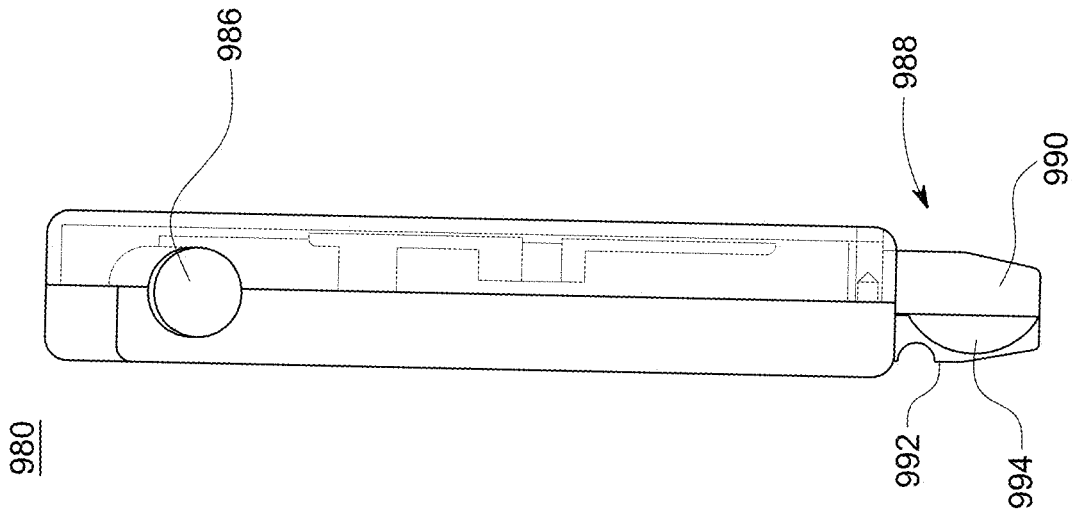
FIG. 76 is an end view of the laser device of FIG. 66, in accordance with an aspect of the present invention.
Figure 75:
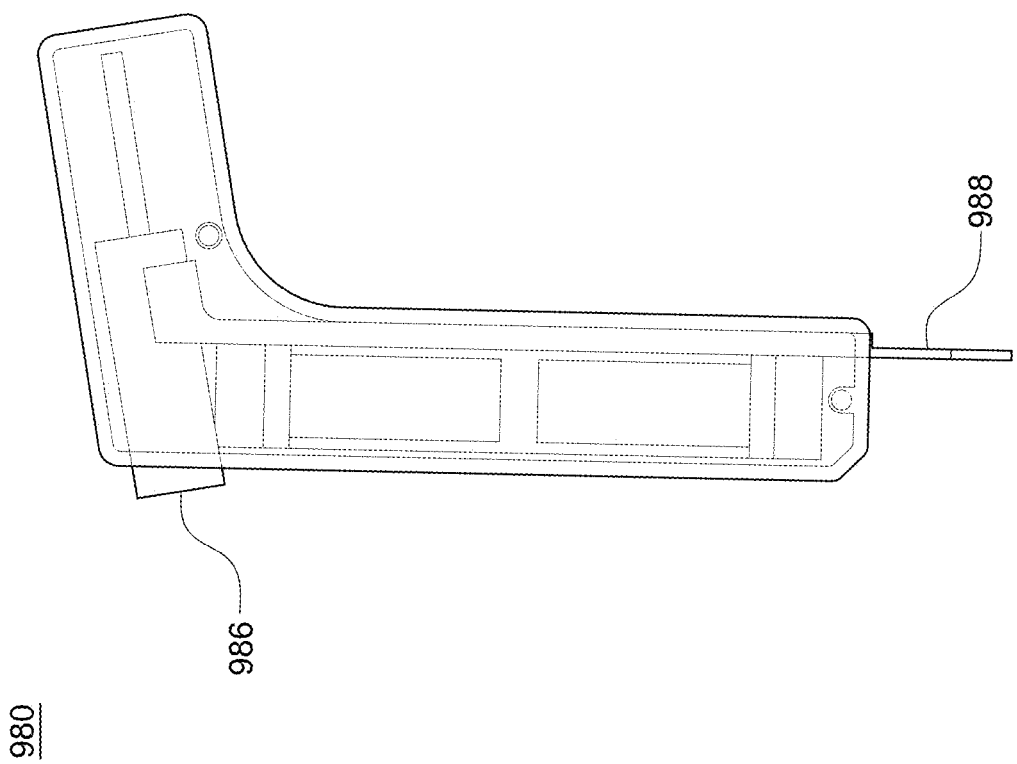
FIG. 75 is a side view of the laser device of FIG. 66, in accordance with an aspect of the present invention.
Figure 77:
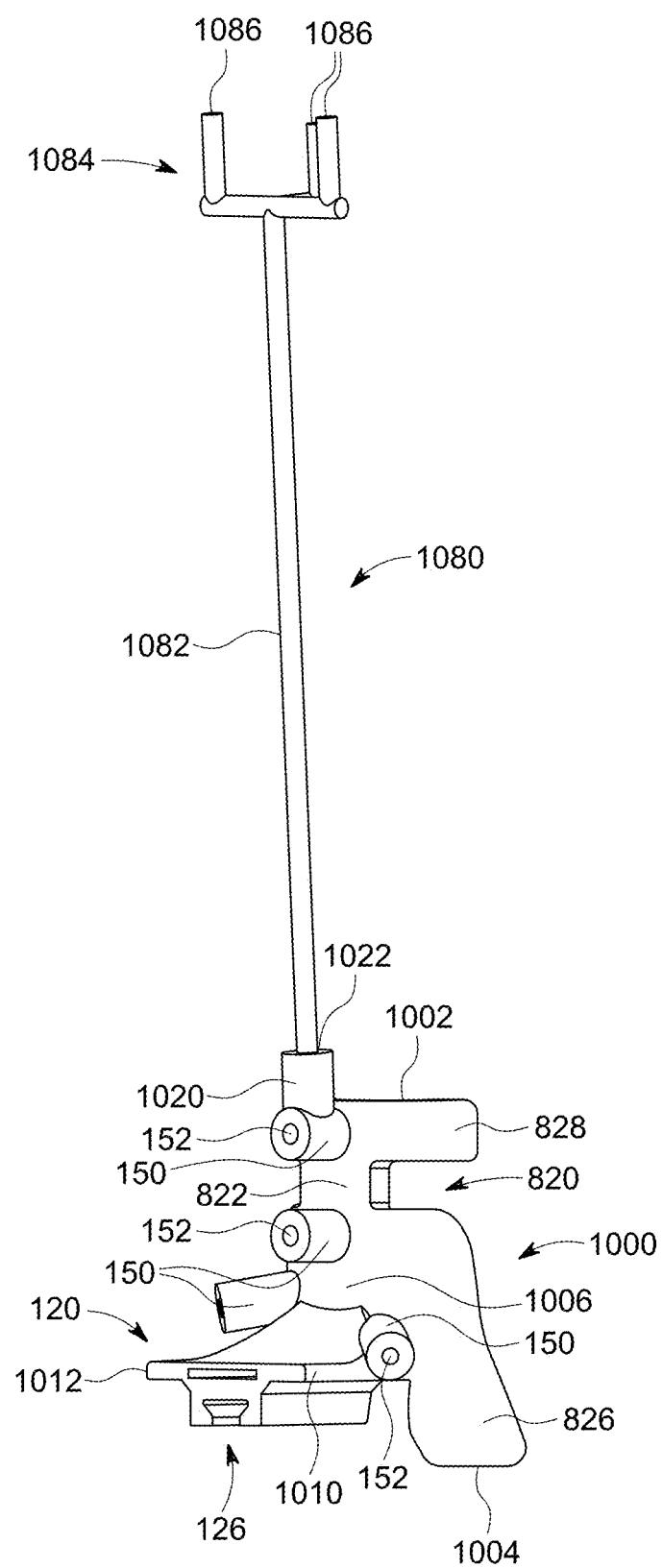
FIG. 77 is a first perspective view of another alignment guide with a coupled alignment member, in accordance with an aspect of the present invention.
Figure 78:
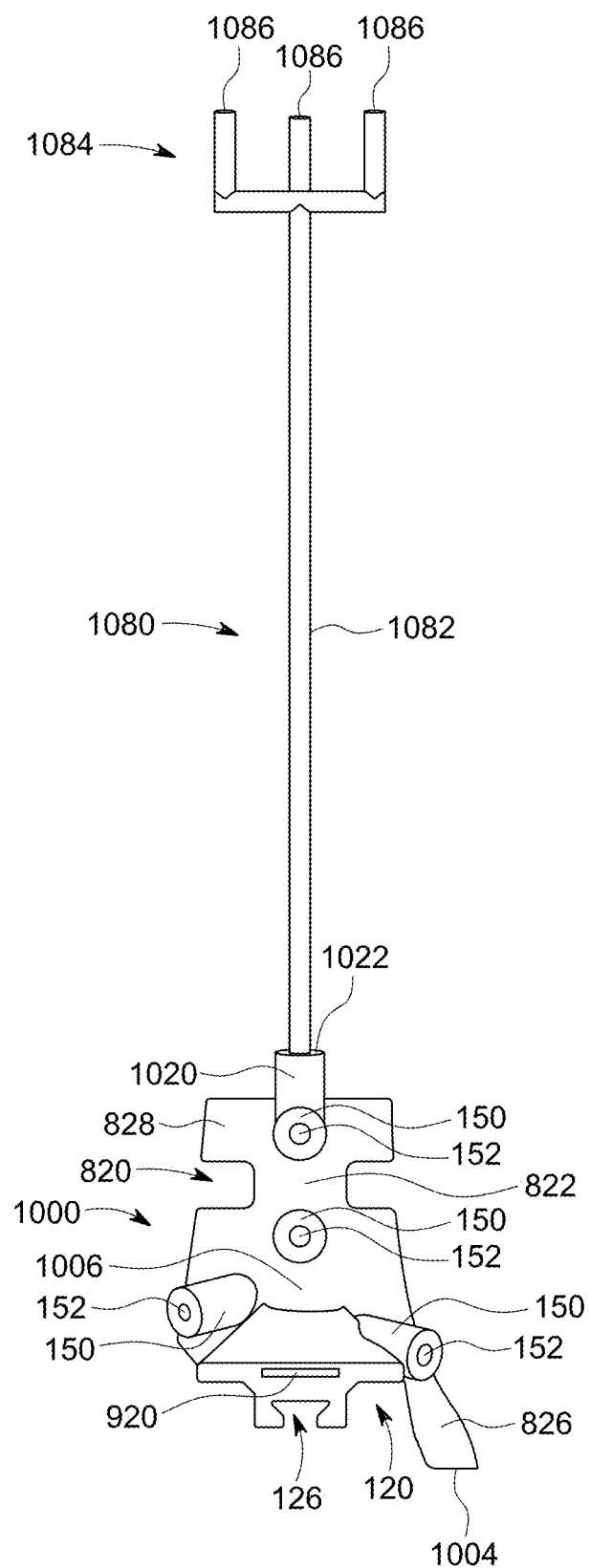
FIG. 78 is a front view of the alignment guide and coupled alignment member of FIG. 77, in accordance with an aspect of the present invention.
Figure 79:
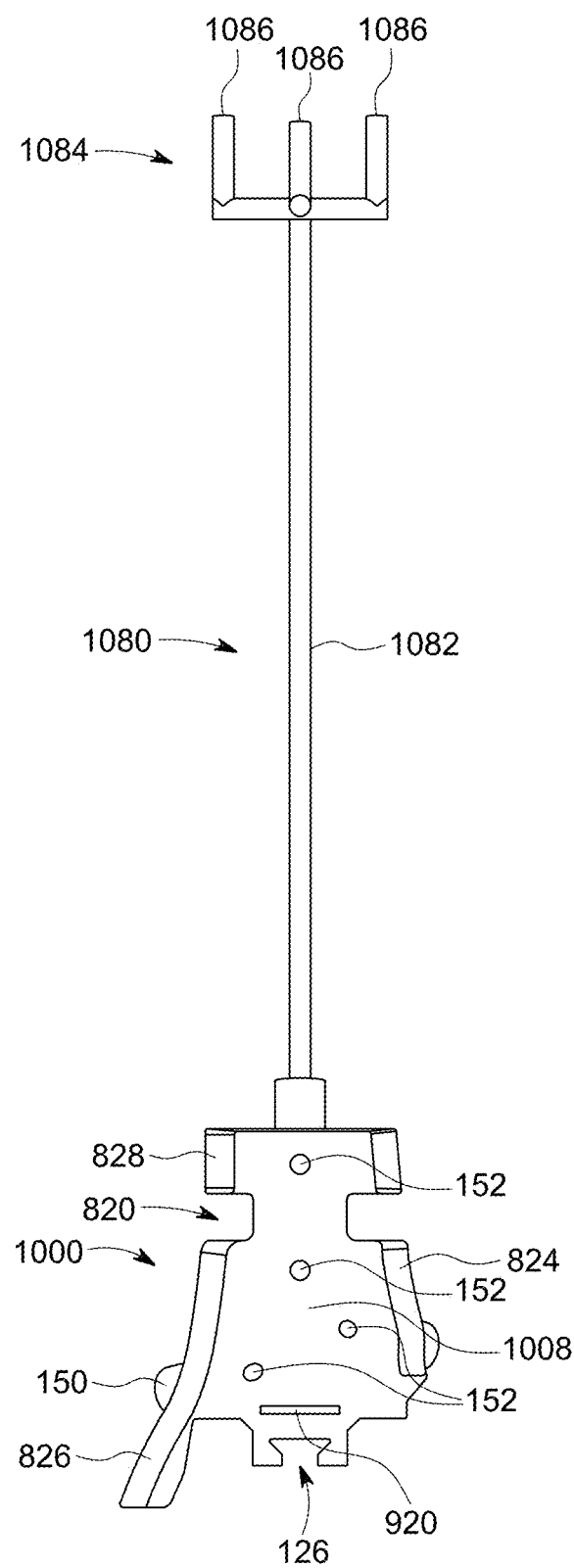
FIG. 79 is a back view of the alignment guide and coupled alignment member of FIG. 77, in accordance with an aspect of the present invention.
Figure 80:
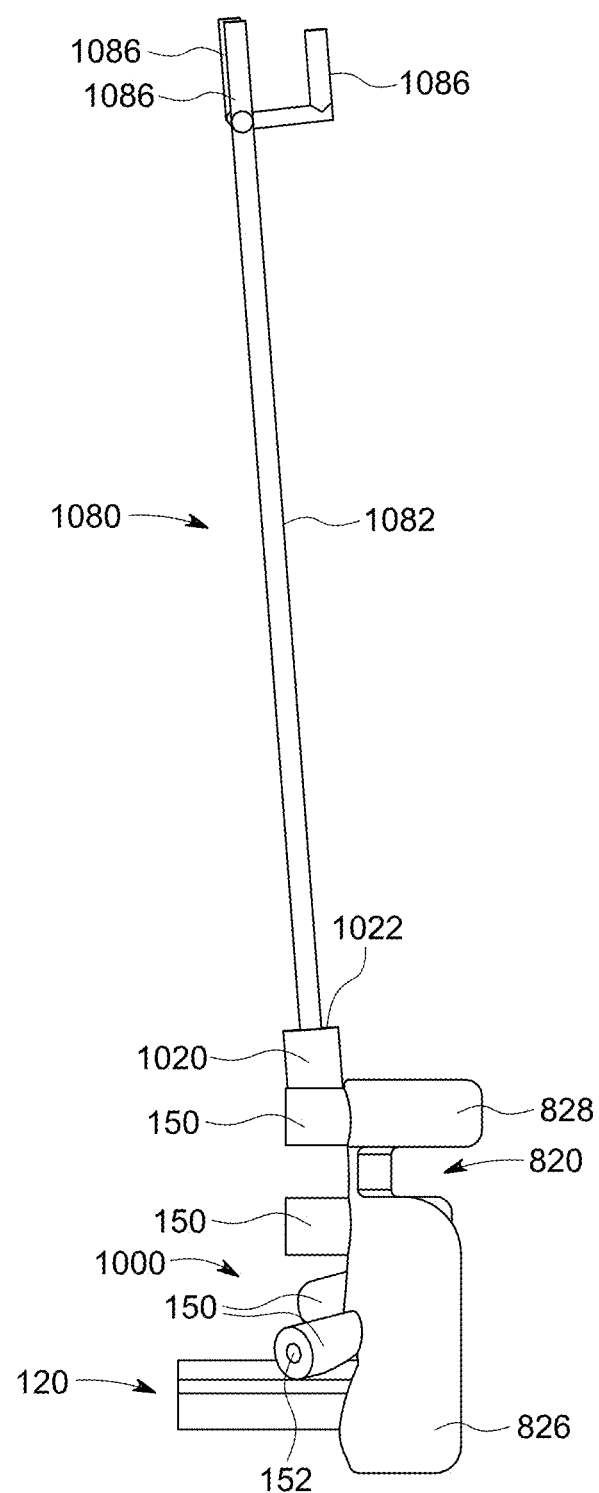
FIG. 80 is a first side view of the alignment guide and coupled alignment member of FIG. 77, in accordance with an aspect of the present invention.
Figure 81:
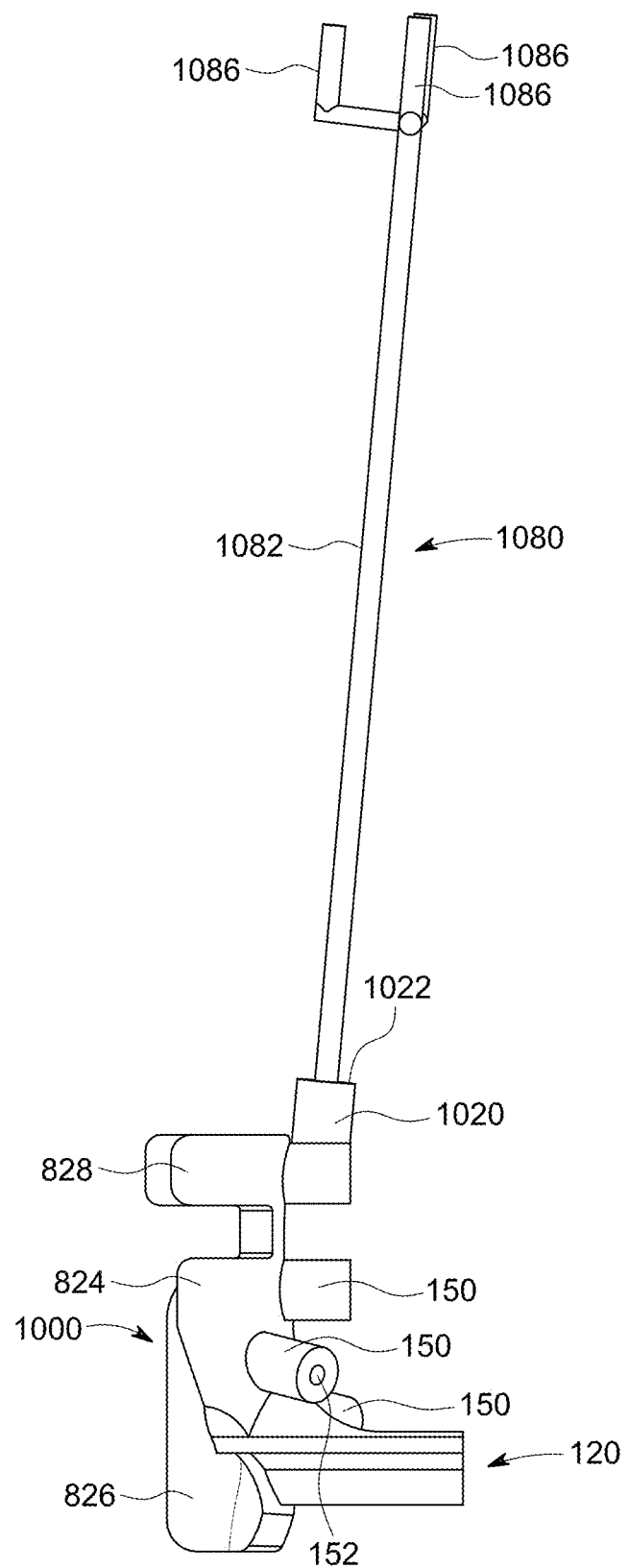
FIG. 81 is a second side view of the alignment guide and coupled alignment member of FIG. 77, in accordance with an aspect of the present invention.
Figures 82, 83:
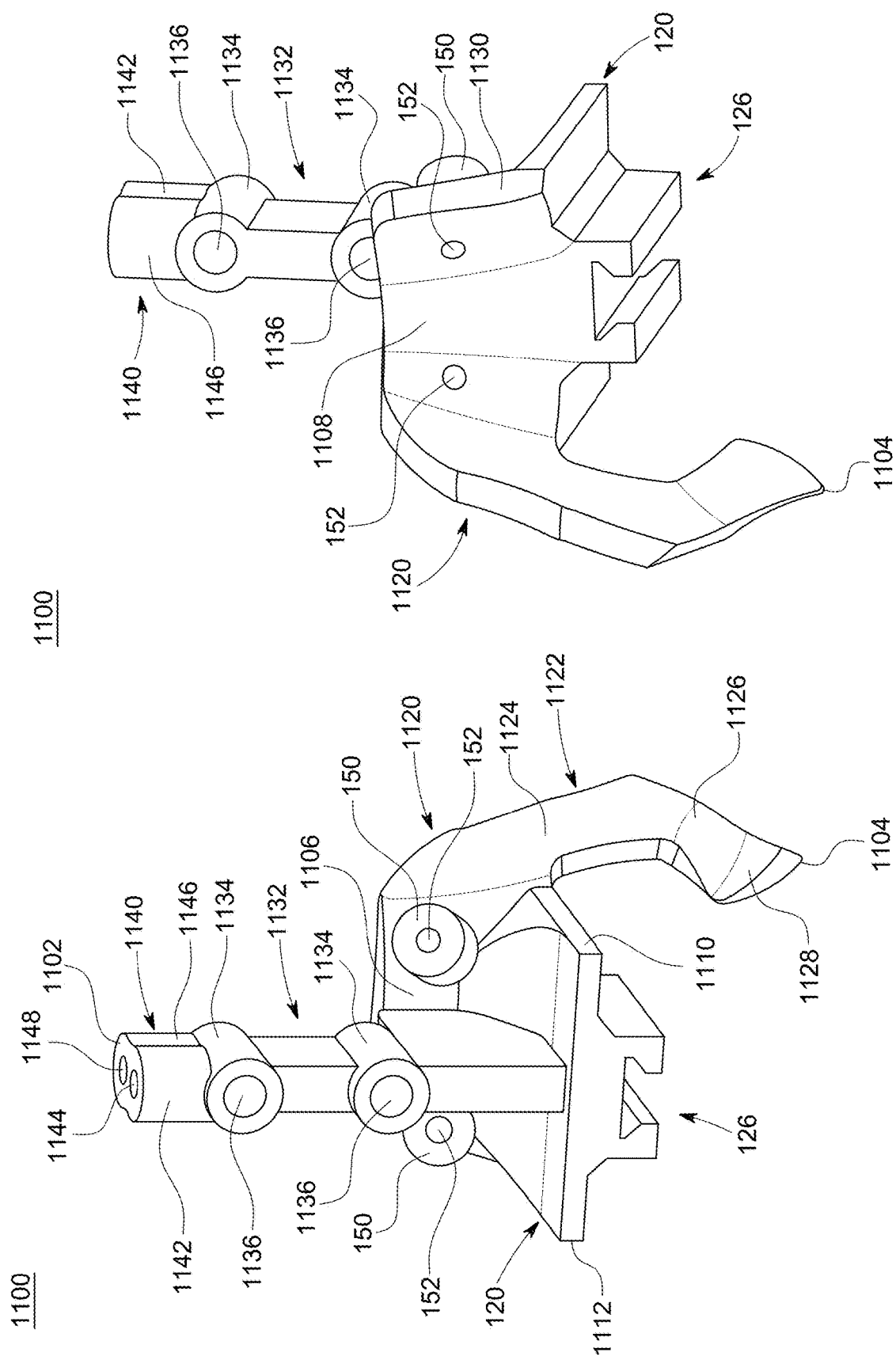
FIG. 82 is first perspective view of another alignment guide, in accordance with an aspect of the present invention.
FIG. 83 is a second perspective view of the alignment guide of FIG. 82, in accordance with an aspect of the present invention.
Figure 86:
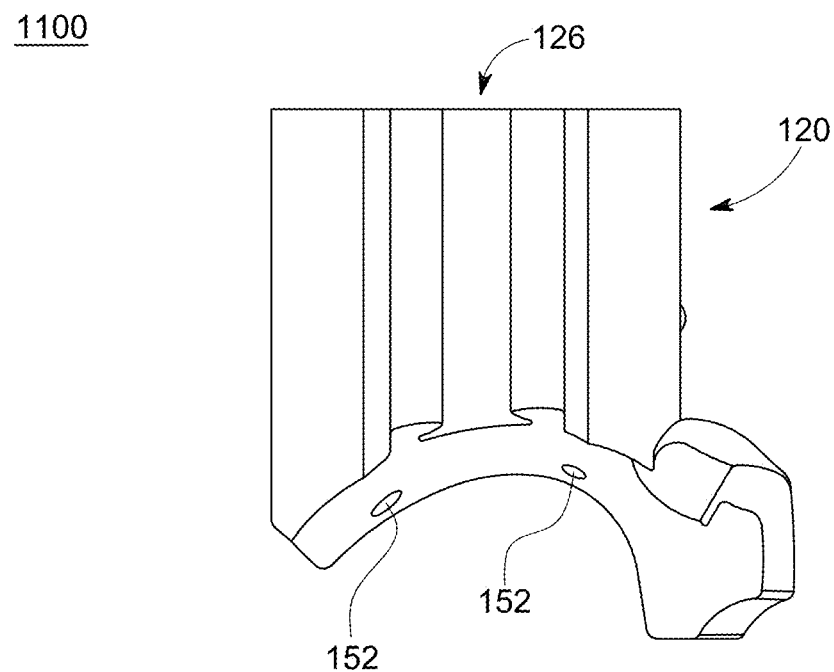
FIG. 86 is a first end view of the alignment guide of FIG. 82, in accordance with an aspect of the present invention.
Figure 87:
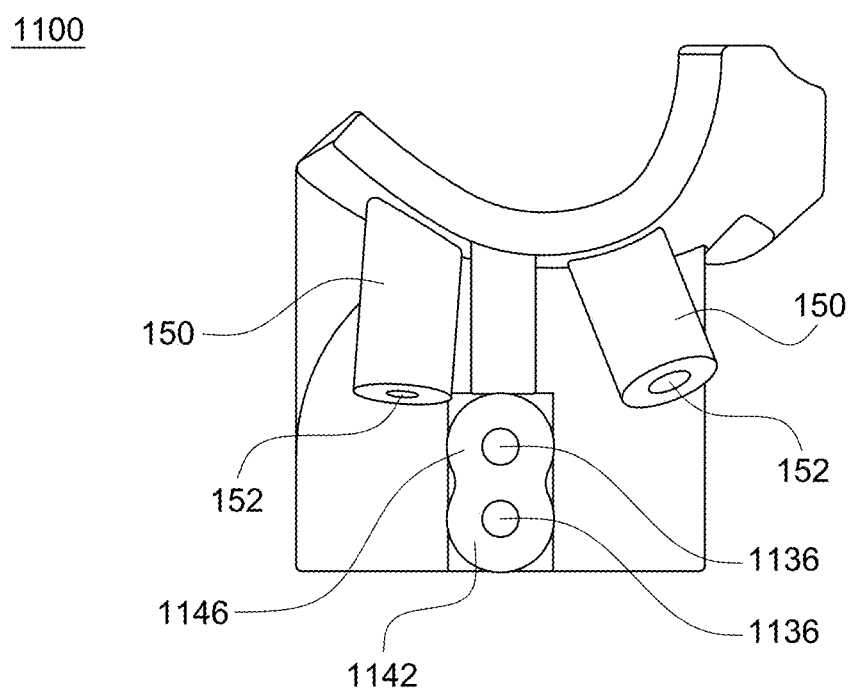
FIG. 87 is a second end view of the alignment guide of FIG. 82, in accordance with an aspect of the present invention.
Figure 98:
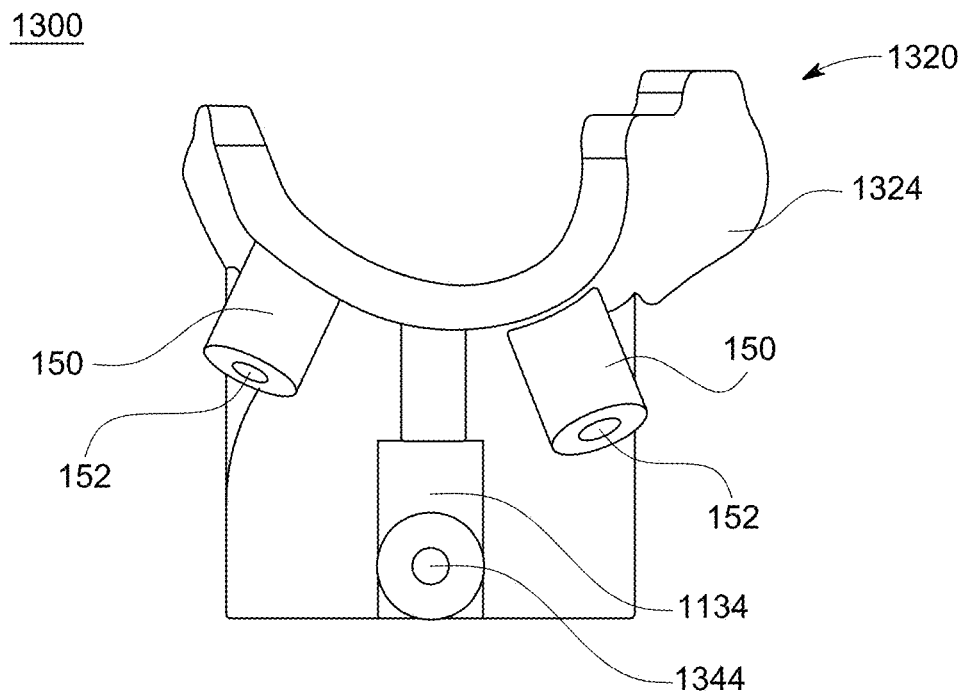
FIG. 98 is a first end view of the alignment guide of FIG. 94, in accordance with an aspect of the present invention.
Figure 99:
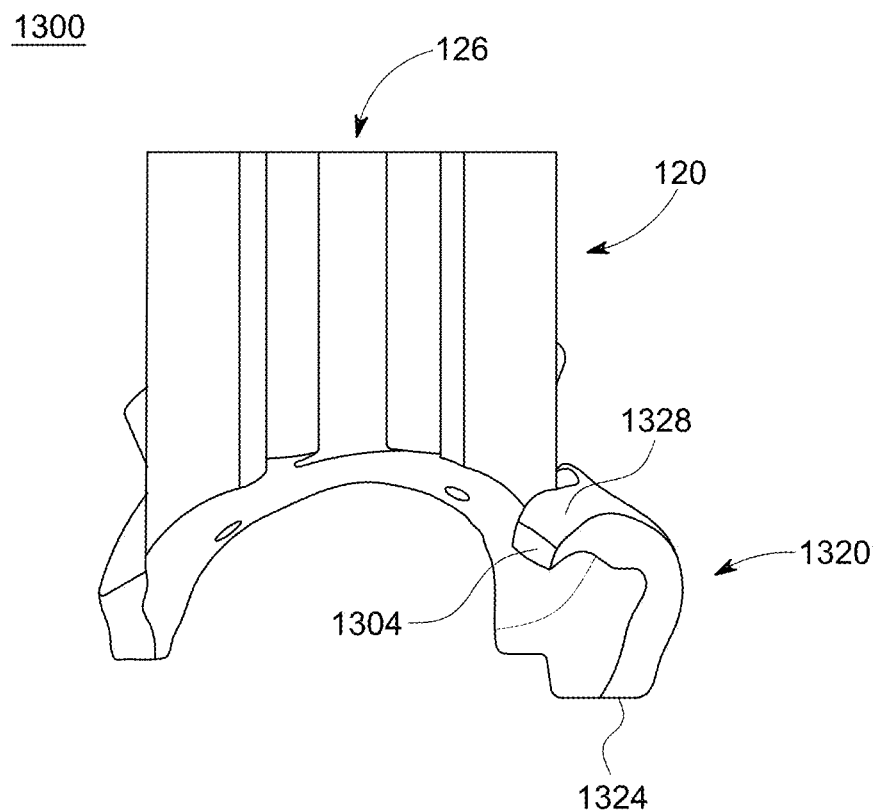
FIG. 99 is a back end view of the alignment guide of FIG. 94, in accordance with an aspect of the present invention.
Figure 103:
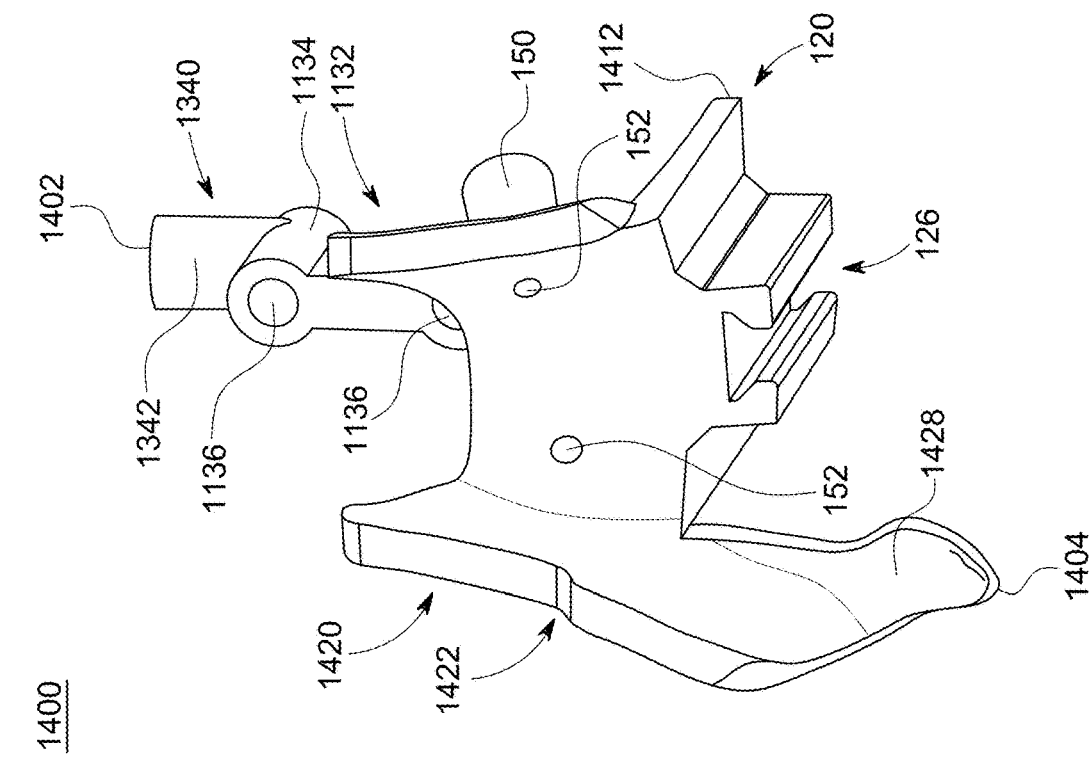
FIG. 103 is a second perspective view of the alignment guide of FIG. 102, in accordance with an aspect of the present invention.
Figure 102:
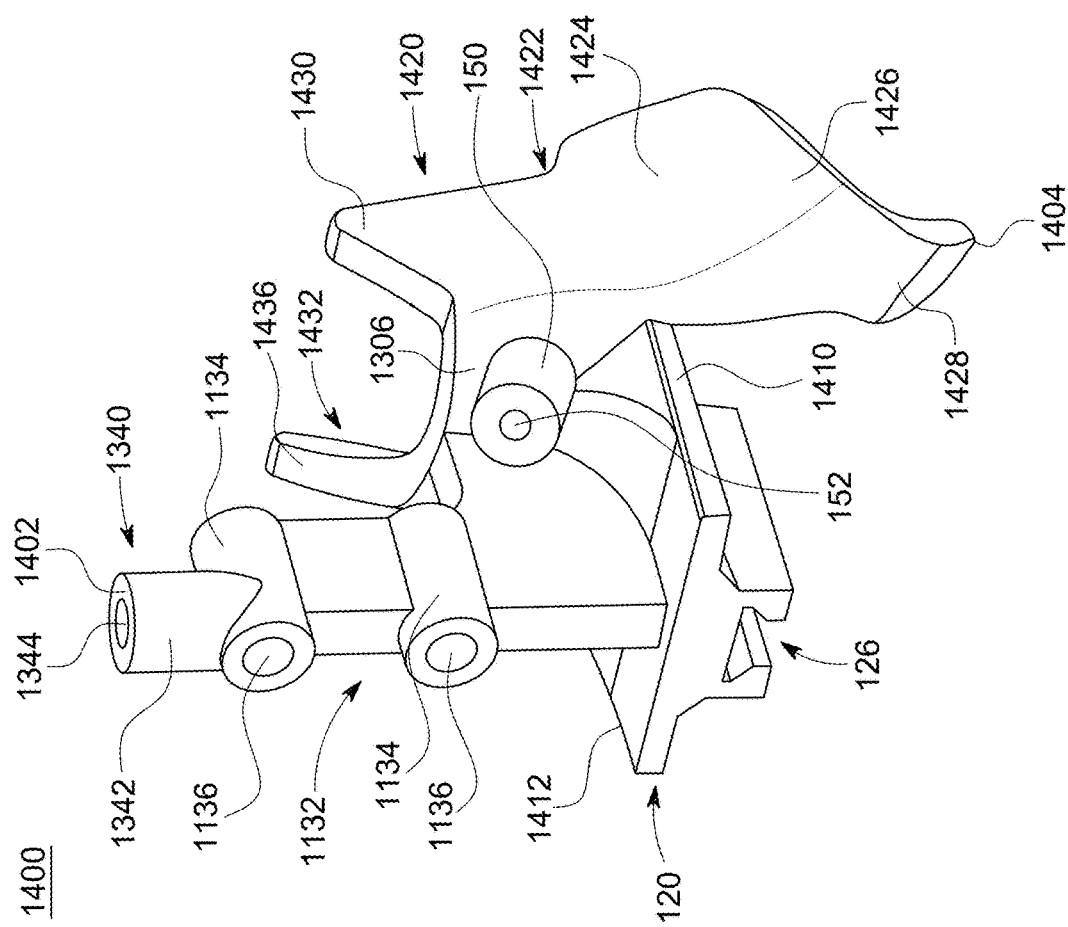
FIG. 102 is a first perspective view of another alignment guide, in accordance with an aspect of the present invention.
Figure 107:
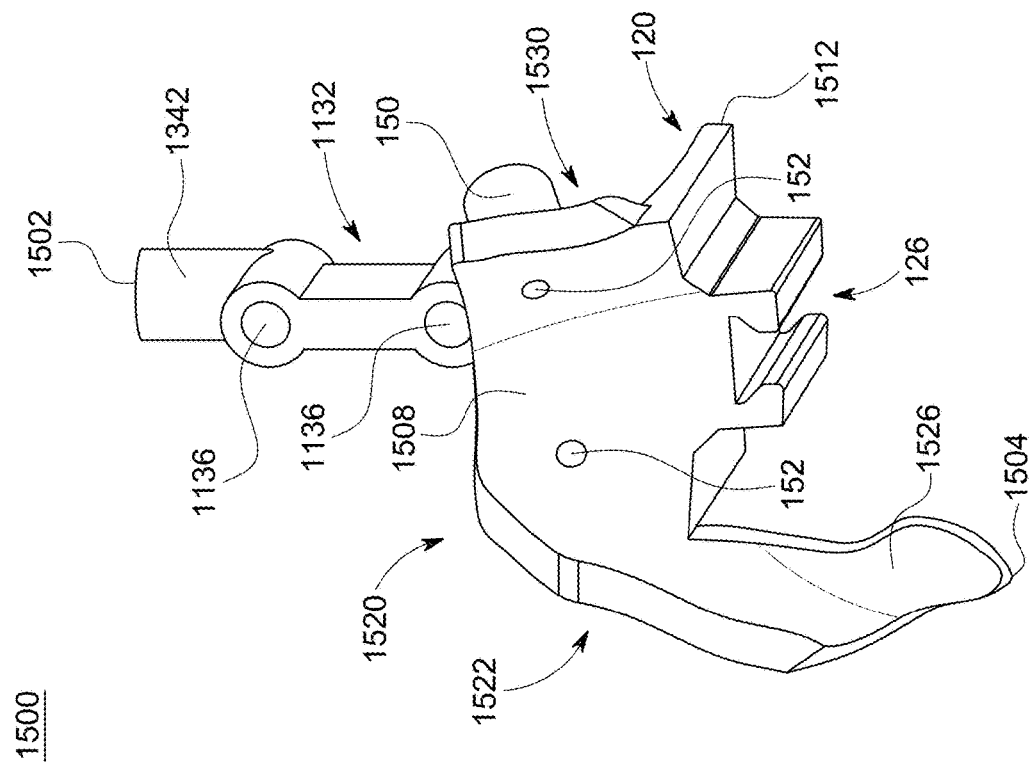
FIG. 107 is a second perspective view of the alignment guide of FIG. 106, in accordance with an aspect of the present invention.
Figure 106:
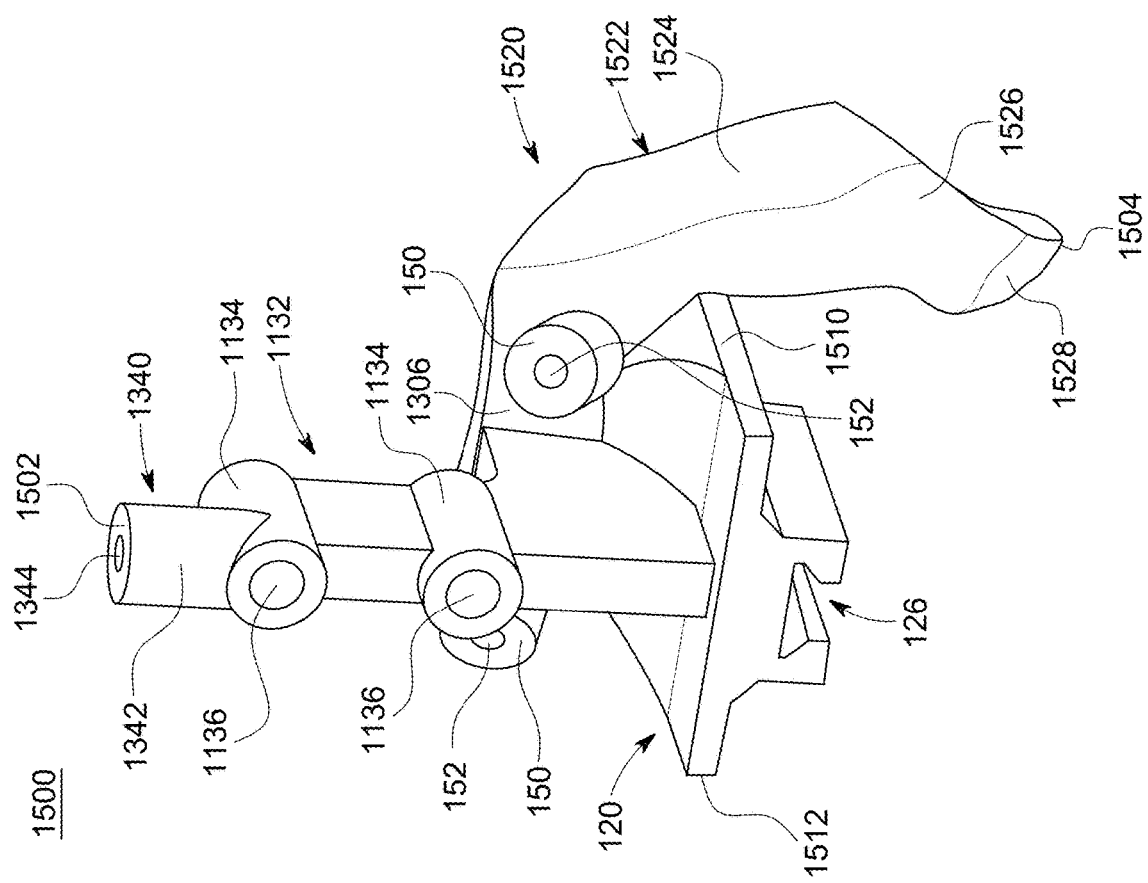
FIG. 106 is a first perspective view of yet another alignment guide, in accordance with an aspect of the present invention.
Figures 110, 111:
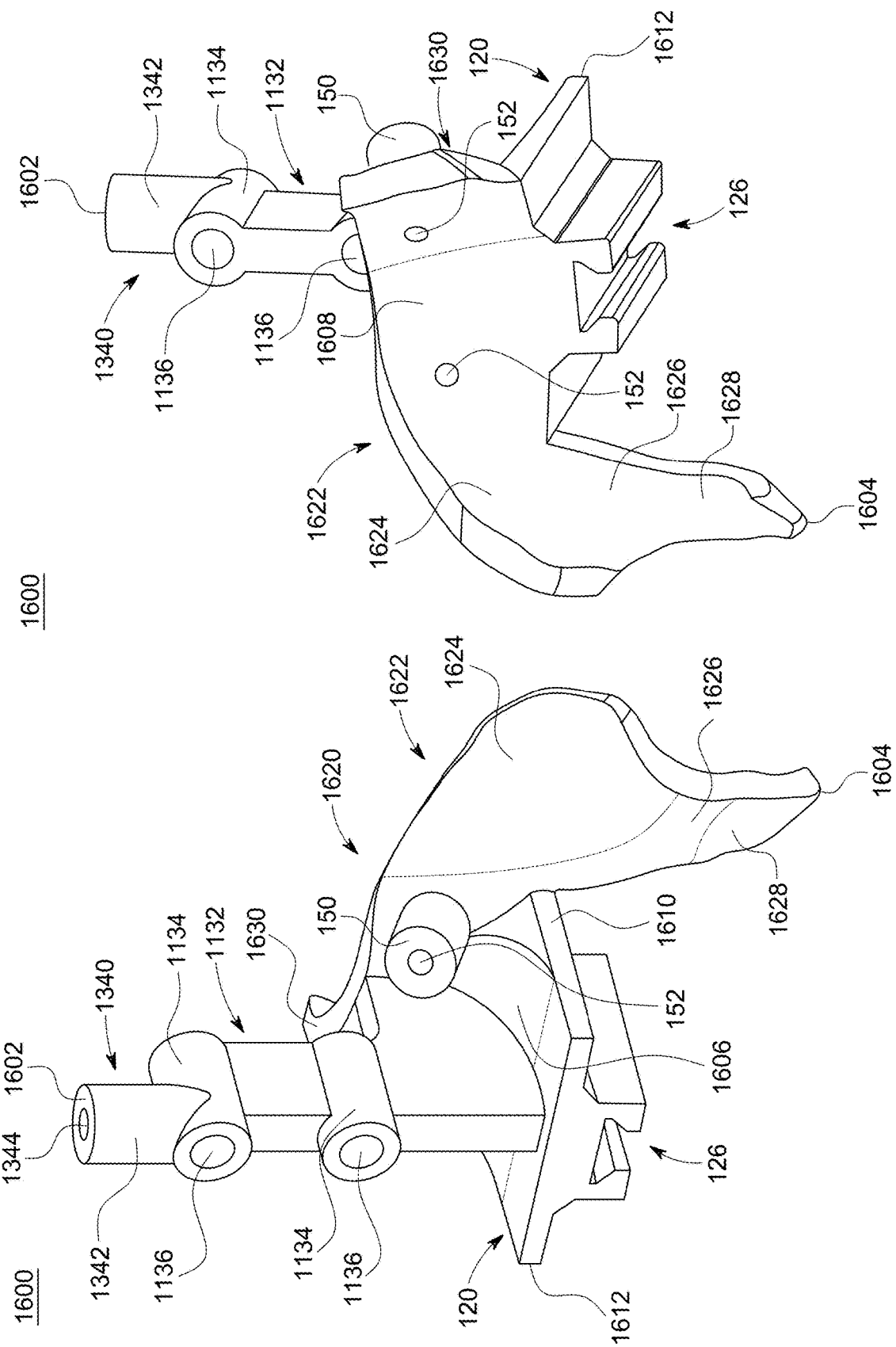
FIG. 110 is a first perspective view of another alignment guide, in accordance with an aspect of the present invention.
FIG. 111 is a second perspective view of the alignment guide of FIG. 110, in accordance with an aspect of the present invention.
Figures 112, 113:
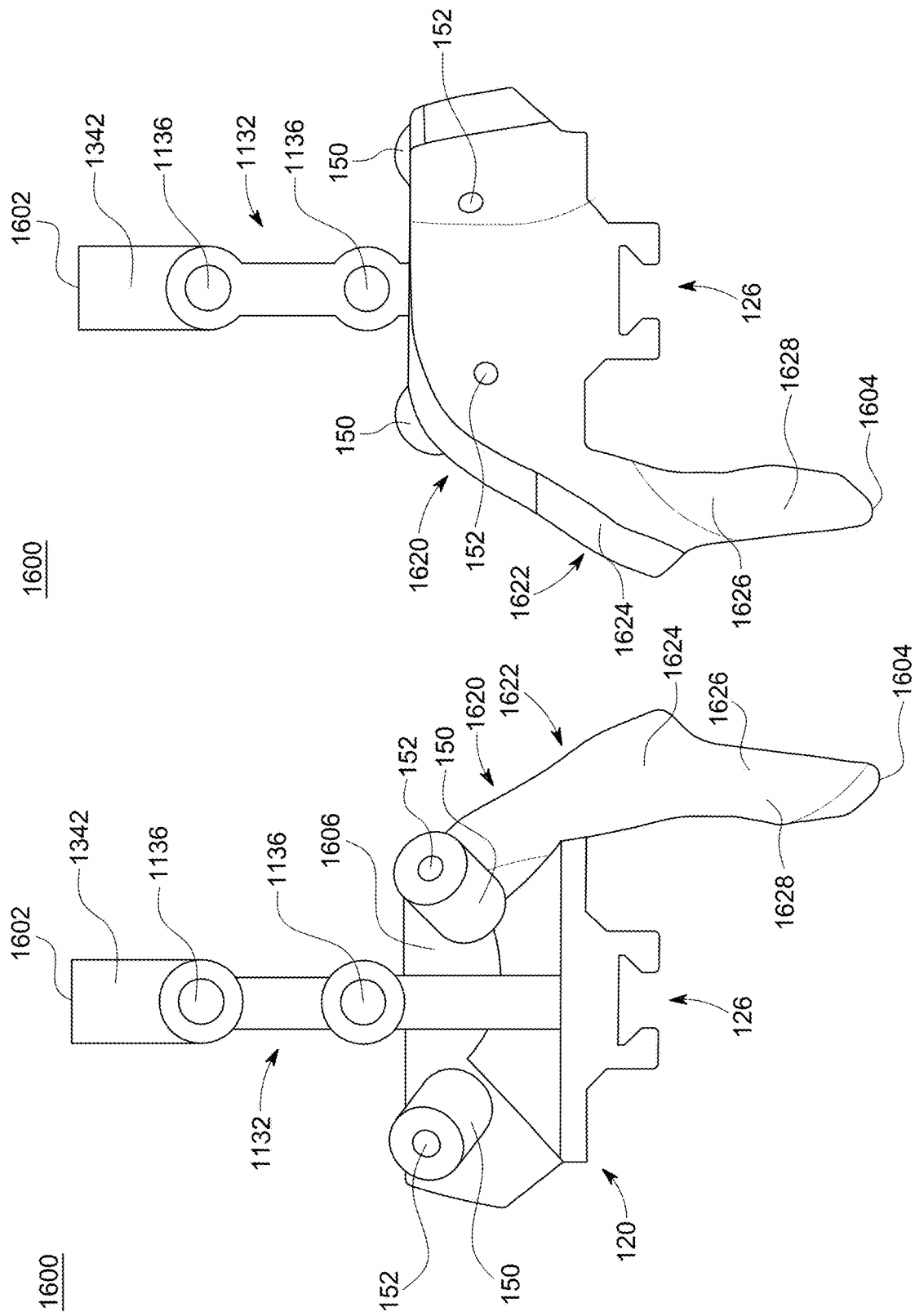
FIG. 112 is a front view of the alignment guide of FIG. 110, in accordance with an aspect of the present invention.
FIG. 113 is a back view of the alignment guide of FIG. 110, in accordance with an aspect of the present invention.
Figure 115:
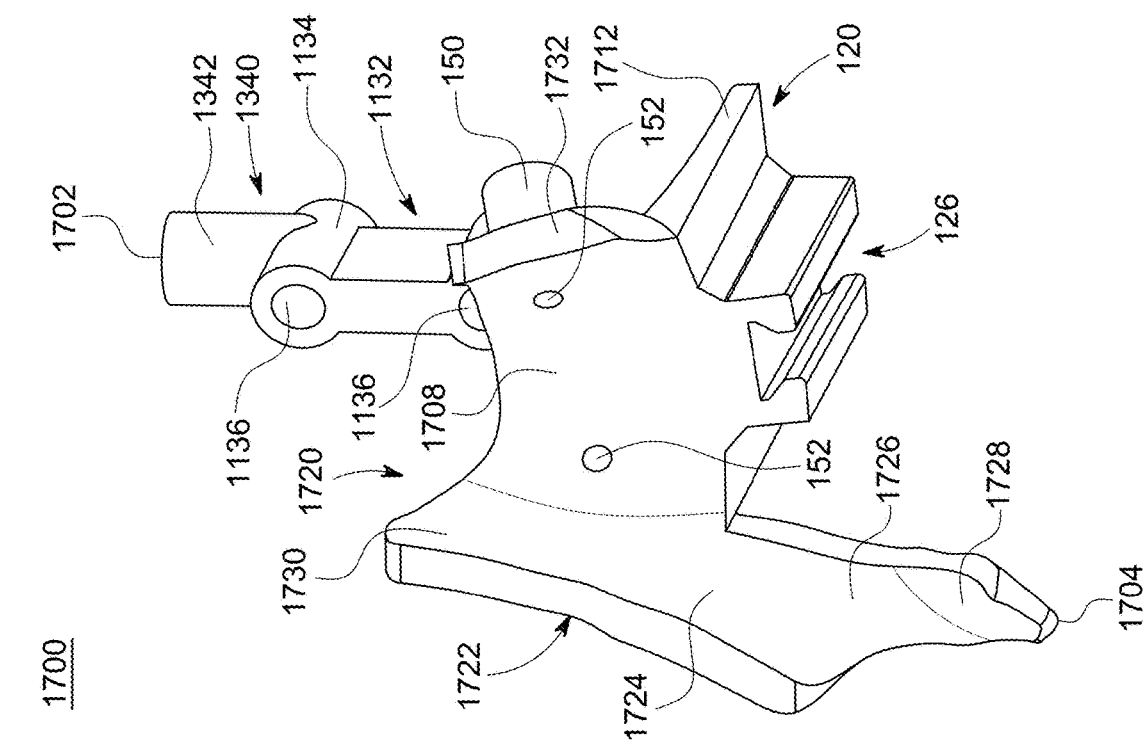
FIG. 115 is a second perspective view of the alignment guide of FIG. 114, in accordance with an aspect of the present invention.
Figure 114:
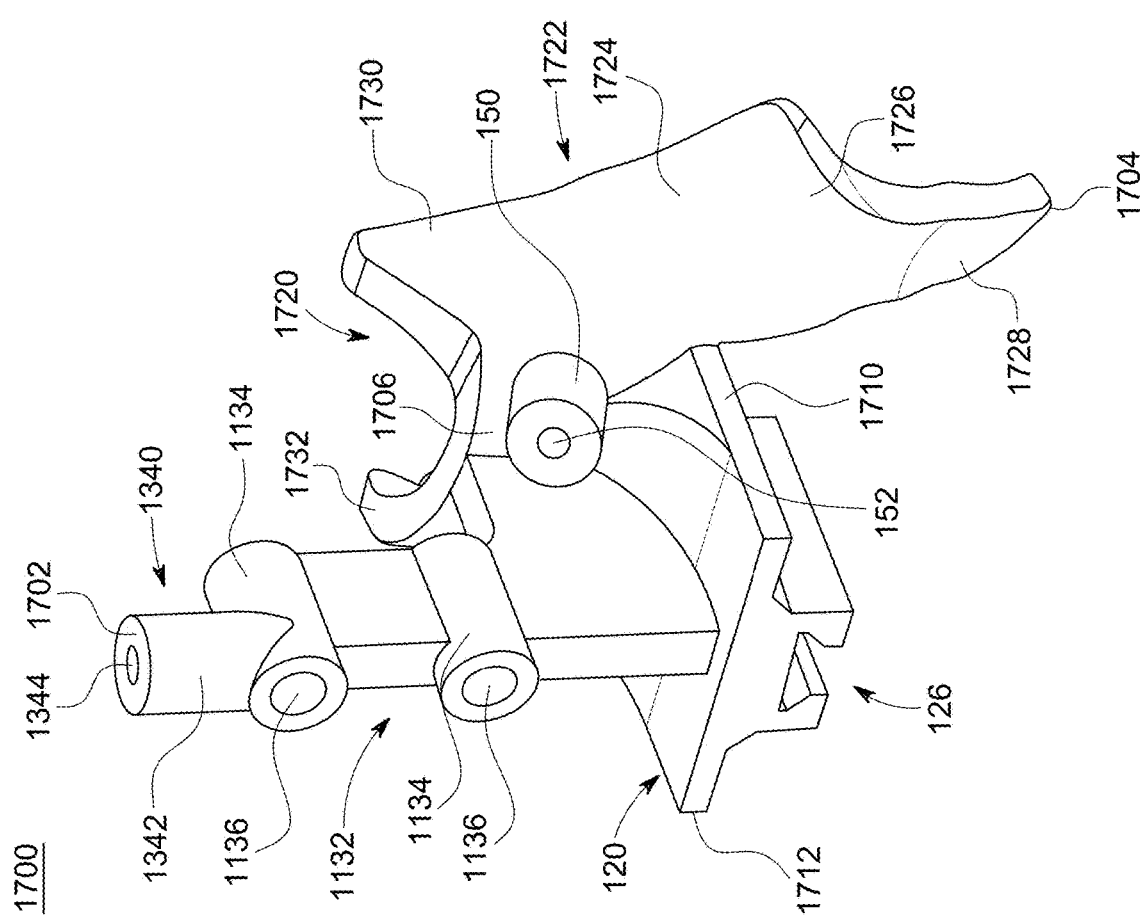
FIG. 114 is a first perspective view of yet another alignment guide, in accordance with an aspect of the present invention.
Figures 116, 117:
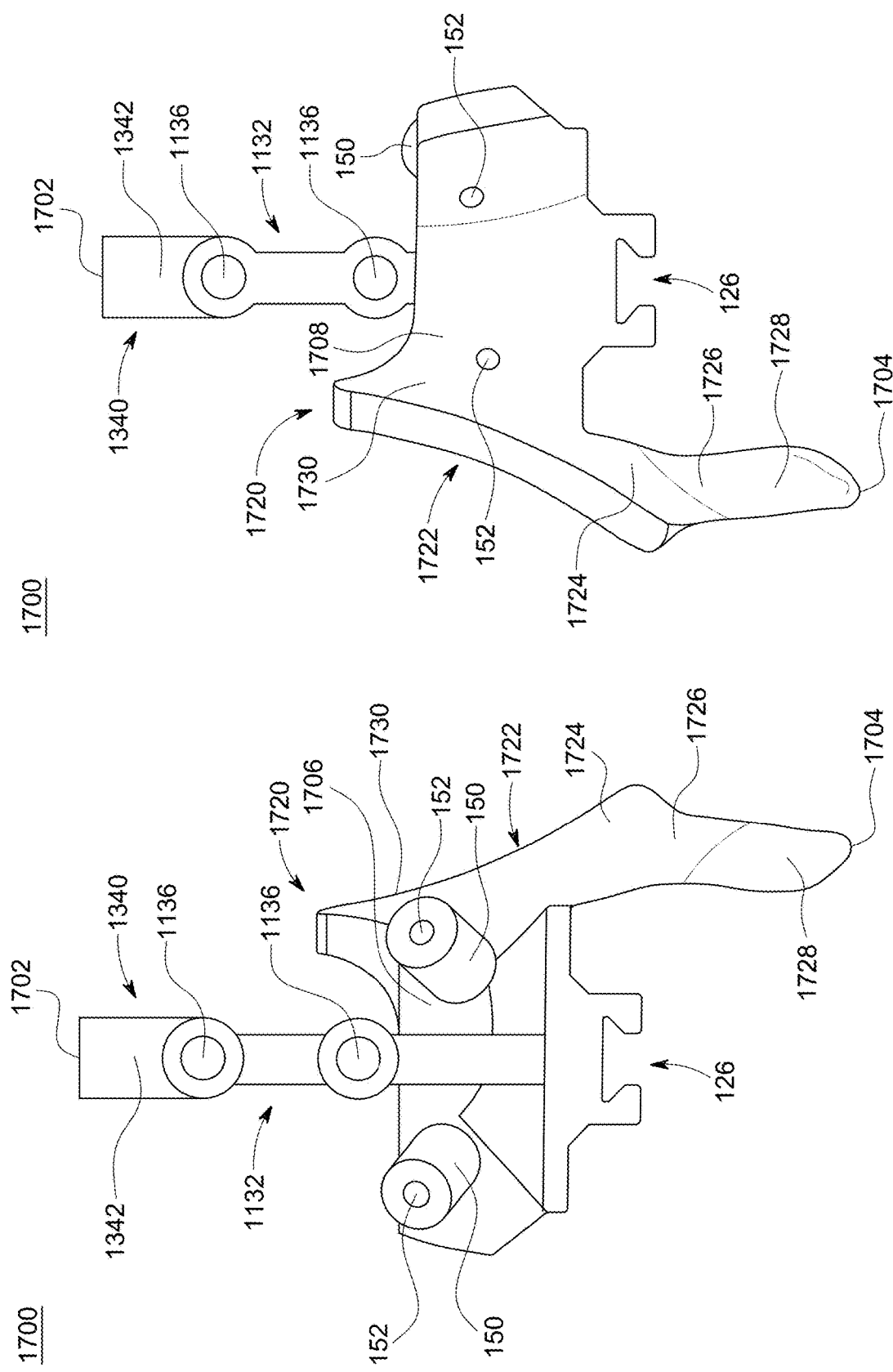
FIG. 116 is a front view of the alignment guide of FIG. 114, in accordance with an aspect of the present invention.
FIG. 117 is a back view of the alignment guide of FIG. 114, in accordance with an aspect of the present invention.
Figure 119:
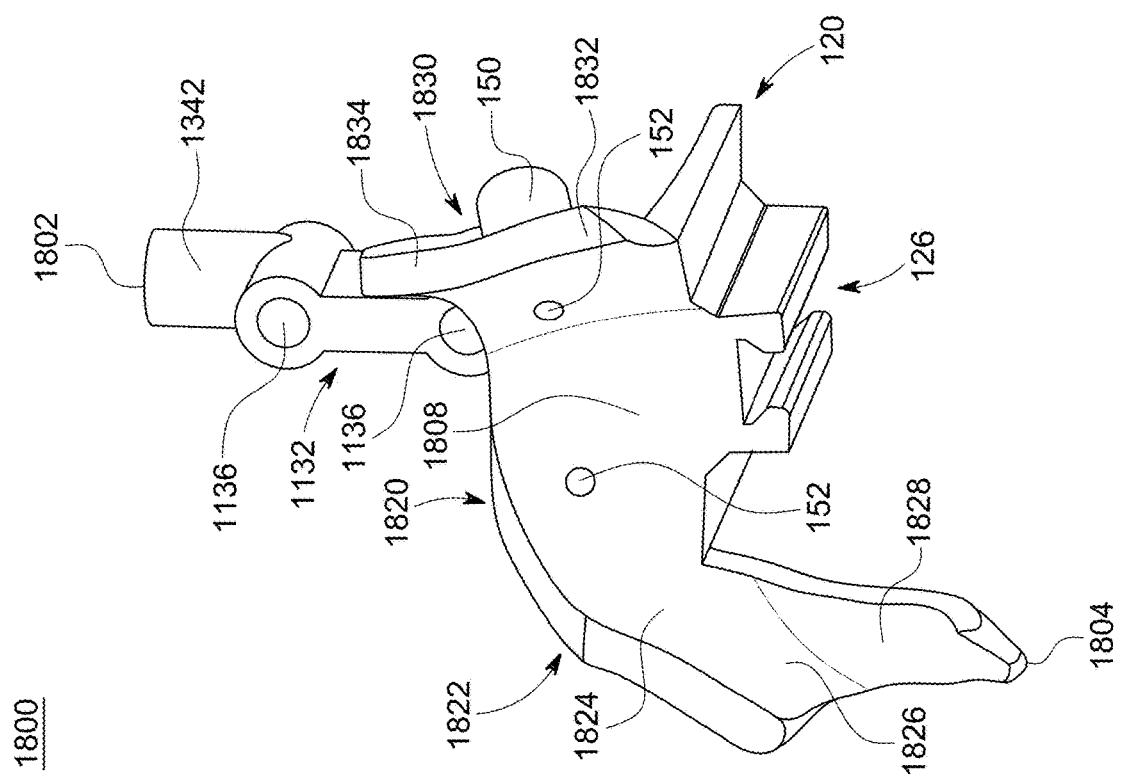
FIG. 119 is a second perspective view of the alignment guide of FIG. 118, in accordance with an aspect of the present invention.
Figure 118:
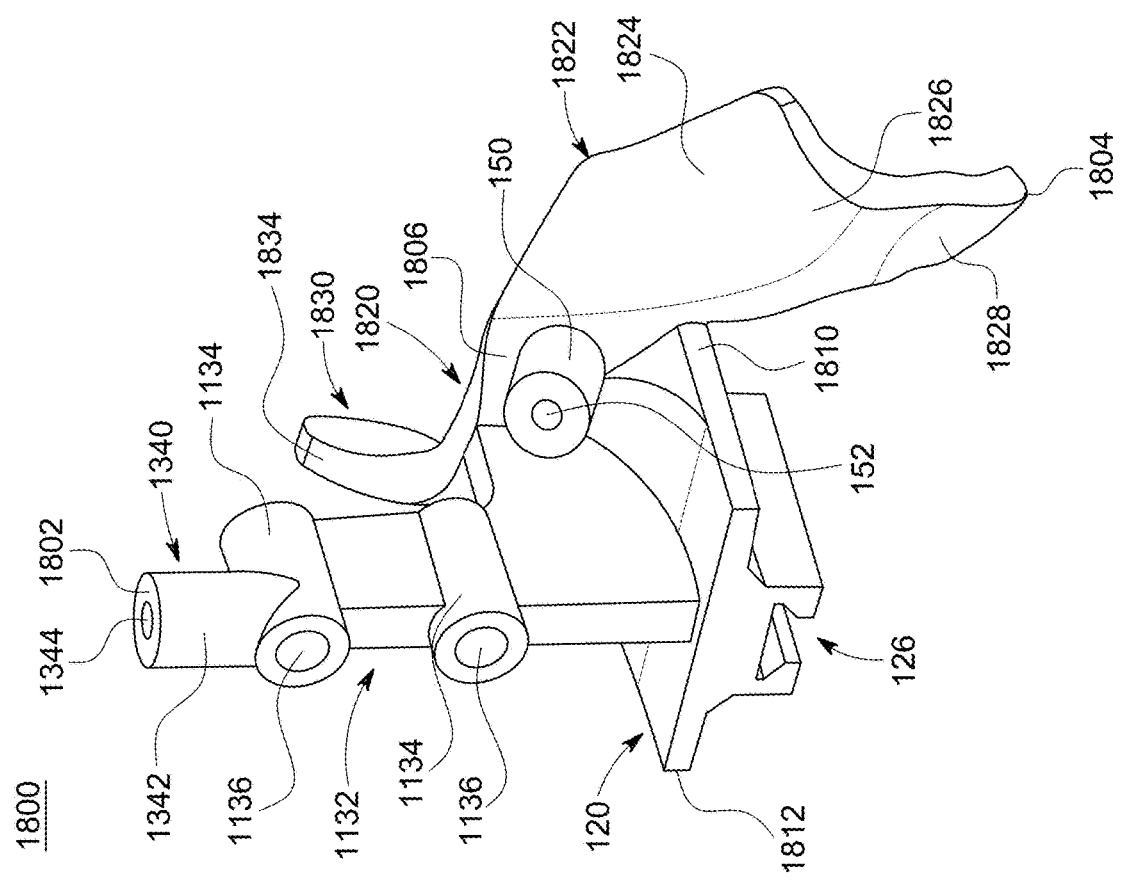
FIG. 118 is a first perspective view of another alignment guide, in accordance with an aspect of the present invention.
Figures 124, 125:
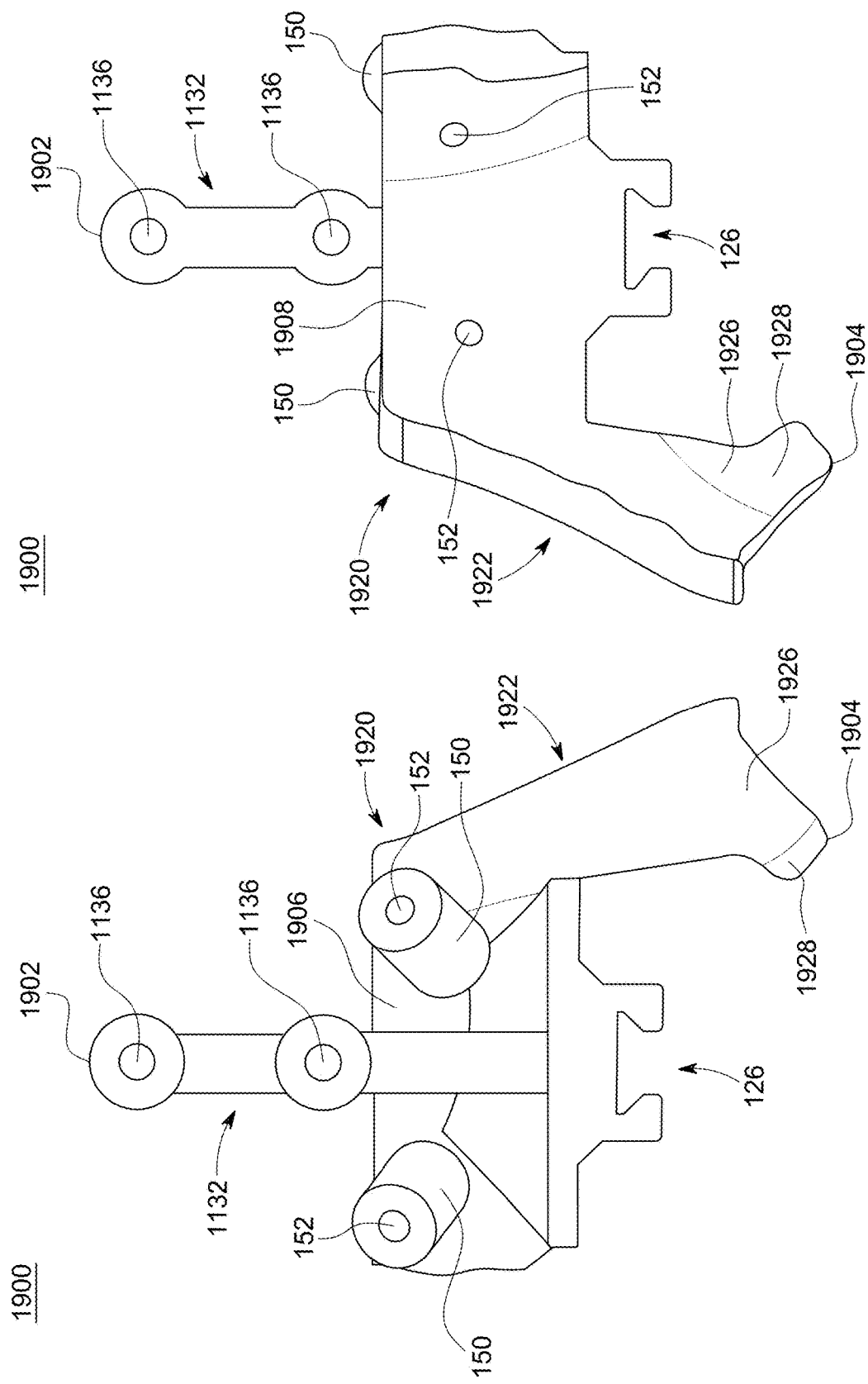
Figure 126:
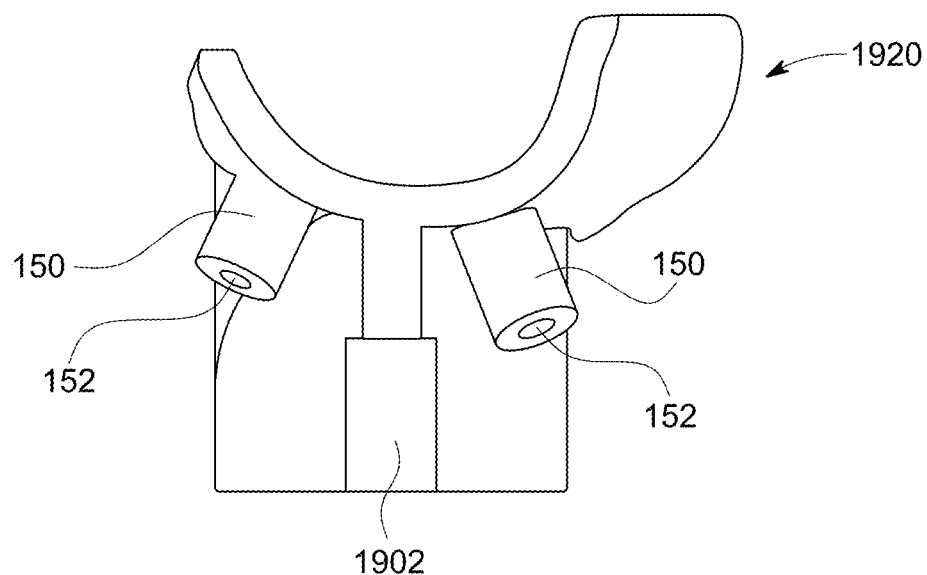
Figure 127:
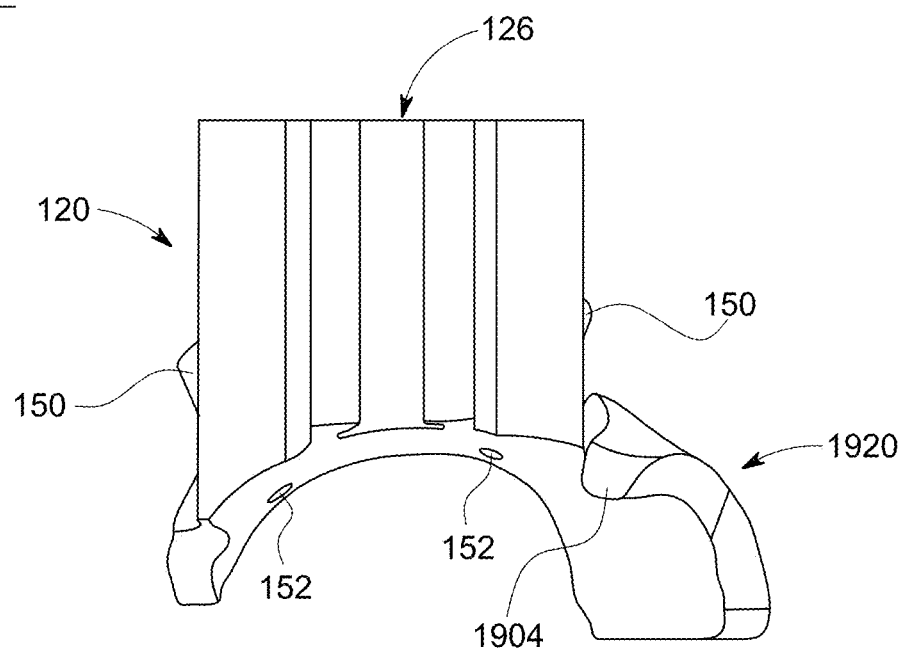

Referring now to FIGS. 64 and 65, another alignment guide 900 is shown. The alignment guide 900 may be, for example, similar to the alignment guide 800 and further include a slot for receiving an alignment tool, such as a laser, as shown in FIGS. 66-76. The guide 900 includes a first or proximal end 902, a second or distal end 904, a first or anterior surface 906, a second or posterior surface 908, a first or medial side 910, and a second or lateral side 912. The guide 900 also includes the base portion 120 extending away from the body 820 as described in greater detail above and which will not be described again here for brevity sake. The second or posterior surface 908 of the body 820 is also formed to match or correspond to the distal end of a patient's tibia. The base portion 120 may also include a slot 920 for receiving a laser device 980. As shown in FIGS. 72-76, the laser device 980 may include a first portion 982 and a second portion 984 coupled together to form, for example, an "L" shaped device. The first portion 982 may be coupled to the second portion 984 at a first end. The first portion 982 may include a laser 986 extending through the first portion to shine the laser 986 relative to a patient's ankle bones. The second portion 984 may also include a tab or extension 988 extending away from the second end of the second portion 984. The tab 988 may be, for example, configured or sized and shaped to engage the slot 920 of the base portion 120. The tab 988 may include a first member 990 on a first side, a second member 992 on a second side, and a through hole 994 extending through a portion of the second member 992. The second member 992 allows for deflection of the tab 988 for insertion into and retention within the slot 920. The laser device 980 may be as described in greater detail in U.S. Application No. WO 2019/213122 filed Apr. 30, 2019 entitled Laser-Based Implant Alignment and Resection Guide Systems and Related Methods, which is hereby incorporated by reference in its entirety and which will not be described again here for brevity sake.

Referring now to FIGS. 77-81, another alignment guide 1000 is shown. The alignment guide 1000 is similar to, for example, alignment guides 800, 900 and further includes an alignment tower 1020 extending away from the first or proximal end 1002 of the alignment guide 1000. The alignment tower 1020 may receive an alignment tool 1080. The guide 1000 includes a first or proximal end 1002, a second or distal end 1004, a first or anterior surface 1006, a second or posterior surface 1008, a first or medial side 1010, and a second or lateral side 1012. The guide 1000 also includes the base portion 120 extending away from the body 820 as described in greater detail above and which will not be described again here for brevity sake. The second or posterior surface 1008 of the body 820 is also formed to match or correspond to the distal end of a patient's tibia. The alignment tower 1020 extends away from the first end 1002 with the longitudinal axis of the alignment tower 1020 extending in the same direction as the longitudinal axis of the body 820. The alignment tower 1020 may also include an opening 1022 extending from a first end of the alignment tower 1020 toward the body 820. The alignment tool 1080 may have a shaft member 1082 with a first end received within the hole 1022 of the alignment tower 1020. The alignment tower 1020 may also have an alignment portion 1084 coupled to the second end of the shaft member 1082. The alignment portion 1084 may include at least one leg member 1086 extending away from the shaft member 1082. In the depicted embodiment, the at least one leg member 1086 is three leg members 1086 spaced apart. The three leg members 1086 may be, for example, positioned in a triangular shape.

Referring now to FIGS. 82-89, another alignment guide 1100 is shown. The alignment guide 1100 includes a first or proximal end 1102, a second or distal end 1104, a first or anterior surface 1106, a second or posterior surface 1108, a first or medial side 1110, and a second or lateral side 1112. The alignment guide 1100 includes a base portion 120, a body portion 1120, a pin tower portion 1132, and an alignment tower 1140. The base portion 120 may extend out from the body 1120 of the alignment guide 1100 in an anterior direction. The base portion may include a fastening system 126 extending away from the bottom surface 124 of the base portion 120. The base portion 120 and fastening system 126 may be as described above in greater detail and will not be described again here for brevity sake.

The body 1120 may be formed using imaging, such as CT scans or other tissue determining images. The second or posterior surface 1108 of the body 1120 is formed to match or correspond to the distal end of a patient's tibia. The body 1120 includes a medial protrusion 1122 and a lateral protrusion 1130. The medial protrusion 1122 extends away from the first side 1110 and extends in a distal direction past the base portion 120 and the fastener 126. The medial protrusion 1122 includes a first portion 1124 coupled to and extending away from the body 1120, a second portion 1126 coupled to and extending away from the first portion 1124, and a third portion 1128 coupled to and extending away from the second portion 1126 and which wraps around the anterior aspect (for example, apex) of a tibia and/or, more specifically, the notch of Harty, if present, and at the junction of the medial malleolus and anterior tibial plafond, extending inferior along the medial malleolus. The first portion 1124 may extend, for example, in an inferior and posterior direction away from the anterior surface 1106 of the body 1120. The first portion 1124 may be, for example, positioned generally perpendicular to an anterior surface of the base portion 120. The second portion 1126 may extend away from the first portion 1124, for example, in an anterior direction and at an angle with respect to the longitudinal axis of the guide 1100. The third portion 1128 may extend, for example, in a direction toward the lateral side of the guide 1100 and at an angle with respect to the longitudinal axis of the guide 1100. The lateral protrusion 1130 extends away from the second side 1112 and matches the patient's anatomy. The lateral protrusion 1130 may, for example, wrap around the posterior aspect of the tibia to allow the guide 1100 to couple to or grip the patient's tibia making additional fasteners optional. The body 1120 may also include at least one pin tower 150 extending away from the first surface 1106 of the body 1120. The at least one pin tower 150 may also include a through hole 152 extending through each pin tower 150 and the body 1120. As shown, the body 1120 may include two pin towers 150. For example, the body 1120 may include at least one pin tower 150 positioned on a medial side of the body 1120 and at least one pin tower 150 positioned on a lateral side of the body 1120. Alternative arrangements of the pin towers 150 are also contemplated in order to place the fixation pins in a position for use with the rest of the total ankle procedure.

The body 1120 may also include a pin tower portion 1132 extending in a proximal direction toward the first end 1102. The pin tower portion 1132 may extend from a top surface 122 of the base portion 120. The pin tower portion 1132 may include at least one pin tower 1134 extending through the pin tower portion 1132. The pin towers 1134 may be, for example, integral, monolithic, a single piece, or of one piece construct with the pin tower portion 1132. The at least one pin tower 1134 may be, for example, two pin towers 1134. The two pin towers 1134 may be, for example, spaced apart from each other along the length of the pin tower portion 1132. Each pin tower 1134 may include a through hole 1136 extending through the pin towers 1134 from an anterior side 1106 to a posterior side 1108 of the guide 1100. The alignment tower 1140 may include, for example, two protrusions 1142, 1146 each including an opening 1144, 1148 configured or sized and shaped for receiving an alignment tool (not shown). The two protrusions 1142, 1146 may be overlapping protrusions to form the alignment tower 1140. The alignment tower 1140 is positioned at the first end 1102 of the pin tower portion 1132. The alignment tower 1140 may, for example, be coupled to and extend away from a pin tower 1134 of the pin tower portion 1132.

Another alignment guide 1200 is shown in FIGS. 90-93. The alignment guide 1200 may be, for example, similar to alignment guide 1100 with varying protrusions. The alignment guide 1200 includes a first or proximal end 1202, a second or distal end 1204, a first or anterior surface 1206, a second or posterior surface 1208, a first or medial side 1210, and a second or lateral side 1212. The alignment guide 1200 includes a base portion 120, a body portion 1220, a pin tower portion 1132, and an alignment tower 1140. The base portion 120 may extend out from the body 1220 of the alignment guide 1200 in an anterior direction. The base portion 120 may be as described above in greater detail and will not be described again here for brevity sake.

The body 1220 may be formed using imaging, such as CT scans or other tissue determining images. The second or posterior surface 1208 of the body 1220 is formed to match or correspond to the distal end of a patient's tibia. The body 1220 includes a medial protrusion 1222 and a lateral protrusion 1230. The medial protrusion 1222 extends away from the first side 1210 and extends in a distal direction past the base portion 120 and the fastener 126. The medial protrusion 1222 includes a first portion 1224 coupled to and extending away from the body 1220, a second portion 1226 coupled to and extending away from the first portion 1224, and a third portion 1228 coupled to and extending away from the second portion 1226 and which wraps around the anterior aspect (for example, apex) of a tibia and/or, more specifically, the notch of Harty, if present, and at the junction of the medial malleolus and anterior tibial plafond, extending inferior along the medial malleolus. The first portion 1224, second portion 1226 and third portion 1228 may be positioned, for example, similar to the first portion 1124, second portion 1126, and third portion 1128, respectively, of the guide 1100, which will not be described again here for brevity sake. The first portion 1224 may be, for example, larger in an anterior-posterior direction than the first portion 1124. The second portion 1226 may be, for example, larger in a medial-lateral direction and wrap around more of the tibia than the second portion 1126. The third portion 1228 may, for example, extend further in an inferior direction than the third portion 1128 forming a more pointed end portion. The lateral protrusion 1230 may be, for example, the same or similar to the lateral protrusion 1130, which is described in greater detail above and will not be described again here for brevity sake. The body 1220 may also include at least one pin tower 150 extending away from the first surface 1206 of the body 1220. The at least one pin tower 150 may be two pin towers 150. The pin towers 150 may be as described above in greater detail with respect to guide 1100 and which will not be described again here for brevity sake.

The guide 1200 may also include a pin tower portion 1132 extending in a proximal direction from the body 1220 toward the first end 1202. The pin tower portion 1132 may be as described above with reference to guide 1100 and which will not be described again here for brevity sake. The guide 1200 may further include an alignment tower 1140 which may be coupled to and extending away from a pin tower 1134 of the pin tower portion 1132. The alignment tower 1140 may be as described above with reference to guide 1100 and which will not be described again here for brevity sake.

Referring now to FIGS. 94-101, another alignment guide 1300 is shown. The alignment guide 1300 includes a first or proximal end 1302, a second or distal end 1304, a first or anterior surface 1306, a second or posterior surface 1308, a first or medial side 1310, and a second or lateral side 1312. The alignment guide 1300 includes a base portion 120, a body portion 1320, a pin tower portion 1132, and an alignment tower 1340. The base portion 120 may extend out from the body 1320 of the alignment guide 1300 in an anterior direction. The base portion 120 may include a fastening system 126 extending away from the bottom surface 124 of the base portion 120. The base portion 120 and fastening system 126 may be as described above in greater detail and will not be described again here for brevity sake.

The body 1320 may be formed using imaging, such as CT scans or other tissue determining images. The second or posterior surface 1308 of the body 1320 is formed to match or correspond to the distal end of a patient's tibia. The body 1320 includes a medial protrusion 1322 and a lateral protrusion 1332. The medial protrusion 1322 extends away from the first side 1310 and extends in a distal direction past the base portion 120 and the fastener 126. The medial protrusion 1322 includes a first portion 1324, a second portion 1326, a third portion 1328, and a fourth portion 1330. The first portion 1324 may be coupled to and extend away from the body 1320. The second portion 1326 may be coupled to and extend away from the first portion 1324. The third portion 1128 may be coupled to and extend away from the second portion 1126 and wrap around the anterior aspect (for example, apex) of a tibia and/or, more specifically, the notch of Harty, if present, and at the junction of the medial malleolus and anterior tibial plafond, extending inferior along the medial malleolus. The fourth portion 1330 may be coupled to and extend away from the first portion 1324 in a superior direction. The first portion 1324 may extend, for example, in an inferior and posterior direction away from the anterior surface 1306 of the body 1320. The first portion 1324 may be, for example, positioned generally perpendicular to an anterior surface of the base portion 120. The second portion 1326 may extend away from the first portion 1324, for example, in an anterior direction and at an angle with respect to the longitudinal axis of the guide 1300. The third portion 1328 may extend, for example, in a direction toward the lateral side of the guide 1300 and at an angle with respect to the longitudinal axis of the guide 1300. The fourth portion 1330 may extend, for example, in a superior direction to a point below the top of the pin tower portion 1132. The fourth portion 1330 may extend in an anterior-posterior direction to a point. The fourth portion 1330 may be, for example, triangularly shaped. The lateral protrusion 1332 extends away from the second side 1312 and matches the patient's anatomy. The lateral protrusion 1332 may include a first portion 1334 and a second portion 1336 extending away from the first portion 1334. The first portion 1334 may extend, for example, in an anterior-posterior direction from the anterior surface 1306 of the body 1320. The second portion 1336 may extend away from the first portion 1334, for example, in a superior direction to a point below the top of the pin tower portion 1132. The second portion 1336 may extend, for example, in an anterior-posterior direction from the first surface 1306 of the body 1320. The second portion 1336 may be, for example, triangularly shaped. The lateral protrusion 1332 may, for example, wrap around the posterior aspect of the tibia to allow the guide 1300 to couple to or grip the patient's tibia making additional fasteners optional. The body 1320 may also include at least one pin tower 150 extending away from the first surface 1306 of the body 1320. The at least one pin tower 150 may also include a through hole 152 extending through each pin tower 150 and the body 1320. As shown, the body 1320 may include two pin towers 150. For example, the body 1320 may include at least one pin tower 150 positioned on a medial side of the body 1320 and at least one pin tower 150 positioned on a lateral side of the body 1320. Alternative arrangements of the pin towers 150 are also contemplated in order to place the fixation pins in a position for use with the rest of the total ankle procedure.

The body 1320 may also include a pin tower portion 1132 extending in a proximal direction toward the first end 1102. The pin tower portion 1132 may be as described above and which will not be described again here for brevity sake. The alignment tower 1340 may include, for example, a single protrusion 1342 including an opening 1344 configured or sized and shaped for receiving an alignment tool (not shown). The protrusions 1342 may be positioned, for example, offset from a longitudinal axis of the pin tower portion 1132. The alignment tower 1340 is positioned at the first end 1302 of the pin tower portion 1132. The alignment tower 1340 may, for example, be coupled to and extend away from a pin tower 1134 of the pin tower portion 1132.

Yet another alignment guide 1400 is shown in FIGS. 102-105. The alignment guide 1400 may be, for example, similar to alignment guide 1300 with varying protrusion portions based on patient anatomy. The alignment guide 1400 includes a first or proximal end 1402, a second or distal end 1404, a first or anterior surface 1406, a second or posterior surface 1408, a first or medial side 1410, and a second or lateral side 1412. The alignment guide 1400 includes a base portion 120, a body portion 1420, a pin tower portion 1132, and an alignment tower 1340. The base portion 120 may extend out from the body 1420 of the alignment guide 1400 in an anterior direction. The base portion 120 may include a fastening system 126 extending away from the bottom surface 124 of the base portion 120. The base portion 120 and fastening system 126 may be as described above in greater detail and will not be described again here for brevity sake.

The body 1420 may be formed using imaging, such as CT scans or other tissue determining images. The second or posterior surface 1408 of the body 1420 is formed to match or correspond to the distal end of a patient's tibia. The body 1420 includes a medial protrusion 1422 and a lateral protrusion 1432. The medial protrusion 1422 extends away from the first side 1410, in a proximal direction toward the alignment tower 1340, and in a distal direction past the base portion 120 and the fastener 126. The medial protrusion 1422 includes a first portion 1424, a second portion 1426, a third portion 1428, and a fourth portion 1430. The first portion 1424 may be coupled to and extend away from the body 1420. The first portion 1424 may be, for example, larger than the first portion 1324 in an anterior-posterior direction. The second portion 1426 may be coupled to and extend away from the first portion 1424. The third portion 1428 may be coupled to and extend away from the second portion 1426 and wrap around the anterior aspect (for example, apex) of a tibia and/or, more specifically, the notch of Harty, if present, and at the junction of the medial malleolus and anterior tibial plafond, extending inferior along the medial malleolus. The fourth portion 1430 may be coupled to and extend away from the first portion 1424 in a superior direction. The first portion 1424 may extend, for example, in an inferior and posterior direction away from the anterior surface 1406 of the body 1420. The first portion 1424 may be, for example, positioned generally perpendicular to an anterior surface of the base portion 120. The second portion 1426 may extend away from the first portion 1424, for example, in an anterior direction and at an angle with respect to the longitudinal axis of the guide 1400. The third portion 1428 may extend, for example, in a direction toward the lateral side of the guide 1400 and at an angle with respect to the longitudinal axis of the guide 1400. The fourth portion 1430 may extend, for example, in a superior direction to a point below the top of the pin tower portion 1132. The fourth portion 1430 may extend in an anterior-posterior direction to a point. The fourth portion 1430 may be, for example, triangularly shaped. The lateral protrusion 1432 extends away from the second side 1412 and matches the patient's anatomy. The lateral protrusion 1432 may include a first portion 1434 and a second portion 1436 extending away from the first portion 1434. The first portion 1434 may extend, for example, in an anterior-posterior direction from the anterior surface 1406 of the body 1420. The second portion 1436 may extend away from the first portion 1434, for example, in a superior direction to a point below the top of the pin tower portion 1132. The second portion 1436 may also extend, for example, in an anterior-posterior direction from the first surface 1406 of the body 1420. The second portion 1336 may be, for example, triangularly shaped. The lateral protrusion 1432 may, for example, wrap around the posterior aspect of the tibia to allow the guide 1400 to couple to or grip the patient's tibia making additional fasteners optional. The body 1420 may also include at least one pin tower 150 extending away from the first surface 1406 of the body 1420. The at least one pin tower 150 may also include a through hole 152 extending through each pin tower 150 and the body 1420. As shown, the body 1420 may include two pin towers 150. For example, the body 1420 may include at least one pin tower 150 positioned on a medial side of the body 1420 and at least one pin tower 150 positioned on a lateral side of the body 1420. Alternative arrangements of the pin towers 150 are also contemplated in order to place the fixation pins in a position for use with the rest of the total ankle procedure.

The body 1420 may also include the pin tower portion 1132 extending in a proximal direction toward the first end 1302. The pin tower portion 1132 may be as described above and which will not be described again here for brevity sake. The alignment tower 1340 may be as described above with reference to guide 1300 and which will not be described again here for brevity sake.

Referring now to FIGS. 106-109, another guide 1500 is shown. The alignment guide 1500 may be, for example, similar to alignment guide 1300, 1400 with varying protrusion portions based on patient anatomy. The alignment guide 1500 includes a first or proximal end 1502, a second or distal end 1504, a first or anterior surface 1506, a second or posterior surface 1508, a first or medial side 1510, and a second or lateral side 1512. The alignment guide 1500 includes a base portion 120, a body portion 1520, a pin tower portion 1132, and an alignment tower 1340. The base portion 120 may extend out from the body 1520 of the alignment guide 1500 in an anterior direction. The base portion 120 may include a fastening system 126 extending away from the bottom surface 124 of the base portion 120. The base portion 120 and fastening system 126 may be as described in greater detail above and which will not be described again here for brevity sake.

The body 1520 may be formed using imaging, such as CT scans or other tissue determining images. The second or posterior surface 1508 of the body 1520 is formed to match or correspond to the distal end of a patient's tibia. The body 1520 includes a medial protrusion 1522 and a lateral protrusion 1532. The medial protrusion 1522 extends away from the first side 1510, in a proximal direction toward the alignment tower 1340, and in a distal direction past the base portion 120 and the fastener 126. The medial protrusion 1522 includes a first portion 1524, a second portion 1526, and a third portion 1528. The first portion 1524 may be coupled to and extend away from the body 1520. The first portion 1524 may be, for example, smaller than the first portions 1324, 1424 in an anterior-posterior direction. The second portion 1526 may be coupled to and extend away from the first portion 1524. The third portion 1528 may be coupled to and extend away from the second portion 1526 and wrap around the anterior aspect (for example, apex) of a tibia and/or, more specifically, the notch of Harty, if present, and at the junction of the medial malleolus and anterior tibial plafond, extending inferior along the medial malleolus. The first portion 1524 may extend, for example, in an inferior and posterior direction away from the anterior surface 1506 of the body 1520. The first portion 1524 may be, for example, positioned generally perpendicular to an anterior surface of the base portion 120. The second portion 1526 may extend away from the first portion 1524, for example, in an anterior direction and at an angle with respect to the longitudinal axis of the guide 1500. The third portion 1528 may extend, for example, in a direction toward the lateral side of the guide 1500 and at an angle with respect to the longitudinal axis of the guide 1500. The lateral protrusion 1530 extends away from the second side 1412 and matches the patient's anatomy. The lateral protrusion 1532 may, for example, wrap around the posterior aspect of the tibia to allow the guide 1500 to couple to or grip the patient's tibia making additional fasteners optional.

The body 1520 may also include at least one pin tower 150 extending away from the first surface 1506 of the body 1520. The at least one pin tower 150 may also include a through hole 152 extending through each pin tower 150 and the body 1520. As shown, the body 1520 may include two pin towers 150. For example, the body 1520 may include at least one pin tower 150 positioned on a medial side of the body 1520 and at least one pin tower 150 positioned on a lateral side of the body 1520. Alternative arrangements of the pin towers 150 are also contemplated in order to place the fixation pins in a position for use with the rest of the total ankle procedure. The body 1520 may also include the pin tower portion 1132 extending in a proximal direction toward the first end 1502. The pin tower portion 1132 may be as described above with reference to at least guide 1100 and which will not be described again here for brevity sake. The alignment tower 1340 may also be as described above with reference to guide 1300 and which will not be described again here for brevity sake.

Another alignment guide 1600 is shown in FIGS. 110-113. The alignment guide 1600 may include, for example, features that are similar to the features of alignment guides 1300, 1400, 1500. The alignment guide 1600 may also include protrusion portions different than the protrusion portions of the alignment guides 1300, 1400, 1500 based on desired coverage of a patient's anatomy. The alignment guide 1600 includes a first or proximal end 1602, a second or distal end 1604, a first or anterior surface 1606, a second or posterior surface 1608, a first or medial side 1610, and a second or lateral side 1612. The alignment guide 1600 includes a base portion 120, a body portion 1620, a pin tower portion 1132, and an alignment tower 1340. The base portion 120 may extend out from the body 1620 of the alignment guide 1600 in an anterior direction. The base portion 120 may include a fastening system 126 extending away from the bottom surface 124 of the base portion 120. The base portion 120 and fastening system 126 may be as described in greater detail above and which will not be described again here for brevity sake.

The body 1620 may be formed using imaging, such as CT scans or other tissue determining images. The second or posterior surface 1608 of the body 1620 is formed to match or correspond to the distal end of a patient's tibia. The body 1620 includes a medial protrusion 1622 and a lateral protrusion 1630. The medial protrusion 1622 extends away from the first side 1610, in a proximal direction toward the alignment tower 1340, and in a distal direction past the base portion 120 and the fastener 126. The medial protrusion 1622 includes a first portion 1624, a second portion 1626, and a third portion 1628. The first portion 1624 may be coupled to and extend away from the body 1620. The first portion 1624 may be, for example, larger than the first portions 1324, 1424, 1524 in an anterior-posterior direction. The second portion 1626 may be coupled to and extend away from the first portion 1624. The third portion 1628 may be coupled to and extend away from the second portion 1626 and wrap around the anterior aspect (for example, apex) of a tibia and/or, more specifically, the notch of Harty, if present, and at the junction of the medial malleolus and anterior tibial plafond, extending inferior along the medial malleolus. The first portion 1624 may extend, for example, in an inferior and posterior direction away from the anterior surface 1606 of the body 1620. The first portion 1624 may be, for example, positioned generally perpendicular to an anterior surface of the base portion 120. The second portion 1626 may extend away from the first portion 1624, for example, in an anterior direction and at an angle with respect to the longitudinal axis of the guide 1600. The third portion 1628 may extend, for example, in an inferior direction and terminate in a point. The lateral protrusion 1630 extends away from the second side 1612 and matches the patient's anatomy. The lateral protrusion 1632 may, for example, wrap around the posterior aspect of the tibia to allow the guide 1600 to couple to or grip the patient's tibia making additional fasteners optional.

The body 1620 may also include at least one pin tower 150 extending away from the first surface 1606 of the body 1620. The at least one pin tower 150 may also include a though hole 152 extending through each pin tower 150 and the body 1620. As shown, the body 1620 may include two pin towers 150. For example, the body 1620 may include at least one pin tower 150 positioned on a medial side of the body 1620 and at least one pin tower 150 positioned on a lateral side of the body 1620. Alternative arrangements of the pin towers 150 are also contemplated in order to place the fixation pins in a position for use with the rest of the total ankle procedure. The body 1620 may also include the pin tower portion 1132 extending in a proximal direction toward the first end 1602. The pin tower portion 1132 may be as described above with reference to at least guide 1100 and which will not be described again here for brevity sake. The alignment tower 1340 may also be as described above with reference to guide 1300 and which will not be described again here for brevity sake.

Still another alignment guide 1700 is shown in FIGS. 114-117. The alignment guide 1700 may have, for example, features that are similar to the features of alignment guides 1300, 1400, 1500, 1600. The alignment guide 1700 may also include at least one protrusion portion that is different than the protrusion portions of the alignment guides 1300, 1400, 1500, 1600 based on desired coverage of a patient's anatomy. The alignment guide 1700 includes a first or proximal end 1702, a second or distal end 1704, a first or anterior surface 1706, a second or posterior surface 1708, a first or medial side 1710, and a second or lateral side 1712. The alignment guide 1700 also includes a base portion 120, a body portion 1720, a pin tower portion 1132, and an alignment tower 1340. The base portion 120 may extend out from the body 1720 of the alignment guide 1700 in an anterior direction. The base portion 120 may include a fastening system 126 extending away from the bottom surface 124 of the base portion 120. The base portion 120 and fastening system 126 may be as described in greater detail above and which will not be described again here for brevity sake.

The body 1720 may be formed using imaging, such as CT scans or other tissue determining images. The second or posterior surface 1708 of the body 1720 is formed to match or correspond to the exterior surface of the distal end of a patient's tibia. The body 1720 includes a medial protrusion 1722 and a lateral protrusion 1732. The medial protrusion 1722 extends away from the first side 1710, in a proximal direction toward the alignment tower 1340, and in a distal direction past the base portion 120 and the fastener 126. The medial protrusion 1722 may be, for example, larger than the medial protrusions 1322, 1422, 1522, 1622 in superior-inferior direction. The medial protrusion 1722 includes a first portion 1724, a second portion 1726, a third portion 1728, and a fourth portion 1730. The first portion 1724 may be coupled to and extend away from the body 1720. The second portion 1726 may be coupled to and extend away from the first portion 1724. The third portion 1728 may be coupled to and extend away from the second portion 1726 and wrap around the anterior aspect (for example, apex) of a tibia and/or, more specifically, the notch of Harty, if present, and at the junction of the medial malleolus and anterior tibial plafond, extending inferior along the medial malleolus. The fourth portion 1730 may be coupled to and extend away from the first portion 1724 in a superior direction.

In addition, the first portion 1724 may extend, for example, in an inferior and posterior direction away from the anterior surface 1706 of the body 1720. The first portion 1724 may be, for example, positioned generally perpendicular to an anterior surface of the base portion 120. The second portion 1726 may extend away from the first portion 1724, for example, in an anterior direction and at an angle with respect to the longitudinal axis of the guide 1700. The third portion 1728 may extend, for example, in an inferior direction and terminate in a point. The fourth portion 1730 may extend, for example, in a superior direction to a point below the top of the pin tower portion 1132. The fourth portion 1730 may be, for example, triangularly shaped. The lateral protrusion 1732 extends away from the second side 1712 and matches the patient's anatomy. The lateral protrusion 1732 may, for example, wrap around the posterior aspect of the tibia to allow the guide 1700 to couple to or grip the patient's tibia making additional fasteners optional.

The body 1720 may also include at least one pin tower 150 extending away from the first surface 1706 of the body 1720. The at least one pin tower 150 may also include a though hole 152 extending through each pin tower 150 and the body 1720. As shown, the body 1720 may include two pin towers 150. For example, the body 1720 may include at least one pin tower 150 positioned on a medial side of the body 1720 and at least one pin tower 150 positioned on a lateral side of the body 1720. Alternative arrangements of the pin towers 150 are also contemplated in order to place the fixation pins in a position for use with the rest of the total ankle procedure. The body 1720 may also include the pin tower portion 1132 extending in a proximal direction toward the first end 1702. The pin tower portion 1132 may be as described above with reference to at least guide 1100 and which will not be described again here for brevity sake. The alignment tower 1340 may also be as described above with reference to guide 1300 and which will not be described again here for brevity sake.

Referring now to FIGS. 118-121 another alignment guide 1800 is shown. The alignment guide 1800 may have, for example, features that are similar to the features of alignment guides 1300, 1400, 1500, 1600, 1700. The alignment guide 1800 may also include at least one protrusion portion that is different than the protrusion portions of the alignment guides 1300, 1400, 1500, 1600, 1700 based on desired coverage of a patient's anatomy. The alignment guide 1800 includes a first or proximal end 1802, a second or distal end 1804, a first or anterior surface 1806, a second or posterior surface 1808, a first or medial side 1810, and a second or lateral side 1812. The alignment guide 1800 also includes a base portion 120, a body portion 1820, a pin tower portion 1132, and an alignment tower 1340. The base portion 120 may extend out from the body 1820 of the alignment guide 1800 in an anterior direction. The base portion 120 may include a fastening system 126 extending away from the bottom surface 124 of the base portion 120. The base portion 120 and fastening system 126 may be as described in greater detail above and which will not be described again here for brevity sake.

The body 1820 may be formed using imaging, such as CT scans or other tissue determining images. The second or posterior surface 1808 of the body 1820 is formed to match or correspond to the exterior surface of the distal end of a patient's tibia. The body 1820 includes a medial protrusion 1822 and a lateral protrusion 1830. The medial protrusion 1822 extends away from the first side 1810, in a proximal direction toward the alignment tower 1340, and in a distal direction past the base portion 120 and the fastener 126. The medial protrusion 1822 may have, for example, a different shape than the medial protrusions 1322, 1422, 1522, 1622, 1722. The medial protrusion 1822 also includes a first portion 1824, a second portion 1826, and a third portion 1828. The first portion 1824 may be coupled to and extend away from the body 1820. The second portion 1826 may be coupled to and extend away from the first portion 1824. The third portion 1828 may be coupled to and extend away from the second portion 1826 and wrap around the anterior aspect (for example, apex) of a tibia and/or, more specifically, the notch of Harty, if present, and at the junction of the medial malleolus and anterior tibial plafond, extending inferior along the medial malleolus.

In addition, the first portion 1824 may extend, for example, in an inferior and posterior direction away from the anterior surface 1806 of the body 1820. The first portion 1824 may be, for example, sloped or curved on a superior surface as the first portion 1824 extends away from the body 1820. The second portion 1826 may extend away from the first portion 1824, for example, forming an anterior surface that may be parallel with the longitudinal axis of the guide 1800. The third portion 1828 may extend, for example, in an inferior direction and terminate in a point at the second end 1804. The lateral protrusion 1830 extends away from the second side 1812 and matches the patient's anatomy. The lateral protrusion 1830 may include a first portion 1832 and a second portion 1834 extending away from the first portion 1832. The first portion 1832 may extend, for example, in an anterior-posterior direction from the anterior surface 1806 of the body 1820. The second portion 1834 may extend away from the first portion 1832, for example, in a superior direction to a point below the top of the pin tower portion 1132. The second portion 1834 may extend, for example, in an anterior-posterior direction from the first surface 1806 of the body 1820. The second portion 1834 may be, for example, triangularly shaped. The lateral protrusion 1830 may, for example, wrap around the posterior aspect of the tibia to allow the guide 1800 to couple to or grip the patient's tibia making additional fasteners optional.

The body 1820 may also include at least one pin tower 150 extending away from the first surface 1806 of the body 1820. The at least one pin tower 150 may also include a though hole 152 extending through each pin tower 150 and the body 1820. As shown, the body 1820 may include two pin towers 150. For example, the body 1820 may include at least one pin tower 150 positioned on a medial side of the body 1820 and at least one pin tower 150 positioned on a lateral side of the body 1820. Alternative arrangements of the pin towers 150 are also contemplated in order to place the fixation pins in a position for use with the rest of the total ankle procedure. The body 1820 may also include the pin tower portion 1132 extending in a proximal direction toward the first end 1802. The pin tower portion 1132 may be as described above with reference to at least guide 1100 and which will not be described again here for brevity sake. The alignment tower 1340 may also be as described above with reference to guide 1300 and which will not be described again here for brevity sake.

Another alignment guide 1900 is shown in FIGS. 122-129. The alignment guide 1900 includes a first or proximal end 1902, a second or distal end 1904, a first or anterior surface 1906, a second or posterior surface 1908, a first or medial side 1910, and a second or lateral side 1912. The alignment guide 1900 includes a body portion 1920, a pin tower portion 1132, a base portion 120, and at least one protrusion 1922, 1930, such as a medial or lateral protrusion. The base portion 120 may extend out from the body 1920 of the alignment guide 1900 in an anterior direction. The base portion 120 may include a fastening system 126 extending away from the bottom surface 124 of the base portion 120. The base portion 120 and fastening system 126 may be as described above in greater detail and will not be described again here for brevity sake.

The body 1920 may be formed using imaging, such as CT scans or other tissue determining images. The second or posterior surface 1908 of the body 1920 is formed to match or correspond to the exterior surface of the distal end of a patient's tibia. The body 1920 includes a medial protrusion 1922 and a lateral protrusion 1930. The medial protrusion 1922 extends away from the first side 1910 and extends in a distal direction past the base portion 120 and the fastener 126. The medial protrusion 1922 includes a first portion 1924 coupled to and extending away from the body 1920, a second portion 1926 coupled to and extending away from the first portion 1924, and a third portion 1928 coupled to and extending away from the second portion 1926 and which wraps around the anterior aspect (for example, apex) of a tibia and/or, more specifically, the notch of Harty, if present, and at the junction of the medial malleolus and anterior tibial plafond, extending inferior along the medial malleolus. The first portion 1924 may extend, for example, in an inferior and posterior direction away from the anterior surface 1906 of the body 1920. The first portion 1924 may be, for example, positioned generally perpendicular to an anterior surface of the base portion 120. The second portion 1926 may extend away from the first portion 1924, for example, in an anterior direction and at an angle with respect to the longitudinal axis of the guide 1900. The third portion 1928 may extend, for example, in a direction toward the lateral side of the guide 1900 and at an angle with respect to the longitudinal axis of the guide 1900. The lateral protrusion 1930 extends away from the second side 1912 and matches the patient's anatomy. The lateral protrusion 1930 may, for example, wrap around the posterior aspect of the tibia to allow the guide 1900 to couple to or grip the patient's tibia making additional fasteners optional. The body 1920 may also include at least one pin tower 150 extending away from the first surface 1906 of the body 1920. The at least one pin tower 150 may also include a through hole 152 extending through each pin tower 150 and the body 1920. As shown, the body 1920 may include two pin towers 150. For example, the body 1920 may include at least one pin tower 150 positioned on a medial side of the body 1920 and at least one pin tower 150 positioned on a lateral side of the body 1920. Alternative arrangements of the pin towers 150 are also contemplated in order to place the fixation pins in a position for use with the rest of the total ankle procedure.

The body 1920 may also include a pin tower portion 1132 extending in a proximal direction to the first end 1902. The pin tower portion 1132 may extend from a top surface 122 of the base portion 120. The pin tower portion 1132 may include at least one pin tower 1134 extending through the pin tower portion 1132. The pin towers 1134 may be, for example, integral, monolithic, a single piece, or of one-piece construction with the pin tower portion 1132. The at least one pin tower 1134 may be, for example, two pin towers 1134. The two pin towers 1134 may be, for example, spaced apart from each other along the length of the pin tower portion 1132. Each pin tower 1134 may include a through hole 1136 extending through the pin towers 1134 from an anterior side 1906 to a posterior side 1908 of the guide 1900.

Referring now to FIGS. 130-133, another alignment guide 2000 is shown. The alignment guide 2000 may have, for example, features similar to the alignment guide 1900 with varying protrusion portions based on patient anatomy. The alignment guide 2000 includes a first or proximal end 2002, a second or distal end 2004, a first or anterior surface 2006, a second or posterior surface 2008, a first or medial side 2010, and a second or lateral side 2012. The alignment guide 2000 includes a body portion 2020, a pin tower portion 1132, a base portion 120, and at least one protrusion 2022, 2030, such as a medial or lateral protrusion. The base portion 120 may extend out from the body 2020 of the alignment guide 2000 in an anterior direction. The base portion 120 may include a fastening system 126 extending away from the bottom surface 124 of the base portion 120. The base portion 120 and fastening system 126 may be as described above in greater detail and will not be described again here for brevity sake.

The body 2020 may be formed using imaging, such as CT scans or other tissue determining images. The second or posterior surface 2008 of the body 2020 is formed to match or correspond to the exterior surface of the distal end of a patient's tibia. The body 2020 includes a medial protrusion 2022 and a lateral protrusion 2030. The medial protrusion 2022 extends away from the first side 2010 and extends in a distal direction past the base portion 120 and the fastener 126. The medial protrusion 2022 includes a first portion 2024 coupled to and extending away from the body 2020, a second portion 2026 coupled to and extending away from the first portion 2024, and a third portion 2028 coupled to and extending away from the second portion 2026 and which wraps around the anterior aspect (for example, apex) of a tibia and/or, more specifically, the notch of Harty, if present, and at the junction of the medial malleolus and anterior tibial plafond, extending inferior along the medial malleolus. The first portion 2024 may extend, for example, in an inferior and posterior direction away from the anterior surface 2006 of the body 2020. The first portion 1924 may be, for example, positioned generally perpendicular to an anterior surface of the base portion 120. The second portion 2026 may extend away from the first portion 2024, for example, in an anterior direction and at an angle with respect to the longitudinal axis of the guide 2000. The third portion 2028 may extend, for example, in a direction toward the lateral side of the guide 2000 and at an angle with respect to the longitudinal axis of the guide 2000. The lateral protrusion 2030 extends away from the second side 2012 and matches the patient's anatomy. The lateral protrusion 2030 may include a first portion 2032 and a second portion 2034 extending away from the first portion 2032. The first portion 2032 may extend, for example, in an anterior-posterior direction from the anterior surface 2006 of the body 2020. The second portion 2034 may extend away from the first portion 2032, for example, in a superior direction to a point below the top of the pin tower portion 1132. The second portion 2034 may also extend, for example, in an anterior-posterior direction from the first surface 2006 of the body 2020. The second portion 2034 may be, for example, triangularly shaped. The lateral protrusion 2030 may, for example, wrap around the posterior aspect of the tibia to allow the guide 2000 to couple to or grip the patient's tibia making additional fasteners optional.

The body 2020 may also include at least one pin tower 150 extending away from the first surface 2006 of the body 2020. The at least one pin tower 150 may also include a through hole 152 extending through each pin tower 150 and the body 2020. As shown, the body 2020 may include two pin towers 150. For example, the body 2020 may include at least one pin tower 150 positioned on a medial side of the body 2020 and at least one pin tower 150 positioned on a lateral side of the body 2020. Alternative arrangements of the pin towers 150 are also contemplated in order to place the fixation pins in a position for use with the rest of the total ankle procedure. The body 2020 may also include the pin tower portion 1132 extending in a proximal direction toward the first end 2002. The pin tower portion 1132 may be as described above with reference to at least guide 1100 and which will not be described again here for brevity sake.

FIGS. 134-137 shown another alignment guide 2100. The alignment guide 2100 may have, for example, features similar to alignment guide 1900, 2000 with varying protrusion portions based on patient anatomy. The alignment guide 2100 includes a first or proximal end 2102, a second or distal end 2104, a first or anterior surface 2106, a second or posterior surface 2108, a first or medial side 2110, and a second or lateral side 2112. The alignment guide 2100 includes a body portion 2120, a pin tower portion 1132, a base portion 120, and at least one protrusion 2122, 2130, such as a medial or lateral protrusion. The base portion 120 may extend out from the body 2120 of the alignment guide 2100 in an anterior direction. The base portion 120 may include a fastening system 126 extending away from the bottom surface 124 of the base portion 120. The base portion 120 and fastening system 126 may be as described above in greater detail and will not be described again here for brevity sake.

The body 2120 may be formed using imaging, such as CT scans or other tissue determining images. The second or posterior surface 2108 of the body 2120 is formed to match or correspond to the exterior surface of the distal end of a patient's tibia. The body 2120 includes a medial protrusion 2122 and a lateral protrusion 2130. The medial protrusion 2122 extends away from the first side 2110 and extends in a distal direction past the base portion 120 and the fastener 126. The medial protrusion 2122 includes a first portion 2124 coupled to and extending away from the body 2120, a second portion 2126 coupled to and extending away from the first portion 2124, and a third portion 2128 coupled to and extending away from the second portion 2126 and which wraps around the anterior aspect (for example, apex) of a tibia and/or, more specifically, the notch of Harty, if present, and at the junction of the medial malleolus and anterior tibial plafond, extending inferior along the medial malleolus. The medial protrusion 2122 may be as described in greater detail above with reference to medial protrusion 1922 and which will not be described again here for brevity sake. The lateral protrusion 2130 extends away from the second side 2112 and matches the patient's anatomy. The lateral protrusion 2130 may, for example, wrap around the posterior aspect of the tibia to allow the guide 2100 to couple to or grip the patient's tibia making additional fasteners optional.

The body 2120 may also include at least one pin tower 150 extending away from the first surface 2106 of the body 2120. The at least one pin tower 150 may also include a through hole 152 extending through each pin tower 150 and the body 2120. As shown, the body 2120 may include two pin towers 150. For example, the body 2120 may include at least one pin tower 150 positioned on a medial side of the body 2120 and at least one pin tower 150 positioned on a lateral side of the body 2120. Alternative arrangements of the pin towers 150 are also contemplated in order to place the fixation pins in a position for use with the rest of the total ankle procedure. The body 2120 may also include the pin tower portion 1132 extending in a proximal direction toward the first end 2102. The pin tower portion 1132 may be as described above with reference to at least guide 1100 and which will not be described again here for brevity sake.

Referring now to FIGS. 138-141, another alignment guide 2200 is shown. The alignment guide 2200 may be, for example, similar to alignment guide 1900, 2000, 2100 with varying protrusion portions based on patient anatomy. The alignment guide 2200 includes a first or proximal end 2202, a second or distal end 2204, a first or anterior surface 2206, a second or posterior surface 2208, a first or medial side 2210, and a second or lateral side 2212. The alignment guide 2200 includes a body portion 2220, a pin tower portion 2232, a base portion 120, and at least one protrusion 2222, 2230, such as a medial or lateral protrusion. The base portion 120 may extend out from the body 2220 of the alignment guide 2200 in an anterior direction. The base portion 120 may include a fastening system 126 extending away from the bottom surface 124 of the base portion 120. The base portion 120 and fastening system 126 may be as described above in greater detail and will not be described again here for brevity sake.

The body 2220 may be formed using imaging, such as CT scans or other tissue determining images. The second or posterior surface 2208 of the body 2220 is formed to match or correspond to the exterior surface of the distal end of a patient's tibia. The body 2220 includes a medial protrusion 2222 and a lateral protrusion 2230. The medial protrusion 2222 extends away from the first side 2210 and extends in a distal direction past the base portion 120 and the fastener 126. The medial protrusion 2222 includes a first portion 2224 coupled to and extending away from the body 2220, a second portion 2226 coupled to and extending away from the first portion 2224, and a third portion 2228 coupled to and extending away from the second portion 2226 and which wraps around the anterior aspect (for example, apex) of a tibia and/or, more specifically, the notch of Harty, if present, and at the junction of the medial malleolus and anterior tibial plafond, extending inferior along the medial malleolus. The medial protrusion 2222 may be as described in greater detail above with reference to medial protrusion 1922 and which will not be described again here for brevity sake. The lateral protrusion 2230 extends away from the second side 2212 and matches the patient's anatomy. The lateral protrusion 2230 may, for example, wrap around the posterior aspect of the tibia to allow the guide 2200 to couple to or grip the patient's tibia making additional fasteners optional.

The body 2220 may also include at least one pin tower 150 extending away from the first surface 2206 of the body 2220. The at least one pin tower 150 may also include a through hole 152 extending through each pin tower 150 and the body 2220. As shown, the body 2220 may include two pin towers 150. For example, the body 2220 may include at least one pin tower 150 positioned on a medial side of the body 2220 and at least one pin tower 150 positioned on a lateral side of the body 2220. Alternative arrangements of the pin towers 150 are also contemplated in order to place the fixation pins in a position for use with the rest of the total ankle procedure. The body 2220 may also include the pin tower portion 2232 extending in a proximal direction toward the first end 2202. The pin tower portion 2232 may be, for example, similar to pin tower portion 1132 and including a length that is larger than the length of the pin tower portion 2232. The at least one pin tower 1134 and through hole 1136 may be as described above with reference to at least guide 1100 and which will not be described again here for brevity sake.

A method for using the guides 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 may include making an incision on the anterior side of the ankle joint. The incision may be as known by one of ordinary skill in the art for total ankle replacements. The incision may then be spread open to clear soft tissue around the ankle joint. The periosteum surrounding the bone can either be cleared for guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 that has no tissue offset, i.e. matches the bone exactly, or left intact for a guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 that includes a tissue offset, i.e. leaves a small space off of the scanned bone to account for soft tissue. The guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 can then be placed onto the tibia and then adjusted until it locks into the bone features on the guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200. After the guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 is appropriately placed on the bone, converging pins may be used to secure the guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 in place. With the guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 securely in place, a resection block can be installed using a fastening mechanism, for example, dovetail features, between the resection blocks and the guides 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200. Once the guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 is in place, the surgeon can complete alignment checks to verify alignment is in the desired location. The alignment checks may include interfacing with other instrumentation (not shown) to verify the coronal and sagittal planes and the joint line. If the alignment is found to be in the desired location, then the surgeon may proceed with the total ankle resection procedure using a normal or standard technique.

However, if the alignment is found not to be at the desired location, then the surgeon can place pins through the pin towers on the guide 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 or a separate, modular attachment that correspond to a fast-track guide or standard alignment guide. The pin towers and modular attachment may be dimensioned based on the dovetail feature to transfer the alignment achieved in the patient specific guides 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 to the fast-track or standard alignment guides. Transferring the position allows the surgeon to make minor adjustments without having to re-complete all alignment steps. The minor adjustments allow for users to maintain portions of the alignment from the patient specific guides 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 and only adjust the desired portions. After the desired adjustments are made, the surgeon can then proceed with the procedure using a normal or standard technique.

Referring now to FIGS. 142-149, a talus guide 2300 is shown. The talus guide 2300 may include a base portion 2310 on an anterior side of the guide 2300. The talus guide 2300 may also include a first member 2312 and a second member 2316 and each member 2312, 2316 may extend from the base portion 2310 to a posterior side of the guide 2300. The first member 2312 may be positioned adjacent to and overlapping with the second member 2316. The first and second members 2312, 2316 may extend away from the base portion 2310, for example, perpendicularly. The first member 2312 may include a first through hole 2314 extending, for example, through the entire first member 2312 and the base portion 2310. The second member 2316 may also include a second through hole 2318 extending, for example, through the entire second member 2316 and the base portion 2310.

The guide 2300 may also include a third member 2320 and a fourth member 2326. A portion of the third member 2320 may be coupled to a posterior end of the first member 2312 and a portion of the anterior end of the third member 2320 may be coupled to the base portion 2310. The third member 2320 may also extend away from a superior or upper surface of the first member 2312 at an angle as the third member 2320 extends from the posterior end to the anterior end. The posterior end of the third member 2320 may, for example, overlap with the first member 2312 and the third member 2320 may be positioned offset from a longitudinal axis of the first member 2312. The third member 2320 may also include a third through hole 2322 extending, for example, through the entire third member 2320 from anterior surface to a posterior surface. The second or posterior end of the third member 2320 may be, for example, situated to position the through hole 2322 of the third member 2320 generally adjacent to the through hole 2314 of the first member 2312. In addition, the third member 2320 may have an angled or tapered surface 2324 positioned at the anterior end on a top or superior surface on a side opposite the portion of the third member 2320 coupled to the base portion 2310.

A portion of the fourth member 2326 may be coupled to a second or posterior end of the second member 2316 and a portion of the first or anterior end of the fourth member 2326 may be coupled to the base portion 2310. The fourth member 2326 may also extend away from a superior or upper surface of the second member 2316 at an angle as the fourth member 2326 extends from the posterior end to the anterior end. The posterior end of the fourth member 2326 may, for example, overlap with the second member 2316 and the fourth member 2326 may be positioned offset from a longitudinal axis of the second member 2316. The fourth member 2326 may also include a fourth through hole 2328 extending, for example, through the entire fourth member 2326 from anterior surface to a posterior surface. The second or posterior end of the fourth member 2326 may be, for example, situated to position the through hole 2328 of the fourth member 2326 generally adjacent to the through hole 2318 of the second member 2316. In addition, the fourth member 2326 may have an angled or tapered surface 2330 positioned at the anterior end on a top or superior surface on a side opposite the portion of the fourth member 2326 coupled to the base portion 2310.

The second or posterior surface of the guide 2300 may include, for example, a second or posterior surface 2340. The second surface 2340 may include a first or upper portion 2342, a second or lower portion 2344, and an extension portion 2346 extending away from a first side of the first portion 2342. The first portion 2342 may include, for example, five lobes, which include the superior or upper surfaces of the members 2312, 2316, 2320, 2326 and a fifth lobe 2348 positioned on a second side of the first portion 2342. The lobes formed from the upper surface of the members 2312, 2316, 2320, 2326 may be positioned, for example, between the fifth lobe 2348 and the extension portion 2346. The upper surface of the members 2312, 2316, 2320, 2326 and the upper surface of the fifth lobe 2348 may be, for example, curved as they extend in a superior direction from the first portion 2342. The second or lower portion 2344 may also be, for example, curved as the second portion 2344 extends from the first portion 2342. The second portion 2344 may curve to be positioned, for example, generally perpendicular to the first portion 2342. The extension portion 2346 may extend away from the first portion 2342 at, for example, an angle. The second surface 2340 may be formed using imaging, such as CT scans or other tissue determining images. The second surface 2340 of the guide 2300 may be formed to match or correspond to the exterior surface of the proximal end of a patient's talus.

The above disclosure describes a portion of a total ankle replacement (TAR) procedure and the devices used in that procedure. Additional understanding of the TAR procedure may be found in U.S. Provisional Application No. 62/779,436 filed Dec. 13, 2018 and entitled Joint Replacement Systems and Methods of Use and Assembly, International Application No. PCT/US2019/029009 filed Apr. 24, 2019 and entitled Implants and Methods of Use and Assembly, U.S. Provisional Application No. 62/779,092 filed Dec. 13, 2018 and entitled Instruments, Guides and Related Methods for Total Ankle Replacement, International Application No. PCT/US2019/066404 filed Dec. 13, 2019 and entitled Instruments, Guides and Related Methods for Total Ankle Replacement, U.S. Provisional Application No. 62/890,611 filed Aug. 22, 2019 and entitled Patient Specific Instruments and Methods of Use, U.S. Provisional Application No. 62/899,703 filed Sep. 12, 2019 and entitled Joint Replacement Alignment Guides, Systems and Methods Use and Assembly of, International Application No. PCT/US2019/066408 filed Dec. 13, 2019 and entitled Joint Replacement Alignment Guides, Systems and Methods of Use and Assembly, U.S. Provisional Application No. 62/899,655 filed Sep. 12, 2019 and entitled Alignment Instruments and Methods for Use in Total Ankle Replacement, International Application No. PCT/US2019/066149 filed Dec. 13, 2019 and entitled Alignment Instruments and Methods for Use in Total Ankle Replacement, U.S. Provisional Application No. 62/899,740 filed Sep. 12, 2019 and entitled Joint Replacement Alignment Guides, Systems and Methods of Use and Assembly, International Application No. PCT/US2019/066393 filed Dec. 13, 2019 and entitled Joint Replacement Alignment Guides, Systems and Methods of Use and Assembly, U.S. Provisional Application No. 62/898,615 filed Sep. 11, 2019 and entitled Resection Guides, Sweeping Reamers, and Methods for Use in Total Ankle Replacement, International Application No. PCT/US2019/064948 filed Dec. 6, 2019 and entitled Resection Guides, Sweeping Reamers, and Methods for Use in Total Ankle Replacement, U.S. Provisional Application No. 62/898,854 filed Sep. 11, 2019 and entitled Distractors Having Attachable Paddles, Impaction Devices, and Methods for Use in Total Ankle Replacement, International Application No. PCT/US2019/066398 filed Dec. 13, 2019 and entitled Distractors Having Attachable Paddles, Impaction Devices, and Methods for Use in Total Ankle Replacement, U.S. Provisional Application No. 62/899,646 filed Sep. 12, 2019 and entitled Trial Insert Assembly, International Application No. PCT/US2019/065025 filed Dec. 6, 2019 and entitled Trial Insert Assembly, U.S. Provisional Application No. 62/899,460 filed Sep. 12, 2019 and entitled Total Ankle Replacement Surgical Method, International Application No. PCT/US2019/066409 filed Dec. 13, 2019 and entitled Total Ankle Replacement Surgical Method, which are each hereby incorporated herein in their entireties.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of guides 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 may be used interchangeably and in alternative combinations as would be modified or altered by one of skill in the art. Further, the steps of the surgical methods associated with the guides 100, 180, 190, 200, 250, 300, 400, 450, 500, 700, 750, 800, 900, 1000, 1100, 1200, 1300, 1400, 1500, 1600, 1700, 1800, 1900, 2000, 2100, 2200 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiment, the invention is now claimed to be:

1. An alignment guide, comprising:
   a body with a first surface and a second surface, wherein the body further comprises:
      a medial protrusion extending away from a medial side of the body, wherein the medial protrusion comprises:
         a first portion extending away from the body in a posterior-medial direction;
         a second portion extending away from a distal end of the first portion, wherein the second portion extends in at least a lateral direction from the first portion; and
         a third portion extending away from the second portion in at least a distal direction; and
      a lateral protrusion extending away from a lateral side of the body;
   a base portion coupled to and extending away from the first surface of the body; and
   a tower portion coupled to and extending away from a top surface of the body.

2. The alignment guide of claim 1, wherein the second surface of the body is formed to correspond to an exterior surface of a patient's bone.

3. The alignment guide of claim 2, wherein the second surface of the body is formed using medical imaging.

4. The alignment guide of claim 1, wherein the medial protrusion further comprises:
   a fourth portion extending away from a proximal end of the first portion.

5. The alignment guide of claim 4, wherein the fourth portion tapers as the fourth portion extends away from the first portion to a point.

6. The alignment guide of claim 1, wherein the lateral protrusion comprises:
   a first portion extending away from the body in a posterior-lateral direction.

7. The alignment guide of claim 6, wherein the lateral protrusion further comprises:
   a second portion extending away from a proximal end of the first portion.

8. The alignment guide of claim 7, wherein the second portion of the lateral protrusion tapers as the second portion extends away from the first portion of the lateral protrusion to a point.

9. The alignment guide of claim 1, wherein the medial protrusion comprises:
   at least one cutout extending through at least a portion of the medial protrusion.

10. The alignment guide of claim 1, wherein the base portion further comprises:
    a fastening system extending away from a bottom surface of the base portion.

11. The alignment guide of claim 10, wherein the fastening system comprises:
    a channel extending in an anterior-posterior direction along a bottom surface of the fastening system;
    wherein the channel forms a first leg spaced apart from a second leg, wherein the first leg includes a first undercut extending from the channel into the first leg, and wherein the second leg includes a second undercut extending from the channel into the second leg.

12. The alignment guide of claim 10, wherein the tower portion further comprises:
    at least one pin tower forming at least one through hole extending through at least the tower portion from an anterior surface to a posterior surface of the tower portion.

13. The alignment guide of claim 12, wherein the tower portion is removable from the body.

14. The alignment guide of claim 12, wherein the at least one pin tower comprises:
    a first pin tower positioned near a first end of the alignment guide; and
    a second pin tower positioned between the first pin tower and the body.

15. The alignment guide of claim 12, wherein the tower portion further comprises:
    at least one elastic region positioned along a length of the tower portion.

16. The alignment guide of claim 12, wherein the alignment guide further comprises:
    an alignment tower coupled to and extending away from a superior surface of the tower portion.

17. The alignment guide of claim 16, wherein the alignment tower comprises:
    at least one protrusion with an opening extending into the at least one protrusion from a first end of the alignment guide toward the tower portion.

18. The alignment guide of claim 17, wherein the at least one protrusion comprises:

a first protrusion; and
a second protrusion;
wherein the protrusions are positioned aligned in an anterior-posterior direction, and wherein the protrusions at least partially overlap.

19. The alignment guide of claim 12, further comprising:
an alignment tool for insertion into at least one through hole of the tower portion.

20. The alignment guide of claim 1, wherein the base portion further comprises:
a slot extending into the base portion from an anterior surface of the base portion.

21. The alignment guide of claim 20, wherein the slot is configured to receive a coupling member of a laser.

22. The alignment guide of claim 1, further comprising:
at least one coupling member extending away from at least one of a medial side and a lateral side of the tower portion at a proximal end.

23. The alignment guide of claim 22, wherein the at least one coupling member curves in a posterior direction as the at least one coupling member extends away from the tower portion.

24. An alignment guide, comprising:
a body;
a base portion extending away from a first surface of the body;
a first member extending away from the base portion to a posterior side of the alignment guide in a generally perpendicular direction; and
a second member extending away from the base portion to a posterior side of the alignment guide in a generally perpendicular direction; and
wherein the first member is positioned adjacent to and overlapping with the second member, wherein the first member comprises a first through hole extending through the first member from an anterior side to a posterior side, and wherein the second member comprises a second through hole extending through the second member from an anterior side to a posterior side.

25. The alignment guide of claim 24, wherein an interior surface corresponds to bones of a patient.

26. The alignment guide of claim 24, further comprising:
a third member coupled to a posterior end of the first member and extending away from the posterior end of the first member at an angle along an anterior posterior direction;
a fourth member coupled to a posterior end of the second member extending away from the posterior end of the second member at an angle along an anterior posterior direction.

27. The alignment guide of claim 26, wherein the third member comprises a third through hole extending through the third member from an anterior side to a posterior side, and wherein the fourth member comprises a fourth through hole extending through the fourth member from an anterior side to a posterior side.

28. The alignment guide of claim 27, wherein at least a portion of the third member overlaps with at least a portion of the first member, and wherein at least a portion of the fourth member overlaps with at least a portion of the second member.

29. The alignment guide of claim 28, wherein an interior surface corresponds to bones of a patient, and wherein the interior surface comprises:
a first portion;
a second portion extending away from a posterior end of the first portion, wherein the second portion extends in an anterior direction from the first portion; and
at least one extension portion extending away from the first portion in at least one of a medial direction and a lateral direction.

30. The alignment guide of claim 29, wherein the interior surface is curved between the first portion and the second portion.

* * * * *